US011535836B2

(12) United States Patent
Zhang et al.

(10) Patent No.: US 11,535,836 B2
(45) Date of Patent: *Dec. 27, 2022

(54) VARIANT G6P G7P GLUCOAMYLASE COMPOSITIONS AND METHODS

(71) Applicant: Fornia BioSolutions, Inc., Hayward, CA (US)

(72) Inventors: Xiyun Zhang, San Ramon, CA (US); Jie Yang, Foster City, CA (US); Goutami Banerjee, Hayward, CA (US); Khin Oo, Daly City, CA (US); Marielle De Jesus Palatino, Stockton, CA (US); Eric Lin Hu, Millbrae, CA (US); Imad N. Sawaya, Redwood City, CA (US); Tatsuya Fukushima, Fremont, CA (US); Jijiao Zeng, Albany, CA (US); Wenhua Lu, Dublin, CA (US)

(73) Assignee: Fornia Biosolutions, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/681,678

(22) Filed: Nov. 12, 2019

(65) Prior Publication Data
US 2020/0199560 A1 Jun. 25, 2020

Related U.S. Application Data

(60) Provisional application No. 62/784,193, filed on Dec. 21, 2018.

(51) Int. Cl.
*C12N 9/34* (2006.01)
*C12N 15/52* (2006.01)
(Continued)

(52) U.S. Cl.
CPC ............. *C12N 9/2428* (2013.01); *C12N 1/14* (2013.01); *C12N 1/16* (2013.01); *C12N 1/20* (2013.01); *C12N 15/52* (2013.01); *C12N 15/70* (2013.01); *C12N 15/74* (2013.01); *C12N 15/80* (2013.01); *C12N 15/81* (2013.01); *C12P 19/14* (2013.01); *C12Y 302/01003* (2013.01)

(58) Field of Classification Search
None
See application file for complete search history.

(56) References Cited

U.S. PATENT DOCUMENTS 9,598,680 B1 3/2017 Zhang et al.
9,670,472 B1 6/2017 Yang et al.
(Continued)

FOREIGN PATENT DOCUMENTS

WO   WO 2011/020852 A1   2/2011
WO   WO 2011/022465 A1   2/2011
WO   WO 2014/028258 A1   2/2014

OTHER PUBLICATIONS

UniProt Accession No. A0A2C5X2Z5_9PEZI, published Dec. 20, 2017 (Year: 2017).*

(Continued)

*Primary Examiner* — Richard C Ekstrom
(74) *Attorney, Agent, or Firm* — Morgan, Lewis & Bockius LLP

(57) ABSTRACT

The invention is directed to novel variant glucoamylases.

21 Claims, 49 Drawing Sheets

Specification includes a Sequence Listing.

(51) Int. Cl.

| | |
|---|---|
| *C12N 15/70* | (2006.01) |
| *C12N 15/74* | (2006.01) |
| *C12N 15/80* | (2006.01) |
| *C12N 15/81* | (2006.01) |
| *C12N 1/14* | (2006.01) |
| *C12N 1/16* | (2006.01) |
| *C12N 1/20* | (2006.01) |
| *C12P 19/14* | (2006.01) |

(56) References Cited

U.S. PATENT DOCUMENTS

| | | |
|---|---|---|
| 10,035,997 B2 | 7/2018 | Yang et al. |
| 10,053,678 B2 | 8/2018 | Zhang et al. |
| 10,227,578 B2 | 3/2019 | Zhang et al. |
| 10,927,357 B2 * | 2/2021 | Yang .................. C12P 19/14 |
| 2018/0037879 A1 | 2/2018 | Zhang et al. |
| 2020/0199560 A1 * | 6/2020 | Zhang .................. C12N 1/14 |

OTHER PUBLICATIONS

U.S. Appl. No. 16/783,970, filed Feb. 6, 2020.
Annex to Form PCT/ISA/206, Communication Relating to the Results of the Partial International Search for International application No. PCT/US2019/061019, dated Feb. 11, 2020, 12 pages.
Norouzian et al., "Fungal glucoamylases", Biotechnology Advances, Elsevier Publishing, Barking, GB, vol. 24, No. 1, Jan. 1, 2006, pp. 80-85.
Coutinho et al., "Structure-Function Relationships in the Catalytic and Starch Binding Domains of Glucoamylase", Protein Engineering, Oxford Univ. Press, Surrey, GB vol. 7, No. 3, Mar. 1, 1994, pp. 393-400.
Evans et al., "Activity and thermal stability of genetically truncated forms of Aspergillus glucoamylase", Gene, Elsevier, Amsterdam, NL, vol. 91, No. 1, Jan. 1, 1990, pp. 131-134.
GenBank accession No. KKA29558.1, hypothetical protein TD95_001685 [Thielaviopsis punctulata], retrieved from the Internet on Mar. 23, 2020. https://www.ncbi.nlm.nih.gov/protein/802103406/.
International Search Report and Written Opinion for International Application No. PCT/US2019/061019, mailed Apr. 9, 2020, 21 pages.

* cited by examiner

FIGURE 1

```
SP (Signal Peptide): AA 1-22 (Bold and Italicized)
CD (Catalytic Domain; GH15): AA 42-457
SBD (Starch Binding Domain; CBM20): AA 515-606 (Bold and Underlined)

1                                                        50
G6P    MVFLKSAIAA STWLLAATGV VASPVSKRAT LDEFISTERP LALERLLCNI
G7P    MVFLKSAIAA STWLLAATGV VASPVSKRAT LDEFISTERP LALERLLCNI 51                                                       100
G6P    GPTGCRASGA ASGVVIASPS RSDPDYYYTW TRDAALVFKE IVDSVETNTT
G7P    GPTGCRASGA ASGVVIASPS RSDPDYYYTW TRDAALVFKE IVDSVETNTT 101                                                      150
G6P    LLLPEIENYV TAQAYLQTVT NPSGSLSDGA GLGEPKFNVD MTPFTGAWGR
G7P    LLLPEIENYV TAQAYLQTVT NPSGSLSDGA GLGEPKFNVD MTPFTGAWGR 151                                                      200
G6P    PQRDGPALRA TAMIAYYNYL LNNNATTDCG LWQIIQNDLN YVAQYWNQTG
G7P    PQRDGPALRA TAMIAYYNYL LNNNATTDCG LWQIIQNDLN YVAQYWNQTG 201                                                      250
G6P    YDLWEEVPGS SFFTVAAQYR ALVEGSTLAA KLGKSHSAYD TVAPQILCYL
G7P    YDLWEEVPGS SFFTVAAQYR ALVEGSTLAA KLGKSHSAYD TVAPQILCYL 251                                                      300
G6P    QSFWSSSKGY IVANTQTASW VSRSGLDANT PLTAIHLFDP ELGCDDSTFQ
G7P    QSFWSSSKGY IVANTQTASW VSRSGLDANT PLTAIHLFDP ELGCDDSTFQ 301                                                      350
G6P    PCSPKQLITT KKLVDSFRSI YAINSGKSAG DALAVGRYAE DVYYNGNPWY
G7P    PCSPKQLITT KKLVDSFRSI YAINSGKSAG DALAVGRYAE DVYYNGNPWY 351                                                      400
G6P    LCTLAVAEQL YDAVYTWKLE GSITVTSVSL PFFTDLLPSL TTGTYASGST
G7P    LCTLAVAEQL YDAVYTWKLE GSITVTSVSL PFFTDLLPSL TTGTYASGST 401                                                      450
G6P    TFESIISAVT TYADGFVSIV QTYTPSDGAL SEQYSKYNGQ QLSAPDLTWS
G7P    TFESIISAVT TYADGFVSIV QTYTPSDGAL SEQYSKYNGQ QLSAPDLTWS 451                                                      500
G6P    YAAFLSATER RDSVVPAGWA GASSVSVPGA CAATTVVGTY AAASNCGTPG
G7P    YAAFLSATER RDSVVPAGWA GASSVSVPGA CAATTVVGTY AAASNCGTPG 501                                                      550
G6P    SGSGGNGGSS GNALVTFNEL ATTYYGENIK LVGSTAAFGS WSPSAGILLS
G7P    SGSGGNGGSS GNAL------ ---------- ---------- ----------

551                                                      600
G6P    ASSYTASNPL WTTTVSVPQG STVEFKFIRV GSDGSITWES GNNKVLTVGS
G7P    ---------- ---------- ---------- ---------- ----------

601        620
G6P    SATSVTVSAS WNGAYSVSSS
G7P    ---------- ----------
```

FIGURE 3A

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00056676 | 1.1 | 0 | 0.7 | 0.1 | K508S | |
| CL00056681 | 1.6 | 0 | 1.5 | 0 | Y412F | |
| CL00056711 | 1.3 | 0 | 1.1 | 0 | V551D | |
| CL00056770 | 1.6 | 0 | 1.6 | 0.1 | S518I | |
| CL00056875 | 1.4 | 0 | 1.2 | 0.1 | V551* | |
| CL00056882 | 1.3 | 0 | 0.8 | 0.1 | Y503T | |
| CL00056934 | 1.1 | 0 | 0.9 | 0 | V551R | |
| CL00056979 | 1.6 | 0 | 1.2 | 0.1 | I525* | |
| CL00057022 | 1.2 | 0 | 1 | 0.1 | V551S | |
| CL00057034 | 1.1 | 0 | 1 | 0.1 | S522G | |
| CL00057107 | 1.4 | 0 | 1.4 | 0.1 | S522* | |
| CL00057123 | 1.5 | 0.1 | 1.4 | 0.2 | T513* | |
| CL00057173 | 1.2 | 0 | 1 | 0.1 | Y503L | |
| CL00057188 | 1.2 | 0 | 0.7 | 0 | Y503G | |
| CL00057210 | 1.3 | 0 | 0.9 | 0.1 | Y503N | |
| CL00057219 | 1.3 | 0 | 1 | 0.1 | Y503K | |
| CL00057229 | 1.2 | 0 | 0.8 | 0.1 | R557P | |
| CL00057230 | 1.2 | 0 | 0.8 | 0.2 | S560* | |
| CL00057237 | 1.4 | 0 | 0.9 | 0 | V545D | |
| CL00057728 | 1.2 | 0 | 1 | 0.1 | A262S | |
| CL00057745 | 1.2 | 0 | 1 | 0.1 | A491V | |
| CL00057761 | 1.1 | 0 | 0.9 | 0 | T98S/Q161P/F516L | |
| CL00057798 | 1.1 | 0 | 0.9 | 0 | T98S/Q161P/N570P | |

FIGURE 3B

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00057832 | 1.2 | 0 | 1.1 | 0 | Q161P | |
| CL00057960 | 1.1 | 0 | 1.1 | 0.1 | T98S/Q161P | |
| CL00058104 | 1.7 | 0.1 | 1.3 | 0 | A514* | |
| CL00058130 | 1.7 | 0 | 1.3 | 0 | S549* | |
| CL00058208 | 1.4 | 0 | 1.3 | 0 | L526I | |
| CL00058270 | 1.8 | 0 | 1.5 | 0 | S549D | |
| CL00058285 | 1.4 | 0 | 1.1 | 0 | V65I | |
| CL00058305 | 1.7 | 0 | 1.3 | 0 | F555R | |
| CL00058322 | 1.9 | 0 | 1.4 | 0 | L509* | |
| CL00058346 | 2 | 0.1 | 1.5 | 0 | T500* | |
| CL00058384 | 2 | 0 | 1.4 | 0 | N506* | |
| CL00058420 | 1.3 | 0.1 | 1.1 | 0 | F555K | |
| CL00058580 | 1.4 | 0 | 1.2 | 0 | V558* | |
| CL00058610 | 1.3 | 0.1 | 1.2 | 0 | L526N | |
| CL00058704 | 1.1 | 0.1 | 1.1 | 0 | L526S | |
| CL00058734 | 1.4 | 0.1 | 1.3 | 0 | L509* | |
| CL00058790 | 1.4 | 0 | 0.9 | 0 | F555S | |
| CL00058830 | 1.6 | 0.1 | 1.4 | 0 | S520* | |
| CL00058933 | 1.3 | 0.1 | 1 | 0 | F555N | |
| CL00058938 | 1.1 | 0 | 0.9 | 0 | L509P | |
| CL00059037 | 1.2 | 0.1 | 1.1 | 0 | S563L | |
| CL00059051 | 1.4 | 0 | 1.1 | 0 | S563* | |
| CL00059137 | 1.6 | 0 | 1.3 | 0.1 | G524* | |

FIGURE 3C

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00059172 | 1.6 | 0.1 | 1.3 | 0 | I556P | |
| CL00059221 | 1.6 | 0 | 1.3 | 0 | G559N | |
| CL00059245 | 1.7 | 0 | 1.3 | 0 | S544* | |
| CL00059293 | 1.6 | 0 | 1.3 | 0 | V510* | |
| CL00059349 | 1.4 | 0.1 | 1.2 | 0.1 | I564N | |
| CL00059363 | 1.5 | 0 | 1.1 | 0 | I564* | |
| CL00059374 | 1.8 | 0 | 1.2 | 0 | T550* | |
| CL00059547 | 1.5 | 0 | 1.3 | 0 | I556* | |
| CL00059600 | 1.4 | 0 | 1.3 | 0 | S544Q | |
| CL00059601 | 1.2 | 0.1 | 1 | 0.1 | G569* | |
| CL00059617 | 1.2 | 0 | 1.1 | 0 | G559S | |
| CL00059650 | 1.3 | 0 | 1.2 | 0 | I564T | |
| CL00059710 | 1.2 | 0.1 | 1.3 | 0 | S544E | |
| CL00059836 | 2.1 | 0 | 1.6 | 0.1 | Y502* | |
| CL00059862 | 1.5 | 0.1 | 1 | 0 | V510G | |
| CL00059894 | 1.4 | 0 | 1.1 | 0.1 | I556D | |
| CL00059920 | 1.3 | 0 | 1 | 0.1 | I556R | |
| CL00059953 | 1.2 | 0 | 1.2 | 0 | V510S | |
| CL00059954 | 1.1 | 0.1 | 1.1 | 0.1 | S544N | |
| CL00059987 | 1.2 | 0 | 1 | 0 | I564S | |
| CL00060048 | 2.1 | 0 | 1.4 | 0 | G569I | |
| CL00060086 | 1.3 | 0.1 | 1.2 | 0 | T550D/F555S | |
| CL00064405 | 1.6 | 0.1 | 1.7 | 0.1 | A-15L | |

FIGURE 3D

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00064407 | 2.1 | 0 | 2.3 | 0.1 | V-20A | |
| CL00064429 | 1.7 | 0 | 1.8 | 0 | V-20G | |
| CL00064502 | 1.7 | 0.1 | 1.8 | 0 | K-17F | |
| CL00064526 | 3.2 | 0 | 3.6 | 0.1 | V-20R | |
| CL00064627 | 2.5 | 0 | 2.8 | 0 | V-20M | |
| CL00064685 | 3.2 | 0.1 | 3.7 | 0.1 | V-20K | |
| CL00064847 | 1.6 | 0 | 1.7 | 0 | V-20W | |
| CL00064854 | 2 | 0.1 | 2.4 | 0.1 | L-18F | |
| CL00064858 | 1.5 | 0.1 | 1.6 | 0.1 | W-9Y | |
| CL00064981 | 2.3 | 0 | 2.6 | 0.1 | V-20Q | |
| CL00065006 | 2 | 0.1 | 2.4 | 0.1 | L-18I | |
| CL00065044 | 2.8 | 0.1 | 2.4 | 0.2 | A-15F | |
| CL00065046 | 2.8 | 0.1 | 3.1 | 0.2 | V-20T | |
| CL00065141 | 1.5 | 0.1 | 1.6 | 0 | K-17Y | |
| CL00065179 | 1.9 | 0.1 | 1.8 | 0.2 | V-20L | |
| CL00065194 | 3.3 | 0.2 | 3.7 | 0.1 | V-20I | |
| CL00065257 | 1.3 | 0.1 | 1.1 | 0.1 | T-10V | |
| CL00065290 | 1.5 | 0.1 | 1.7 | 0.1 | K-17N | |
| CL00065321 | 1.4 | 0.1 | 1.7 | 0 | L-18Y | |
| CL00065355 | 1.4 | 0.1 | 1.3 | 0.1 | V-1F | |
| CL00065384 | 3.4 | 0.2 | 4.1 | 0.3 | V-20F | |
| CL00065388 | 1.4 | 0.1 | 1.3 | 0 | T-10F | |
| CL00065394 | 1.2 | 0.1 | 1.1 | 0 | A-12V | |

FIGURE 3E

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00065400 | 1.5 | 0.1 | 1.8 | 0.1 | A-15V | |
| CL00065402 | 2.2 | 0.1 | 2.6 | 0 | A-15I | |
| CL00065463 | 1.8 | 0.1 | 1.9 | 0.2 | V-20A/T258S | |
| CL00065484 | 1.1 | 0.2 | 1 | 0 | A108S | |
| CL00065818 | 1.2 | 0.1 | 1.2 | 0.1 | G158S | |
| CL00066007 | 1 | 0.1 | 1.1 | 0.1 | S215A | |
| CL00066051 | 1.3 | 0.1 | 1.1 | 0.1 | I298V | |
| CL00066239 | 1.2 | 0.1 | 1.3 | 0.1 | K212Y | |
| CL00066275 | 1.3 | 0.1 | 1.3 | 0.1 | T89N | |
| CL00066610 | 1.4 | 0.1 | 0.4 | 0.1 | V65I/Y412F/Y503S/S518I | |
| CL00066636 | 1.6 | 0 | 1.1 | 0 | Y412F/Y503S/I564T | |
| CL00066648 | 1.5 | 0.1 | 1.2 | 0.3 | Y412F/Y503E | |
| CL00066653 | 1.5 | 0 | 1 | 0.1 | Y412F/Y503E/S518I | |
| CL00066677 | 1.4 | 0.1 | 1.2 | 0.2 | Y503E | |
| CL00066701 | 1.5 | 0.1 | 0.7 | 0.1 | V65I/Y412F/Y503S | |
| CL00066705 | 1.6 | 0.1 | 1 | 0.2 | V65I/Y503E | |
| CL00066706 | 1.4 | 0 | 0.9 | 0 | Y503D/S518I/I564N | |
| CL00066722 | 1.5 | 0 | 1.1 | 0.1 | Y503E/S518L | |
| CL00066769 | 1.6 | 0 | 1 | 0.2 | V65I/Y503E/S544Q | |
| CL00066776 | 1.6 | 0 | 0.8 | 0.2 | V65I/Y503S | |
| CL00066783 | 1.5 | 0 | 1.3 | 0.1 | Y503E/S544E | |
| CL00066793 | 1.6 | 0.1 | 0.6 | 0.1 | V65I/Y503E/S544E/I564N | |
| CL00066814 | 1.4 | 0 | 1.2 | 0.1 | Y503S | |

FIGURE 3F

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00066844 | 1.5 | 0.1 | 0.9 | 0.1 | V65I/Y412F/Y503E | |
| CL00066850 | 1.1 | 0.1 | 0.8 | 0.1 | Y503E/S518I/S544Q | |
| CL00066863 | 1.4 | 0 | 1 | 0 | Y503* | |
| CL00066864 | 1.5 | 0.1 | 0.6 | 0.1 | V65I/Y503E/S518M | |
| CL00066894 | 1.3 | 0.1 | 0.9 | 0.1 | Y412F/S518L | |
| CL00066949 | 1.3 | 0 | 1.2 | 0.1 | Y503E/S544Q | |
| CL00066957 | 1.3 | 0.1 | 0.5 | 0 | V65I/Y412F/Y503E/S544E/I564T/G569I | |
| CL00066959 | 1.5 | 0 | 1.2 | 0.1 | Y412F/Y503S | |
| CL00066990 | 1.4 | 0 | 1 | 0 | Y503E/I564T | |
| CL00067337 | 1.5 | 0 | 1.8 | 0.2 | K5H | |
| CL00067453 | 1.5 | 0 | 1.7 | 0.1 | K5T | |
| CL00067557 | 1.3 | 0 | 1.6 | 0.1 | K5P | |
| CL00067779 | 1.5 | 0.1 | 1.8 | 0.1 | K5N | |
| CL00067926 | 1.4 | 0.1 | 1.7 | 0.2 | K5Q | |
| CL00067965 | 1.4 | 0.1 | 1.9 | 0.1 | K5S | |
| CL00068001 | 1.5 | 0 | 1.7 | 0.1 | K5Y | |
| CL00068144 | 1.9 | 0 | 2 | 0 | S549D/F555D/G559N | |
| CL00068216 | 1.5 | 0 | 1.4 | 0.1 | S549D/F555R | |
| CL00068226 | 1.5 | 0 | 0.9 | 0 | K508T/L526N/S549D/G559N | |
| CL00068279 | 1.4 | 0 | 0.8 | 0 | K508T/G559N | |
| CL00068303 | 1.7 | 0 | 1.8 | 0 | F555D/I556P/G559N | |
| CL00068335 | 1.7 | 0 | 1.6 | 0.1 | S549D/F555R/I556P/G559N | |
| CL00068338 | 1.6 | 0.1 | 1.7 | 0.1 | F555D | |

FIGURE 3G

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00068375 | 1.6 | 0.1 | 1.6 | 0.1 | F555R/I556P | |
| CL00068376 | 1.3 | 0.1 | 1 | 0 | K508T | |
| CL00068377 | 1.7 | 0.1 | 1.9 | 0 | L526I/F555R/I556P | |
| CL00068381 | 1.9 | 0.1 | 2 | 0.1 | F555R/I556P/G559N | |
| CL00068384 | 1.1 | 0.1 | 1.1 | 0 | K508T/I556P/G559N | |
| CL00068415 | 1.7 | 0 | 1.7 | 0.1 | F555D/I556P | |
| CL00068429 | 1.5 | 0 | 1.5 | 0 | K508T/L526N/A534T/S549D/I556P | |
| CL00068430 | 1.3 | 0 | 0.8 | 0 | K508T/L526I/S549D/G559N | |
| CL00068440 | 1.5 | 0.1 | 1.4 | 0.1 | K508N/L526I/S549E/F555L/G559N | |
| CL00068442 | 1.5 | 0 | 1.6 | 0 | L526N/S549D/F555D/I556P | |
| CL00068526 | 1.6 | 0 | 1.6 | 0.1 | L526I/F555D/G559N | |
| CL00068530 | 1.6 | 0.1 | 1.5 | 0.1 | A38V/F555R | |
| CL00068539 | 1.3 | 0.1 | 1.1 | 0.1 | A39F/T540N/T542N | |
| CL00068540 | 1.2 | 0.1 | 0.7 | 0.1 | L498T/T542N/T581N/T584N | |
| CL00068547 | 1.4 | 0 | 1.3 | 0 | T540N | |
| CL00068560 | 1.1 | 0 | 1.1 | 0.2 | T542N | |
| CL00068609 | 1.4 | 0 | 1.1 | 0 | T542N/T581N/T584N | |
| CL00068646 | 1.2 | 0 | 1.1 | 0 | S535Y/T542N | |
| CL00068686 | 1.2 | 0.1 | 0.9 | 0.1 | T540N/T584N | |
| CL00068695 | 1.4 | 0 | 0.8 | 0 | T540N/T542N/T581N/T584N | |
| CL00068711 | 1.2 | 0 | 0.7 | 0 | L498T/T581N/T584N | |
| CL00068722 | 1.3 | 0 | 0.9 | 0 | L498T/T584N | |
| CL00068745 | 1.5 | 0 | 0.9 | 0 | L498T/T542N/T581N | |

FIGURE 3H

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00068804 | 1.4 | 0 | 1.2 | 0 | P121S/T542N/T584N | |
| CL00068849 | 1.5 | 0 | 0.9 | 0 | L498T/T542N | |
| CL00068861 | 1.4 | 0 | 1 | 0 | S535Y/T540N/T542N/T581N | |
| CL00071862 | 1.4 | 0 | 1.1 | 0 | Q419P/P423R | |
| CL00072100 | 1.1 | 0 | 0.9 | 0 | L79F/Q419P | |
| CL00072204 | 1.3 | 0 | 1.1 | 0 | Q419P/P423V | |
| CL00072207 | 1.2 | 0 | 1 | 0 | Q419P/P423R/T533R | |
| CL00072249 | 1.1 | 0 | 0.9 | 0 | S36P/Q419P | |
| CL00072311 | 1.2 | 0 | 1 | 0.1 | Q419P | |
| CL00072327 | 1.4 | 0.1 | 1.1 | 0 | Q419P/P423G | |
| CL00072404 | 1.2 | 0.1 | 0.9 | 0.1 | S36P/T400L/Q419P/P423G | |
| CL00072557 | 1.3 | 0.1 | 1 | 0 | S50Q/Q419P/P423R | |
| CL00072561 | 1.3 | 0.1 | 0.9 | 0 | S50Q/Q419P/P423R/G457S/E497V/P521S | |
| CL00072611 | 1.5 | 0.1 | 1.2 | 0.1 | E68N | |
| CL00072941 | 1.4 | 0 | 0.9 | 0 | E68S | |
| CL00073028 | 1.7 | 0.1 | 1.3 | 0 | E68Y | |
| CL00073034 | 1.4 | 0.1 | 1.2 | 0 | S188T | |
| CL00073178 | 1.6 | 0.1 | 1.8 | 0.1 | W519* | |
| CL00073261 | 1.3 | 0.1 | 1.1 | 0.1 | S188H | |
| CL00073292 | 1.4 | 0.1 | 1.2 | 0 | E68K | |
| CL00073363 | 1.2 | 0.1 | 0.9 | 0 | S188W | |
| CL00074746 | 1.1 | 0 | 0.8 | 0 | G124T | |
| CL00074858 | 1.1 | 0 | 1.1 | 0.1 | G124S | |

FIGURE 3I

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00074937 | 1.2 | 0 | 1 | 0.1 | G124P | |
| CL00074995 | 1.2 | 0 | 0.7 | 0.1 | N27A | |
| CL00075131 | 1.1 | 0 | 1.1 | 0 | F122M | |
| CL00075670 | 1.2 | 0 | 0.9 | 0.1 | P47T | |
| CL00076055 | 1.5 | 0 | 1.2 | 0.1 | Y321F | |
| CL00076065 | 1.1 | 0 | 0.7 | 0 | A422G | |
| CL00076211 | 1.2 | 0 | 0.9 | 0.1 | T192A | |
| CL00076269 | 1.6 | 0 | 1.1 | 0.1 | Y321W | |
| CL00076372 | 1.1 | 0 | 0.9 | 0 | H264M | |
| CL00076394 | 1.1 | 0 | 0.5 | 0 | Y321L | |
| CL00076399 | 1.4 | 0 | 0.9 | 0 | A422S | |
| CL00076824 | 1 | 0 | 1.1 | 0 | L420K | |
| CL00077439 | 1.4 | 0 | 1.5 | 0.1 | V-20R/A-15I | |
| CL00077470 | 1.6 | 0 | 1.8 | 0 | A-15F/S188T | |
| CL00077535 | 2 | 0.1 | 1.2 | 0.1 | V-20F/A-15I/Y321F/A422S | |
| CL00077536 | 2.1 | 0.1 | 2.2 | 0.2 | V-20F/A-15F/S188H/Q419P | |
| CL00077543 | 1.9 | 0 | 2.1 | 0.1 | A-15F/K5H/Y321W | |
| CL00077548 | 1.9 | 0 | 1.9 | 0.2 | A-15F/K5N/Y321F | |
| CL00077552 | 2 | 0 | 2.2 | 0.1 | V-20F/Y321F | |
| CL00077562 | 1.9 | 0 | 2.2 | 0 | V-20F/A-15I | |
| CL00077578 | 2 | 0 | 2.3 | 0 | A-15F/K5P/S188H | |
| CL00077580 | 2 | 0.1 | 0.8 | 0 | V-20F/E68S/S188H/A422S | |
| CL00077607 | 1.9 | 0 | 0.4 | 0.1 | V-20F/S188T/Y321F/Q419P/A422S | |

FIGURE 3J

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00077623 | 2.1 | 0 | 0.7 | 0.1 | V-20F/K5H/S188H/Y321F/A422S | |
| CL00077630 | 2 | 0 | 1.7 | 0.2 | V-20F/A422S | |
| CL00077637 | 1.9 | 0 | 1.6 | 0.1 | A-15I/S188H/Y321W/Q419P | |
| CL00077651 | 1.9 | 0 | 1.4 | 0.1 | A-15F/S188H/A422S | |
| CL00077663 | 2 | 0 | 1.4 | 0 | V-20F/S188H/A422S/V545A | |
| CL00077675 | 2 | 0 | 2.2 | 0 | V-20F/A-15I/Q419P | |
| CL00077681 | 2.1 | 0 | 2.3 | 0.1 | V-20F/K5Q/A422S | |
| CL00077697 | 1.9 | 0 | 1.8 | 0 | V-20R/A-15I/K5S/E68K/Y321W | |
| CL00077705 | 1.9 | 0 | 1.1 | 0.1 | A-15F/K5H/Y321F/A422S | |
| CL00077708 | 2 | 0 | 2.7 | 0.1 | V-20F/A-15F/K5N | |
| CL00077709 | 2 | 0.1 | 2.4 | 0.1 | V-20F/S188H/Y321W/Q419P | |
| CL00077715 | 1.9 | 0 | 2 | 0 | A-15I/Y321F | |
| CL00077745 | 1.9 | 0 | 1.7 | 0.1 | A-15F/K5Y/A422S | |
| CL00077768 | 2 | 0 | 2 | 0.1 | V-20F/A-15F/Q419P/A422S | |
| CL00077808 | 2.1 | 0 | 2 | 0.1 | V-20F/K5Y/S188H/A422S | |
| CL00077834 | 2 | 0 | 2.1 | 0.1 | V-20T/A-15I/K5T/A422S | |
| CL00077838 | 2 | 0 | 2.4 | 0.1 | V-20T/A-15I/K5T/Y321W | |
| CL00077884 | 1.6 | 0 | 0.7 | 0.1 | V-20R/A-15F/Y321W/A422S | |
| CL00077900 | 1.7 | 0 | 2 | 0.1 | A-15F/A-13T | |
| CL00077946 | 2 | 0 | 1.8 | 0.2 | V-20F/Q419P/A422S | |
| CL00078318 | 1.9 | 0 | 2.1 | 0.1 | A-15I/K5P/Y321F | |
| CL00078339 | 2 | 0 | 2.3 | 0.1 | V-20F/A-15F/Y321W | |
| CL00078341 | 2.1 | 0 | 0.8 | 0 | V-20F/A-15F/K5H/S188H/Y321F/A422S | |

FIGURE 3K

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00078450 | 1.8 | 0.1 | 1.1 | 0.1 | A-15I/E68K/A422S | |
| CL00078639 | 1.7 | 0 | 1.2 | 0 | Y321F/A422S | |
| CL00078734 | 1.8 | 0.2 | 1.2 | 0.1 | V-20T/A-15F/K5H/Y321F | |
| CL00078791 | 2 | 0 | 0.9 | 0.1 | V-20T/A-15I/K5T/Y321F/Q419P/A422S | |
| CL00078804 | 2 | 0 | 2 | 0 | K5T/E68Y/S188T | |
| CL00078810 | 1.8 | 0 | 1.9 | 0 | K5S/E68Y/S188H | |
| CL00078811 | 1.3 | 0 | 1.4 | 0 | K5N/S188H | |
| CL00078813 | 1.7 | 0 | 1.4 | 0 | K5T/E68S/S188T | |
| CL00078831 | 1.9 | 0 | 1.9 | 0.1 | K5H/E68Y/S188P | |
| CL00078858 | 1.9 | 0 | 1.9 | 0.1 | K5P/E68Y/S188T | |
| CL00078867 | 1.8 | 0 | 1.6 | 0.1 | K5T/E68K/S188H | |
| CL00078868 | 1.8 | 0 | 1.5 | 0 | K5P/E68K/S188T | |
| CL00078882 | 1.9 | 0 | 1.8 | 0.1 | K5H/E68Y/S188T | |
| CL00078885 | 1.5 | 0 | 1.5 | 0 | K5T/S188H | |
| CL00078894 | 1.8 | 0 | 1.5 | 0 | K5T/E68N/S188T | |
| CL00078923 | 1.8 | 0 | 1.7 | 0 | K5Y/E68Y/S188T | |
| CL00078928 | 2 | 0.1 | 1.9 | 0.1 | K5S/E68Y/S188T | |
| CL00078945 | 1.8 | 0 | 1.6 | 0 | K5Q/E68K/S188H | |
| CL00078947 | 1.7 | 0 | 1.5 | 0 | K5P/E68N/S188H | |
| CL00078962 | 1.8 | 0 | 1.6 | 0 | K5P/E68N/S188T | |
| CL00078998 | 2 | 0 | 2 | 0.1 | K5P/E68Y/S188H | |
| CL00079092 | 1.9 | 0.1 | 1.8 | 0.1 | K5Y/E68Y/S188H | |
| CL00079114 | 1.5 | 0 | 1.5 | 0 | K5S/S188T | |

FIGURE 3L

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00079128 | 1.6 | 0 | 1.1 | 0.3 | K5H/E68N/S188H | |
| CL00079146 | 1.6 | 0 | 1.8 | 0 | K5P/S188H | |
| CL00079147 | 1.8 | 0 | 1.5 | 0 | K5H/S46T/E68K/S188H | |
| CL00079158 | 1.8 | 0 | 1.6 | 0.1 | K5H/E68K/S188T | |
| CL00079186 | 2 | 0 | 2.2 | 0.1 | K5Q/E68Y/S188T | |
| CL00079194 | 1.5 | 0 | 1 | 0 | K5Y/E68N/S188H | |
| CL00104219 | 1.3 | 0 | 1 | 0 | V42I/S188H/A195V/Y412F/Q419P | |
| CL00104243 | 1.6 | 0 | 1.6 | 0 | L19I/V42I/E68Y/N168S/S188H/A195V/Y412F | |
| CL00104257 | 1.2 | 0 | 1.1 | 0 | L311V | |
| CL00104268 | 1.1 | 0 | 1.2 | 0 | E11S/V42I/T57S/D118N/N168S/S188H/A195V/L311V | |
| CL00104313 | 1.8 | 0.1 | 1.6 | 0.1 | E11S/V42I/D53N/E68Y/N168S/S188H/A195V/L311V/Y412F | |
| CL00104326 | 3.5 | 0.1 | 1.6 | 0.1 | E11S/L19I/V42I/I69L/Y321W/Y412F/Q419P | |
| CL00104420 | 1.9 | 0 | 2 | 0.1 | E11S/L19I/V42I/E68Y/D118N/S188H/A195V/L311V/Y412F | |
| CL00104449 | 1.3 | 0 | 1.3 | 0 | E11S/L19I/T57S/M119E/S188H/A195V/L311V/Y412F | |
| CL00104460 | 2.5 | 0.2 | 1.6 | 0.3 | E11S/V42I/A317P/Y412F/Q419P | |
| CL00104476 | 2.1 | 0 | 0.6 | 0 | L19I/T57S/I69L/D118N/N168S/S188H/A195V/L311V/A317P/Y321F/Y412F/Q419P | |
| CL00104486 | 1.8 | 0.1 | 1.8 | 0.1 | E11S/E68Y/S188H/A195V/L311V/Y412F | |

FIGURE 3M

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00104496 | 1.6 | 0 | 1.7 | 0.1 | E11S/L19I/V42I/E68Y/I69L/D118N/N168S/S188H/A195V/L311V/Y412F | |
| CL00104517 | 3.4 | 0.1 | 1.6 | 0.2 | E11S/L19I/V42I/S188H/A195V/L311V/Y321W/Y412F/Q419P | |
| CL00104530 | 2.4 | 0 | 1.8 | 0 | E11S/L19I/N168S/S188H/A195V/L311V/A317P/Y321F/Y412F | |
| CL00104549 | 1.9 | 0 | 2.1 | 0.1 | E11S/V42I/E68Y/Y412F | |
| CL00104558 | 1.9 | 0.1 | 2 | 0.2 | E11S/L19I/V42I/E68Y/Y412F | |
| CL00104569 | 1.6 | 0.1 | 1.5 | 0.2 | E11S/V42I/E68Y/S188H/A195V/Y412F | |
| CL00104619 | 3.3 | 0 | 1.8 | 0.1 | E11S/L19I/V42I/T57S/I69L/S188H/A195V/L311V/Y321W/Y412F | |
| CL00104621 | 2.1 | 0.1 | 2.1 | 0.2 | E11S/L19I/D53N/E68Y/S188H/A195V/L311V/Y412F | |
| CL00104632 | 2.9 | 0.1 | 1.4 | 0 | E11S/V42I/E68Y/S188H/A195V/L311V/Y321W/Y412F | |
| CL00104637 | 2.5 | 0.1 | 1.6 | 0.2 | E11S/V42I/E68Y/S188H/A195V/L311V/Y412F/Q419P | |
| CL00104654 | 3.6 | 0 | 1.2 | 0 | E11S/L19I/V42I/E68Y/S188H/A195V/L311V/A317P/Y321W/Y412F/Q419P | |
| CL00104675 | 2.3 | 0 | 1.8 | 0 | E11S/L19I/D53N/I69L/S188H/A195V/L311V/Q419P | |
| CL00104694 | 3.3 | 0.1 | 1.5 | 0 | E11S/V42I/E68Y/N168S/L311V/A317P/Y321W/Y412F | |

FIGURE 3N

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00104695 | 2.5 | 0.1 | 1.1 | 0.1 | E11S/E68Y/I69L/S188H/A195V/L311V/A317P/Y321F/Y412F | |
| CL00104699 | 2.4 | 0.1 | 0.9 | 0 | E11S/V42I/T57S/E68Y/I69L/S188H/A195V/L311V/A317P/Y321F | |
| CL00104703 | 1.9 | 0 | 0.6 | 0 | E11S/D53N/T57S/L311V/Y321F/Y412F/Q419P | |
| CL00104731 | 3.7 | 0.1 | 1.5 | 0 | E11S/L19I/S188H/A195V/L311V/A317P/Y321W/Y412F/Q419P | |
| CL00104742 | 1.9 | 0 | 1.7 | 0.1 | E11S/L19I/I69L/S188H/A195V/L311V/A317P | |
| CL00104751 | 2.4 | 0 | 1.7 | 0 | E11S/V42I/I69L/N168S/S188H/A195V/L311V/A317P/Y412F/Q419P | |
| CL00104753 | 1.9 | 0.1 | 1.9 | 0.1 | E11S/V42I/E68Y/S188H/A195V/L311V/Y412F | |
| CL00104755 | 2.8 | 0 | 1.7 | 0 | E11S/V42I/I69L/S188H/A195V/L311V/A317P/Y321F/Y412F | |
| CL00104774 | 1.1 | 0 | 1.3 | 0.1 | E11S/Y412F | |
| CL00104796 | 1.8 | 0 | 2 | 0.1 | E11S/L19I/V42I/E68Y/I69L/S188H/A195V/Y412F | |
| CL00104807 | 3.1 | 0.1 | 1.7 | 0.1 | E11S/L19I/V42I/D53N/T57S/S188H/A195V/L311V/Y321W/Y412F | |
| CL00104819 | 1.9 | 0 | 1.7 | 0.1 | V42I/E68Y/Y412F | |
| CL00104821 | 2.3 | 0.1 | 0.8 | 0 | E11S/L19I/V42I/D53N/T57S/E68Y/I69L/N168S/S188H/A195V/L311V/A317P/Y321F | |

FIGURE 3O

| Colony Tracking Number | PF* at pH 4.3, 30°C, 72hr | PF* STD | PF* at pH 4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00104823 | 3.9 | 0.1 | 1.9 | 0.1 | E11S/L19I/V42I/D53N/T57S/I69L/S188H/A195V/L311V/A317P/Y321W/Y412F | |
| CL00104826 | 2.6 | 0 | 1.7 | 0 | E11S/V42I/A317P/Y321F | |
| CL00104845 | 1.9 | 0 | 2.1 | 0.1 | E11S/V42I/T57S/E68Y/D118N/S188H/A195V/L311V/Y412F | |
| CL00104861 | 1.8 | 0 | 1.8 | 0.1 | E11S/L19I/V42I/E68Y/I69L/D118N/N168S/S188H/A195V/L311V/Y412F/Q419P | |
| CL00104873 | 1.7 | 0 | 1.8 | 0.1 | E11S/V42I/D53N/E68Y/S188H/A195V/L311V/Y412F | |
| CL00104881 | 1.3 | 0 | 1.7 | 0.1 | E11S/I69L/D118N/S188H/A195V/L311V/Y412F | |
| CL00106170 | 3 | 0 | 1.3 | 0.1 | V42I/D53N/T57S/E68Y/M141L/N168S/T261A/Y321W/E38IN/Y412F | |
| CL00106232 | 1.2 | 0.1 | 0.9 | 0 | E11S/V42I/S188H/L347N/Y412F/S434T | c18t |
| CL00106250 | 2.2 | 0 | 1.2 | 0.1 | D53N/T57S/E68Y/D118N/M119E/L311V/E348I/Y412F | |
| CL00106260 | 1.3 | 0.1 | 1.2 | 0 | D118N/N168S/S188H/L347N/E348I/S382D/T388Q/V395L | |
| CL00106263 | 2.6 | 0.1 | 0.8 | 0 | E68Y/I69L/N168S/S188H/A195V/L311V/A317P/Y321W/Y412F/Q419P | |
| CL00106337 | 2.4 | 0.1 | 1.1 | 0.1 | E11S/E68Y/V88I/A317P/Y321F/S355D | c18t |
| CL00106367 | 2.2 | 0.1 | 1.4 | 0.1 | D53N/I69L/L79Y/M119E/T261A/L311V/L347N/E348I/Q419P | |

FIGURE 3P

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00106370 | 2.1 | 0 | 0.8 | 0.1 | V42I/E68Y/I69L/D118N/M119E/M141L/L311V/A317P/Y321F/L347N | |
| CL00106384 | 2.9 | 0.1 | 1.3 | 0 | E11S/L19I/E68Y/I69L/L79Y/M141L/N168S/T261A/A317P/Y321W/L347N | c18t |
| CL00106393 | 2.5 | 0.1 | 1.1 | 0 | E11S/V42I/E68Y/I69L/L311V/Y321W/S434T | c18t |
| CL00106401 | 2.3 | 0.1 | 1.1 | 0 | E11S/V42I/D53N/N168S/L311V/A317P/Y321W | c18t |
| CL00106406 | 1.7 | 0 | 0.9 | 0 | E11S/E68Y/I69L/D118N/N168S/Y321F/Y412F | c18t |
| CL00106414 | 3.2 | 0.1 | 1 | 0.1 | V42I/D53N/T57S/L311V/Y321W/S355D/Y412F/Q419P | |
| CL00106459 | 1 | 0 | 1.1 | 0.05 | T89S | |
| CL00106462 | 1.7 | 0 | 1.5 | 0 | V42I/E68Y/L311V/L347N/L364I/Y412F | |
| CL00106463 | 1.9 | 0 | 1 | 0 | E11S/D118N/M119E/M141L/L311V/Y321W/L347N | |
| CL00106480 | 1.7 | 0 | 0.7 | 0 | V42I/D53N/T57S/M119E/M141L/A317P/Y321F/Q419P | |
| CL00106506 | 2.3 | 0.2 | 1 | 0.1 | T57S/I69L/T89S/S188H/A195V/T261A/L311V/A317P/Y321W/F394Y/Y412F | c18t |
| CL00106512 | 1.4 | 0.1 | 0.9 | 0.1 | Y321F/Y412F | |
| CL00106513 | 2 | 0 | 1.3 | 0.1 | V42I/T57S/E68Y/I69L/T89S/M119E/T261A/A317P/Y412F/S434T | |
| CL00106521 | 2 | 0.1 | 1.6 | 0.2 | E11S/V42I/E68Y/L311V/A317P/S434T | c18t |
| CL00106554 | 1.9 | 0.1 | 1.3 | 0.1 | V42I/D53N/T57S/E68Y/I69L/S434T | |

FIGURE 3Q

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00106581 | 2.5 | 0.1 | 1 | 0.1 | V42I/E68Y/Y321W | |
| CL00106604 | 1.1 | 0.1 | 0.9 | 0.1 | L311V/L347N/E348I/S355D/L364I/S434T | |
| CL00106662 | 2.8 | 0 | 0.2 | 0 | E11S/D53N/T57S/E68Y/V88I/T89S/M119E/A317P/Y321W | c18t |
| CL00106700 | 2.7 | 0.1 | 1.3 | 0.1 | D53N/E68Y/I69L/T89S/L311V/A317P/S355D/Q419P | |
| CL00106794 | 2.7 | 0 | 1.3 | 0 | V42I/E68Y/A317P/Y321F/Y412F | c18t |
| CL00106812 | 2.8 | 0 | 1.4 | 0.1 | L19I/I69L/T89S/L311V/A317P/Y321F/S355D/L364I/Y412F | |
| CL00106835 | 2 | 0.1 | 0.4 | 0.1 | V42I/D53N/T57S/E68Y/I69L/M141L/S188H/A195V/L311V/A317P/Y321F/Y412F/S434T | |
| CL00106838 | 2.9 | 0.1 | 0.6 | 0 | T57S/V88I/A317P/Y321W/Q419P | c18t |
| CL00106849 | 3.1 | 0.1 | 1.3 | 0.1 | E11S/L19I/V42I/D53N/E68Y/L311V/A317P/Y321W/Y412F | |
| CL00106861 | 1.5 | 0.1 | 1.3 | 0.2 | E11S/V42I/D53N/E68Y/I69L/S188H/A195V/E348I | |
| CL00106905 | 2.5 | 0.1 | 1.2 | 0.1 | L19I/V42I/T57S/I69L/V88I/M119E/T261A/A317P/Y321F/Y412F | |
| CL00106923 | 1.4 | 0.1 | 0.8 | 0.1 | D53N/E68Y/D118N/M119E/M141L/T261A/L347N/E348I/S355D/L364I/S434T | |
| CL00106927 | 1 | 0 | 1.2 | 0.1 | E11S/T261A/L347N/E348I/S355D/S434T | c18t |
| CL00106932 | 1 | 0.1 | 1.1 | 0.2 | M119E/S188H/E348I | |
| CL00106955 | 1.9 | 0.1 | 0.9 | 0.1 | E11S/A317P/Y321F/L347N | c18t |

FIGURE 3R

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00106980 | 1.5 | 0.1 | 1.4 | 0.1 | E11S/E68Y/I69L/T261A/L364I | |
| CL00106990 | 1.1 | 0 | 0.5 | 0.01 | D118N/M119E/N168S/S188H/A195V/L311V/Y321W/L347N/F394Y | |
| CL00107035 | 2.2 | 0.1 | 1.1 | 0 | E11S/L311V/Y321W/E348I/S355D/L364I/Y412F | |
| CL00107039 | 1.5 | 0.1 | 0.9 | 0.1 | V42I/D53N/T57S/I69L/V88I/L347N/E348I/F394Y/V395L/S434T | |
| CL00107056 | 3.2 | 0.1 | 1.1 | 0.1 | E11S/D53N/T89S/N168S/S188H/T261A/L311V/A317P/Y321W/S355D/Y412F | |
| CL00107069 | 3.3 | 0.1 | 1.1 | 0 | L19I/V42I/D53N/L79Y/T89S/N168S/T261A/L311V/Y321W/Y412F/Q419P/S434T | |
| CL00107071 | 1.7 | 0 | 0.4 | 0 | L79Y/V88I/D118N/M119E/T261A/Y321F/L364I/Y412F | |
| CL00107087 | 2.6 | 0.2 | 1.3 | 0.2 | V42I/E68Y/T89S/M141L/T261A/L311V/Y321F/E348I/L364I | |
| CL00107108 | 1.8 | 0.1 | 1.7 | 0.2 | V42I/E68Y/D118N/S188H/T261A/Y412F/S434T | |
| CL00107144 | 2.7 | 0.2 | 1 | 0.1 | E11S/D53N/E68Y/I69L/T89S/Y321W/E348I/S355D | c18t |
| CL00107146 | 1.9 | 0.1 | 1.1 | 0.1 | M119E/L311V/Y321F | |
| CL00107149 | 1.1 | 0 | 1.1 | 0.13 | L311V/L347N/E348I | |
| CL00107165 | 2.3 | 0.1 | 1.3 | 0.1 | E11S/V42I/A317P/Y321F/L347N/Y412F | c18t |
| CL00107166 | 2.9 | 0.1 | 1.6 | 0.1 | E11S/L19I/V42I/E68Y/A317P/Y321F/L364I/Y412F | |

FIGURE 3S

| Colony Tracking Number | PF* at pH4.3, 30°C, 72hr | PF* STD | PF* at pH4.3, 60°C, 72hr | PF* STD | AA Mutation w.r.t. G6P (CL00025225) (Numbering starts from mature protein; negative number indicates mutations at the SP region) | Silent Mutation w.r.t. G6P (CL00025225) (Numbering starts from mature protein; negative number indicates mutations at the SP region) |
|---|---|---|---|---|---|---|
| CL00107167 | 1.9 | 0 | 2 | 0.1 | D53N/E68Y/T89S/T261A | c18t |
| CL00107172 | 2.6 | 0.1 | 1.1 | 0.1 | I69L/S188H/A195V/L311V/A317P/Y321W/V395L/Y412F | |
| CL00107195 | 1.9 | 0 | 1.4 | 0 | V42I/D53N/E68Y/V88I/T89S/D118N/L311V/Y412F/S434T | |
| CL00107199 | 1.6 | 0 | 1.7 | 0.2 | E11S/V42I/E68Y/I69L/L311V/E348I | |
| CL00107218 | 2 | 0 | 1.1 | 0.1 | V42I/Y321W | |
| CL00107370 | 1.7 | 0 | 1.5 | 0.1 | E68Y/T261A/L311V/L347N/E348I/S434T | |
| CL00107391 | 1.4 | 0 | 1.3 | 0 | E11S/E68Y/I69L/L79Y | |
| CL00107403 | 2 | 0.1 | 1.3 | 0.1 | V42I/D53N/E68Y/S188H/A195V/T261A/L311V/Y321F/S355D/S434T | |
| CL00107437 | 1.7 | 0 | 1.6 | 0 | L19I/V42I/S188H/A195V/S382D/V395L/Q419P | |
| CL00107448 | 1.8 | 0.3 | 0.9 | 0.2 | E11S/L19I/V42I/D53N/T57S/M119E/L311V/Y321W/L347N/F394Y/Y412F | |
| CL00107450 | 1.3 | 0.1 | 1 | 0.1 | L9P/E11S/D53N/T57S/E68Y/M119E/M141L/E348I/Y412F | |
| CL00107453 | 2.8 | 0.1 | 1.6 | 0 | L19I/V42I/I69L/L311V/Y321W/L347N | c18t |

FIGURE 4A

| Colony Tracking Number | PF* at pH4.3, 30°C, 72hr | PF* STD | PF* at pH4.3, 60°C, 72hr | PF* STD | AA Mutation w.r.t. G7P (CL00077366) (Numbering starts from mature protein; negative number indicates mutations at the SP region) | Silent Mutation w.r.t.G7P (CL00077366) (Numbering starts from mature protein; negative number indicates mutations at the SP region) |
|---|---|---|---|---|---|---|
| CL00079234 | 1.7 | 0 | 1.7 | 0.1 | K5T/S188T | |
| CL00079308 | 1.3 | 0 | 0.9 | 0.1 | S188H | |
| CL00079327 | 1.9 | 0 | 1.5 | 0.1 | K5T/E68K/S188H | |
| CL00079363 | 1.7 | 0 | 1.2 | 0 | K5Y/S188H | |
| CL00079381 | 1.3 | 0 | 1.4 | 0.1 | E68K | |
| CL00079388 | 1.8 | 0 | 1.6 | 0.1 | K5Q/E68K/S188T | |
| CL00079550 | 1.3 | 0 | 1.4 | 0.1 | K5N | |
| CL00079574 | 1.7 | 0 | 1.4 | 0.2 | K5N/E68Y/S188T | |
| CL00079599 | 1.6 | 0 | 1.2 | 0 | K5H/S188H | |
| CL00079618 | 1.9 | 0 | 1.3 | 0.1 | K5S/E68Y/S188H | |
| CL00079650 | 1.8 | 0 | 1.7 | 0 | K5S/E68Y/S188T | |
| CL00079652 | 1.8 | 0 | 1.7 | 0.1 | K5Y/E68Y | |
| CL00079662 | 1.6 | 0 | 0.9 | 0.1 | K5S/E68S/S188T | |
| CL00079669 | 1.5 | 0 | 0.9 | 0.1 | K5H/E68S/S188H | |
| CL00079678 | 1.6 | 0 | 1.3 | 0 | K5H/E68K/S188T | |
| CL00079692 | 1.6 | 0 | 1.5 | 0.1 | K5P/S188H | |
| CL00079693 | 1.5 | 0 | 1 | 0 | K5Y/E68K | |
| CL00079722 | 1.3 | 0.1 | 0.9 | 0 | K5T/S188H | |
| CL00079739 | 1.1 | 0 | 0.9 | 0 | S188T | |
| CL00079746 | 1.3 | 0 | 1.3 | 0.1 | K5T | |
| CL00079776 | 1.2 | 0 | 0.9 | 0.1 | K5S/S188H | |
| CL00079792 | 1.3 | 0 | 0.8 | 0.1 | E68Y/S188H | |

FIGURE 4B

| Colony Tracking Number | PF* at pH4.3, 30°C, 72hr | PF* STD | PF* at pH4.3, 60°C, 72hr | PF* STD | AA Mutation w.r.t. G7P (CL00077366) (Numbering starts from mature protein; negative number indicates mutations at the SP region) | Silent Mutation w.r.t. G7P (CL00077366) (Numbering starts from mature protein; negative number indicates mutations at the SP region) |
|---|---|---|---|---|---|---|
| CL00079796 | 1.4 | 0 | 1.1 | 0.1 | E68Y/S188T | |
| CL00079800 | 1.3 | 0 | 1.2 | 0.1 | K5P | |
| CL00079819 | 1.9 | 0 | 1.3 | 0.1 | A-15F/K5T/Y321F | |
| CL00079997 | 1.8 | 0 | 1.9 | 0 | V-20F/A-15I | |
| CL00080026 | 2.1 | 0 | 1.8 | 0.2 | V-20F/K5Q/S188H/Q419P | |
| CL00080035 | 1.7 | 0 | 1 | 0 | A-15I/Y321F | |
| CL00080064 | 1.9 | 0 | 1.2 | 0 | V-20F/A422S | |
| CL00080088 | 1.9 | 0 | 0.7 | 0 | A-15F/K5P/E68Y/S188T/A422S | |
| CL00080150 | 2 | 0 | 1.5 | 0.1 | V-20F/A-15I/A422S | |
| CL00080153 | 1.7 | 0.1 | 1.5 | 0 | V-20T/A-15I/Q419P | |
| CL00080167 | 2.2 | 0 | 1.9 | 0.3 | V-20F/K5N/S188H/Q419P | |
| CL00080198 | 1.9 | 0 | 0.3 | 0 | V-20F/Y321W/A422S | |
| CL00080238 | 2 | 0 | 1.8 | 0 | V-20F/E68K/Q419P | |
| CL00080291 | 1.5 | 0 | 0.8 | 0 | Y321F | |
| CL00080332 | 1.9 | 0 | 0.6 | 0.1 | A-15F/S188H/Y321W/Q419P | |
| CL00080342 | 2 | 0 | 1.5 | 0.1 | V-20F/Y321F | |
| CL00080386 | 1.8 | 0 | 1.1 | 0 | A-15F/Y321F | |
| CL00080420 | 1.7 | 0 | 0 | 0 | V-20F/E68S/S188T/Y321W/A422S | |
| CL00080426 | 2.1 | 0 | 1.4 | 0.1 | V-20F/A-15F/K5Q/Q419P/A422S | |
| CL00080434 | 1.2 | 0 | 0.6 | 0 | V-20I/A-15I/Y321F | |
| CL00080447 | 1.5 | 0 | 0.7 | 0 | S188T/Y321F | |
| CL00080473 | 1.4 | 0 | 0.4 | 0 | S188T/Q419P/A422S | |

FIGURE 4C

| Colony Tracking Number | PF* at pH4.3, 30°C, 72hr | PF* STD | PF* at pH4.3, 60°C, 72hr | PF* STD | AA Mutation w.r.t. G7P (CL00077366) (Numbering starts from mature protein; negative number indicates mutations at the SP region) | Silent Mutation w.r.t. G7P (CL00077366) (Numbering starts from mature protein; negative number indicates mutations at the SP region) |
|---|---|---|---|---|---|---|
| CL00080498 | 1.9 | 0 | 2.1 | 0.1 | V-20T/A-15I/K5Q | |
| CL00080518 | 1.8 | 0 | 1.2 | 0.1 | A-15I/Y321W | |
| CL00080520 | 2 | 0 | 2.3 | 0 | V-20F/A-15F/K5Q | |
| CL00080526 | 2.2 | 0 | 1.1 | 0.1 | V-20F/K5H/S188T/Q419P/A422S | |
| CL00080531 | 1.9 | 0 | 1.4 | 0.1 | V-20T/A-15I/K5H/A422S | |
| CL00080559 | 1.9 | 0 | 0.8 | 0.2 | A-15F/S188H/Y321W | |
| CL00080560 | 1.8 | 0 | 0.9 | 0 | A-15F/Q419P/A422S | |
| CL00080583 | 2.1 | 0 | 1.6 | 0 | V-20F/K5N/A422S | |
| CL00080586 | 1.9 | 0 | 1.5 | 0.2 | V-20F/A-15I/S188H | |
| CL00080593 | 1.5 | 0 | 0.3 | 0 | E68Y/S188H/Y321F/Q419P | |
| CL00080649 | 2 | 0 | 1.7 | 0.2 | V-20F/A-15F/K5N/A422S | |
| CL00080654 | 1.9 | 0 | 1.3 | 0.1 | V-20F/A-15I/Y321F | |
| CL00080712 | 2.1 | 0 | 2.1 | 0.2 | V-20F/K5Q/S188H | |
| CL00080759 | 1.8 | 0 | 1.9 | 0.1 | V-20F | |
| CL00092425 | 1.1 | 0 | 1.3 | 0.1 | E11S/Y55F/M141L/N168S/T388Q | |
| CL00092508 | 1.2 | 0 | 1.4 | 0.1 | E11S/T31N/Y55F/M141L/N168S/T388Q | |
| CL00092528 | 1.3 | 0 | 1.4 | 0.1 | L19I/A195V | |
| CL00092589 | 1.2 | 0 | 1.3 | 0.1 | E11S | |
| CL00092592 | 1.1 | 0.1 | 0.9 | 0.1 | E11S/L19I/Y55F/A108- | |
| CL00092612 | 1 | 0 | 1.1 | 0.1 | M141L/N168S/Y227F/T362Q/T388Q/D440Q | |
| CL00092673 | 1.2 | 0 | 1.3 | 0.1 | E11S/M141L | |
| CL00092705 | 1.1 | 0 | 1.2 | 0.1 | E11S/L19I/I44V/Y145A/T155A/D309S/L311V/Y412F/S472T | |

FIGURE 4D

| Colony Tracking Number | PF* at pH4.3, 30°C, 72hr | PF* STD | PF* at pH4.3, 60°C, 72hr | PF* STD | AA Mutation w.r.t. G7P (CL00077366) (Numbering starts from mature protein; negative number indicates mutations at the SP region) | Silent Mutation w.r.t. G7P (CL00077366) (Numbering starts from mature protein; negative number indicates mutations at the SP region) |
|---|---|---|---|---|---|---|
| CL00092765 | 1.1 | 0 | 1.1 | 0.1 | D309S/L311V | |
| CL00092788 | 1 | 0 | 1.1 | 0.1 | E11S/L19I/T31N/Y55F/A125P/N168S/Y227F | |
| CL00092851 | 1.2 | 0 | 1.3 | 0 | L19I/D309S/L311V/Y412F/A460S/S472T | |
| CL00092884 | 1.2 | 0 | 1.4 | 0 | E11S/L19I/N168S/Y227F/D309S/L311V/D440Q | |
| CL00093036 | 1.1 | 0 | 1.1 | 0.1 | S472T | |
| CL00093105 | 1.1 | 0 | 1.2 | 0 | L19I/Y412F | |
| CL00093189 | 1.1 | 0 | 1.2 | 0 | E11S/L19I/Y145A/A460S/S472T | |
| CL00093270 | 1.5 | 0.1 | 1.4 | 0 | E11S/M141L/N168S/D309S/L311V/T362Q/L364I/Y412F/A460S/S472T | |
| CL00093271 | 1.1 | 0 | 1.3 | 0.1 | E11S/Y55F/M141L/N168S/L311V/T362Q/L364I/A460S/S472T | |
| CL00093292 | 1.2 | 0.1 | 1.4 | 0.2 | E11S/L19I/Y55F/M141L/N168S/Y227F | |
| CL00093322 | 1.1 | 0 | 1.1 | 0 | L19I/T155A/A407S/Y412F/S472T | |
| CL00093357 | 1.2 | 0 | 0.6 | 0 | D53N/L149I/N150D/P186E/A317P | |
| CL00093437 | 1.2 | 0 | 0.9 | 0.1 | V42I/S103D/D106T/P186E/A317P/S434T/G478S | |
| CL00093443 | 1.2 | 0 | 1.1 | 0.1 | A317P/G478S | |
| CL00093519 | 1.1 | 0.1 | 0.7 | 0.1 | C26N/V42I/L149I/A317P/S355D/A374N | |
| CL00093549 | 1.2 | 0 | 1.1 | 0.1 | V42I/S103D/D106T/A317P | |
| CL00093569 | 1.3 | 0 | 1 | 0 | D53N/S434T | |
| CL00093612 | 1.2 | 0 | 1 | 0 | /S103D/A317P/V342I | |
| CL00093709 | 1.1 | 0 | 0.9 | 0 | A256V/A317P | |
| CL00093794 | 1.1 | 0 | 1 | 0 | V42I/P186E | |
| CL00093848 | 1.2 | 0 | 1.1 | 0 | A317P/V342I/G478S | |

FIGURE 4E

| Colony Tracking Number | PF* at pH4.3, 30°C, 72hr | PF* STD | PF* at pH4.3, 60°C, 72hr | PF* STD | AA Mutation w.r.t. G7P (CL00077366) (Numbering starts from mature protein; negative number indicates mutations at the SP region) | Silent Mutation w.r.t.G7P (CL00077366) (Numbering starts from mature protein; negative number indicates mutations at the SP region) |
|---|---|---|---|---|---|---|
| CL00093868 | 1.1 | 0 | 0.9 | 0 | I224V/A256V/A317P/G478S | |
| CL00093885 | 1.2 | 0.1 | 0.8 | 0.1 | V42I/L149I/N150D/A317P/G478S | |
| CL00093899 | 1.1 | 0 | 0.8 | 0 | V42I/S103D/P186E/A317P/V342I/S355D/A374N/A391G | |
| CL00093937 | 1.2 | 0 | 0.9 | 0 | P186E/A317P/G478S | |
| CL00093964 | 1.1 | 0 | 0.9 | 0 | D53N/G446S | |
| CL00093967 | 1.2 | 0 | 0.9 | 0 | A256V/A317P/G478S | |
| CL00094025 | 1.5 | 0.1 | 1 | 0.1 | V42I/D53N/T57S/L149I/A317P/G478S | |
| CL00094029 | 1.2 | 0.1 | 0.3 | 0 | C26N/V42I/D53N/T57S/N150D/P186E/A317P/V342I/G478S | |
| CL00094148 | 1.2 | 0 | 1.2 | 0 | V42I/S355D | |
| CL00094205 | 1.1 | 0 | 0.6 | 0 | V42I/N150D/P186E/A317P | |
| CL00094221 | 1.2 | 0 | 1.2 | 0 | V42I/S434T/G478S | |
| CL00094247 | 1.3 | 0 | 0.1 | 0 | C26N/D53N/T57S/S103D/Q161P/A317P/G478S | |
| CL00094292 | 1.2 | 0 | 1 | 0 | V42I/A256V/A317P/S434T | |
| CL00094338 | 1.1 | 0 | 0.9 | 0 | V42I/S103D/A317P/A391G/G478S | |
| CL00094502 | 1.3 | 0 | 0.7 | 0.3 | E68Y/I69L/G178T/Y179F/S213T/H214C | |
| CL00094638 | 1.2 | 0 | 0.9 | 0.1 | E68Y/I69L/E85Q/N86Q/F394Y/V395L | |
| CL00094787 | 1.1 | 0 | 1 | 0.1 | E68Y/I69L | |
| CL00094853 | 0.8 | 0.1 | 2.8 | 0.2 | D118N/M119E | |
| CL00095012 | 1.1 | 0 | 0.7 | 0 | E68Y/I69L/V97I/T98S/A246S/S247G/T261G/A262S/L347N/E348I | |
| CL00095048 | 1.2 | 0 | 0.9 | 0 | E68Y/I69L/S452A/V453S | |
| CL00095171 | 1.2 | 0 | 1 | 0 | E68Y/I69L/S452A/V453S | |
| CL00095255 | 1.4 | 0.1 | 0.8 | 0.1 | E68Y/I69L/E85Q/N86Q/L347N/E348I/Q418T/Q419P | |

FIGURE 4F

| Colony Tracking Number | PF* at pH4.3, 30°C, 72hr | PF* STD | PF* at pH4.3, 60°C, 72hr | PF* STD | AA Mutation w.r.t. G7P (CL00077366) (Numbering starts from mature protein; negative number indicates mutations at the SP region) | Silent Mutation w.r.t. G7P (CL00077366) (Numbering starts from mature protein; negative number indicates mutations at the SP region) |
|---|---|---|---|---|---|---|
| CL00095346 | 1.2 | 0.1 | 0.9 | 0.1 | E68Y/I69L/E85Q/N86Q/S204N/T205A | |
| CL00095398 | 1.1 | 0 | 0.9 | 0 | A208T/K209R/E381N/S382D/Q418T/Q419P/A469S/A470T | |
| CL00095409 | 1.1 | 0 | 0.7 | 0.1 | E381N/S382D/Q418T/Q419P/T436S/E437A/A469S/A470T | |
| CL00095435 | 1.2 | 0.1 | 0.9 | 0 | Q418T/Q419P/A469S/A470T | |
| CL00095537 | 1.2 | 0 | 1.4 | 0.2 | R7C | |
| CL00095704 | 1.1 | 0 | 0.9 | 0.1 | V170I/A171T/E381N/S382D/Q418T/Q419P/A469S/A470T | |
| CL00095795 | 1.1 | 0 | 0.7 | 0.1 | F394Y/V395L/Q418T/Q419P/T436S/E437A/A469S/A470T | |
| CL00096040 | 1.1 | 0 | 0.6 | 0 | T78K/L79D/Q418T/Q419P/A469S/A470T | |
| CL00096149 | 1.3 | 0.1 | 0.6 | 0.1 | E68Y/I69L/V88I/T89S/T352S/V353I/Q399E/T400K/A469S/A470T | |
| CL00096609 | 1.1 | 0 | 1.2 | 0 | L94V | |
| CL00098118 | 1.1 | 0 | 0.6 | 0 | S72A/V73F/A153S/S306A/T476W | |
| CL00098393 | 1.2 | 0 | 1.3 | 0.1 | T370V/G475V | |
| CL00100850 | 1.2 | 0 | 0.2 | 0 | R49H/S72A/V73F/A92T/Y93K/A153S/S306A/T476W | |
| CL00101324 | 1.4 | 0.1 | 1.2 | 0.2 | E68Y/I69L/T219S/V220Q/A307E/S355D/L492P | |
| CL00101411 | 1.5 | 0 | 1.3 | 0 | E11S/V42I/L149I/I224V/A317P/T388Q/A460S/G478S | |
| CL00101447 | 1.4 | 0 | 1.2 | 0.1 | Y412F/Q418T/Q419P/A469S/A470T/ | |
| CL00102286 | 2 | 0.1 | 0.8 | 0 | L19I/D53N/I69L/V88I/S188H/A195V/Y321W/Y412F | c18t |
| CL00102294 | 1.8 | 0 | 1 | 0 | V42I/D118N/M119E/T261A/L311V/Y321W/S355D | |
| CL00102315 | 1.1 | 0.1 | 1 | 0 | E11S/T57S/T89S | |
| CL00102318 | 1.7 | 0 | 0.5 | 0 | E11S/V42I/L79Y/D118N/M141L/L311V/A317P/Y321F | |
| CL00102323 | 1.8 | 0 | 1.1 | 0 | V42I/D53N/E68Y/A317P/L347N | |
| CL00102344 | 1.4 | 0 | 0.3 | 0 | I69L/S188H/A195V/A317P/Y321F/L364I/S434T | c18t |

FIGURE 4G

| Colony Tracking Number | PF* at pH4.3, 30°C, 72hr | PF* STD | PF* at pH4.3, 60°C, 72hr | PF* STD | AA Mutation w.r.t. G7P (CL00077366) (Numbering starts from mature protein; negative number indicates mutations at the SP region) | Silent Mutation w.r.t.G7P (CL00077366) (Numbering starts from mature protein; negative number indicates mutations at the SP region) |
|---|---|---|---|---|---|---|
| CL00102346 | 1.7 | 0 | 0.7 | 0 | T57S/A195V/T261A/L311V/Y321F/L347N/E348I/S434T | c18t |
| CL00102373 | 1.7 | 0.1 | 1.2 | 0 | E11S/V42I/T57S/E68Y/S188H/A195V/T261A | |
| CL00102389 | 1.9 | 0 | 0.6 | 0 | T57S/N168S/T261A/A317P/Y321W/V395L/Y412F | |
| CL00102427 | 1.7 | 0 | 0.8 | 0 | E11S/D53N/E68Y/D118N/S188H/A195V/Y412F/Q419P | c18t |
| CL00102431 | 1.4 | 0.1 | 0.9 | 0 | E11S/V42I/D118N/M141L/N168S/Y321W/Y412F | c18t |
| CL00102460 | 2 | 0 | 1 | 0 | E11S/D53N/T57S/E68Y/T89S/E381N/Y412F/Q419P/S434T | c18t/g27a |
| CL00102470 | 1.8 | 0 | 1 | 0 | E11S/D53N/T57S/V88I/T89S/S188H/A195V/L311V/L347N/Y412F | |
| CL00102475 | 1.4 | 0 | 1.1 | 0 | A317P/Y412F | |
| CL00102514 | 1.9 | 0 | 0.5 | 0 | I69L/T89S/L311V/A317P/Y321F/Y412F/S434T | c18t |
| CL00102518 | 1.8 | 0 | 1.1 | 0 | V42I/D53N/T57S/E68Y/V88I/Y412F | c18t |
| CL00102544 | 1.9 | 0.1 | 0.8 | 0 | E11S/T57S/V88I/M141L/T261A/Y321W/L364I/Y412F | |
| CL00102552 | 1.8 | 0.1 | 0.7 | 0.1 | V42I/I69L/S188H/A317P/Y321W/Y412F | |
| CL00102559 | 2.2 | 0.1 | 0.8 | 0 | E11S/V42I/D53N/T57S/L79Y/T89S/L311V/Y321W/Y412F | c18t |
| CL00102590 | 1.1 | 0 | 1 | 0 | L19I/M141L/N168S/S188H/A195V/L311V/S355D/S434T | c18t |
| CL00102622 | 1.5 | 0 | 0.7 | 0 | S188H/A195V/T261A/L311V/Y321F/L347N/E348I | |
| CL00102639 | 1.1 | 0 | 1 | 0 | E11S/L19I/D53N/T57S/N168S/L347N | c18t |
| CL00102644 | 1.7 | 0 | 0.9 | 0 | E11S/I69L/M119E/A195V/T261A/A317P/Y321W/L347N/Y412F | c18t |
| CL00102654 | 1.7 | 0 | 0.5 | 0 | L79Y/V88I/T261A/A317P/Y321F/L364I/Y412F | |
| CL00102693 | 1.7 | 0 | 0.6 | 0.1 | E11S/V42I/E68Y/T89S/L311V/Y321F/T388Q/F394Y/V395L/Q419P | c18t |
| CL00102703 | 1.8 | 0 | 0.6 | 0.1 | D53N/E68Y/V88I/M141L/N168S/Y321W/Y412F | |
| CL00102722 | 1.7 | 0.1 | 0.7 | 0.1 | E11S/I69L/L311V/A317P/Y321F/L347N/Y412F | |

FIGURE 4H

| Colony Tracking Number | PF* at pH4.3, 30°C, 72hr | PF* STD | PF* at pH4.3, 60°C, 72hr | PF* STD | AA Mutation w.r.t. G7P (CL00077366) (Numbering starts from mature protein; negative number indicates mutations at the SP region) | Silent Mutation w.r.t. G7P (CL00077366) (Numbering starts from mature protein; negative number indicates mutations at the SP region) |
|---|---|---|---|---|---|---|
| CL00102724 | 1.1 | 0 | 0.9 | 0 | D53N/T57S/M141L | c18t |
| CL00102736 | 1.1 | 0 | 1.1 | 0 | D53N/V88I/T89S/D118N/E348I/S355D | |
| CL00102786 | 1.5 | 0 | 0.8 | 0.1 | E11S/S188H/A195V/A317P/L347N/E348I/Y412F/Q419P/S434T | |
| CL00102887 | 1.7 | 0 | 1 | 0 | E11S/D53N/I69L/V88I/A317P/Q419P | c18t |
| CL00102949 | 1.2 | 0 | 0.8 | 0 | E68Y/I69L/V88I/N168S/L364I/Q419P | |
| CL00102960 | 2 | 0 | 1.1 | 0.1 | E11S/V42I/V88I/T261A/Y321F/E348I/S355D | |
| CL00102971 | 1.6 | 0 | 1.9 | 0.1 | E11S/V42I/T57S/I69L/A195V/L347N/E348I/S355D | |
| CL00103030 | 1.7 | 0 | 0.7 | 0 | L19I/T89S/A317P/Y321F/S434T | |
| CL00103041 | 1.7 | 0 | 0.7 | 0 | E11S/V42I/L79Y/L311V/A317P/Y321W/L347N/E348I/L364I/Y412F | c18t |
| CL00103056 | 1.2 | 0 | 0.9 | 0 | D53N/T57S/L347N/E348I/Y412F | c18t |
| CL00103062 | 1.9 | 0 | 1.1 | 0 | D53N/T57S/E68Y/L79Y/Y412F/S434T | c18t |
| CL00103082 | 1.3 | 0 | 1.2 | 0.1 | L19I/V88I/T89S/A317P | |
| CL00103089 | 1.4 | 0 | 0.7 | 0.1 | M119E/M141L/N168S/L311V/Y321F | |
| CL00103169 | 1.5 | 0.1 | 1 | 0.1 | E11S/T89S/Y321W | c18t |
| CL00103174 | 1.4 | 0 | 1.1 | 0.1 | E11S/M141L/T261A/A317P/Y412F/S434T | |
| CL00103220 | 1.7 | 0 | 0.8 | 0.1 | V42I/L79Y/S188H/A195V/L311V/Y321F/S355D | |
| CL00103230 | 2.1 | 0.1 | 1.1 | 0.1 | V42I/E68Y/V88I/T261A/Y321W/L347N/E348I | |
| CL00103241 | 1.7 | 0 | 0.8 | 0 | L19I/E68Y/I69L/M141L/Y321F/L347N/S355D/E381N/Y412F | |
| CL00103271 | 2.1 | 0.1 | 0.5 | 0 | V42I/D53N/I69L/L79Y/D118N/T261A/L311V/A317P/Y321F/L347N/Y412F | |
| CL00103283 | 1.6 | 0 | 1.2 | 0.1 | E68Y/S355D/L364I/S382D/T388Q/Q419P | |

FIGURE 4I

| Colony Tracking Number | PF* at pH4.3, 30°C, 72hr | PF* STD | PF* at pH4.3, 60°C, 72hr | PF* STD | AA Mutation w.r.t. G7P (CL00077366) (Numbering starts from mature protein; negative number indicates mutations at the SP region) | Silent Mutation w.r.t.G7P (CL00077366) (Numbering starts from mature protein; negative number indicates mutations at the SP region) |
|---|---|---|---|---|---|---|
| CL00103294 | 2.1 | 0 | 1.2 | 0.1 | E11S/L19I/V42I/E68Y/I69L/D118N/M141L/Y321W/L347N | |
| CL00103327 | 2.1 | 0 | 0.7 | 0 | /E11S/V42I/E68Y/M141L/A317P/Y321F/E348I/S355D | |
| CL00103338 | 1.2 | 0 | 0.6 | 0 | E11S/V42I/E68Y/I69L/V88I/T89S/D118N/M119E/S188H/A195V/A317P/L347N/Y412F/Q419P | |
| CL00103402 | 1.8 | 0.1 | 0.6 | 0 | V42I/V88I/L311V/A317P/Y321F/L347N/E348I/T388Q/V395L/S434T | c18t |
| CL00103473 | 1.8 | 0.1 | 0.9 | 0.1 | T261A/A317P/Y321W/E348I | c18t |
| CL00103533 | 1.3 | 0 | 1.1 | 0.1 | E11S/V42I/E68Y/I69L/D118N/M119E/Y412F | |
| CL00103543 | 1.5 | 0 | 1.4 | 0.1 | E11S/V42I/T57S/I69L/L311V | |
| CL00103580 | 1.1 | 0.1 | 1.2 | 0.2 | V42I/Y412F | |
| CL00103581 | 1.6 | 0 | 1.6 | 0.1 | E11S/L19I/E68Y/M119E/N168S/Y412F/Q419P | |
| CL00103584 | 1.2 | 0 | 1.3 | 0.1 | L19I/L311V/Y412F | |
| CL00103587 | 1.3 | 0 | 1.6 | 0 | E11S/V42I/M119E/Y412F | |
| CL00103592 | 2.1 | 0.1 | 0.8 | 0.1 | E11S/L19I/V42I/D53N/S188H/A195V/L311V/Y321F/Y412F | |
| CL00103629 | 1.4 | 0 | 1.4 | 0.2 | E11S/L19I/V42I/T57S/D118N/N168S/L311V/Y412F | |
| CL00103631 | 2.1 | 0.1 | 0.9 | 0.1 | E11S/L19I/V42I/D53N/T57S/N168S/A317P/Y321W/Y412F | |
| CL00103662 | 2.2 | 0 | 0.1 | 0 | L19I/V42I/D53N/T57S/E68Y/N168S/S188H/A195V/L311V/Y321W/Y412F/Q419P | |
| CL00103665 | 2.2 | 0.1 | 0.8 | 0 | L19I/D53N/T57S/L311V/Y321W/Y412F | |
| CL00103699 | 2.2 | 0 | 0.6 | 0 | E11S/T57S/Y321W/Y412F/Q419P | |
| CL00103712 | 1.3 | 0 | 0.9 | 0 | D53N/S188H/A195V/L311V/Y412F | |
| CL00103729 | 1.7 | 0 | 0.4 | 0 | V42I/D53N/S188H/A195V/L311V/Y321F/Y412F | |

FIGURE 4J

| Colony Tracking Number | PF* at pH4.3, 30°C, 72hr | PF* STD | PF* at pH4.3, 60°C, 72hr | PF* STD | AA Mutation w.r.t. G7P (CL00077366) (Numbering starts from mature protein; negative number indicates mutations at the SP region) | Silent Mutation w.r.t.G7P (CL00077366) (Numbering starts from mature protein; negative number indicates mutations at the SP region) |
|---|---|---|---|---|---|---|
| CL00103736 | 1.4 | 0 | 1.1 | 0.1 | L19I/M119E/N168S/S188H/A195V/L311V/Y412F/Q419P | |
| CL00103748 | 2.6 | 0 | 0.7 | 0.1 | E11S/V42I/S188H/A195V/L311V/A317P/Y321W/Y412F/Q419P | |
| CL00103790 | 1.3 | 0.1 | 1.5 | 0.2 | E11S/V42I/M119E/N168S/L311V/Y412F | |
| CL00103809 | 2.2 | 0.1 | 0.8 | 0.2 | E11S/V42I/N168S/L311V/A317P/Y321W/Y412F/Q419P | |
| CL00103816 | 2.4 | 0.1 | 0.4 | 0 | E11S/V42I/D53N/E68Y/S188H/A195V/L311V/A317P/Y321F/Y412F | |
| CL00103817 | 1.4 | 0 | 1.3 | 0 | E11S/L19I/D53N/N168S/A195V/Y412F/Q419P | |
| CL00103834 | 1.3 | 0 | 1.5 | 0.1 | E11S/L19I/V42I/L311V/Y412F | |
| CL00103836 | 1.2 | 0 | 0.9 | 0.2 | V42I/D53N/N168S/L311V/Y412F | |
| CL00103877 | 1.4 | 0 | 1.2 | 0.2 | E11S/L311V/Y412F | |
| CL00103888 | 2.5 | 0 | 0.5 | 0 | E11S/D53N/T57S/L311V/Y321W/Y412F | |
| CL00103889 | 2 | 0 | 1 | 0.1 | E11S/L311V/Y321W/Y412F | |
| CL00103893 | 1.8 | 0.1 | 1.4 | 0 | E11S/V42I/I69L/D118N/N168S/L311V/A317P/Y412F/Q419P | |
| CL00103897 | 1.8 | 0 | 1.4 | 0.1 | E11S/V42I/E68Y/Y412F/Q419P | |
| CL00103983 | 1.4 | 0 | 1.2 | 0.1 | E11S/L19I/D53N/L311V | |
| CL00103984 | 1.7 | 0 | 1.6 | 0 | E11S/L19I/V42I/L311V/Y412F/Q419P | |
| CL00104003 | 2.3 | 0 | 0.5 | 0.1 | L19I/V42I/D53N/T57S/I69L/N168S/S188H/A195V/L311V/A317P/Y321W | |
| CL00104045 | 2 | 0 | 0.6 | 0 | E11S/L19I/V42I/T57S/L311V/A317P/Y321F/Y412F | |
| CL00104054 | 1.9 | 0 | 0.7 | 0.1 | L19I/V42I/I69L/D118N/N168S/L311V/Y321W/Y412F/Q419P | |
| CL00104057 | 2 | 0 | 1.3 | 0.1 | E11S/V42I/D53N/E68Y/S188H/A195V/Y412F | |
| CL00104062 | 2.6 | 0 | 1.1 | 0.2 | E11S/L19I/V42I/D53N/T57S/N168S/L311V/Y321W/Y412F | |

FIGURE 4K

| Colony Tracking Number | PF* at pH4.3, 30°C, 72hr | PF* STD | PF* at pH4.3, 60°C, 72hr | PF* STD | AA Mutation w.r.t. G7P (CL00077366) (Numbering starts from mature protein; negative number indicates mutations at the SP region) | Silent Mutation w.r.t.G7P (CL00077366) (Numbering starts from mature protein; negative number indicates mutations at the SP region) |
|---|---|---|---|---|---|---|
| CL00104074 | 1.5 | 0 | 1.4 | 0.2 | E11S/V42I/L311V/Y412F | |
| CL00104085 | 2 | 0 | 1 | 0 | E11S/L19I/V42I/N168S/A195V/L311V/Y321F/Y412F | |
| CL00104098 | 1.7 | 0 | 1.2 | 0.1 | E11S/V42I/S188H/L311V/Y412F | |
| CL00104099 | 1.7 | 0 | 0.3 | 0 | L19I/V42I/T57S/E68Y/M119E/S188H/A195V/L311V/Y321F/Y412F | |
| CL00104112 | 1.1 | 0 | 0.8 | 0.1 | E11S/L19I/V42I/D53N/N168S/S188H/A195V | |
| CL00104158 | 2.1 | 0.1 | 1.2 | 0.1 | E11S/L19I/V42I/T57S/E68Y/A195V/L311V/Y321W | |
| CL00104196 | 1.3 | 0 | 1.2 | 0.2 | E11S/L19I/V42I | |

FIGURE 5A

| Position (Numbering starts from mature protein; negative number indicates mutations at the SP region) | G6P/G7P Residue | Particular Variants | Position (Numbering starts from mature protein; negative number indicates mutations at the SP region) | G6P Residue | Particular Variants |
|---|---|---|---|---|---|
| -20 | V | A, F, G, I, K, L, M, Q, R, T, W | 497 | E | V |
| -18 | L | F, I, Y | 498 | L | T |
| -17 | K | F, N, Y | 500 | T | * |
| -15 | A | F, I, L, V | 502 | Y | * |
| -13 | A | T | 503 | Y | *, D, E, G, K, L, N, S, T |
| -12 | A | V | 506 | N | * |
| -10 | T | F, V | 508 | K | N, S, T |
| -9 | W | Y | 509 | L | *, P |
| -1 | V | F | 510 | V | *, G, S |
| 5 | K | H, N, P, Q, S, T, Y | 513 | T | * |
| 27 | N | A | 514 | A | * |
| 36 | S | P | 516 | F | L |
| 38 | A | V | 518 | S | I, L, M |
| 39 | A | F | 519 | W | * |
| 46 | S | T | 520 | S | * |
| 47 | P | T | 521 | P | S |
| 50 | S | Q | 522 | S | *, G |
| 65 | V | I | 524 | G | * |
| 68 | E | K, N, S, Y | 525 | I | * |
| 79 | L | F | 526 | L | I, N, S |

FIGURE 5B

| Position (Numbering starts from mature protein; negative number indicates mutations at the SP region) | G6P/G7P Residue | Particular Variants | Position (Numbering starts from mature protein; negative number indicates mutations at the SP region) | G6P Residue | Particular Variants |
|---|---|---|---|---|---|
| 89 | T | N | 533 | T | R |
| 98 | T | S | 534 | A | T |
| 108 | A | S | 535 | S | Y |
| 121 | P | S | 540 | T | N |
| 122 | F | M | 542 | T | N |
| 124 | G | P, S, T | 544 | S | *, E, N, Q |
| 158 | G | S | 545 | V | A, D |
| 161 | Q | P | 549 | S | *, D, E |
| 188 | S | H, P, T, W | 550 | T | *, D |
| 192 | T | A | 551 | V | *, D, R, S |
| 212 | K | Y | 555 | F | D, K, L, N, R, S |
| 215 | S | A | 556 | I | *, D, P, R |
| 258 | T | S | 557 | R | P |
| 262 | A | S | 558 | V | * |
| 264 | H | M | 559 | G | N, S |
| 298 | I | V | 560 | S | * |
| 321 | Y | F, L, W | 563 | S | *, L |
| 400 | T | L | 564 | I | *, N, S, T |
| 412 | Y | F | 569 | G | *, I |
| 419 | Q | P | 570 | N | P |
| 420 | L | K | 581 | T | N |

FIGURE 5C

| Position (Numbering starts from mature protein; negative number indicates mutations at the SP region) | G6P/G7P Residue | Particular Variants | Position (Numbering starts from mature protein; negative number indicates mutations at the SP region) | G6P Residue | Particular Variants |
|---|---|---|---|---|---|
| 422 | A | G, S | 584 | T | N |
| 423 | P | G, R, V | | | |
| 457 | G | S | | | |
| 491 | A | V | | | |

FIGURE 7A

>G6P preprotein amino acid sequence SEQ ID NO:1
*MVFLKSAIAASTWLLAATGVVA*SPVSKRATLDEFISTERPLALERLLCNIGPTGCRASGAAS
GVVIASPSRSDPDYYYTWTRDAALVFKEIVDSVETNTTLLLPEIENYVTAQAYLQTVTNPS
GSLSDGAGLGEPKFNVDMTPFTGAWGRPQRDGPALRATAMIAYYNYLLNNNATTDCGL
WQIIQNDLNYVAQYWNQTGYDLWEEVPGSSFFTVAAQYRALVEGSTLAAKLGKSHSAYD
TVAPQILCYLQSFWSSSKGYIVANTQTASWVSRSGLDANTPLTAIHLFDPELGCDDSTFQPC
SPKQLITTKKLVDSFRSIYAINSGKSAGDALAVGRYAEDVYYNGNPWYLCTLAVAEQLYD
AVYTWKLEGSITVTSVSLPFFTDLLPSLTTGTYASGSTTFESIISAVTTYADGFVSIVQTYTPS
DGALSEQYSKYNGQQLSAPDLTWSYAAFLSATERRDSVVPAGWAGASSVSVPGACAATT
VVGTYAAASNCGTPGSGSGGNGGSSGNALVTFNELATTYYGENIKLVGSTAAFGSWSPSA
GILLSASSYTASNPLWTTTVSVPQGSTVEFKFIRVGSDGSITWESGNNKVLTVGSSATSVTV
SASWNGAYSVSSS >G6P preprotein-encoding nucleic acid sequence SEQ ID NO:2
*ATGGTTTTCCTCAAGTCGGCCATCGCCGCTTCCACCTGGCTCTTGGCTGCCACTGGCGTC*
*GTTGCC*TCGCCTGTTTCCAAGCGCGCTACGCTGGACGAGTTCATCAGCACCGAGCGTCC
CTTGGCTCTGGAGCGCCTGCTCTGCAACATTGGTCCTACTGGTTGCCGTGCTTCGGGAG
CTGCCTCGGGAGTCGTTATCGCCTCGCCGTCCCGCAGCGATCCGGACTACTACACT
TGGACCCGTGATGCTGCTCTGGTCTTTAAGGAGATTGTCGACTCTGTCGAGACTAACAC
CACTCTGCTGCTGCCAGAGATTGAGAACTACGTTACTGCCCAGGCTTACCTGCAGACC
GTGACGAACCCCTCGGGTTCGCTGTCGGATGGTGCTGGTCTGGGCGAGCCCAAGTTCA
ACGTCGATATGACTCCCTTCACTGGTGCCTGGGGTCGTCCTCAGCGTGATGGTCCGGCT
CTGCGTGCTACGGCTATGATCGCCTACTACAACTACCTGCTCAACAACAACGCCACTA
CCGACTGTGGTCTGTGGCAGATTATCCAGAACGACCTGAATTACGTCGCTCAGTACTG
GAACCAAACTGGTTACGACCTGTGGGAGGAGGTTCCGGGTTCATCCTTTTTCACTGTTG
CTGCTCAGTACAGAGCTCTCGTTGAGGGTTCTACCCTTGCTGCCAAGCTCGGCAAGTCT
CACTCGGCCTACGACACTGTCGCTCCGCAGATTCTGTGCTACTTGCAGAGCTTCTGGTC
ATCCAGCAAGGGCTACATTGTCGCCAACACCCAGACTGCCAGCTGGGTCTCGCGGTCC
GGTCTTGATGCCAACACTCCCTTGACTGCCATCCACCTATTTGACCCTGAACTTGGCTG
CGATGACTCGACTTTCCAGCCCTGCTCGCCCAAGCAGCTTATCACTACTAAGAAGCTCG
TTGACTCGTTCCGCTCCATCTATGCCATCAACTCGGGCAAGTCTGCTGGTGATGCTTTG
GCTGTTGGTCGTTACGCCGAGGACGTCTACTACAACGGCAACCCCTGGTACCTGTGCA
CTTTGGCTGTTGCAGAGCAGCTTTACGATGCAGTTTACACTTGGAAGCTCGAGGGCTCC
ATCACCGTCACCTCTGTCTCGCTGCCCTTCTTCACTGACCTGCTGCCCTCGCTGACCACT
GGCACCTACGCTTCGGGCTCGACCACCTTCGAATCCATCATCTCTGCTGTGACTACCTA
CGCTGATGGCTTTGTCAGTATTGTCCAGACCTACACTCCCTCTGACGGCGCTCTGTCTG
AGCAGTACTCCAAGTACAACGGCCAGCAGCTGTCGGCTCCCGACCTGACCTGGTCGTA
CGCCGCTTTCCTATCTGCCACTGAGCGCCGTGACAGCGTTGTCCCTGCCGGCTGGGCTG
GTGCCTCGTCTGTCTCTGTCCCGGCGCCTGCGCTGCTACCACCGTTGTCGGAACCTAC
GCTGCTGCCTCCAACTGCGGTACTCCTGGCTCTGGCTCGGGCGGCAACGGTGGCTCGA
GCGGTAACGCCCTGGTGACTTTCAACGAGCTGGCTACTACCTACTACGGCGAGAACAT
TAAGCTTGTCGGCAGCACAGCTGCTTTCGGTTCGTGGTCGCCCTCAGCTGGTATTCTCC
TGTCTGCCTCGTCGTACACGGCCAGCAACCCTCTGTGGACTACCACCGTGTCGGTTCCC
CAGGGCTCGACCGTTGAGTTCAAGTTCATCCGTGTTGGCTCCGACGGCAGCATCACGT
GGGAGAGCGGCAACAACAAGGTGTTGACGGTTGGCTCTTCGGCCACGAGCGTCACTGT
TTCTGCCAGCTGGAACGGCGCCTACTCGGTGTCTAGCTCTTAATAG

FIGURE 7B

>G7P preprotein amino acid sequence SEQ ID NO:3
*MVFLKSAIAASTWLLAATGVVA*SPVSKRATLDEFISTERPLALERLLCNIGPTGCRASGAAS
GVVIASPSRSDPDYYYTWTRDAALVFKEIVDSVETNTTLLLPEIENYVTAQAYLQTVTNPS
GSLSDGAGLGEPKFNVDMTPFTGAWGRPQRDGPALRATAMIAYYNYLLNNNATTDCGL
WQIIQNDLNYVAQYWNQTGYDLWEEVPGSSFFTVAAQYRALVEGSTLAAKLGKSHSAYD
TVAPQILCYLQSFWSSSKGYIVANTQTASWVSRSGLDANTPLTAIHLFDPELGCDDSTFQPC
SPKQLITTKKLVDSFRSIYAINSGKSAGDALAVGRYAEDVYYNGNPWYLCTLAVAEQLYD
AVYTWKLEGSITVTSVSLPFFTDLLPSLTTGTYASGSTTFESIISAVTTYADGFVSIVQTYTPS
DGALSEQYSKYNGQQLSAPDLTWSYAAFLSATERRDSVVPAGWAGASSVSVPGACAATT
VVGTYAAASNCGTPGSGSGGNGGSSGNAL >G7P preprotein-encoding nucleic acid sequence SEQ ID NO:4
*ATGGTTTTCCTCAAGTCGGCCATCGCCGCTTCCACCTGGCTCTTGGCTGCCACTGGCGTC*
*GTTGCC*TCGCCTGTTTCCAAGCGCGCTACGCTGGACGAGTTCATCAGCACCGAGCGTCC
CTTGGCTCTGGAGCGCCTGCTCTGCAACATTGGTCCTACTGGTTGCCGTGCTTCGGGAG
CTGCCTCGGGAGTCGTTATCGCCTCGCCGTCCCGCAGCGATCCGGACTACTACTACACT
TGGACCCGTGATGCTGCTCTGGTCTTTAAGGAGATTGTCGACTCTGTCGAGACTAACAC
CACTCTGCTGCTGCCAGAGATTGAGAACTACGTTACTGCCCAGGCTTACCTGCAGACC
GTGACGAACCCCTCGGGTTCGCTGTCGGATGGTGCTGGTCTGGGCGAGCCCAAGTTCA
ACGTCGATATGACTCCCTTCACTGGTGCCTGGGGTCGTCCTCAGCGTGATGGTCCGGCT
CTGCGTGCTACGGCTATGATCGCCTACTACAACTACCTGCTCAACAACAACGCCACTA
CCGACTGTGGTCTGTGGCAGATTATCCAGAACGACCTGAATTACGTCGCTCAGTACTG
GAACCAAACTGGTTACGACCTGTGGGAGGAGGTTCCGGGTTCATCCTTTTTCACTGTTG
CTGCTCAGTACAGAGCTCTCGTTGAGGGTTCTACCCTTGCTGCCAAGCTCGGCAAGTCT
CACTCGGCCTACGACACTGTCGCTCCGCAGATTCTGTGCTACTTGCAGAGCTTCTGGTC
ATCCAGCAAGGGCTACATTGTCGCCAACACCCAGACTGCCAGCTGGGTCTCGCGGTCC
GGTCTTGATGCCAACACTCCCTTGACTGCCATCCACCTATTTGACCCTGAACTTGGCTG
CGATGACTCGACTTTCCAGCCCTGCTCGCCCAAGCAGCTTATCACTACTAAGAAGCTCG
TTGACTCGTTCCGCTCCATCTATGCCATCAACTCGGGCAAGTCTGCTGGTGATGCTTTG
GCTGTTGGTCGTTACGCCGAGGACGTCTACTACAACGGCAACCCCTGGTACCTGTGCA
CTTTGGCTGTTGCAGAGCAGCTTTACGATGCAGTTTACACTTGGAAGCTCGAGGGCTCC
ATCACCGTCACCTCTGTCTCGCTGCCCTTCTTCACTGACCTGCTGCCCTCGCTGACCACT
GGCACCTACGCTTCGGGCTCGACCACCTTCGAATCCATCATCTCTGCTGTGACTACCTA
CGCTGATGGCTTTGTCAGTATTGTCCAGACCTACACTCCCTCTGACGGCGCTCTGTCTG
AGCAGTACTCCAAGTACAACGGCCAGCAGCTGTCGGCTCCCGACCTGACCTGGTCGTA
CGCCGCTTTCCTATCTGCCACTGAGCGCCGTGACAGCGTTGTCCCTGCCGGCTGGGCTG
GTGCCTCGTCTGTCTCTGTGCCCGGCGCCTGCGCTGCTACCACCGTTGTCGGAACCTAC
GCTGCTGCCTCCAACTGCGGTACTCCTGGCTCTGGCTCGGGCGGCAACGGTGGCTCGA
GCGGTAACGCCCTGTAATAG

FIGURE 7C

>Variant1 (Y321F with Starch Binding Domain) preprotein amino acid sequence SEQ ID NO:5
*MVFLKSAIAASTWLLAATGVVA*SPVSKRATLDEFISTERPLALERLLCNIGPTGCRASGAAS
GVVIASPSRSDPDYYYTWTRDAALVFKEIVDSVETNTTLLLPEIENYVTAQAYLQTVTNPS
GSLSDGAGLGEPKFNVDMTPFTGAWGRPQRDGPALRATAMIAYYNYLLNNNATTDCGL
WQIIQNDLNYVAQYWNQTGYDLWEEVPGSSFFTVAAQYRALVEGSTLAAKLGKSHSAYD
TVAPQILCYLQSFWSSSKGYIVANTQTASWVSRSGLDANTPLTAIHLFDPELGCDDSTFQPC
SPKQLITTKKLVDSFRSIYAINSGKSAGDALAVGRYAEDVFYNGNPWYLCTLAVAEQLYD
AVYTWKLEGSITVTSVSLPFFTDLLPSLTTGTYASGSTTFESIISAVTTYADGFVSIVQTYTPS
DGALSEQYSKYNGQQLSAPDLTWSYAAFLSATERRDSVVPAGWAGASSVSVPGACAATT
VVGTYAAASNCGTPGSGSGGNGGSSGNALVTFNELATTYYGENIKLVGSTAAFGSWSPSA
GILLSASSYTASNPLWTTTVSVPQGSTVEFKFIRVGSDGSITWESGNNKVLTVGSSATSVTV
SASWNGAYSVSSS >Variant1 (Y321F with Starch Binding Domain) preprotein-encoding nucleic acid sequence SEQ
ID NO:6
*ATGGTTTTCCTCAAGTCGGCCATCGCCGCTTCCACCTGGCTCTTGGCTGCCACTGGCGTC
GTTGCC*TCGCCTGTTTCCAAGCGCGCTACGCTGGACGAGTTCATCAGCACCGAGCGTCC
CTTGGCTCTGGAGCGCCTGCTCTGCAACATTGGTCCTACTGGTTGCCGTGCTTCGGGAG
CTGCCTCGGGAGTCGTTATCGCCTCGCCGTCCCGCAGCGATCCGGACTACTACTACACT
TGGACCCGTGATGCTGCTCTGGTCTTTAAGGAGATTGTCGACTCTGTCGAGACTAACAC
CACTCTGCTGCTGCCAGAGATTGAGAACTACGTTACTGCCCAGGCTTACCTGCAGACC
GTGACGAACCCCTCGGGTTCGCTGTCGGATGGTGCTGGTCTGGGCGAGCCCAAGTTCA
ACGTCGATATGACTCCCTTCACTGGTGCCTGGGGTCGTCCTCAGCGTGATGGTCCGGCT
CTGCGTGCTACGGCTATGATCGCCTACTACAACTACCTGCTCAACAACAACGCCACTA
CCGACTGTGGTCTGTGGCAGATTATCCAGAACGACCTGAATTACGTCGCTCAGTACTG
GAACCAAACTGGTTACGACCTGTGGGAGGAGGTTCCGGGTTCATCCTTTTTCACTGTTG
CTGCTCAGTACAGAGCTCTCGTTGAGGGTTCTACCCTTGCTGCCAAGCTCGGCAAGTCT
CACTCGGCCTACGACACTGTCGCTCCGCAGATTCTGTGCTACTTGCAGAGCTTCTGGTC
ATCCAGCAAGGGCTACATTGTCGCCAACACCCAGACTGCCAGCTGGGTCTCGCGGTCC
GGTCTTGATGCCAACACTCCCTTGACTGCCATCCACCTATTTGACCCTGAACTTGGCTG
CGATGACTCGACTTTCCAGCCCTGCTCGCCCAAGCAGCTTATCACTACTAAGAAGCTCG
TTGACTCGTTCCGCTCCATCTATGCCATCAACTCGGGCAAGTCTGCTGGTGATGCTTTG
GCTGTTGGTCGTTACGCCGAGGACGTCTTCTACAACGGCAACCCCTGGTACCTGTGCAC
TTTGGCTGTTGCAGAGCAGCTTTACGATGCAGTTTACACTTGGAAGCTCGAGGGCTCCA
TCACCGTCACCTCTGTCTCGCTGCCCTTCTTCACTGACCTGCTGCCCTCGCTGACCACTG
GCACCTACGCTTCGGGCTCGACCACCTTCGAATCCATCATCTCTGCTGTGACTACCTAC
GCTGATGGCTTTGTCAGTATTGTCCAGACCTACACTCCCTCTGACGGCGCTCTGTCTGA
GCAGTACTCCAAGTACAACGGCCAGCAGCTGTCGGCTCCCGACCTGACCTGGTCGTAC
GCCGCTTTCCTATCTGCCACTGAGCGCCGTGACAGCGTTGTCCCTGCCGGCTGGGCTGG
TGCCTCGTCTGTCTCTGTGCCCGGCGCCTGCGCTGCTACCACCGTTGTCGGAACCTACG
CTGCTGCCTCCAACTGCGGTACTCCTGGCTCTGGCTCGGGCGGCAACGGTGGCTCGAG
CGGTAACGCCCTGGTGACTTTCAACGAGCTGGCTACTACCTACTACGGCGAGAACATT
AAGCTTGTCGGCAGCACAGCTGCTTTCGGTTCGTGGTCGCCCTCAGCTGGTATTCTCCT
GTCTGCCTCGTCGTACACGGCCAGCAACCCTCTGTGGACTACCACCGTGTCGGTTCCCC
AGGGCTCGACCGTTGAGTTCAAGTTCATCCGTGTTGGCTCCGACGGCAGCATCACGTG
GGAGAGCGGCAACAACAAGGTGTTGACGGTTGGCTCTTCGGCCACGAGCGTCACTGTT
TCTGCCAGCTGGAACGGCGCCTACTCGGTGTCTAGCTCTTAATAG*

FIGURE 7D

>Variant2 (S188H/Y321W/Q419P with Starch Binding Domain) preprotein amino acid sequence SEQ ID NO:7

*MVFLKSAIAASTWLLAATGVVA*SPVSKRATLDEFISTERPLALERLLCNIGPTGCRASGAAS
GVVIASPSRSDPDYYYTWTRDAALVFKEIVDSVETNTTLLLPEIENYVTAQAYLQTVTNPS
GSLSDGAGLGEPKFNVDMTPFTGAWGRPQRDGPALRATAMIAYYNYLLNNNATTDCGL
WQIIQNDLNYVAQYWNQTGYDLWEEVPGHSFFTVAAQYRALVEGSTLAAKLGKSHSAY
DTVAPQILCYLQSFWSSSKGYIVANTQTASWVSRSGLDANTPLTAIHLFDPELGCDDSTFQP
CSPKQLITTKKLVDSFRSIYAINSGKSAGDALAVGRYAEDVWYNGNPWYLCTLAVAEQLY
DAVYTWKLEGSITVTSVSLPFFTDLLPSLTTGTYASGSTTFESIISAVTTYADGFVSIVQTYTP
SDGALSEQYSKYNGQPLSAPDLTWSYAAFLSATERRDSVVPAGWAGASSVSVPGACAATT
VVGTYAAASNCGTPGSGSGGNGGSSGNALVTFNELATTYYGENIKLVGSTAAFGSWSPSA
GILLSASSYTASNPLWTTTVSVPQGSTVEFKFIRVGSDGSITWESGNNKVLTVGSSATSVTV
SASWNGAYSVSSS

>Variant2 (S188H/Y321W/Q419P with Starch Binding Domain) preprotein-encoding nucleic acid sequence SEQ ID NO:8

*ATGGTTTTCCTCAAGTCGGCCATCGCCGCTTCCACCTGGCTCTTGGCTGCCACTGGCGTC
GTTGCC*TCGCCTGTTTCCAAGCGCGCTACGCTGGACGAGTTCATCAGCACCGAGCGTCC
CTTGGCTCTGGAGCGCCTGCTCTGCAACATTGGTCCTACTGGTTGCCGTGCTTCGGGAG
CTGCCTCGGGAGTCGTTATCGCCTCGCCGTCCCGCAGCGATCCGGACTACTACACT
TGGACCCGTGATGCTGCTCTGGTCTTTAAGGAGATTGTCGACTCTGTCGAGACTAACAC
CACTCTGCTGCTGCCAGAGATTGAGAACTACGTTACTGCCCAGGCTTACCTGCAGACC
GTGACGAACCCCTCGGGTTCGCTGTCGGATGGTGCTGGTCTGGGCGAGCCCAAGTTCA
ACGTCGATATGACTCCCTTCACTGGTGCCTGGGGTCGTCCTCAGCGTGATGGTCCGGCT
CTGCGTGCTACGGCTATGATCGCCTACTACAACTACCTGCTCAACAACAACGCCACTA
CCGACTGTGGTCTGTGGCAGATTATCCAGAACGACCTGAATTACGTCGCTCAGTACTG
GAACCAAACTGGTTACGACCTGTGGGAGGAGGTTCCGGGTCACTCCTTTTTCACTGTTG
CTGCTCAGTACAGAGCTCTCGTTGAGGGTTCTACCCTTGCTGCCAAGCTCGGCAAGTCT
CACTCGGCCTACGACACTGTCGCTCCGCAGATTCTGTGCTACTTGCAGAGCTTCTGGTC
ATCCAGCAAGGGCTACATTGTCGCCAACACCCAGACTGCCAGCTGGGTCTCGCGGTCC
GGTCTTGATGCCAACACTCCCTTGACTGCCATCCACCTATTTGACCCTGAACTTGGCTG
CGATGACTCGACTTTCCAGCCCTGCTCGCCCAAGCAGCTTATCACTACTAAGAAGCTCG
TTGACTCGTTCCGCTCCATCTATGCCATCAACTCGGGCAAGTCTGCTGGTGATGCTTTG
GCTGTTGGTCGTTACGCCGAGGACGTCTGGTACAACGGCAACCCCTGGTACCTGTGCA
CTTTGGCTGTTGCAGAGCAGCTTTACGATGCAGTTTACACTTGGAAGCTCGAGGGCTCC
ATCACCGTCACCTCTGTCTCGCTGCCCTTCTTCACTGACCTGCTGCCCTCGCTGACCACT
GGCACCTACGCTTCGGGCTCGACCACCTTCGAATCCATCATCTCTGCTGTGACTACCTA
CGCTGATGGCTTTGTCAGTATTGTCCAGACCTACACTCCCTCTGACGGCGCTCTGTCTG
AGCAGTACTCCAAGTACAACGGCCAGCCCCTGTCGGCTCCCGACCTGACCTGGTCGTA
CGCCGCTTTCCTATCTGCCACTGAGCGCCGTGACAGCGTTGTCCCTGCCGGCTGGGCTG
GTGCCTCGTCTGTCTCTGTGCCCGGCGCCTGCGCTGCTACCACCGTTGTCGGAACCTAC
GCTGCTGCCTCCAACTGCGGTACTCCTGGCTCTGGCTCGGGCGGCAACGGTGGCTCGA
GCGGTAACGCCCTGGTGACTTTCAACGAGCTGGCTACTACCTACTACGGCGAGAACAT
TAAGCTTGTCGGCAGCACAGCTGCTTTCGGTTCGTGGTCGCCCTCAGCTGGTATTCTCC
TGTCTGCCTCGTCGTACACGGCCAGCAACCCTCTGTGGACTACCACCGTGTCGGTTCCC
CAGGGCTCGACCGTTGAGTTCAAGTTCATCCGTGTTGGCTCCGACGGCAGCATCACGT
GGGAGAGCGGCAACAACAAGGTGTTGACGGTTGGCTCTTCGGCCACGAGCGTCACTGT
TTCTGCCAGCTGGAACGGCGCCTACTCGGTGTCTAGCTCTTAATAG*

FIGURE 7E

>Variant1 (Y321F without Starch Binding Domain) preprotein amino acid sequence SEQ ID NO:9
*MVFLKSAIAASTWLLAATGVVA*SPVSKRATLDEFISTERPLALERLLCNIGPTGCRASGAAS
GVVIASPSRSDPDYYYTWTRDAALVFKEIVDSVETNTTLLLPEIENYVTAQAYLQTVTNPS
GSLSDGAGLGEPKFNVDMTPFTGAWGRPQRDGPALRATAMIAYYNYLLNNNATTDCGL
WQIIQNDLNYVAQYWNQTGYDLWEEVPGSSFFTVAAQYRALVEGSTLAAKLGKSHSAYD
TVAPQILCYLQSFWSSSKGYIVANTQTASWVSRSGLDANTPLTAIHLFDPELGCDDSTFQPC
SPKQLITTKKLVDSFRSIYAINSGKSAGDALAVGRYAEDVFYNGNPWYLCTLAVAEQLYD
AVYTWKLEGSITVTSVSLPFFTDLLPSLTTGTYASGSTTFESIISAVTTYADGFVSIVQTYTPS
DGALSEQYSKYNGQQLSAPDLTWSYAAFLSATERRDSVVPAGWAGASSVSVPGACAATT
VVGTYAAASNCGTPGSGSGGNGGSSGNAL >Variant1 (Y321F without Starch Binding Domain) preprotein-encoding nucleic acid sequence
SEQ ID NO:10
*ATGGTTTTCCTCAAGTCGGCCATCGCCGCTTCCACCTGGCTCTTGGCTGCCACTGGCGTC
GTTGCC*TCGCCTGTTTCCAAGCGCGCTACGCTGGACGAGTTCATCAGCACCGAGCGTCC
CTTGGCTCTGGAGCGCCTGCTCTGCAACATTGGTCCTACTGGTTGCCGTGCTTCGGGAG
CTGCCTCGGGAGTCGTTATCGCCTCGCCGTCCCGCAGCGATCCGGACTACTACACT
TGGACCCGTGATGCTGCTCTGGTCTTTAAGGAGATTGTCGACTCTGTCGAGACTAACAC
CACTCTGCTGCTGCCAGAGATTGAGAACTACGTTACTGCCCAGGCTTACCTGCAGACC
GTGACGAACCCCTCGGGTTCGCTGTCGGATGGTGCTGGTCTGGGCGAGCCCAAGTTCA
ACGTCGATATGACTCCCTTCACTGGTGCCTGGGGTCGTCCTCAGCGTGATGGTCCGGCT
CTGCGTGCTACGGCTATGATCGCCTACTACAACTACCTGCTCAACAACAACGCCACTA
CCGACTGTGGTCTGTGGCAGATTATCCAGAACGACCTGAATTACGTCGCTCAGTACTG
GAACCAAACTGGTTACGACCTGTGGGAGGAGGTTCCGGGTTCATCCTTTTTCACTGTTG
CTGCTCAGTACAGAGCTCTCGTTGAGGGTTCTACCCTTGCTGCCAAGCTCGGCAAGTCT
CACTCGGCCTACGACACTGTCGCTCCGCAGATTCTGTGCTACTTGCAGAGCTTCTGGTC
ATCCAGCAAGGGCTACATTGTCGCCAACACCCAGACTGCCAGCTGGGTCTCGCGGTCC
GGTCTTGATGCCAACACTCCCTTGACTGCCATCCACCTATTTGACCCTGAACTTGGCTG
CGATGACTCGACTTTCCAGCCCTGCTCGCCCAAGCAGCTTATCACTACTAAGAAGCTCG
TTGACTCGTTCCGCTCCATCTATGCCATCAACTCGGGCAAGTCTGCTGGTGATGCTTTG
GCTGTTGGTCGTTACGCCGAGGACGTCTTCTACAACGGCAACCCCTGGTACCTGTGCAC
TTTGGCTGTTGCAGAGCAGCTTTACGATGCAGTTTACACTTGGAAGCTCGAGGGCTCCA
TCACCGTCACCTCTGTCTCGCTGCCCTTCTTCACTGACCTGCTGCCCTCGCTGACCACTG
GCACCTACGCTTCGGGCTCGACCACCTTCGAATCCATCATCTCTGCTGTGACTACCTAC
GCTGATGGCTTTGTCAGTATTGTCCAGACCTACACTCCCTCTGACGGCGCTCTGTCTGA
GCAGTACTCCAAGTACAACGGCCAGCAGCTGTCGGCTCCCGACCTGACCTGGTCGTAC
GCCGCTTTCCTATCTGCCACTGAGCGCCGTGACAGCGTTGTCCCTGCCGGCTGGGCTGG
TGCCTCGTCTGTCTCTGTGCCCGGCGCCTGCGCTGCTACCACCGTTGTCGGAACCTACG
CTGCTGCCTCCAACTGCGGTACTCCTGGCTCTGGCTCGGGCGGCAACGGTGGCTCGAG
CGGTAACGCCCTGTAATAG

FIGURE 7F

>Variant2 (S188H/Y321W/Q419P without Starch Binding Domain) preprotein amino acid sequence SEQ ID NO:11
*MVFLKSAIAASTWLLAATGVVA*SPVSKRATLDEFISTERPLALERLLCNIGPTGCRASGAAS
GVVIASPSRSDPDYYYTWTRDAALVFKEIVDSVETNTTLLLPEIENYVTAQAYLQTVTNPS
GSLSDGAGLGEPKFNVDMTPFTGAWGRPQRDGPALRATAMIAYYNYLLNNNATTDCGL
WQIIQNDLNYVAQYWNQTGYDLWEEVPGHSFFTVAAQYRALVEGSTLAAKLGKSHSAY
DTVAPQILCYLQSFWSSSKGYIVANTQTASWVSRSGLDANTPLTAIHLFDPELGCDDSTFQP
CSPKQLITTKKLVDSFRSIYAINSGKSAGDALAVGRYAEDVWYNGNPWYLCTLAVAEQLY
DAVYTWKLEGSITVTSVSLPFFTDLLPSLTTGTYASGSTTFESIISAVTTYADGFVSIVQTYTP
SDGALSEQYSKYNGQPLSAPDLTWSYAAFLSATERRDSVVPAGWAGASSVSVPGACAATT
VVGTYAAASNCGTPGSGSGGNGGSSGNAL >Variant2 (S188H/Y321W/Q419P without Starch Binding Domain) preprotein-encoding nucleic acid sequence SEQ ID NO:12
*ATGGTTTTCCTCAAGTCGGCCATCGCCGCTTCCACCTGGCTCTTGGCTGCCACTGGCGTC*
*GTTGCC*TCGCCTGTTTCCAAGCGCGCTACGCTGGACGAGTTCATCAGCACCGAGCGTCC
CTTGGCTCTGGAGCGCCTGCTCTGCAACATTGGTCCTACTGGTTGCCGTGCTTCGGGAG
CTGCCTCGGGAGTCGTTATCGCCTCGCCGTCCCGCAGCGATCCGGACTACTACTACACT
TGGACCCGTGATGCTGCTCTGGTCTTTAAGGAGATTGTCGACTCTGTCGAGACTAACAC
CACTCTGCTGCTGCCAGAGATTGAGAACTACGTTACTGCCCAGGCTTACCTGCAGACC
GTGACGAACCCCTCGGGTTCGCTGTCGGATGGTGCTGGTCTGGGCGAGCCCAAGTTCA
ACGTCGATATGACTCCCTTCACTGGTGCCTGGGGTCGTCCTCAGCGTGATGGTCCGGCT
CTGCGTGCTACGGCTATGATCGCCTACTACAACTACCTGCTCAACAACAACGCCACTA
CCGACTGTGGTCTGTGGCAGATTATCCAGAACGACCTGAATTACGTCGCTCAGTACTG
GAACCAAACTGGTTACGACCTGTGGGAGGAGGTTCCGGGTCACTCCTTTTTCACTGTTG
CTGCTCAGTACAGAGCTCTCGTTGAGGGTTCTACCCTTGCTGCCAAGCTCGGCAAGTCT
CACTCGGCCTACGACACTGTCGCTCCGCAGATTCTGTGCTACTTGCAGAGCTTCTGGTC
ATCCAGCAAGGGCTACATTGTCGCCAACACCCAGACTGCCAGCTGGGTCTCGCGGTCC
GGTCTTGATGCCAACACTCCCTTGACTGCCATCCACCTATTTGACCCTGAACTTGGCTG
CGATGACTCGACTTTCCAGCCCTGCTCGCCCAAGCAGCTTATCACTACTAAGAAGCTCG
TTGACTCGTTCCGCTCCATCTATGCCATCAACTCGGGCAAGTCTGCTGGTGATGCTTTG
GCTGTTGGTCGTTACGCCGAGGACGTCTGGTACAACGGCAACCCCTGGTACCTGTGCA
CTTTGGCTGTTGCAGAGCAGCTTTACGATGCAGTTTACACTTGGAAGCTCGAGGGCTCC
ATCACCGTCACCTCTGTCTCGCTGCCCTTCTTCACTGACCTGCTGCCCTCGCTGACCACT
GGCACCTACGCTTCGGGCTCGACCACCTTCGAATCCATCATCTCTGCTGTGACTACCTA
CGCTGATGGCTTTGTCAGTATTGTCCAGACCTACACTCCCTCTGACGGCGCTCTGTCTG
AGCAGTACTCCAAGTACAACGGCCAGCCCTGTCGGCTCCCGACCTGACCTGGTCGTA
CGCCGCTTTCCTATCTGCCACTGAGCGCCGTGACAGCGTTGTCCCTGCCGGCTGGGCTG
GTGCCTCGTCTGTCTCTGTGCCCGGCGCCTGCGCTGCTACCACCGTTGTCGGAACCTAC
GCTGCTGCCTCCAACTGCGGTACTCCTGGCTCTGGCTCGGGCGGCAACGGTGGCTCGA
GCGGTAACGCCCTGTAATAG

FIGURE 7G

>G6P mature protein amino acid sequence SEQ ID NO:13
SPVSKRATLDEFISTERPLALERLLCNIGPTGCRASGAASGVVIASPSRSDPDYYYTWTRDA
ALVFKEIVDSVETNTTLLLPEIENYVTAQAYLQTVTNPSGSLSDGAGLGEPKFNVDMTPFT
GAWGRPQRDGPALRATAMIAYYNYLLNNNATTDCGLWQIIQNDLNYVAQYWNQTGYDL
WEEVPGSSFFTVAAQYRALVEGSTLAAKLGKSHSAYDTVAPQILCYLQSFWSSSKGYIVA
NTQTASWVSRSGLDANTPLTAIHLFDPELGCDDSTFQPCSPKQLITTKKLVDSFRSIYAINSG
KSAGDALAVGRYAEDVYYNGNPWYLCTLAVAEQLYDAVYTWKLEGSITVTSVSLPFFTD
LLPSLTTGTYASGSTTFESIISAVTTYADGFVSIVQTYTPSDGALSEQYSKYNGQQLSAPDLT
WSYAAFLSATERRDSVVPAGWAGASSVSVPGACAATTVVGTYAAASNCGTPGSGSGGNG
GSSGNALVTFNELATTYYGENIKLVGSTAAFGSWSPSAGILLSASSYTASNPLWTTTVSVPQ
GSTVEFKFIRVGSDGSITWESGNNKVLTVGSSATSVTVSASWNGAYSVSSS >G6P mature protein-encoding nucleic acid sequence SEQ ID NO:14
TCGCCTGTTTCCAAGCGCGCTACGCTGGACGAGTTCATCAGCACCGAGCGTCCCTTGGC
TCTGGAGCGCCTGCTCTGCAACATTGGTCCTACTGGTTGCCGTGCTTCGGGAGCTGCCT
CGGGAGTCGTTATCGCCTCGCCGTCCCGCAGCGATCCGGACTACTACTACACTTGGAC
CCGTGATGCTGCTCTGGTCTTTAAGGAGATTGTCGACTCTGTCGAGACTAACACCACTC
TGCTGCTGCCAGAGATTGAGAACTACGTTACTGCCCAGGCTTACCTGCAGACCGTGAC
GAACCCCTCGGGTTCGCTGTCGGATGGTGCTGGTCTGGGCGAGCCCAAGTTCAACGTC
GATATGACTCCCTTCACTGGTGCCTGGGGTCGTCCTCAGCGTGATGGTCCGGCTCTGCG
TGCTACGGCTATGATCGCCTACTACAACTACCTGCTCAACAACAACGCCACTACCGAC
TGTGGTCTGTGGCAGATTATCCAGAACGACCTGAATTACGTCGCTCAGTACTGGAACC
AAACTGGTTACGACCTGTGGGAGGAGGTTCCGGGTTCATCCTTTTTCACTGTTGCTGCT
CAGTACAGAGCTCTCGTTGAGGGTTCTACCCTTGCTGCCAAGCTCGGCAAGTCTCACTC
GGCCTACGACACTGTCGCTCCGCAGATTCTGTGCTACTTGCAGAGCTTCTGGTCATCCA
GCAAGGGCTACATTGTCGCCAACACCCAGACTGCCAGCTGGGTCTCGCGGTCCGGTCT
TGATGCCAACACTCCCTTGACTGCCATCCACCTATTTGACCCTGAACTTGGCTGCGATG
ACTCGACTTTCCAGCCCTGCTCGCCCAAGCAGCTTATCACTACTAAGAAGCTCGTTGAC
TCGTTCCGCTCCATCTATGCCATCAACTCGGGCAAGTCTGCTGGTGATGCTTTGGCTGT
TGGTCGTTACGCCGAGGACGTCTACTACAACGGCAACCCCTGGTACCTGTGCACTTTG
GCTGTTGCAGAGCAGCTTTACGATGCAGTTTACACTTGGAAGCTCGAGGGCTCCATCA
CCGTCACCTCTGTCTCGCTGCCCTTCTTCACTGACCTGCTGCCCTCGCTGACCACTGGC
ACCTACGCTTCGGGCTCGACCACCTTCGAATCCATCATCTCTGCTGTGACTACCTACGC
TGATGGCTTTGTCAGTATTGTCCAGACCTACACTCCCTCTGACGGCGCTCTGTCTGAGC
AGTACTCCAAGTACAACGGCCAGCAGCTGTCGGCTCCCGACCTGACCTGGTCGTACGC
CGCTTTCCTATCTGCCACTGAGCGCCGTGACAGCGTTGTCCCTGCCGGCTGGGCTGGTG
CCTCGTCTGTCTCTGTGCCCGGCGCCTGCGCTGCTACCACCGTTGTCGGAACCTACGCT
GCTGCCTCCAACTGCGGTACTCCTGGCTCTGGCTCGGGCGGCAACGGTGGCTCGAGCG
GTAACGCCCTGGTGACTTTCAACGAGCTGGCTACTACCTACTACGGCGAGAACATTAA
GCTTGTCGGCAGCACAGCTGCTTTCGGTTCGTGGTCGCCCTCAGCTGGTATTCTCCTGT
CTGCCTCGTCGTACACGGCCAGCAACCCTCTGTGGACTACCACCGTGTCGGTTCCCCAG
GGCTCGACCGTTGAGTTCAAGTTCATCCGTGTTGGCTCCGACGGCAGCATCACGTGGG
AGAGCGGCAACAACAAGGTGTTGACGGTTGGCTCTTCGGCCACGAGCGTCACTGTTTC
TGCCAGCTGGAACGGCGCCTACTCGGTGTCTAGCTCTTAATAG

FIGIRE 7H

\>G7P mature protein amino acid sequence SEQ ID NO:15
SPVSKRATLDEFISTERPLALERLLCNIGPTGCRASGAASGVVIASPSRSDPDYYYTWTRDA
ALVFKEIVDSVETNTTLLLPEIENYVTAQAYLQTVTNPSGSLSDGAGLGEPKFNVDMTPFT
GAWGRPQRDGPALRATAMIAYYNYLLNNNATTDCGLWQIIQNDLNYVAQYWNQTGYDL
WEEVPGSSFFTVAAQYRALVEGSTLAAKLGKSHSAYDTVAPQILCYLQSFWSSSKGYIVA
NTQTASWVSRSGLDANTPLTAIHLFDPELGCDDSTFQPCSPKQLITTKKLVDSFRSIYAINSG
KSAGDALAVGRYAEDVYYNGNPWYLCTLAVAEQLYDAVYTWKLEGSITVTSVSLPFFTD
LLPSLTTGTYASGSTTFESIISAVTTYADGFVSIVQTYTPSDGALSEQYSKYNGQQLSAPDLT
WSYAAFLSATERRDSVVPAGWAGASSVSVPGACAATTVVGTYAAASNCGTPGSGSGGNG
GSSGNAL \>G7P mature protein-encoding nucleic acid sequence SEQ ID NO:16
TCGCCTGTTTCCAAGCGCGCTACGCTGGACGAGTTCATCAGCACCGAGCGTCCCTTGGC
TCTGGAGCGCCTGCTCTGCAACATTGGTCCTACTGGTTGCCGTGCTTCGGGAGCTGCCT
CGGGAGTCGTTATCGCCTCGCCGTCCCGCAGCGATCCGGACTACTACTACACTTGGAC
CCGTGATGCTGCTCTGGTCTTTAAGGAGATTGTCGACTCTGTCGAGACTAACACCACTC
TGCTGCTGCCAGAGATTGAGAACTACGTTACTGCCCAGGCTTACCTGCAGACCGTGAC
GAACCCCTCGGGTTCGCTGTCGGATGGTGCTGGTCTGGGCGAGCCCAAGTTCAACGTC
GATATGACTCCCTTCACTGGTGCCTGGGGTCGTCCTCAGCGTGATGGTCCGGCTCTGCG
TGCTACGGCTATGATCGCCTACTACAACTACCTGCTCAACAACAACGCCACTACCGAC
TGTGGTCTGTGGCAGATTATCCAGAACGACCTGAATTACGTCGCTCAGTACTGGAACC
AAACTGGTTACGACCTGTGGGAGGAGGTTCCGGGTTCATCCTTTTTCACTGTTGCTGCT
CAGTACAGAGCTCTCGTTGAGGGTTCTACCCTTGCTGCCAAGCTCGGCAAGTCTCACTC
GGCCTACGACACTGTCGCTCCGCAGATTCTGTGCTACTTGCAGAGCTTCTGGTCATCCA
GCAAGGGCTACATTGTCGCCAACACCCAGACTGCCAGCTGGGTCTCGCGGTCCGGTCT
TGATGCCAACACTCCCTTGACTGCCATCCACCTATTTGACCCTGAACTTGGCTGCGATG
ACTCGACTTTCCAGCCCTGCTCGCCCAAGCAGCTTATCACTACTAAGAAGCTCGTTGAC
TCGTTCCGCTCCATCTATGCCATCAACTCGGGCAAGTCTGCTGGTGATGCTTTGGCTGT
TGGTCGTTACGCCGAGGACGTCTACTACAACGGCAACCCCTGGTACCTGTGCACTTTG
GCTGTTGCAGAGCAGCTTTACGATGCAGTTTACACTTGGAAGCTCGAGGGCTCCATCA
CCGTCACCTCTGTCTCGCTGCCCTTCTTCACTGACCTGCTGCCCTCGCTGACCACTGGC
ACCTACGCTTCGGGCTCGACCACCTTCGAATCCATCATCTCTGCTGTGACTACCTACGC
TGATGGCTTTGTCAGTATTGTCCAGACCTACACTCCCTCTGACGGCGCTCTGTCTGAGC
AGTACTCCAAGTACAACGGCCAGCAGCTGTCGGCTCCCGACCTGACCTGGTCGTACGC
CGCTTTCCTATCTGCCACTGAGCGCCGTGACAGCGTTGTCCCTGCCGGCTGGGCTGGTG
CCTCGTCTGTCTCTGTGCCCGGCGCCTGCGCTGCTACCACCGTTGTCGGAACCTACGCT
GCTGCCTCCAACTGCGGTACTCCTGGCTCTGGCTCGGGCGGCAACGGTGGCTCGAGCG
GTAACGCCCTGTAATAG

FIGURE 7I

>Variant1 (Y321F with Starch Binding Domain) mature protein amino acid sequence SEQ ID NO:17
SPVSKRATLDEFISTERPLALERLLCNIGPTGCRASGAASGVVIASPSRSDPDYYYTWTRDA
ALVFKEIVDSVETNTTLLLPEIENYVTAQAYLQTVTNPSGSLSDGAGLGEPKFNVDMTPFT
GAWGRPQRDGPALRATAMIAYYNYLLNNNATTDCGLWQIIQNDLNYVAQYWNQTGYDL
WEEVPGSSFFTVAAQYRALVEGSTLAAKLGKSHSAYDTVAPQILCYLQSFWSSSKGYIVA
NTQTASWVSRSGLDANTPLTAIHLFDPELGCDDSTFQPCSPKQLITTKKLVDSFRSIYAINSG
KSAGDALAVGRYAEDVFYNGNPWYLCTLAVAEQLYDAVYTWKLEGSITVTSVSLPFFTD
LLPSLTTGTYASGSTTFESIISAVTTYADGFVSIVQTYTPSDGALSEQYSKYNGQQLSAPDLT
WSYAAFLSATERRDSVVPAGWAGASSVSVPGACAATTVVGTYAAASNCGTPGSGSGGNG
GSSGNALVTFNELATTYYGENIKLVGSTAAFGSWSPSAGILLSASSYTASNPLWTTTVSVPQ
GSTVEFKFIRVGSDGSITWESGNNKVLTVGSSATSVTVSASWNGAYSVSSS >Variant1 (Y321F with Starch Binding Domain) mature protein-encoding nucleic acid sequence SEQ ID NO:18
TCGCCTGTTTCCAAGCGCGCTACGCTGGACGAGTTCATCAGCACCGAGCGTCCCTTGGC
TCTGGAGCGCCTGCTCTGCAACATTGGTCCTACTGGTTGCCGTGCTTCGGGAGCTGCCT
CGGGAGTCGTTATCGCCTCGCCGTCCCGCAGCGATCCGGACTACTACTACACTTGGAC
CCGTGATGCTGCTCTGGTCTTTAAGGAGATTGTCGACTCTGTCGAGACTAACACCACTC
TGCTGCTGCCAGAGATTGAGAACTACGTTACTGCCCAGGCTTACCTGCAGACCGTGAC
GAACCCCTCGGGTTCGCTGTCGGATGGTGCTGGTCTGGGCGAGCCCAAGTTCAACGTC
GATATGACTCCCTTCACTGGTGCCTGGGGTCGTCCTCAGCGTGATGGTCCGGCTCTGCG
TGCTACGGCTATGATCGCCTACTACAACTACCTGCTCAACAACAACGCCACTACCGAC
TGTGGTCTGTGGCAGATTATCCAGAACGACCTGAATTACGTCGCTCAGTACTGGAACC
AAACTGGTTACGACCTGTGGGAGGAGGTTCCGGGTTCATCCTTTTCACTGTTGCTGCT
CAGTACAGAGCTCTCGTTGAGGGTTCTACCCTTGCTGCCAAGCTCGGCAAGTCTCACTC
GGCCTACGACACTGTCGCTCCGCAGATTCTGTGCTACTTGCAGAGCTTCTGGTCATCCA
GCAAGGGCTACATTGTCGCCAACACCCAGACTGCCAGCTGGGTCTCGCGGTCCGGTCT
TGATGCCAACACTCCCTTGACTGCCATCCACCTATTTGACCCTGAACTTGGCTGCGATG
ACTCGACTTTCCAGCCCTGCTCGCCCAAGCAGCTTATCACTACTAAGAAGCTCGTTGAC
TCGTTCCGCTCCATCTATGCCATCAACTCGGGCAAGTCTGCTGGTGATGCTTTGGCTGT
TGGTCGTTACGCCGAGGACGTCTTCTACAACGGCAACCCCTGGTACCTGTGCACTTTGG
CTGTTGCAGAGCAGCTTTACGATGCAGTTTACACTTGGAAGCTCGAGGGCTCCATCAC
CGTCACCTCTGTCTCGCTGCCCTTCTTCACTGACCTGCTGCCCTCGCTGACCACTGGCA
CCTACGCTTCGGGCTCGACCACCTTCGAATCCATCATCTCTGCTGTGACTACCTACGCT
GATGGCTTTGTCAGTATTGTCCAGACCTACACTCCCTCTGACGGCGCTCTGTCTGAGCA
GTACTCCAAGTACAACGGCCAGCAGCTGTCGGCTCCCGACCTGACCTGGTCGTACGCC
GCTTTCCTATCTGCCACTGAGCGCCGTGACAGCGTTGTCCCTGCCGGCTGGGCTGGTGC
CTCGTCTGTCTCTGTGCCCGGCGCCTGCGCTGCTACCACCGTTGTCGGAACCTACGCTG
CTGCCTCCAACTGCGGTACTCCTGGCTCTGGCTCGGCGGCAACGGTGGCTCGAGCGG
TAACGCCCTGGTGACTTTCAACGAGCTGGCTACTACCTACTACGGCGAGAACATTAAG
CTTGTCGGCAGCACAGCTGCTTTCGGTTCGTGGTCGCCCTCAGCTGGTATTCTCCTGTC
TGCCTCGTCGTACACGGCCAGCAACCCTCTGTGGACTACCACCGTGTCGGTTCCCCAGG
GCTCGACCGTTGAGTTCAAGTTCATCCGTGTTGGCTCCGACGGCAGCATCACGTGGGA
GAGCGGCAACAACAAGGTGTTGACGGTTGGCTCTTCGGCCACGAGCGTCACTGTTTCT
GCCAGCTGGAACGGCGCCTACTCGGTGTCTAGCTCTTAATAG

FIGURE 7J

>Variant2 (S188H/Y321W/Q419P with Starch Binding Domain) mature protein amino acid sequence SEQ ID NO:19
SPVSKRATLDEFISTERPLALERLLCNIGPTGCRASGAASGVVIASPSRSDPDYYYTWTRDA
ALVFKEIVDSVETNTTLLLPEIENYVTAQAYLQTVTNPSGSLSDGAGLGEPKFNVDMTPFT
GAWGRPQRDGPALRATAMIAYYNYLLNNNATTDCGLWQIIQNDLNYVAQYWNQTGYDL
WEEVPGHSFFTVAAQYRALVEGSTLAAKLGKSHSAYDTVAPQILCYLQSFWSSSKGYIVA
NTQTASWVSRSGLDANTPLTAIHLFDPELGCDDSTFQPCSPKQLITTKKLVDSFRSIYAINSG
KSAGDALAVGRYAEDVWYNGNPWYLCTLAVAEQLYDAVYTWKLEGSITVTSVSLPFFTD
LLPSLTTGTYASGSTTFESIISAVTTYADGFVSIVQTYTPSDGALSEQYSKYNGQPLSAPDLT
WSYAAFLSATERRDSVVPAGWAGASSVSVPGACAATTVVGTYAAASNCGTPGSGSGGNG
GSSGNALVTFNELATTYYGENIKLVGSTAAFGSWSPSAGILLSASSYTASNPLWTTTVSVPQ
GSTVEFKFIRVGSDGSITWESGNNKVLTVGSSATSVTVSASWNGAYSVSSS >Variant2 (S188H/Y321W/Q419P with Starch Binding Domain) mature protein-encoding nucleic acid sequence SEQ ID NO:20
TCGCCTGTTTCCAAGCGCGCTACGCTGGACGAGTTCATCAGCACCGAGCGTCCCTTGGC
TCTGGAGCGCCTGCTCTGCAACATTGGTCCTACTGGTTGCCGTGCTTCGGGAGCTGCCT
CGGGAGTCGTTATCGCCTCGCCGTCCCGCAGCGATCCGGACTACTACTACACTTGGAC
CCGTGATGCTGCTCTGGTCTTTAAGGAGATTGTCGACTCTGTCGAGACTAACACCACTC
TGCTGCTGCCAGAGATTGAGAACTACGTTACTGCCCAGGCTTACCTGCAGACCGTGAC
GAACCCCTCGGGTTCGCTGTCGGATGGTGCTGGTCTGGGCGAGCCCAAGTTCAACGTC
GATATGACTCCCTTCACTGGTGCCTGGGGTCGTCCTCAGCGTGATGGTCCGGCTCTGCG
TGCTACGGCTATGATCGCCTACTACAACTACCTGCTCAACAACAACGCCACTACCGAC
TGTGGTCTGTGGCAGATTATCCAGAACGACCTGAATTACGTCGCTCAGTACTGGAACC
AAACTGGTTACGACCTGTGGGAGGAGGTTCCGGGTCACTCCTTTTCACTGTTGCTGCT
CAGTACAGAGCTCTCGTTGAGGGTTCTACCCTTGCTGCCAAGCTCGGCAAGTCTCACTC
GGCCTACGACACTGTCGCTCCGCAGATTCTGTGCTACTTGCAGAGCTTCTGGTCATCCA
GCAAGGGCTACATTGTCGCCAACACCCAGACTGCCAGCTGGGTCTCGCGGTCCGGTCT
TGATGCCAACACTCCCTTGACTGCCATCCACCTATTTGACCCTGAACTTGGCTGCGATG
ACTCGACTTTCCAGCCCTGCTCGCCCAAGCAGCTTATCACTACTAAGAAGCTCGTTGAC
TCGTTCCGCTCCATCTATGCCATCAACTCGGGCAAGTCTGCTGGTGATGCTTTGGCTGT
TGGTCGTTACGCCGAGGACGTCTGGTACAACGGCAACCCCTGGTACCTGTGCACTTTG
GCTGTTGCAGAGCAGCTTTACGATGCAGTTTACACTTGGAAGCTCGAGGGCTCCATCA
CCGTCACCTCTGTCTCGCTGCCCTTCTTCACTGACCTGCTGCCCTCGCTGACCACTGGC
ACCTACGCTTCGGGCTCGACCACCTTCGAATCCATCATCTCTGCTGTGACTACCTACGC
TGATGGCTTTGTCAGTATTGTCCAGACCTACACTCCCTCTGACGGCGCTCTGTCTGAGC
AGTACTCCAAGTACAACGGCCAGCCCCTGTCGGCTCCCGACCTGACCTGGTCGTACGC
CGCTTTCCTATCTGCCACTGAGCGCCGTGACAGCGTTGTCCCTGCCGGCTGGGCTGGTG
CCTCGTCTGTCTCTGTGCCCGGCGCCTGCGCTGCTACCACCGTTGTCGGAACCTACGCT
GCTGCCTCCAACTGCGGTACTCCTGGCTCTGGCTCGGGCGGCAACGGTGGCTCGAGCG
GTAACGCCCTGGTGACTTTCAACGAGCTGGCTACTACCTACTACGGCGAGAACATTAA
GCTTGTCGGCAGCACAGCTGCTTTCGGTTCGTGGTCGCCCTCAGCTGGTATTCTCCTGT
CTGCCTCGTCGTACACGGCCAGCAACCCTCTGTGGACTACCACCGTGTCGGTTCCCCAG
GGCTCGACCGTTGAGTTCAAGTTCATCCGTGTTGGCTCCGACGGCAGCATCACGTGGG
AGAGCGGCAACAACAAGGTGTTGACGGTTGGCTCTTCGGCCACGAGCGTCACTGTTTC
TGCCAGCTGGAACGGCGCCTACTCGGTGTCTAGCTCTTAATAG

FIGURE 7K

>Variant1 (Y321F without Starch Binding Domain) mature protein amino acid sequence SEQ ID NO:21
SPVSKRATLDEFISTERPLALERLLCNIGPTGCRASGAASGVVIASPSRSDPDYYYTWTRDA
ALVFKEIVDSVETNTTLLLPEIENYVTAQAYLQTVTNPSGSLSDGAGLGEPKFNVDMTPFT
GAWGRPQRDGPALRATAMIAYYNYLLNNNATTDCGLWQIIQNDLNYVAQYWNQTGYDL
WEEVPGSSFFTVAAQYRALVEGSTLAAKLGKSHSAYDTVAPQILCYLQSFWSSSKGYIVA
NTQTASWVSRSGLDANTPLTAIHLFDPELGCDDSTFQPCSPKQLITTKKLVDSFRSIYAINSG
KSAGDALAVGRYAEDVFYNGNPWYLCTLAVAEQLYDAVYTWKLEGSITVTSVSLPFFTD
LLPSLTTGTYASGSTTFESIISAVTTYADGFVSIVQTYTPSDGALSEQYSKYNGQQLSAPDLT
WSYAAFLSATERRDSVVPAGWAGASSVSVPGACAATTVVGTYAAASNCGTPGSGSGGNG
GSSGNAL >Variant1 (Y321F without Starch Binding Domain) mature protein-encoding nucleic acid sequence SEQ ID NO:22
TCGCCTGTTTCCAAGCGCGCTACGCTGGACGAGTTCATCAGCACCGAGCGTCCCTTGGC
TCTGGAGCGCCTGCTCTGCAACATTGGTCCTACTGGTTGCCGTGCTTCGGGAGCTGCCT
CGGGAGTCGTTATCGCCTCGCCGTCCCGCAGCGATCCGGACTACTACTACACTTGGAC
CCGTGATGCTGCTCTGGTCTTTAAGGAGATTGTCGACTCTGTCGAGACTAACACCACTC
TGCTGCTGCCAGAGATTGAGAACTACGTTACTGCCCAGGCTTACCTGCAGACCGTGAC
GAACCCCTCGGGTTCGCTGTCGGATGGTGCTGGTCTGGGCGAGCCCAAGTTCAACGTC
GATATGACTCCCTTCACTGGTGCCTGGGGTCGTCCTCAGCGTGATGGTCCGGCTCTGCG
TGCTACGGCTATGATCGCCTACTACAACTACCTGCTCAACAACAACGCCACTACCGAC
TGTGGTCTGTGGCAGATTATCCAGAACGACCTGAATTACGTCGCTCAGTACTGGAACC
AAACTGGTTACGACCTGTGGGAGGAGGTTCCGGGTTCATCCTTTTTCACTGTTGCTGCT
CAGTACAGAGCTCTCGTTGAGGGTTCTACCCTTGCTGCCAAGCTCGGCAAGTCTCACTC
GGCCTACGACACTGTCGCTCCGCAGATTCTGTGCTACTTGCAGAGCTTCTGGTCATCCA
GCAAGGGCTACATTGTCGCCAACACCCAGACTGCCAGCTGGGTCTCGCGGTCCGGTCT
TGATGCCAACACTCCCTTGACTGCCATCCACCTATTTGACCCTGAACTTGGCTGCGATG
ACTCGACTTTCCAGCCCTGCTCGCCCAAGCAGCTTATCACTACTAAGAAGCTCGTTGAC
TCGTTCCGCTCCATCTATGCCATCAACTCGGGCAAGTCTGCTGGTGATGCTTTGGCTGT
TGGTCGTTACGCCGAGGACGTCTTCTACAACGGCAACCCCTGGTACCTGTGCACTTTGG
CTGTTGCAGAGCAGCTTTACGATGCAGTTTACACTTGGAAGCTCGAGGGCTCCATCAC
CGTCACCTCTGTCTCGCTGCCCTTCTTCACTGACCTGCTGCCCTCGCTGACCACTGGCA
CCTACGCTTCGGGCTCGACCACCTTCGAATCCATCATCTCTGCTGTGACTACCTACGCT
GATGGCTTTGTCAGTATTGTCCAGACCTACACTCCCTCTGACGGCGCTCTGTCTGAGCA
GTACTCCAAGTACAACGGCCAGCAGCTGTCGGCTCCCGACCTGACCTGGTCGTACGCC
GCTTTCCTATCTGCCACTGAGCGCCGTGACAGCGTTGTCCCTGCCGGCTGGGCTGGTGC
CTCGTCTGTCTCTGTGCCCGGCGCCTGCGCTGCTACCACCGTTGTCGGAACCTACGCTG
CTGCCTCCAACTGCGGTACTCCTGGCTCTGGCTCGGGCGGCAACGGTGGCTCGAGCGG
TAACGCCCTGTAATAG

FIGURE 7L

>Variant2 (S188H/Y321W/Q419P without Starch Binding Domain) mature protein amino acid sequence SEQ ID NO:23
SPVSKRATLDEFISTERPLALERLLCNIGPTGCRASGAASGVVIASPSRSDPDYYYTWTRDA
ALVFKEIVDSVETNTTLLLPEIENYVTAQAYLQTVTNPSGSLSDGAGLGEPKFNVDMTPFT
GAWGRPQRDGPALRATAMIAYYNYLLNNNATTDCGLWQIIQNDLNYVAQYWNQTGYDL
WEEVPGHSFFTVAAQYRALVEGSTLAAKLGKSHSAYDTVAPQILCYLQSFWSSSKGYIVA
NTQTASWVSRSGLDANTPLTAIHLFDPELGCDDSTFQPCSPKQLITTKKLVDSFRSIYAINSG
KSAGDALAVGRYAEDVWYNGNPWYLCTLAVAEQLYDAVYTWKLEGSITVTSVSLPFFTD
LLPSLTTGTYASGSTTFESIISAVTTYADGFVSIVQTYTPSDGALSEQYSKYNGQPLSAPDLT
WSYAAFLSATERRDSVVPAGWAGASSVSVPGACAATTVVGTYAAASNCGTPGSGSGGNG
GSSGNAL >Variant2 (S188H/Y321W/Q419P without Starch Binding Domain) mature protein-encoding nucleic acid sequence SEQ ID NO:24
TCGCCTGTTTCCAAGCGCGCTACGCTGGACGAGTTCATCAGCACCGAGCGTCCCTTGGC
TCTGGAGCGCCTGCTCTGCAACATTGGTCCTACTGGTTGCCGTGCTTCGGGAGCTGCCT
CGGGAGTCGTTATCGCCTCGCCGTCCCGCAGCGATCCGGACTACTACTACACTTGGAC
CCGTGATGCTGCTCTGGTCTTTAAGGAGATTGTCGACTCTGTCGAGACTAACACCACTC
TGCTGCTGCCAGAGATTGAGAACTACGTTACTGCCCAGGCTTACCTGCAGACCGTGAC
GAACCCCTCGGGTTCGCTGTCGGATGGTGCTGGTCTGGGCGAGCCCAAGTTCAACGTC
GATATGACTCCCTTCACTGGTGCCTGGGGTCGTCCTCAGCGTGATGGTCCGGCTCTGCG
TGCTACGGCTATGATCGCCTACTACAACTACCTGCTCAACAACAACGCCACTACCGAC
TGTGGTCTGTGGCAGATTATCCAGAACGACCTGAATTACGTCGCTCAGTACTGGAACC
AAACTGGTTACGACCTGTGGGAGGAGGTTCCGGGTCACTCCTTTTTCACTGTTGCTGCT
CAGTACAGAGCTCTCGTTGAGGGTTCTACCCTTGCTGCCAAGCTCGGCAAGTCTCACTC
GGCCTACGACACTGTCGCTCCGCAGATTCTGTGCTACTTGCAGAGCTTCTGGTCATCCA
GCAAGGGCTACATTGTCGCCAACACCCAGACTGCCAGCTGGGTCTCGCGGTCCGGTCT
TGATGCCAACACTCCCTTGACTGCCATCCACCTATTTGACCCTGAACTTGGCTGCGATG
ACTCGACTTTCCAGCCCTGCTCGCCCAAGCAGCTTATCACTACTAAGAAGCTCGTTGAC
TCGTTCCGCTCCATCTATGCCATCAACTCGGGCAAGTCTGCTGGTGATGCTTTGGCTGT
TGGTCGTTACGCCGAGGACGTCTGGTACAACGGCAACCCCTGGTACCTGTGCACTTTG
GCTGTTGCAGAGCAGCTTTACGATGCAGTTTACACTTGGAAGCTCGAGGGCTCCATCA
CCGTCACCTCTGTCTCGCTGCCCTTCTTCACTGACCTGCTGCCCTCGCTGACCACTGGC
ACCTACGCTTCGGGCTCGACCACCTTCGAATCCATCATCTCTGCTGTGACTACCTACGC
TGATGGCTTTGTCAGTATTGTCCAGACCTACACTCCCTCTGACGGCGCTCTGTCTGAGC
AGTACTCCAAGTACAACGGCCAGCCCCTGTCGGCTCCCGACCTGACCTGGTCGTACGC
CGCTTTCCTATCTGCCACTGAGCGCCGTGACAGCGTTGTCCCTGCCGGCTGGGCTGGTG
CCTCGTCTGTCTCTGTGCCCGGCGCCTGCGCTGCTACCACCGTTGTCGGAACCTACGCT
GCTGCCTCCAACTGCGGTACTCCTGGCTCTGGCTCGGGCGGCAACGGTGGCTCGAGCG
GTAACGCCCTGTAATAG

FIGURE 7M

>Amino acid sequence of wild type glucoamylase mature protein with Starch Binding Domain SEQ ID NO:25
SPVSKRATLDEFISTERPLALEKLLCNIGSTGCRASGASSGVVLASPSTSNPDYYYTWTRDA
ALVFKEIVDSVETNTTLLLPEIENYVTAQAYLQTVTNPSGSLSDGAGLAEPKFNADLTQFTG
AWGRPQRDGPALRATAMIAYYNYLLNNNATTDCGLWQIIQNDLNYVAQYWNQTGYDL
WEEVPGSSFFTVAAQYRALVEGSTLAAKLGKSHSAYDTVAPQILCYLQSFWSSSKGYIVA
NTQTASWVSRSGLDANTPLTAIHLFDPELGCDDSTFQPCSPKQLITTKKLVDSFRSIYAINSG
KSAGTALAVGRYAEDVYYNGNPWYLCTLAVAEQLYDAVYTWKLEGSITVTSVSLPFFTD
LLPSLTTGTYASGSTTFESIISAVTTYADGFVSIVQTYTPSDGALSEQYNKANGQQLSAQDL
TWSYAAFLSATERRDSVVPAGWAGASSVSVPGACAATTVVGTYAAASNCGTPGSGSGGN
GGSSGNALVTFNELATTYYGENIKLVGSTAAFGSWSPSAGILLSASSYTASNPLWTTTVSVP
QGSTVEFKFIRVGSDGSITWESGNNKVLTVGSSATSVTVSASWNGAYSVSSS >Amino acid sequence of wild type signal peptide SEQ ID NO:26
*MVFLKSAIAASTWLLAATGVVA*

VARIANT G6P G7P GLUCOAMYLASE COMPOSITIONS AND METHODS

CROSS REFERENCE TO RELATED APPLICATIONS

This application claims priority to U.S. Provisional Patent Application No. 62/784,193, filed on Dec. 21, 2018, which is expressly incorporated by reference in its entirety.

SEQUENCE LISTING

The instant application contains a Sequence Listing which has been submitted electronically in ASCII format and is hereby incorporated by reference in its entirety. Said ASCII copy, created on Oct. 30, 2019, is named 114095-5008_ST25.txt and is 92 kilobytes in size.

FIELD OF THE INVENTION

This invention relates to variant glucoamylases, polynucleotides encoding the variant glucoamylases, methods of producing the variant glucoamylases, and methods of using the variant glucoamylases. Also described are the use of glucoamylases of the invention for varying from starch conversion to produce fermentation products, such as ethanol, and syrups, such as glucose, as well as animal feedstocks. The invention also relates to compositions comprising one or more variant glucoamylases of the invention.

BACKGROUND OF THE INVENTION

Glucoamylase (1,4-alpha-D-glucan glucohydrolase, EC 3.2.1.3) is an enzyme, which catalyzes the release of D-glucose from the non-reducing ends of starch or related oligosaccharide and polysaccharide molecules. Glucoamylases are produced by several filamentous fungi and yeast, with those from *Aspergillus* being generally most important for commercial purposes.

Commercially, glucoamylases are used to convert starch containing material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese) industries.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world.

The end product may also be a commercial feedstock, fed to agricultural animals. Furthermore, glucoamylase has significant applications in food, textile and pharmaceutical industries. In the food industry for an example, glucoamylase is used to improve bread crust color and produce low-calorie beer. Another key application of glucoamylase is as a digestive aid when used together with a cocktail of other enzymes.

However, there remains a need in the art for variant glucoamylases with increased activity, thermoactivity, thermostability and pH stability. The present invention meets this need and provides variant glucoamylases with improved properties compared to a parent glucoamylase.

It is an object of the present invention to provide variant glucoamylase enzymes having glucoamylase activity and polynucleotides encoding the variant glucoamylase enzymes and methods of using the variant glucoamylase enzymes in various processes.

BRIEF SUMMARY OF THE INVENTION

Accordingly, the present invention provides isolated wild-type glucoamylases as well as variant glucoamylases and methods of using them. The amino acid sequence numbers and nucleic acid sequence numbers of the present invention are listed in Table 1.

TABLE 1

Amino acid sequence numbers and nucleic acid sequence numbers. Variant 1 comprises an amino acid substitution Y321F. Variant 2 comprises amino acid substitutions S188H/Y321W/Q419P.

| | |
|---|---|
| G6P preprotein | SEQ ID NO: 1 |
| G7P preprotein | SEQ ID NO: 3 |
| Variant 1 preprotein w.r.t. G6P preprotein | SEQ ID NO: 5 |
| Variant 2 preprotein w.r.t. G6P preprotein | SEQ ID NO: 7 |
| Variant 1 preprotein w.r.t. G7P preprotein | SEQ ID NO: 9 |
| Variant 2 preprotein w.r.t. G7P preprotein | SEQ ID NO: 11 |
| G6P mature protein | SEQ ID NO: 13 |
| G7P mature protein | SEQ ID NO: 15 |
| Variant 1 mature protein w.r.t. G6P mature protein | SEQ ID NO: 17 |
| Variant 2 mature protein w.r.t. G6P mature protein | SEQ ID NO: 19 |
| Variant 1 mature protein w.r.t. G7P mature protein | SEQ ID NO: 21 |
| Variant 2 mature protein w.r.t. G7P mature protein | SEQ ID NO: 23 |
| Wild type mature protein (including the Starch Binding Domain) | SEQ ID NO: 25 |
| Wild type signal peptide | SEQ ID NO: 26 |
| N.A. encoding G6P preprotein | SEQ ID NO: 2 |
| N.A. encoding G7P preprotein | SEQ ID NO: 4 |
| N.A. encoding Variant 1 preprotein w.r.t. G6P preprotein | SEQ ID NO: 6 |
| N.A. encoding Variant 2 preprotein w.r.t. G6P preprotein | SEQ ID NO: 8 |
| N.A. encoding Variant 1 preprotein w.r.t. G7P preprotein | SEQ ID NO: 10 |
| N.A. encoding Variant 2 preprotein w.r.t. G7P preprotein | SEQ ID NO: 12 |
| N.A. encoding G6P mature protein | SEQ ID NO: 14 |
| N.A. encoding G7P mature protein | SEQ ID NO: 16 |
| N.A. encoding Variant 1 mature protein w.r.t. G6P mature protein | SEQ ID NO: 18 |
| N.A. encoding Variant 2 mature protein w.r.t. G6P mature protein | SEQ ID NO: 20 |
| N.A. encoding Variant 1 mature protein w.r.t. G7P mature protein | SEQ ID NO: 22 |
| N.A. encoding Variant 2 mature protein w.r.t. G7P mature protein | SEQ ID NO: 24 | w.r.t. represents "with respect to".

In some aspects, the invention provides a composition comprising a variant glucoamylase enzyme, wherein the variant glucoamylase exhibits at least 95% identity to SEQ ID NO:15, wherein said variant glucoamylase enzyme has at least 1.1 fold better activity as compared to SEQ ID NO:25 under a condition selected from the group consisting of thermoactivity at about 30° C., thermoactivity at about 35°

C., thermoactivity at about 40° C., thermoactivity at about 50° C., thermoactivity at about 60° C. and thermoactivity at about 70° C.

In some aspects, the invention provides a composition comprising a variant glucoamylase enzyme having SEQ ID NO:15.

In an additional aspect, the invention provides a composition comprising a variant glucoamylase enzyme comprising at least one amino acid substitution as compared to SEQ ID NO:15, wherein said amino acid substitution is at a position number selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, wherein said variant enzyme is at least 95% identical to SEQ ID NO:15.

In a further aspect, the invention provides a composition comprising a variant glucoamylase enzyme comprising at least one amino acid substitution as compared to SEQ ID NO:15, wherein said amino acid substitution is at a position number selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, wherein said variant glucoamylase enzyme has at least 1.1 fold better activity as compared to SEQ ID NO:15 under a condition selected from the group consisting of thermoactivity at about 30° C., thermoactivity at about 35° C., thermoactivity at about 40° C., thermoactivity at about 50° C., thermoactivity at about 60° C. and thermoactivity at about 70° C.; and wherein said variant enzyme is at least 95% identical to SEQ ID NO:15.

In an additional aspect, the invention provides a composition comprising the variant glucoamylase enzyme as described herein exhibiting at least 96%, 97%, 98%, or 99% identity to SEQ ID NO:15.

In a further aspect, the invention provides a composition comprising a variant glucoamylase enzyme as described herein, wherein said amino acid substitution(s) occur at one of said positions, two of said positions, three of said positions, four of said positions, five of said positions, six of said positions, seven of said positions, eight of said positions, nine of said positions, ten of said positions, eleven of said positions, twelve of said positions, thirteen of said positions or fourteen of said positions.

In some aspects, the invention provides a composition comprising a variant glucoamylase enzyme as described herein, wherein said amino acid substitution(s) is at a position number selected from the group consisting of 5, 68, 188, 321, 419, 422, 7, 11, 19, 26, 31, 42, 44, 49, 53, 55, 57, 69, 72, 73, 78, 79, 85, 86, 88, 89, 92, 93, 94, 97, 98, 103, 106, 118, 119, 125, 141, 145, 149, 150, 153, 155, 161, 168, 170, 171, 178, 179, 186, 195, 204, 205, 208, 209, 213, 214, 219, 220, 224, 227, 246, 247, 256, 261, 262, 306, 307, 309, 311, 317, 342, 347, 348, 352, 353, 355, 362, 364, 370, 374, 381, 382, 388, 391, 394, 395, 399, 400, 407, 412, 418, 434, 436, 437, 440, 446, 452, 453, 460, 469, 470, 472, 475, 476, 478 and 492.

In an additional aspect, the invention provides a composition comprising a variant glucoamylase enzyme as described herein, wherein said amino acid substitution(s) is selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, T400L, Y412F, L420K, A422G, P423G, P423R, P423V, G457S, A491V, K5P, K5S, K5T, K5Y, K5Q, K5N, K5H, E68K, E68Y, E68S, S188T, S188H, Y321F, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In a further aspect, the invention provides a composition comprising a variant glucoamylase enzyme as described herein, wherein said amino acid substitution(s) is selected from the group consisting of K5P, K5S, K5T, K5Y, K5Q, K5N, K5H, E68K, E68Y, E68S, S188T, S188H, Y321F, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, T98S, S103D, D106T, D118N, M119E, A125P, M141L, Y145A, L149I, N150D, A153S, T155A, Q161P, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, A262S, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Y412F, Q418T, S434T, T436S, E437A, D440Q, G446S, S452A, V453S, A460S, A469S, A470T, S472T, G475V, T476W, G478S, L492P.

In an additional aspect, the invention provides a composition comprising a variant glucoamylase enzyme as described herein, wherein said amino acid substitution(s) is selected from the group consisting of S188H/Y321W/Q419P, K5T/S188T, K5T/E68K/S188H, K5Y/S188H, K5Q/E68K/S188T, K5N/E68Y/S188T, K5H/S188H, K5S/E68Y/S188H, K5S/E68Y/S188T, K5Y/E68Y, K5S/E68S/S188T, K5H/E68S/S188H, K5H/E68K/S188T, K5P/S188H, K5Y/E68K, K5T/S188H, K5S/S188H, E68Y/S188H, E68Y/S188T, K5T/Y321F, K5Q/S188H/Q419P, K5P/E68Y/S188T/A422S, K5N/S188H/Q419P, Y321W/A422S, E68K/Q419P, E68S/S188T/Y321W/A422S, K5Q/Q419P/A422S, S188T/Y321F, S188T/Q419P/A422S, K5H/S188T/Q419P/A422S, K5H/A422S, S188H/Y321W, Q419P/A422S, K5N/A422S, E68Y/S188H/Y321F/Q419P, K5Q/S188H, E11S/Y55F/M141L/N168S/T388Q, E11S/T31N/Y55F/M141L/N168S/T388Q, L19I/A195V, M141L/N168S/Y227F/

T362Q/T388Q/D440Q, E11S/M141L, E11S/L19I/I44V/ Y145A/T155A/D309S/L311V/Y412F/S472T, D309S/ L311V, E11S/L19I/T31N/Y55F/A125P/N168S/Y227F, L19I/D309S/L311V/Y412F/A460S/S472T, E11S/L19I/ N168S/Y227F/D309S/L311V/D440Q, L19I/Y412F, E11S/ L19I/Y145A/A460S/S472T, E11S/M141L/N168S/D309S/ L311V/T362Q/L364I/Y412F/A460S/S472T, E11S/Y55F/ M141L/N168S/L311V/T362Q/L364I/A460S/S472T, E11S/ L19I/Y55F/M141L/N168S/Y227F, L19I/T155A/A407S/ Y412F/S472T, D53N/L149I/N150D/P186E/A317P, V42I/ S103D/D106T/P186E/A317P/S434T/G478S, A317P/ G478S, C26N/V42I/L149I/A317P/S355D/A374N, V42I/ S103D/D106T/A317P, D53N/S434T, /S103D/A317P/ V342I, A256V/A317P, V42I/P186E, A317P/V342I/G478S, I224V/A256V/A317P/G478S, V42I/L149I/N150D/A317P/ G478S, V42I/S103D/P186E/A317P/V342I/S355D/A374N/ A391G, P186E/A317P/G478S, D53N/G446S, A256V/ A317P/G478S, V42I/D53N/T57S/L149I/A317P/G478S, C26N/V42I/D53N/T57S/N150D/P186E/A317P/V342I/ G478S, V42I/S355D, V42I/N150D/P186E/A317P, V42I/ S434T/G478S, C26N/D53N/T57S/S103D/Q161P/A317P/ G478S, V42I/A256V/A317P/S434T, V42I/S103D/A317P/ A391G/G478S, E68Y/I69L/G178T/Y179F/S213T/H214C, E68Y/I69L/E85Q/N86Q/F394Y/V395L, E68Y/I69L, D118N/M119E, E68Y/I69L/V97I/T98S/A246S/S247G/ T261G/A262S/L347N/E348I, E68Y/I69L/S452A/V453S, E68Y/I69L/S452A/V453S, E68Y/I69L/E85Q/N86Q/ L347N/E348I/Q418T/Q419P, E68Y/I69L/E85Q/N86Q/ S204N/T205A, A208T/K209R/E381N/S382D/Q418T/ Q419P/A469S/A470T, E381N/S382D/Q418T/Q419P/ T436S/E437A/A469S/A470T, Q418T/Q419P/A469S/ A470T, V170I/A171T/E381N/S382D/Q418T/Q419P/ A469S/A470T, F394Y/V395L/Q418T/Q419P/T436S/ E437A/A469S/A470T, T78K/L79D/Q418T/Q419P/A469S/ A470T, E68Y/I69L/V88I/T89S/T352S/V353I/Q399E/ T400K/A469S/A470T, S72A/V73F/A153S/S306A/T476W, T370V/G475V, R49H/S72A/V73F/A92T/Y93K/A153S/ S306A/T476W, E68Y/I69L/T219S/V220Q/A307E/S355D/ L492P, E11S/V42I/L149I/I224V/A317P/T388Q/A460S/ G478S, Y412F/Q418T/Q419P/A469S/A470T/, L19I/D53N/ I69L/V88I/S188H/A195V/Y321W/Y412F, V42I/D118N/ M119E/T261A/L311V/Y321W/S355D, E11S/T57S/T89S, E11S/V42I/L79Y/D118N/M141L/L311V/A317P/Y321F, V42I/D53N/E68Y/A317P/L347N, 169L/S188H/A195V/ A317P/Y321F/L364I/S434T, T57S/A195V/T261A/L311V/ Y321F/L347N/E348I/S434T, E11S/V42I/T57S/E68Y/ S188H/A195V/T261A, T57S/N168S/T261A/A317P/ Y321W/V395L/Y412F, E11S/D53N/E68Y/D118N/S188H/ A195V/Y412F/Q419P, E11S/V42I/D118N/M141L/N168S/ Y321W/Y412F, E11S/D53N/T57S/E68Y/T89S/E381N/ Y412F/Q419P/S434T, E11S/D53N/T57S/V88I/T89S/ S188H/A195V/L311V/L347N/Y412F, A317P/Y412F, I69L/ T89S/L311V/A317P/Y321F/Y412F/S434T, V42I/D53N/ T57S/E68Y7V88I/Y412F, E11S/T57S/V88I/M141L/ T261A/Y321W/L364I/Y412F, V42I/I69L/S188H/A317P/ Y321W/Y412F, E11S/V42I/D53N/T57S/L79Y/T89S/ L311V/Y321W/Y412F, L19I/M141L/N168S/S188H/ A195V/L311V/S355D/S434T, S188H/A195V/T261A/ L311V/Y321F/L347N/E348I, E11S/L19I/D53N/T57S/ N168S/L347N, E11S/I69L/M119E/A195V/T261A/A317P/ Y321W/L347N/Y412F, L79Y/V88I/T261A/A317P/Y321F/ L364I/Y412F, E11S/V42I/E68Y/T89S/L311V/Y321F/ T388Q/F394 Y/V395L/Q419P, D53N/E68Y/V88I/M141L/ N168S/Y321W/Y412F, E11S/I69L/L311V/A317P/Y321F/ L347N/Y412F, D53N/T57S/M141L, D53N/V88I/T89S/ D118N/E348I/S355D, E11S/S188H/A195V/A317P/L347N/ E348I/Y412F/Q419P/S434T, E11S/D53N/I69L/V88I/ A317P/Q419P, E68Y/I69L/V88I/N168S/L364I/Q419P, E11S/V42I/V88I/T261A/Y321F/E348I/S355D, E11S/V42I/ T57S/I69L/A195V/L347N/E348I/S355D, L19I/T89S/ A317P/Y321F/S434T, E11S/V42I/L79Y/L311V/A317P/ Y321W/L347N/E348I/L364I/Y412F, D53N/T57S/L347N/ E348I/Y412F, D53N/T57S/E68Y/L79Y/Y412F/S434T, L19I/V88I/T89S/A317P, M119E/M141L/N168S/L311V/ Y321F, E11S/T89S/Y321W, E11S/M141L/T261A/A317P/ Y412F/S434T, V42I/L79Y/S188H/A195V/L311V/Y321F/ S355D, V42I/E68Y/V88I/T261A/Y321W/L347N/E348I, L19I/E68Y/I69L/M141L/Y321F/L347N/S355D/E381N/ Y412F, V42I/D53N/I69L/L79Y/D118N/T261A/L311V/ A317P/Y321F/L347N/Y412F, E68Y/S355D/L364I/S382D/ T388Q/Q419P, E11S/L19I/V42I/E68Y/I69L/D118N/ M141L/Y321W/L347N, /E11S/V42I/E68Y/M141L/A317P/ Y321F/E348I/S355D, E11S/V42I/E68Y/I69L/V88I/T89S/ D118N/M119E/S188H/A195V/A317P/L347N/Y412F/ Q419P, V42I/V88I/L311V/A317P/Y321F/L347N/E348I/ T388Q/V395L/S434T, T261A/A317P/Y321W/E348I, E11S/V42I/E68Y/I69L/D118N/M119E/Y412F, E11S/V42I/ T57S/I69L/L311V, V42I/Y412F, E11S/L19I/E68Y/M119E/ N168S/Y412F/Q419P, L19I/L311V/Y412F, E11S/V42I/ M119E/Y412F, E11S/L19I/V42I/D53N/S188H/A195V/ L311V/Y321F/Y412F, E11S/L19I/V42I/T57S/D118N/ N168S/L311V/Y412F, L19I/V42I/D53N/T57S/N168S/ A317P/Y321W/Y412F, D53N/T57S/E68Y/N168S/S188H/ A195V/L311V/Y321W/Y412F/Q419P, L19I/D53N/T57S/ L311V/Y321W/Y412F, E11S/T57S/Y321W/Y412F/Q419P, D53N/S188H/A195V/L311V/Y412F, V42I/D53N/S188H/ A195V/L311V/Y321F/Y412F, L19I/M119E/N168S/ S188H/A195V/L311V/Y412F/Q419P, E11S/V42I/S188H/ A195V/L311V/A317P/Y321W/Y412F/Q419P, E11S/V42I/ M119E/N168S/L311V/Y412F, E11S/V42I/N168S/L311V/ A317P/Y321W/Y412F/Q419P, E11S/V42I/D53N/E68Y/ S188H/A195V/L311V/A317P/Y321F/Y412F, E11S/L19I/ D53N/N168S/A195V/Y412F/Q419P, E11S/L19I/V42I/ L311V/Y412F, V42I/D53N/N168S/L311V/Y412F, E11S/ L311V/Y412F, E11S/D53N/T57S/L311V/Y321W/Y412F, E11S/L311V/Y321W/Y412F, E11S/V42I/I69L/D118N/ N168S/L311V/A317P/Y412F/Q419P, E11S/L19I/V42I/ E68Y/Y412F/Q419P, E11S/L19I/D53N/L311V, E11S/L19I/ V42I/L311V/Y412F/Q419P, L19I/V42I/D53N/T57S/I69L/ N168S/S188H/A195V/L311V/A317P/Y321W, E11S/L19I/ V42I/T57S/L311V/A317P/Y321F/Y412F, L19I/V42I/I69L/ D118N/N168S/L311V/Y321W/Y412F/Q419P, E11S/V42I/ D53N/E68Y/S188H/A195V/Y412F, E11S/L19I/V42I/ D53N/T57S/N168S/L311V/Y321W/Y412F, E11S/V42I/ L311V/Y412F, E11S/L19I/V42I/N168S/A195V/L311V/ Y321F/Y412F, E11S/V42I/S188H/L311V/Y412F, L19I/ V42I/T57S/E68Y/M119E/S188H/A195V/L311V/Y321F/ Y412F, E11S/L19I/V42I/D53N/N168S/S188H/A195V, E11S/L19I/V42I/T57S/E68Y/A195V/L311V/Y321W, and E11S/L19I/V42I.

In a further aspect, the invention provides a composition comprising a variant glucoamylase enzyme as described herein, wherein said amino acid substitution is Y321F.

In an additional aspect, the invention provides a composition comprising a variant glucoamylase enzyme as described herein, wherein said amino acid substitutions are S188H/Y321W/Q419P.

In a further aspect, the invention provides a composition comprising a variant glucoamylase enzyme as described herein, wherein said composition comprises an amino acid substitution Y321F, and further comprises at least one amino acid substitution selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, T400L, Y412F, L420K, A422G, P423G, P423R, P423V, G457S, A491V, K5P, K5S, K5T, K5Y, K5Q, K5N, K5H, E68K, E68Y, E68S, S188T, S188H, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In an additional aspect, the invention provides a composition comprising a variant glucoamylase enzyme as described herein, wherein said composition comprises amino acid substitutions S188H/Y321W/Q419P, and further comprises at least one amino acid substitution selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, Y321F, T400L, Y412F, L420K, A422G, P423G, P423R, P423V, G457S, A491V, K5P, K5S, K5T, K5Y, K5Q, K5N, K5H, E68K, E68Y, E68S, S188T, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In an additional aspect, the invention provides a nucleic acid encoding said variant glucoamylase enzyme as described herein.

In some aspects, the invention provides a nucleic acid as described herein, wherein said nucleic acid is codon optimized for a host organism for expression of the variant glucoamylase enzyme in said organism.

In additional aspects, the invention provides a nucleic acid comprising a sequence selected from the group consisting of SEQ ID NO:16, SEQ ID NO:22 or SEQ ID NO:24.

In further aspects, the invention provides an expression vector comprising the nucleic acid as described herein.

In a further aspect, the invention provides a host cell comprising the nucleic acid as described herein.

In a further aspect, the invention provides a host cell comprising the expression vector as described herein.

In an additional aspect, the invention provides the host cell as described herein, wherein said host cell is selected from the group consisting of a bacterial cell, a fungal cell, or a yeast cell.

In some aspects, the invention provides a method of making a variant glucoamylase enzyme comprising: a) culturing the host cell as described herein under conditions wherein said variant glucoamylase enzyme is expressed; and b) recovering said variant glucoamylase enzyme.

In additional aspects, the invention provides a nucleic acid encoding a preprotein comprising a signal peptide and a mature protein, wherein said signal peptide is SEQ ID NO:26 or a variant signal peptide as compared to SEQ ID NO:26, and said variant signal peptide has at least one amino acid substitution at a position number selected from the group consisting of −20, −18, −17, −15, −13, −12, −10, −9, and −1; and wherein said mature protein has SEQ ID NO:15, or is a variant glucoamylase enzyme as compared to SEQ ID NO:15, wherein said variant glucoamylase has at least one amino acid substitution at a position number selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492; and wherein said preprotein is at least 95% identical to SEQ ID NO:3.

In further aspects, the invention provides the nucleic acid encoding the preprotein as described herein, wherein said preprotein exhibits at least 96%, 97%, 98%, or 99% identity to SEQ ID NO:3.

In a further aspect, the invention provides the nucleic acid encoding the preprotein as described herein, wherein said variant signal peptide has amino acid substitution(s) at one of said positions, two of said positions, three of said positions, four of said positions, or five of said positions.

In a further aspect, the invention provides the nucleic acid encoding the preprotein as described herein, wherein said variant glucoamylase enzyme has amino acid substitution(s) at one of said positions, two of said positions, three of said positions, four of said positions, five of said positions, six of said positions, seven of said positions, eight of said positions, nine of said positions, ten of said positions, eleven of said positions, twelve of said positions, thirteen of said positions or fourteen of said positions.

In an additional aspect, the invention provides the nucleic acid encoding the preprotein as described herein, wherein said variant signal peptide has at least one amino acid substitution at a position number −20 or −15.

In an additional aspect, the invention provides the nucleic acid encoding the preprotein as described herein, wherein said variant signal peptide has amino acid substitution(s) selected from the group consisting of V-20A, V-20F, V-20G, V-20I, V-20K, V-20L, V-20M, V-20Q, V-20R, V-20T, V-20W, L-18F, L-18I, L-18Y, K-17F, K-17N, K-17Y, A-15F, A-15I, A-15L, A-15V, A-13T, A-12V, T-10F, T-10V, W-9Y, and V-1F.

In a further aspect, the invention provides the nucleic acid encoding the preprotein as described herein, wherein said variant glucoamylase enzyme has amino acid substitution(s) selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, T400L, Y412F, L420K, A422G, P423G, P423R, P423V, G457S, A491V, K5P, K5S, K5T, K5Y, K5Q, K5N, K5H, E68K, E68Y, E68S, S188T, S188H, Y321F, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In some aspects, the invention provides the nucleic acid encoding the preprotein as described herein, wherein said variant glucoamylase enzyme has amino acid substitution(s) at a position number selected from the group consisting of 5, 68, 188, 321, 419, 420, 422, 7, 11, 19, 26, 31, 42, 44, 49, 53, 55, 57, 69, 72, 73, 78, 79, 85, 86, 88, 89, 92, 93, 94, 97, 98, 103, 106, 118, 119, 125, 141, 145, 149, 150, 153, 155, 161, 168, 170, 171, 178, 179, 186, 195, 204, 205, 208, 209, 213, 214, 219, 220, 224, 227, 246, 247, 256, 261, 262, 306, 307, 309, 311, 317, 342, 347, 348, 352, 353, 355, 362, 364, 370, 374, 381, 382, 388, 391, 394, 395, 399, 400, 407, 412, 418, 434, 436, 437, 440, 446, 452, 453, 460, 469, 470, 472, 475, 476, 478, and 492.

In further aspects, the invention provides the nucleic acid encoding the preprotein as described herein, wherein said variant glucoamylase enzyme has amino acid substitution(s) selected from the group consisting of K5P, K5S, K5T, K5Y, K5Q, K5N, K5H, E68K, E68Y, E68S, S188T, S188H, Y321F, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, T98S, S103D, D106T, D118N, M119E, A125P, M141L, Y145A, L149I, N150D, A153S, T155A, Q161P, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, A262S, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Y412F, Q418T, S434T, T436S, E437A, D440Q, G446S, S452A, V453S, A460S, A469S, A470T, S472T, G475V, T476W, G478S, and L492P.

In a further aspect, the invention provides the nucleic acid encoding the preprotein as described herein, wherein said preprotein has amino acid substitution(s) selected from the group consisting of S188H/Y321W/Q419P, K5T/S188T, K5T/E68K/S188H, K5Y/S188H, K5Q/E68K/S188T, K5N/E68Y/S188T, K5H/S188H, K5S/E68Y/S188H, K5S/E68Y/S188T, K5Y/E68Y, K5S/E68S/S188T, K5H/E68S/S188H, K5H/E68K/S188T, K5P/S188H, K5Y/E68K, K5T/S188H, K5S/S188H, E68Y/S188H, E68Y/S188T, A-15F/K5T/Y321F, V-20F/A-15I, V-20F/K5Q/S188H/Q419P, A-15I/Y321F, V-20F/A422S, A-15F/K5P/E68Y/S188T/A422S, V-20F/A-15I/A422S, V-20T/A-15I/Q419P, V-20F/K5N/S188H/Q419P, V-20F/Y321W/A422S, V-20F/E68K/Q419P, A-15F/S188H/Y321W/Q419P, V-20F/Y321F, A-15F/Y321F, V-20F/E68S/S188T/Y321W/A422S, V-20F/A-15F/K5Q/Q419P/A422S, V-20I/A-15I/Y321F, S188T/Y321F, S188T/Q419P/A422S, V-20T/A-15I/K5Q, A-15I/Y321W, V-20F/A-15F/K5Q, V-20F/K5H/S188T/Q419P/A422S, V-20F/A-15I/K5H/A422S, A-15F/S188H/Y321W, A-15F/ Q419P/A422S, V-20F/K5N/A422S, V-20F/A-15I/S188H, E68Y/S188H/Y321F/Q419P, V-20F/A-15F/K5N/A422S, V-20F/A-15I/Y321F, V-20F/K5Q/S188H, E11S/Y55F/M141L/N168S/T388Q, E11S/T31N/Y55F/M141L/N168S/T388Q, L19I/A195V, M141L/N168S/Y227F/T362Q/T388Q/D440Q, E11S/M141L, E11S/L19I/I44V/Y145A/T155A/D309S/L311V/Y412F/S472T, D309S/L311V, E11S/L19I/T31N/Y55F/A125P/N168S/Y227F, L19I/D309S/L311V/Y412F/A460S/S472T, E11S/L19I/N168S/Y227F/D309S/L311V/D440Q, L19I/Y412F, E11S/L19I/Y145A/A460S/S472T, E11S/M141L/N168S/D309S/L311V/T362Q/L364I/Y412F/A460S/S472T, E11S/Y55F/M141L/N168S/L311V/T362Q/L364I/A460S/S472T, E11S/L19I/Y55F/M141L/N168S/Y227F, L19I/T155A/A407S/Y412F/S472T, D53N/L149I/N150D/P186E/A317P, V42I/S103D/D106T/P186E/A317P/S434T/G478S, A317P/G478S, C26N/V42I/L149I/A317P/S355D/A374N, V42I/S103D/D106T/A317P, D53N/S434T, /S103D/A317P/V342I, A256V/A317P, V42I/P186E, A317P/V342I/G478S, I224V/A256V/A317P/G478S, V42I/L149I/N150D/A317P/G478S, V42I/S103D/P186E/A317P/V342I/S355D/A374N/A391G, P186E/A317P/G478S, D53N/G446S, A256V/A317P/G478S, V42I/D53N/T57S/L149I/A317P/G478S, C26N/V42I/D53N/T57S/N150D/P186E/A317P/V342I/G478S, V42I/S355D, V42I/N150D/P186E/A317P, V42I/S434T/G478S, C26N/D53N/T57S/S103D/Q161P/A317P/G478S, V42I/A256V/A317P/S434T, V42I/S103D/A317P/A391G/G478S, E68Y/I69L/G178T/Y179F/S213T/H214C, E68Y/I69L/E85Q/N86Q/F394Y/V395L, E68Y/I69L, D118N/M119E, E68Y/I69L/V97I/T98S/A246S/S247G/T261G/A262S/L347N/E348I, E68Y/I69L/S452A/V453S, E68Y/I69L/S452A/V453S, E68Y/I69L/E85Q/N86Q/L347N/E348I/Q418T/Q419P, E68Y/I69L/E85Q/N86Q/S204N/T205A, A208T/K209R/E381N/S382D/Q418T/Q419P/A469S/A470T, E381N/S382D/Q418T/Q419P/T436S/E437A/A469S/A470T, Q418T/Q419P/A469S/A470T, V170I/A171T/E381N/S382D/Q418T/Q419P/A469S/A470T, F394Y/V395L/Q418T/Q419P/T436S/E437A/A469S/A470T, T78K/L79D/Q418T/Q419P/A469S/A470T, E68Y/I69L/V88I/T89S/T352S/V353I/Q399E/T400K/A469S/A470T, S72A/V73F/A153S/S306A/T476W, T370V/G475V, R49H/S72A/V73F/A92T/Y93K/A153S/S306A/T476W, E68Y/I69L/T219S/V220Q/A307E/S355D/L492P, E11S/V42I/L149I/I224V/A317P/T388Q/A460S/G478S, Y412F/Q418T/Q419P/A469S/A470T/, L19I/D53N/I69L/V88I/S188H/A195V/Y321W/Y412F, V42I/D118N/M119E/T261A/L311V/Y321W/S355D, E11S/T57S/T89S, E11S/V42I/L79Y/D118N/M141L/L311V/A317P/Y321F, V42I/D53N/E68Y/A317P/L347N, I69L/S188H/A195V/A317P/Y321F/L364I/S434T, T57S/A195V/T261A/L311V/Y321F/L347N/E348I/S434T, E11S/V42I/T57S/E68Y/S188H/A195V/T261A, T57S/N168S/T261A/A317P/Y321W/V395L/Y412F, E11S/D53N/E68Y/D118N/S188H/A195V/Y412F/Q419P, E11S/V42I/D118N/M141L/N168S/Y321W/Y412F, E11S/D53N/T57S/E68Y/T89S/E381N/Y412F/Q419P/S434T, E11S/D53N/T57S/V88I/T89S/S188H/A195V/L311V/L347N/Y412F, A317P/Y412F, I69L/T89S/L311V/A317P/Y321F/Y412F/S434T, V42I/D53N/T57S/E68Y/V88I/Y412F, E11S/T57S/V88I/M141L/T261A/Y321W/L364I/Y412F, V42I/I69L/S188H/A317P/Y321W/Y412F, E11S/V42I/D53N/T57S/L79Y/T89S/L311V/Y321W/Y412F, L19I/M141L/N168S/S188H/A195V/L311V/S355D/S434T, S188H/A195V/T261A/L311V/Y321F/L347N/E348I, E11S/L19I/D53N/T57S/N168S/L347N, E11S/I69L/M119E/A195V/T261A/A317P/Y321W/L347N/Y412F, L79Y/V88I/T261A/A317P/Y321F/L364I/Y412F, E11S/V42I/E68Y/T89S/L311V/Y321F/T388Q/

F394Y/V395L/Q419P, D53N/E68Y/V88I/M141L/N168S/
Y321W/Y412F, E11S/I69L/L311V/A317P/Y321F/L347N/
Y412F, D53N/T57S/M141L, D53N/V88I/T89S/D118N/
E348I/S355D, E11S/S188H/A195V/A317P/L347N/E348I/
Y412F/Q419P/S434T, E11S/D53N/I69L/V88I/A317P/
Q419P, E68Y/I69L/V88I/N168S/L364I/Q419P, E11S/V42I/
V88I/T261A/Y321F/E348I/S355D, E11S/V42I/T57S/I69L/
A195V/L347N/E348I/S355D, L19I/T89S/A317P/Y321F/
S434T, E11S/V42I/L79Y/L311V/A317P/Y321W/L347N/
E348I/L364I/Y412F, D53N/T57S/L347N/E348I/Y412F,
D53N/T57S/E68Y/L79Y/Y412F/S434T, L19I/V88I/T89S/
A317P, M119E/M141L/N168S/L311V/Y321F, E11S/T89S/
Y321W, E11S/M141L/T261A/A317P/Y412F/S434T, V42I/
L79Y/S188H/A195V/L311V/Y321F/S355D, V42I/E68Y/
V88I/T261A/Y321W/L347N/E348I, L19I/E68Y/I69L/
M141L/Y321F/L347N/S355D/E381N/Y412F, V42I/D53N/
I69L/L79Y/D118N/T261A/L311V/A317P/Y321F/L347N/
Y412F, E68Y/S355D/L364I/S382D/T388Q/Q419P, E11S/
L19I/V42I/E68Y/I69L/D118N/M141L/Y321W/L347N,
/E11S/V42I/E68Y/M141L/A317P/Y321F/E348I/S355D,
E11S/V42I/E68Y/I69L/V88I/T89S/D118N/M119E/S188H/
A195V/A317P/L347N/Y412F/Q419P, V42I/V88I/L311V/
A317P/Y321F/L347N/E348I/T388Q/V395L/S434T,
T261A/A317P/Y321W/E348I, E11S/V42I/E68Y/I69L/
D118N/M119E/Y412F, E11S/V42I/T57S/I69L/L311V,
V42I/Y412F, E11S/L19I/E68Y/M119E/N168S/Y412F/
Q419P, L19I/L311V/Y412F, E11S/V42I/M119E/Y412F,
E11S/L19I/V42I/D53N/S188H/A195V/L311V/Y321F/
Y412F, E11S/L19I/V42I/T57S/D118N/N168S/L311V/
Y412F, L19I/V42I/D53N/T57S/N168S/A317P/Y321W/
Y412F, D53N/T57S/E68Y/N168S/S188H/A195V/L311V/
Y321W/Y412F/Q419P, L19I/D53N/T57S/L311V/Y321W/
Y412F, E11S/T57S/Y321W/Y412F/Q419P, D53N/S188H/
A195V/L311V/Y412F, V42I/D53N/S188H/A195V/L311V/
Y321F/Y412F, L19I/M119E/N168S/S188H/A195V/
L311V/Y412F/Q419P, E11S/V42I/S188H/A195V/L311V/
A317P/Y321W/Y412F/Q419P, E11S/V42I/M119E/N168S/
L311V/Y412F, E11S/V42I/N168S/L311V/A317P/Y321W/
Y412F/Q419P, E11S/V42I/D53N/E68Y/S188H/A195V/
L311V/A317P/Y321F/Y412F, E11S/L19I/D53N/N168S/
A195V/Y412F/Q419P, E11S/L19I/V42I/L311V/Y412F,
V42I/D53N/N168S/L311V/Y412F, E11S/L311V/Y412F,
E11S/D53N/T57S/L311V/Y321W/Y412F, E11S/L311V/
Y321W/Y412F, E11S/V42I/I69L/D118N/N168S/L311V/
A317P/Y412F/Q419P, E11S/L19I/V42I/E68Y/Y412F/
Q419P, E11S/L19I/D53N/L311V, E11S/L19I/V42I/L311V/
Y412F/Q419P, L19I/V42I/D53N/T57S/I69L/N168S/
S188H/A195V/L311V/A317P/Y321W, E11S/L19I/V42I/
T57S/L311V/A317P/Y321F/Y412F, L19I/V42I/I69L/
D118N/N168S/L311V/Y321W/Y412F/Q419P, E11S/V42I/
D53N/E68Y/S188H/A195V/Y412F, E11S/L19I/V42I/
D53N/T57S/N168S/L311V/Y321W/Y412F, E11S/V42I/
L311V/Y412F, E11S/L19I/V42I/N168S/A195V/L311V/
Y321F/Y412F, E11S/V42I/S188H/L311V/Y412F, L19I/
V42I/T57S/E68Y/M119E/S188H/A195V/L311V/Y321F/
Y412F, E11S/L19I/V42I/D53N/N168S/S188H/A195V,
E11S/L19I/V42I/T57S/E68Y/A195V/L311V/Y321W, and
E11S/L19I/V42I.

In a further aspect, the invention provides the nucleic acid encoding the preprotein as described herein, wherein said variant glucoamylase enzyme has an amino acid substitution Y321F.

In an additional aspect, the invention provides the nucleic acid encoding the preprotein as described herein, wherein said variant glucoamylase enzyme has amino acid substitutions S188H/Y321W/Q419P.

In a further aspect, the invention provides the nucleic acid encoding the preprotein as described herein, wherein said variant glucoamylase enzyme comprises an amino acid substitution Y321F and further comprises at least one amino acid selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, T400L, Y412F, L420K, A422G, P423G, P423R, P423V, G457S, A491V, K5P, K5S, K5T, K5Y, K5Q, K5N, K5H, E68K, E68Y, E68S, S188T, S188H, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In an additional aspect, the invention provides the nucleic acid encoding the preprotein as described herein, wherein said variant glucoamylase enzyme comprises amino acid substitutions S188H/Y321W/Q419P and further comprises at least one amino acid selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, Y321F, T400L, Y412F, L420K, A422G, P423G, P423R, P423V, G457S, A491V, K5P, K5S, K5T, K5Y, K5Q, K5N, K5H, E68K, E68Y, E68S, S188T, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In some aspects, the invention provides the nucleic acid encoding the preprotein as described herein, wherein the preprotein comprises a sequence selected from the group consisting of SEQ ID NO:3, SEQ ID NO:9 and SEQ ID NO:11.

In additional aspects, the invention provides an expression vector comprising the nucleic acid as described herein.

In further aspects, the invention provides a host cell comprising the nucleic acid as described herein.

In further aspects, the invention provides a host cell comprising the expression vector as described herein.

In an additional aspect, the invention provides a host cell as described herein, wherein said host cell is selected from the group consisting of a bacterial cell, a fungal cell, or a yeast cell.

In a further aspect, the invention provides a method of making a variant glucoamylase enzyme comprising: a) culturing the host cell as described herein under conditions wherein said variant glucoamylase enzyme is expressed; and b) recovering said variant glucoamylase enzyme.

In a further aspect, the invention provides a composition comprising a C-terminally truncated variant glucoamylase enzyme of SEQ ID NO:13, wherein said truncation position is at a position number selected from the group consisting of 493, 500, 502, 503, 506, 509, 510, 513, 514, 519, 520, 522, 524, 525, 544, 549, 550, 551, 556, 558, 560, 563, 564 and 569.

In an additional aspect, the invention provides a composition comprising a variant glucoamylase enzyme comprising at least one amino acid substitution as compared to SEQ ID NO:13, wherein said amino acid substitution is at a position selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 516, 518, 521, 522, 526, 533, 534, 535, 540, 542, 544, 545, 549, 550, 551, 555, 556, 557, 559, 563, 564, 569, 570, 581 584, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, and wherein said variant enzyme is at least 95% identical to SEQ ID NO:13.

In some aspects, the present invention provides a composition comprising a variant glucoamylase enzyme comprising at least one amino acid substitution as compared to SEQ ID NO:13, wherein said amino acid substitution is at a position selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 516, 518, 521, 522, 526, 533, 534, 535, 540, 542, 544, 545, 549, 550, 551, 555, 556, 557, 559, 563, 564, 569, 570, 581 584, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, wherein said variant glucoamylase enzyme has at least 1.1 fold better activity as compared to SEQ ID NO:13 under a condition selected from the group consisting of thermoactivity at about 30° C., thermoactivity at about 35° C., thermoactivity at about 40° C., thermoactivity at about 50° C., thermoactivity at about 60° C. and thermoactivity at about 70° C.; and wherein said variant enzyme is at least 95% identical to SEQ ID NO:13.

In additional aspects, the present invention provides the composition comprising a variant glucoamylase enzyme as described herein, wherein said variant enzyme is at least 96%, 97%, 98%, or 99% identical to SEQ ID NO:13.

In further aspects, the present invention provides the composition comprising a variant glucoamylase enzyme as described herein, wherein said amino acid substitution(s) occurs at one of said positions, two of said positions, three of said positions, four of said positions, five of said positions, six of said positions, seven of said positions, eight of said positions, nine of said positions, ten of said positions, eleven of said positions, twelve of said positions or thirteen of said positions.

In a further aspect, the present invention provides the composition comprising a variant glucoamylase enzyme as described herein, wherein said amino acid substitution(s) is selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321F, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453A, A460S, A469S, A470T, S472T, G475V, T476W, G478S, L492P, and L9P.

In an additional aspect, the present invention provides the composition comprising a variant glucoamylase enzyme as described herein, wherein said amino acid substitution(s) is selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321F, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, L9P, E11S, L19I, V42I, D53N, T57S, I69L, L79Y, V88I, T89S, D118N, M119E, M141L, N168S, A195V, T261A, L311V, A317P, L347N, E348I, S355D, L364I, E381N, S382D, T388Q, F394Y, V395L and S434T.

In a further aspect, the present invention provides the composition comprising a variant glucoamylase enzyme as described herein, wherein said amino acid substitution(s) is selected from the group consisting of S188H/Y321W/ Q419P, T98S/Q161P/F516L, T98S/Q161P/N570P, T98S/ Q161P, T550D/F555S, V65I/Y412F/Y503S/S518I, Y412F/ Y503S/I564T, Y412F/Y503E, Y412F/Y503E/S518I, V65I/

Y412F/Y503S, V65I/Y503E, Y503D/S518I/I564N, Y503E/ S518L, V65I/Y503E/S544Q, V65I/Y503S, Y503E/S544E, V65I/Y503E/S544E/I564N, V65I/Y412F/Y503E, Y503E/ S518I/S544Q, V65I/Y503E/S518M, Y412F/S518L, Y503E/ S544Q, V65I/Y412F/Y503E/S544E/I564T/G569I, Y412F/ Y503S, Y503E/I564T, S549D/F555D/G559N, S549D/ F555R, K508T/L526N/S549D/G559N, K508T/G559N, F555D/I556P/G559N, S549D/F555R/I556P/G559N, F555R/I556P, L526I/F555R/I556P, F555R/I556P/G559N, K508T/I556P/G559N, F555D/I556P, K508T/L526N/ A534T/S549D/I556P, K508T/L526I/S549D/G559N, K508N/L526I/S549E/F555L/G559N, L526N/S549D/ F555D/I556P, L526I/F555D/G559N, A38V/F555R, A39F/ T540N/T542N, L498T/T542N/T581N/T584N, T542N/ T581N/T584N, S535Y/T542N, T540N/T584N, T540N/ T542N/T581N/T584N, L498T/T581N/T584N, L498T/ T584N, L498T/T542N/T581N, P121S/T542N/T584N, L498T/T542N, S535Y/T540N/T542N/T581N, Q419P/ P423R, L79F/Q419P, Q419P/P423V, Q419P/P423R/T533R, S36P/Q419P, Q419P/P423G, S36P/T400L/Q419P/P423G, S50Q/Q419P/P423R, S50Q/Q419P/P423R/G457S/E497V/ P521S, Y321F/A422S, S188H/Q419P, K5H/Y321W, K5N/ Y321F, K5P/S188H, E68S/S188H/A422S, S188T/Y321F/ Q419P/A422S, K5H/S188H/Y321F/A422S, S188H/ Y321W/Q419P, S188H/A422S, S188H/A422S/V545A, K5Q/A422S, K5S/E68K/Y321W, K5H/Y321F/A422S, S188H/Y321W/Q419P, K5Y/A422S, Q419P/A422S, K5Y/ S188H/A422S, K5T/A422S, K5T/Y321W, Y321W/A422S, Q419P/A422S, K5P/Y321F, K5H/S188H/Y321F/A422S, E68K/A422S, Y321F/A422S, K5H/Y321F, K5T/Y321F/ Q419P/A422S, K5T/E68Y/S188T, K5S/E68Y/S188H, K5N/S188H, K5T/E68S/S188T, K5H/E68Y/S188P, K5P/ E68Y/S188T, K5T/E68K/S188H, K5P/E68K/S188T, K5H/ E68Y/S188T, K5T/S188H, K5T/E68N/S188T, K5Y/E68Y/ S188T, K5S/E68Y/S188T, K5Q/E68K/S188H, K5P/E68N/ S188H, K5P/E68N/S188T, K5P/E68Y/S188H, K5Y/E68Y/ S188H, K5S/S188T, K5H/E68N/S188H, K5P/S188H, K5H/ S46T/E68K/S188H, K5H/E68K/S188T, K5Q/E68Y/S188T, K5Y/E68N/S188H, V42I/S188H/A195V/Y412F/Q419P, L19I/V42I/E68Y/N168S/S188H/A195V/Y412F, E11S/ V42I/T57S/D118N/N168S/S188H/A195V/L311V, E11S/ V42I/D53N/E68Y/N168S/S188H/A195V/L311V/Y412F, E11S/L19I/V42I/Y321W/Y412F/Q419P, E11S/L19I/ V42I/E68Y/D118N/S188H/A195V/L311V/Y412F, E11S/ L19I/T57S/M119E/S188H/A195V/L311V/Y412F, E11S/ V42I/A317P/Y412F/Q419P, L19I/T57S/I69L/D118N/ N168S/S188H/A195V/L311V/A317P/Y321F/Y412F/ Q419P, E11S/E68Y/S188H/A195V/L311V/Y412F, E11S/ L19I/V42I/E68Y/I69L/D118N/N168S/S188H/A195V/ L311V/Y412F, E11S/L19I/V42I/S188H/A195V/L311V/ Y321W/Y412F/Q419P, E11S/L19I/N168S/S188H/A195V/ L311V/A317P/Y321F/Y412F, E11S/V42I/E68Y/Y412F, E11S/L19I/V42I/E68Y/Y412F, E11S/V42I/E68Y/S188H/ A195V/Y412F, E11S/L19I/V42I/T57S/I69L/S188H/ A195V/L311V/Y321W/Y412F, E11S/L19I/D53N/E68Y/ S188H/A195V/L311V/Y412F, E11S/V42I/E68Y/S188H/ A195V/L311V/Y321W/Y412F, E11S/V42I/E68Y/S188H/ L311V/Y412F/Q419P, E11S/L19I/V42I/E68Y/S188H/ A195V/L311V/A317P/Y321W/Y412F/Q419P, E11S/L19I/ D53N/I69L/S188H/A195V/L311V/Q419P, E11S/V42I/ E68Y/N168S/L311V/A317P/Y321W/Y412F, E11S/E68Y/ I69L/S188H/A195V/L311V/A317P/Y321F/Y412F, E11S/ V42I/T57S/E68Y/I69L/S188H/A195V/L311V/A317P/ Y321F, E11S/D53N/T57S/L311V/Y321F/Y412F/Q419P, E11S/L19I/S188H/A195V/L311V/A317P/Y321W/Y412F/ Q419P, E11S/L19I/I69L/S188H/A195V/L311V/A317P, E11S/V42I/I69L/N168S/S188H/A195V/L311V/A317P/ Y412F/Q419P, E11S/V42I/E68Y/S188H/A195V/L311V/ Y412F, E11S/V42I/I69L/S188H/A195V/L311V/A195V/ L311V/A317P/Y321F/Y412F, E11S/Y412F, E11S/L19I/ V42I/E68Y/I69L/S188H/A195V/Y412F, E11S/L19I/V42I/ D53N/T57S/S188H/A195V/L311V/Y321W/Y412F, V42I/ E68Y/Y412F, E11S/L19I/V42I/D53N/T57S/E68Y/I69L/ N168S/S188H/A195V/L311V/A317P/Y321F, E11S/L19I/ V42I/D53N/T57S/I69L/S188H/A195V/L311V/A317P/ Y321W/Y412F, E11S/V42I/A317P/Y321F, E11S/V42I/ T57S/E68Y/D118N/S188H/A195V/L311V/Y412F, E11S/ L19I/V42I/E68Y/I69L/D118N/N168S/S188H/A195V/ L311V/Y412F/Q419P, E11S/V42I/D53N/E68Y/S188H/ A195V/L311V/Y412F, E11S/I69L/D118N/S188H/A195V/ L311V/Y412F, V42I/D53N/T57S/E68Y/M141L/N168S/ T261A/Y321W/E381N/Y412F, E11S/V42I/S188H/L347N/ Y412F/S434T, D53N/T57S/E68Y/D118N/M119E/L311V/ E348I/Y412F, D118N/N168S/S188H/L347N/E348I/ S382D/T388Q/V395L, E68Y/I69L/N168S/S188H/A195V/ L311V/A317P/Y321W/Y412F/Q419P, E11S/E68Y/V88I/ A317P/Y321F/S355D, D53N/I69L/L79Y/M119E/T261A/ L311V/L347N/E348I/Q419P, V42I/E68Y/I69L/D118N/ M119E/M141L/L311V/A317P/Y321F/L347N, E11S/L19I/ E68Y/I69L/L79Y/M141L/N168S/T261A/A317P/Y321W/ L347N, E11S/V42I/E68Y/I69L/L311V/Y321W/S434T, E11S/V42I/D53N/N168S/L311V/A317P/Y321W, E11S/ E68Y/I69L/D118N/N168S/Y321F/Y412F, V42I/D53N/ T57S/L311V/Y321W/S355D/Y412F/Q419P, V42I/E68Y/ L311V/L347N/L364I/Y412F, E11S/D118N/M119E/ M141L/L311V/Y321W/L347N, V42I/D53N/T57S/M119E/ M141L/A317P/Y321F/Q419P, T57S/I69L/T89S/S188H/ A195V/T261A/L311V/A317P/Y321W/F394Y/Y412F, Y321F/Y412F, V42I/T57S/E68Y/I69L/T89S/M119E/ T261A/A317P/Y412F/S434T, E11S/V42I/E68Y/L311V/ A317P/S434T, V42I/D53N/T57S/E68Y/I69L/S434T, V42I/ E68Y/Y321W, L311V/L347N/E348I/S355D/L364I/S434T, E11S/D53N/T57S/E68Y/V88I/T89S/M119E/A317P/ Y321W, D53N/E68Y/I69L/T89S/L311V/A317P/S355D/ Q419P, V42I/E68Y/A317P/Y321F/Y412F, L19I/I69L/ T89S/L311V/A317P/Y321F/S355D/L364I/Y412F, V42I/ D53N/T57S/E68Y/I69L/M141L/S188H/A195V/L311V/ A317P/Y321F/Y412F/S434T, T57S/V88I/A317P/Y321W/ Q419P, E11S/L19I/V42I/D53N/E68Y/L311V/A317P/ Y321W/Y412F, E11S/V42I/D53N/E68Y/I69L/S188H/ A95V/E348I, L19J/V42I/T57S/I69L7V88I/M119E/T261A/ A317P/Y321F/Y412F, D53N/E68Y/D118N/M119E/ M141L/T261A/L347N/E348I/S355D/L364I/S434T, E11S/ T261A/L347N/E348I/S355D/S434T, M119E/S188H/ E348I, E11S/A317P/Y321F/L347N, E11S/E68Y/I69 L/T261A/L364I, D118N/M119E/N168S/S188H/A195V/ L311V/Y321W/L347N/F394Y, E11S/L311V/Y321W/ E348I/S355D/L364I/Y412F, V42I/D53N/T57S/I69L/V88I/ L347N/E348I/F394Y/V395L/S434T, E11S/D53N/T89S/N168S/S188H/T261A/L311V/A317P/Y321W/S355D/Y412F, L19I/V42I/D53N/L79Y/T89S/N168S/T261A/L311V/Y321W/Y412F/Q419P/S434T, L79Y/V88I/D118N/M119E/T261A/Y321F/L364I/Y412F, V42I/E68Y/T89S/M141L/T261A/L311V/Y321F/E348I/L364I, V42I/E68Y/D118N/S188H/T261A/Y412F/S434T, E11S/D53N/E68Y/I69L/T89S/Y321W/E348I/S355D, M119E/L311V/Y321F, L311V/L347N/E348I, E11S/V42I/A317P/Y321F/L347N/Y412F, E11S/L19I7V42I/E68Y/A317P/Y321F/L364I/Y412F, D53N/E68Y/T89S/T261A, I69L/S188H/A195V/L311V/A317P/Y321W/V395L/Y412F, V42I/D53N/E68Y/V88I/T89S/D118N/L311V/Y412F/S434T, E11S/V42I/E68Y/I69L/L311V/E348I, V42I/Y321W, E68Y/T261A/L311V/L347N/E348I/S434T, E11S/E68Y/I69L/L79Y, V42I/D53N/E68Y/S188H/A195V/T261A/L311V/Y321F/

S355D/S434T, L19I/V42I/S188H/A195V/S382D/V395L/Q419P, E11S/L19I/V42I/D53N/T57S/M119E/L311V/Y321W/L347N/F394Y/Y412F, L9P/E11S/D53N/T57S/E68Y/M119E/M141L/E348I/Y412F and L19I/V42I/I69L/L311V/Y321W/L347N.

In an additional aspect, the present invention provides the composition comprising a variant glucoamylase enzyme as described herein, wherein said amino acid substitution is Y321F.

In some aspects, the present invention provides the composition comprising a variant glucoamylase enzyme as described herein, wherein said amino acid substitutions are S188H/Y321W/Q419P.

In a further aspect, the present invention provides the composition comprising at least one variant glucoamylase enzyme as described herein, wherein said amino acid substitutions comprise Y321F, and further comprise at least one amino acid substitution selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In an additional aspect, the present invention provides the composition comprising at least one variant glucoamylase enzyme as described herein, wherein said amino acid substitutions comprise S188H/Y321W/Q419P, and further comprise at least one amino acid substitution selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188P, S188T, S188W, T192A, K212Y, S215A, T258S, A262S, H264M, I298V, Y321F, Y321L, T400L, Y412F, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In additional aspects, the present invention provides a composition comprising a variant glucoamylase enzyme, wherein said variant glucoamylase enzyme comprises at least one amino acid substitution as compared to SEQ ID NO:13 as described herein, and further comprises a C-terminal amino acid truncation at a position number selected from the group consisting of 493, 500, 502, 503, 506, 509, 510, 513, 514, 519, 520, 522, 524, 525, 544, 549, 550, 551, 556, 558, 560, 563, 564 and 569.

In some aspects, the invention provides a nucleic acid encoding said variant glucoamylase enzyme as described herein.

In further aspects, the invention provides a nucleic acid as described herein, wherein said nucleic acid is codon optimized for a host organism for expression of the variant glucoamylase enzyme in said organism.

In additional aspects, the invention provides a nucleic acid comprising a sequence selected from the group consisting of SEQ ID NO:18 or SEQ ID NO:20.

In further aspects, the invention provides an expression vector comprising the nucleic acid as described herein.

In a further aspect, the invention provides a host cell comprising the nucleic acid as described herein.

In a further aspect, the invention provides a host cell comprising the expression vector as described herein.

In an additional aspect, the invention provides the host cell as described herein, wherein said host cell is selected from the group consisting of a bacterial cell, a fungal cell, or a yeast cell.

In some aspects, the invention provides a method of making a variant glucoamylase enzyme comprising: a) culturing the host cell as described herein under conditions wherein said variant glucoamylase enzyme is expressed; and b) recovering said variant glucoamylase enzyme.

In an additional aspect, the invention provides a nucleic acid encoding a preprotein comprising a signal peptide and a mature protein, wherein said signal peptide is SEQ ID:26 or a variant signal peptide as compared to SEQ ID NO:26, and said variant signal peptide has at least one amino acid substitution at a position number selected from the group consisting of −20, −18, −17, −15, −13, −12, −10, −9, and −1; and wherein said mature protein has SEQ ID NO:13 or is a variant glucoamylase enzyme as compared to SEQ ID NO:13, wherein said variant glucoamylase has at least one amino acid substitution at a position number selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 516, 518, 521, 522, 526, 533, 534, 535, 540, 542, 544, 545, 549, 550, 551, 555, 556, 557, 559, 563, 564, 569, 570, 581, 584; 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492; and wherein said preprotein is at least 95% identical to SEQ ID NO:1; and wherein said preprotein is not SEQ ID NO:1.

In a further aspect, the invention provides the nucleic acid encoding the preprotein as described herein, wherein said preprotein exhibits at least 96%, 97%, 98%, or 99% identity to SEQ ID NO:1.

In a further aspect, the invention provides the nucleic acid encoding the preprotein as described herein, wherein said variant signal peptide has amino acid substitution(s) at one of said positions, two of said positions, three of said positions, four of said positions, or five of said positions.

In a further aspect, the invention provides the nucleic acid encoding the preprotein as described herein, wherein said variant glucoamylase enzyme has amino acid substitution(s) at one of said positions, two of said positions, three of said positions, four of said positions, five of said positions, six of said positions, seven of said positions, eight of said positions, nine of said positions, ten of said positions, eleven of said positions, twelve of said positions or thirteen of said positions.

In additional aspects, the invention provides the nucleic acid encoding the preprotein as described herein, wherein said variant signal peptide has amino acid substitution(s) selected from the group consisting of V-20A, V-20F, V-20G, V-20I, V-20K, V-20L, V-20M, V-20Q, V-20R, V-20T, V-20W, L-18F, L-18I, L-18Y, K-17F, K-17N, K-17Y, A-15F, A-15I, A-15L, A-15V, A-13T, A-12V, T-10F, T-10V, W-9Y, and V-1F.

In further aspects, the invention provides the nucleic acid encoding the preprotein as described herein, wherein said variant glucoamylase enzyme has amino acid substitution(s) selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321F, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, Y353I, S355D, L362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In an additional aspect, the invention provides the nucleic acid encoding the preprotein as described herein, wherein said variant glucoamylase enzyme has amino acid substitution(s) selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321F, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, L9P, E11S, L19I, V42I, D53N, T57S, I69L, L79Y, V88I, T89S, D118N, M119E, M141L, N168S, A195V, T261A, L311V, A317P, L347N, E348I, S355D, L364I, E381N, S382D, T388Q, F394Y, V395L and S434T.

In a further aspect, the invention provides the nucleic acid encoding the preprotein as described herein, wherein said preprotein has amino acid substitution(s) selected from the group consisting of S188H/Y321W/Q419P, T98S/Q161P/F516L, T98S/Q161P/N570P, T98S/Q161P, T550D/F555S, V-20A/T258S, V65I/Y412F/Y503S/S518I, Y412F/Y503S/I564T, Y412F/Y503E, Y412F/Y503E/S518I, V65I/Y412F/Y503S, V65I/Y503E, Y503D/S518I/I564N, Y503E/S518L, V65I/Y503E/S544Q, V65I/Y503S, Y503E/S544E, V65I/Y503E/S544E/I564N, V65I/Y412F/Y503E, Y503E/S518I/S544Q, V65I/Y503E/S518M, Y412F/S518L, Y503E/S544Q, V65I/Y412F/Y503E/S544E/I564T/G569I, Y412F/Y503S, Y503E/I564T, S549D/F555D/G559N, S549D/F555R, K508T/L526N/S549D/G559N, K508T/G559N, F555D/I556P/G559N, S549D/F555R/I556P/G559N, F555R/I556P, L526I/F555R/I556P, F555R/I556P/G559N, K508T/I556P/G559N, F555D/I556P, K508T/L526N/A534T/S549D/I556P, K508T/L526I/S549D/G559N, K508N/L526I/S549E/F555L/G559N, L526N/S549D/F555D/I556P, L526I/F555D/G559N, A38V/F555R, A39F/T540N/T542N, L498T/T542N/T581N/T584N, T542N/T581N/T584N, S535Y/T542N, T540N/T584N, T540N/T542N/T581N/T584N, L498T/T581N/T584N, L498T/T584N, L498T/T542N/T581N, P121S/T542N/T584N, L498T/T542N, S535Y/T540N/T542N/T581N, Q419P/P423R, L79F/Q419P, Q419P/P423V, Q419P/P423R/T533R, S36P/Q419P, Q419P/P423G, S36P/T400L/Q419P/P423G, S50Q/Q419P/P423R, S50Q/Q419P/P423R/G457S/E497V/P521S, V-20R/A-15I, A-15F/S188T, V-20F/A-15I/Y321F/A422S, V-20F/A-15F/S188H/Q419P, A-15F/K5H/Y321W, A-15F/K5N/Y321F, V-20F/Y321F, V-20F/A-15I, A-15F/K5P/S188H, V-20F/E68S/S188H/A422S, V-20F/S188T/Y321F/Q419P/A422S, V-20F/K5H/S188H/Y321F/A422S, V-20F/A422S, A-15I/S188H/Y321W/Q419P, A-15F/S188H/A422S, V-20F/S188H/A422S/V545A, V-20F/A-15I/Q419P, V-20F/K5Q/A422S, V-20R/A-15I/K5S/E68K/Y321W, A-15F/K5H/Y321F/A422S, V-20F/A-15F/K5N, V-20F/S188H/Y321W/Q419P, A-15I/Y321F, A-15F/K5Y/A422S, V-20F/A-15F/Q419P/A422S, V-20F/K5Y/S188H/A422S, V-20T/A-15I/K5T/A422S, V-20T/A-15I/K5T/Y321W, V-20R/A-15F/Y321W/A422S, A-15F/A-13T, V-20F/Q419P/A422S, A-15I/K5P/Y321F, V-20F/A-15F/Y321W, V-20F/A-15F/K5H/S188H/Y321F/A422S, A-15I/E68K/A422S, Y321F/A422S, V-20T/A-15F/K5H/Y321F, V-20T/A-15I/K5T/Y321F/Q419P/A422S, K5T/E68Y/S188T, K5S/E68Y/S188H, K5N/S188H, K5T/E68S/S188T, K5H/E68Y/S188P, K5P/E68Y/S188T, K5T/E68K/S188H, K5P/E68K/S188T, K5H/E68Y/S188T, K5T/S188H, K5T/E68N/S188T, K5Y/E68Y/S188T, K5S/E68Y/S188T, K5Q/E68K/S188H, K5P/E68N/S188H, K5P/E68N/S188T, K5P/E68Y/S188H, K5Y/E68Y/S188H, K5S/S188T, K5H/E68N/S188H, K5P/S188H, K5H/S46T/E68K/S188H, K5H/E68K/S188T, K5Q/E68Y/S188T, K5Y/E68N/S188H, V42I/S188H/A195V/Y412F/Q419P, L19I/V42I/E68Y/N168S/S188H/A195V/Y412F, E11S/V42I/T57S/D118N/N168S/S188H/A195V/L311V, E11S/V42I/D53N/E68Y/N168S/S188H/A195V/L311V/Y412F, E11S/L19I/V42I/I69L/Y321W/Y412F/Q419P, E11S/L19I/V42I/E68Y/D118N/S188H/A195V/L311V/Y412F, E11S/L19I/T57S/M119E/S188H/A195V/L311V/Y412F, E11S/V42I/A317P/Y412F/Q419P, L19I/T57S/I69L/D118N/N168S/S188H/A195V/L311V/A317P/Y321F/Y412F/Q419P, E11S/E68Y/S188H/A195V/L311V/Y412F, E11S/L19I/V42I/E68Y/I69L/D118N/N168S/S188H/A195V/L311V/Y412F, E11S/L19I/V42I/S188H/A195V/L311V/Y321W/Y412F/Q419P, E11S/L19I/N168S/S188H/A195V/L311V/A317P/Y321F/Y412F, E11S/V42I/E68Y/Y412F, E11S/L19I/V42I/E68Y/Y412F, E11S/V42I/E68Y/S188H/A195V/Y412F, E11S/L19I/V42I/T57S/I69L/S188H/A195V/L311V/Y321W/Y412F, E11S/L19I/D53N/E68Y/S188H/A195V/L311V/Y412F, E11S/V42I/E68Y/S188H/A195V/L311V/Y321W/Y412F, E11S/V42I/E68Y/S188H/L311V/Y412F/Q419P, E11S/L19I/V42I/E68Y/S188H/A195V/L311V/A317P/Y321W/Y412F/Q419P, E11S/L19I/D53N/I69L/S188H/A195V/L311V/Q419P, E11S/V42I/E68Y/N168S/L311V/A317P/Y321W/Y412F, E11S/E68Y/I69L/S188H/A195V/L311V/A317P/Y321F/Y412F, E11S/V42I/T57S/E68Y/I69L/S188H/A195V/L311V/A317P/Y321F, E11S/D53N/T57S/L311V/Y321F/Y412F/Q419P, E11S/L19I/S188H/A195V/L311V/A317P/Y321W/Y412F/Q419P, E11S/L19I/I69L/S188H/A195V/L311V/A317P, E11S/V42I/I69L/N168S/S188H/A195V/L311V/A317P/Y412F/Q419P, E11S/V42I/E68Y/S188H/A195V/L311V/Y412F, E11S/V42I/I69L/S188H/A195V/L311V/A195V/L311V/A317P/Y321F/Y412F, E11S/Y412F, E11S/L19I/V42I/E68Y/I69L/S188H/A195V/Y412F, E11S/L19I/V42I/D53N/T57S/S188H/A195V/L311V/Y321W/Y412F, V42I/E68Y/Y412F, E11S/L19I/V42I/D53N/T57S/E68Y/I69L/N168S/S188H/A195V/L311V/A317P/Y321F, E11S/L19I/V42I/D53N/T57S/I69L/S188H/A195V/L311V/A317P/Y321W/Y412F, E11S/V42I/A317P/Y321F, E11S/V42I/T57S/E68Y/D118N/S188H/A195V/L311V/Y412F, E11S/L19I/V42I/E68Y/I69L/D118N/N168S/S188H/A195V/L311V/Y412F/Q419P, E11S/V42I/D53N/E68Y/S188H/A195V/L311V/Y412F, E11S/I69L/D118N/S188H/A195V/L311V/Y412F, V42I/D53N/T57S/E68Y/M141L/N168S/T261A/Y321W/E381N/Y412F, E11S/V42I/S188H/L347N/Y412F/S434T, D53N/T57S/E68Y/D118N/M119E/L311V/E348I/Y412F, D118N/N168S/S188H/L347N/E348I/S382D/T388Q/V395L, E68Y/I69L/N168S/S188H/A195V/L311V/A317P/Y321W/Y412F/Q419P, E11S/E68Y/V88I/A317P/Y321F/S355D, D53N/I69L/L79Y/M119E/T261A/L311V/L347N/E348I/Q419P, V42I/E68Y/I69L/D118N/M119E/M141L/L311V/A317P/Y321F/L347N, E11S/L19I/E68Y/I69L/L79Y/M141L/N168S/T261A/A317P/Y321W/L347N, E11S/V42I/E68Y/I69L/L311V/Y321W/S434T, E11S/V42I/D53N/N168S/L311V/A317P/Y321W, E11S/E68Y/I69L/D118N/N168S/Y321F/Y412F, V42I/D53N/T57S/L311V/Y321W/S355D/Y412F/Q419P, V42I/E68Y/L311V/L347N/L364I/Y412F, E11S/D118N/M119E/M141L/L311V/Y321W/L347N, V42I/D53N/T57S/M119E/M141L/A317P/Y321F/Q419P, T57S/I69L/T89S/S188H/A195V/T261A/L311V/A317P/Y321W/F394Y/Y412F, Y321F/Y412F, V42I/T57S/E68Y/I69L/T89S/M119E/T261A/A317P/Y412F/S434T, E11S/V42I/E68Y/L311V/A317P/S434T, V42I/D53N/T57S/E68Y/169L/S434T, V42I/E68Y/Y321W, L311V/L347N/E348I/S355D/L364I/S434T, E11S/D53N/T57S/E68Y/V88I/T89S/M119E/A317P/Y321W, D53N/E68Y/I69L/T89S/L311V/A317P/S355D/Q419P, V42I/E68Y/A317P/Y321F/Y412F, L19I/I69L/T89S/L311V/A317P/Y321F/S355D/L364I/Y412F, V42I/D53N/T57S/E68Y/I69L/M141L/S188H/A195V/L311V/A317P/Y321F/Y412F/S434T, T57S/V88I/A317P/Y321W/Q419P, E11S/L19I/V42I/D53N/E68Y/L311V/A317P/Y321W/Y412F, E11S/V42J/D53N/E68Y/I69L/S188H/A95V/E348I, L19J/V42I/T57S/I69L7V88I/M119E/T261A/A317P/Y321F/Y412F, D53N/E68Y/D118N/M119E/M141L/T261A/L347N/E348I/S355D/L364I/S434T, E11S/T261A/L347N/E348I/S355D/S434T, M119E/S188H/E348I, E11S/A317P/Y321F/L347N, E11S/E68Y/I69 L/T261A/L364I, D118N/M119E/N168S/S188H/A195V/L311V/Y321W/L347N/F394Y, E11S/L311V/Y321W/E348I/S355D/L364I/Y412F, V42I/D53N/T57S/I69L/V88I/L347N/E348I/F394Y/V395L/S434T, E11S/D53N/T89S/N168S/S188H/T261A/L311V/A317P/Y321W/S355D/Y412F, L19I/V42I/D53N/L79Y/T89S/N168S/T261A/L311V/Y321W/Y412F/Q419P/S434T, L79Y/V88I/D118N/M119E/T261A/Y321F/L364I/Y412F, V42I/E68Y/T89S/M141L/T261A/L311V/Y321F/E348I/L364I, V42I/E68Y/D118N/S188H/T261A/Y412F/S434T, E11S/D53N/E68Y/I69L/T89S/Y321W/E348I/S355D, M119E/L311V/Y321F, L311V/L347N/E348I, E11S/V42I/A317P/Y321F/L347N/Y412F, E11S/L19I7V42I/E68Y/A317P/Y321F/L364I/Y412F, D53N/E68Y/T89S/T261A, I69L/S188H/A195V/L311V/A317P/Y321W/V395L/Y412F, V42I/D53N/E68Y/V88I/T89S/D118N/L311V/Y412F/S434T, E11S/V42I/E68Y/I69L/L311V/E348I, V42I/Y321W, E68Y/T261A/L311V/L347N/E348I/S434T, E11S/E68Y/I69L/L79Y, V42I/D53N/E68Y/S188H/A195V/T261A/L311V/Y321F/S355D/S434T, L19I/V42I/S188H/A195V/S382D/V395L/Q419P, E11S/L19I/V42I/D53N/T57S/M119E/L311V/Y321W/L347N/F394Y/Y412F, L9P/E11S/D53N/T57S/E68Y/M119E/M141L/E348I/Y412F and L19I/V42I/I69L/L311V/Y321W/L347N.

In a further aspect, the invention provides the nucleic acid encoding the preprotein as described herein, wherein said variant glucoamylase enzyme has an amino acid substitution Y321F.

In an additional aspect, the invention provides the nucleic acid encoding the preprotein as described herein, wherein said variant glucoamylase enzyme has amino acid substitutions S188H/Y321W/Q419P.

In a further aspect, the invention provides the nucleic acid encoding the preprotein as described herein, wherein said variant glucoamylase enzyme comprises an amino acid substitution Y321F, and further comprises K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In an additional aspect, the invention provides the nucleic acid encoding the preprotein as described herein, wherein said variant glucoamylase enzyme comprises amino acid substitutions S188H/Y321W/Q419P, and further comprises K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188P, S188T, S188W, T192A, K212Y, S215A, T258S, A262S, H264M, I298V, Y321F, Y321L, T400L, Y412F, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In some aspects, the invention provides the nucleic acid encoding the preprotein as described herein, wherein the preprotein comprises a sequence having SEQ ID NO:5 or SEQ ID NO:7.

In additional aspects, the invention provides an expression vector comprising the nucleic acid as described herein.

In further aspects, the invention provides a host cell comprising the nucleic acid as described herein.

In further aspects, the invention provides a host cell comprising the expression vector as described herein.

In an additional aspect, the invention provides a host cell as described herein, wherein said host cell is selected from the group consisting of a bacterial cell, a fungal cell, or a yeast cell.

In a further aspect, the invention provides a method of making a variant glucoamylase enzyme comprising: a) culturing the host cell as described herein under conditions wherein said variant glucoamylase enzyme is expressed; and b) recovering said variant glucoamylase enzyme.

In a further aspect, the invention provides the composition as described herein, wherein said composition is a feed supplement.

In an additional aspect, the invention provides a formulation suitable for consumption by an animal, wherein said formulation comprises a variant glucoamylase enzyme as described herein, and at least one consumable components.

In some aspects, the invention provides a method of carbohydrate saccharification from a starch substrate comprising contacting said substrate with a variant glucoamylase enzyme as described herein, wherein said starch is degraded.

BRIEF DESCRIPTION OF THE DRAWINGS

FIG. 1 provides amino acid sequence alignment of G6P and G7P preproteins. The Signal Peptide region is bolded and italicized. The starch binding domain (SBD) is bolded and underlined.

FIGS. 3A-3S provides thermoactivity improvement data for various G6P variant glucoamylases. The variants are shown with respect to (w.r.t.) G6P as set forth in SEQ ID NO:1. * represents C-terminal amino acid truncation. w.r.t. represents "with respect to".

FIGS. 4A-4K provides thermoactivity improvement data for various G7 variant glucoamylases. The variants are shown with respect to (w.r.t.) G7P as set forth in SEQ ID NO:3. w.r.t. represents "with respect to".

FIGS. 5A-5C depict a variant table showing some preferred variants of G6P and G7P in some embodiments of the invention. As described herein, these may be combined in any combination, and with variant sets as outlined herein. * represents C-terminal amino acid truncation.

FIG. 7A depicts the amino acid sequence (SEQ ID NO:1) of G6P preprotein, and the nucleic acid sequence (SEQ ID NO:2) encoding the G6P preprotein; FIG. 7B depicts the amino acid sequence (SEQ ID NO:3) of G7P preprotein, and the nucleic acid sequence (SEQ ID NO:4) encoding the G7P preprotein; FIG. 7C depicts the amino acid sequence (SEQ ID NO:5) of Variant 1 preprotein with Starch Binding Domain (SBD), and the nucleic acid sequence (SEQ ID NO:6) encoding the Variant 1 preprotein with SBD; FIG. 7D depicts the amino acid sequence (SEQ ID NO:7) of Variant 2 preprotein with SBD, and the nucleic acid sequence (SEQ ID NO:8) encoding the Variant 2 preprotein with SBD; FIG. 7E depicts the amino acid sequence (SEQ ID NO:9) of Variant 1 preprotein without SBD, and the nucleic acid sequence (SEQ ID NO:10) encoding the Variant 1 preprotein without SBD; FIG. 7F depicts the amino acid sequence (SEQ ID NO:11) of Variant 2 preprotein without SBD, and the nucleic acid sequence (SEQ ID NO:12) encoding the Variant 2 preprotein without SBD; FIG. 7G depicts the amino acid sequence (SEQ ID NO:13) of G6P mature protein, and the nucleic acid sequence (SEQ ID NO:14) encoding the G6P mature protein; FIG. 7H depicts and the amino acid sequence (SEQ ID NO:15) of G7P mature protein, and the nucleic acid sequence (SEQ ID NO:16) encoding the G7P mature protein; FIG. 7I depicts the amino acid sequence (SEQ ID NO:17) of Variant 1 mature protein with SBD, and the nucleic acid sequence (SEQ ID NO:18) encoding the Variant 1 mature protein with SBD; FIG. 7J depicts the amino acid sequence (SEQ ID NO:19) of Variant 2 mature protein with SBD, and the nucleic acid sequence (SEQ ID NO:20) encoding the Variant 2 mature protein with SBD; FIG. 7K depicts and the amino acid sequence (SEQ ID NO:21) of Variant 1 mature protein without SBD, and the nucleic acid sequence (SEQ ID NO:22) encoding the Variant 1 mature protein without SBD; FIG. 7L depicts the amino acid sequence (SEQ ID NO:23) of Variant 2 mature protein without SBD, and the nucleic acid sequence (SEQ ID NO:24) encoding the Variant 2 mature protein without SBD; FIG. 7M depicts the amino acid sequence (SEQ ID NO:25) of wild type glucoamylase mature protein with SBD, and the amino acid sequence (SEQ ID NO:26) of wild type signal peptide.

DETAILED DESCRIPTION OF THE INVENTION

I. Introduction

Figure 2:
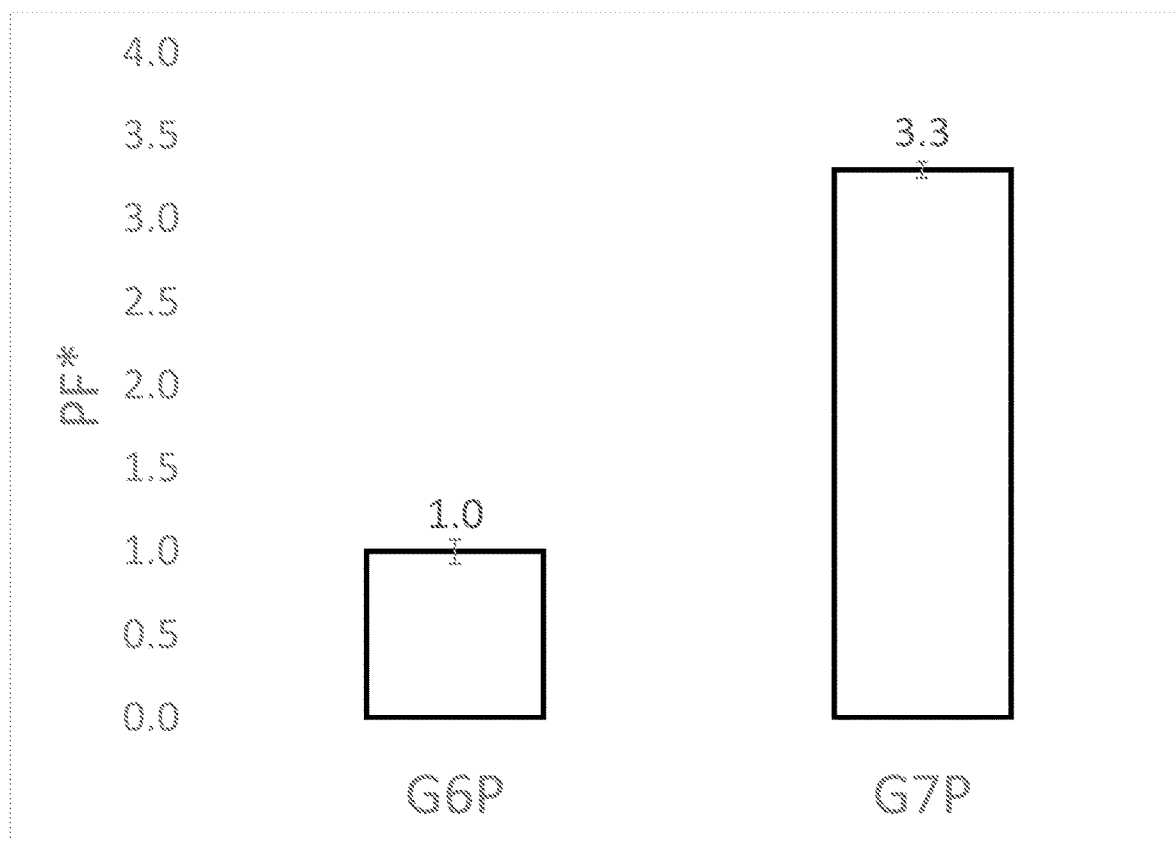
FIG. 2 provides data on thermoactivity comparison of *Pichia pastoris* produced G6P and G7P at 40° C.

Starch is the major carbohydrate reserve polymer found in a number of important food plant sources, including corn, wheat, potatoes, rice, cassava, oats and others. Starch is used as the substrate for the production of glucose, which in turn is used to make a number of products including liquid fuels (sometimes referred to herein as "biofuels"), proteins, sugars and chemicals, and is used extensively in the food industry. The convention conversion of starch to glucose requires a two step process of liquefaction (converting the solid starchy substrate into a more useable mash) and saccharification (breaking down the mash into simple sugars). Glucoamylase is used in saccharification reactions to release glucose as the final end product, which in turn can be used to produce food, beverages and biofuels. Glucoamylases generally have two domains, a catalytic domain for the actual conversion and a starch binding domain (SBD), which allows the phase transfer of a soluble enzyme to the insoluble starch substrate.

However, many of the industrial processes that utilize glucoamylases are run under generally harsh conditions such as high temperature; accordingly, thermoactive and thermostable glucoamylases are desired and provided herein.

II. Definitions

By "exogeneous" in the context of nucleic acid sequences herein is meant that the exogeneous element is not normally associated with the second element in nature, and is thus an artificial or synthetic construct. In many embodiments, the invention provides nucleic acid constructs that comprise the coding sequence of a glucoamylase liked to exogeneous construct sequences such as an exogeneous promoter. For clarity, in general the reference to "exogeneous" is in reference to the glucoamylase and not the host cell. For example, if the host cell is an *A. niger* cell, the promoter that is operably linked to the glucoamylase gene may be endogeneous to *A. niger* but exogeneous to the glucoamylase (for example, the promoter from *A. niger* α-amylase can be linked to the glucoamylases of the invention). Accordingly, in some embodiments, the invention provides nucleic acid constructs that encode both a glucoamylase enzyme (whether wild type or variant) operably linked to exogeneous construct nucleic acid sequences. By "exogeneous construct sequence" herein is meant a construct sequence (whether amino acid or nucleic acid sequences, although as will be appreciated by the context in which the term is used, usually refers to the nucleic acid sequence) that is not normally associated with the nucleic acid encoding the glucoamylase.

Suitable construct sequences that can be included in extrachromosomal or integrating expression vectors include, but are not limited to, selectable markers, purificaiton tags, origin(s) of replication and regulatory sequences including but not limited to promoters (inducible and constituative), enhancers, ribosomal binding sites, start codons, termination codons, Shine-Dalgarno sequences, etc.

By "selection marker" or "selectable marker" or "selection protein" herein is meant a protein that is introduced into a host cell that confers a trait suitable for artificial selection during the growth of the host cells, such that only those cells that contain the selectable marker grow. Thus, a selectable marker is a gene the product of which provides for biocide or viral resistance, resistance to heavy metals, prototrophy to auxotrophs, and the like. Examples of selection markers are outlined below. Accordingly, a "selection gene" is a nucleic acid that encodes a selection protein.

By "extrachromosomal expression vector" (also generally referred to as a "plasmid") herein is meant a self-replicating expression vector (generally a plasmid) that carries genes of interest, which remains within the cell and does not integrate into the genome of the host cell.

By "integrating expression vector" herein is meant a vector that is designed to be inserted into the genome of the host cell, sometimes referred to as "episomes".

By "modification" herein is meant an amino acid substitution, insertion, truncation and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, truncation and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E75D refers to a variant polypeptide, in this case a glucoamylase, in which the glutamic acid at position 75 is replaced with aspartic acid. Multiple mutations are separated by forward slash marks ("/"), e.g., "A114G/I190V/S204A" representing substitutions at positions 114, 190 and 204, respectively (in some cases a "+" can be used). For clarity, a protein which has been engineered to change the nucleic acid coding sequence but not change the starting amino acid (for example, exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "silent mutation" or "silent nucleic acid mutation" as used herein is meant a change in the sequence of nucleotide bases which constitute DNA, without a subsequent change in the amino acid or the function of the overall protein.

By "amino acid insertion" or "insertion" as used herein is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAsp-Glu after position 233 and before position 234.

By "amino acid truncation" as used herein is meant that the elimination of a N-terminal or a C-terminal portion of an amino acid sequence from a particular position of a parent polypeptide sequence. By "C-terminal amino acid truncation" is meant an elimination of an amino acid sequence starting from a particular position to the C-terminus of a parent polypeptide. By "N-terminal amino acid truncation" is meant an elimination of an amino acid sequence starting from N-terminus to a particular position of a parent polypeptide. A "C-terminally truncated variant polypeptide" is meant a variant polypeptide having an amino acid sequence eliminated from a particular position to the C-terminus of a parent polypeptide. For example, a variant polypeptide having a C-terminal amino acid truncation V551* designates a variant polypeptide having an elimination of an amino acid sequence starting from the position 551 to the C-terminus of a parent polypeptide, which means this variant polypeptide ends at position 550.

By "amino acid deletion" or "deletion" as used herein is meant the removal of an amino acid sequence at a particular position in a parent polypeptide sequence. For example, E233- or E233 #, E233( ) or E233 del designates a deletion of glutamic acid at position 233. Additionally, EDA233- or EDA233 # designates a deletion of the sequence GluAspAla that begins at position 233.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. In the present case, some embodiments utilize wild type, G6P or G7P as parent polypeptides.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about seventy amino acid modifications, and preferably from about one to about ten amino acid modifications compared to the parent. As described below, in some embodiments the parent polypeptide is a wild type sequence as set forth in SEQ ID NO:25. As further discussed below, the protein variant sequence herein will preferably possess at least about 80% identity with a parent protein sequence, and most preferably at least about 90% identity, more preferably at least about 95%, 96%, 97%, 98% or 99% identity. Variant protein can refer to the variant protein itself, compositions comprising the protein variant, or the DNA sequence that encodes it. Thus, by "variant glucoamylase" herein is meant a novel glucoamylase that has at least one amino acid modification in the amino acid sequence as compared to a parent glucoamylase enzyme. As discussed herein, in some cases the parent glucoamylase is a wild type glucoamylase (SEQ ID NO:25). In some cases, the parent glucoamylase is a variant glucoamylase, e.g. G6P (SEQ ID NO:13) or G7P (SEQ ID NO:15) protein. Unless otherwise noted or as will be obvious from the context, the variant glucoamylases of the invention are enzymatically active, that is, there is detectable glucoamylase activity using the glucoamylase assay described in the Examples and below.

As used herein, "protein" herein is meant at least two covalently attached amino acids, which includes proteins, polypeptides, oligopeptides and peptides. The peptidyl group generally comprise naturally occurring amino acids and peptide bonds. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Valine 3 (also referred to as Val3 or V3) is a residue at position 3 in the wild type parental enzyme (SEQ ID NO:25) with sequence numbering starting from the mature region.

By "non-naturally occurring modification" as used herein is meant an amino acid modification that is not found in the wild type enzyme.

By "amino acid" and "amino acid identity" as used herein is meant one of the 20 naturally occurring amino acids that are coded for by DNA and RNA.

By "position" as used herein is meant a location in the sequence of a protein. In general, the positive position number is relative to the first amino acid of the mature glucoamylase sequence, e.g. excluding the signal peptide. For example, K5 of G6P (SEQ ID NO:13) represents that the fifth amino acid of G6P counting forward from the mature region is lysine. In the context of a preprotein that includes a signal peptide, the numbering counts backwards from the first amino acid of the mature protein at position "1", with the C-terminus of the signal being "zero" or "0", and the penultimate amino acid being "–1", etc. That is, a 10 amino acid signal peptide using "X" as an amino acid is "X-9/X-8/X-7/X-6/X-5/X-4/X-3/X-2/X-1/X0/X+1 (start of the mature protein)". For example, W-9 of G6P preprotein (SEQ ID NO:1) represents that the tenth amino acid counting backwards from the last amino acid of the signal peptide (or the eleventh amino acid counting backwards from the first amino acid of the mature region) is tryptophan.

The term "glucoamylase" (1,4-alpha-D-glucan glucohydrolase, EC 3.2.1.3) is defined as an enzyme, which catalyzes the release of D-glucose from the non-reducing ends of starch or related oligosaccharide and polysaccharide molecules. For purposes of the present invention, glucoamylase activity is determined according to the procedures described in the Examples herein, for example the Starch Assay to determine glucoamylase activity in Example 3.

The term "coding sequence" refers to a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The term "expression" includes any step involved in the production of a variant glucoamylase described herein, including, but not limited to, transcription, post-transcriptional modification, translation, post-translational modification, and secretion.

The term "expression vector" refers to a linear or circular DNA molecule that comprises a polynucleotide encoding a variant and is operably linked to control sequences that provide for its expression.

The term "fragment" means a polypeptide having one or more (e.g., several) amino acids absent from the amino and/or carboxyl terminus of a mature polypeptide. A "glucoamylase fragment" herein means a portion of an amino acid sequence depicted herein that maintains maintains glucoamylase activity. As shown in FIG. 1, the parental glucoamylase enzyme of the invention (G6P) comprises a SBD and a catalytic domain. In some applications, particularly for starch processing, both domains are desirable. In other applications, only the catalytic domain is desired. In one aspect, a fragment contains at least 250, at least 300, at least 350, or at least 400 amino acid residues, comprising the catalytic domain and having one or more of the substitutions/truncations according to the invention. In some embodiments, the fragment is at least 380, at least 390, at least 400, at least 410 or at least 420 amino acid residues. In some embodiments, the fragment is at least 405, at least 406, at least 407, at least 408, at least 409, at least 410, at least 411, at least 412, at least 413, at least 414, or at least 415 amino acid residues.

The term "host cell" refers to any cell type that is susceptible to transformation, transfection, transduction, or the like with a nucleic acid construct or expression vector comprising a polynucleotide of the present invention, and that allows for expression of the enzyme. The term "host cell" encompasses any progeny of a parent cell that is not identical to the parent cell due to mutations that occur during replication. In many embodiments, the host cell is not a *Thielaviopsis* punctuala cell; that is, the glucoamylase of the invention (including both the wild type sequence of SEQ ID NO:25 and variant enzymes described herein) are not produced in the endogenous host.

The term "improved property" refers to a characteristic associated with a variant glucoamylase enzyme described herein that is improved compared to the parent glucoamylase enzyme. Such improved properties include, but are not limited to, thermoactivity, specific activity, reduced glucose inhibition, reduced isomaltose forming activity, increased activity on maltodextrin DE11-14, increased thermostability (e.g., increased stability at higher temperature), and increased pH stability (e.g., increase stability at higher pH). A further improved property is increased EtOH yield when the variant glucoamylase enzymes is applied in saccharification followed by fermentation on a liquefied mash.

The term "isolated" refers to a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance, etc.). With specific reference to isolated glucoamylases having SEQ ID NO:25, the isolated glucoamylase is generally either: a) purified away from other proteins with which it is normally associated, for example when it is produced in *T. punctuala* but at least some of the other secreted proteins are removed or the host cells are removed; b) when the enzyme is in a concentration not found in nature, or c) when the enzyme is produced in a host cell that is not *T. punctuala*.

The term "mature polypeptide" means a polypeptide in its final form following translation and any post-translational modifications, such as N-terminal processing, C-terminal truncation, glycosylation, phosphorylation, etc.

The phrase "mature polypeptide coding sequence" refers to a polynucleotide that encodes a mature polypeptide having glucoamylase activity.

The term "nucleic acid construct" refers to a nucleic acid molecule, either single-stranded or double-stranded, which is isolated from a naturally occurring gene or is modified to contain segments of nucleic acids in a manner that would not otherwise exist in nature or which is synthetic, and which comprises one or more control sequences.

The term "operably linked" refers to a configuration in which a construct sequence is placed at an appropriate position relative to the coding sequence of a polynucleotide such that the control sequence directs, allows or facilitates expression of the coding sequence.

The terms "parent" or "parent glucoamylase" refer to a glucoamylase to which an alteration is made to produce the variant glucoamylases of the present invention. The parent may be a naturally occurring (wild-type) polypeptide or a variant or fragment thereof. Exemplary parent polypeptides of the present invention are SEQ ID NO:13, SEQ ID NO:15 and SEQ ID NO:25.

The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the-nobrief option) is used as the percent identity and is calculated as follows:

$$(\text{Identical Residues} \times 100)/(\text{Length of Alignment} - \text{Total Number of Gaps in Alignment})$$

For clarity, the alignment is done using the length of the shorter sequence, and the sequence identity is calculated after sequence alignment is done.

The term "subsequence" refers to a polynucleotide having one or more (e.g., several) nucleotides absent from the 5'- and/or 3'-end of a mature polypeptide coding sequence; wherein the subsequence encodes a fragment having glucoamylase activity. In one aspect, a subsequence encodes at least the catalytic domain of the variant according to the invention.

The term "variant" refers to a polypeptide having glucoamylase activity and which comprises an alteration, i.e., a substitution, insertion, truncation and/or deletion, at one or more (e.g., several) positions. A substitution means replacement of the amino acid occupying a position with a different amino acid; a truncation means an elimination of an amino acid sequence starting from a particular position to the C-terminal; a deletion means removal of the amino acid occupying a position; and an insertion means adding an amino acid adjacent to and immediately following the amino acid occupying a position.

The term "wild-type" glucoamylase means a glucoamylase expressed by a naturally occurring microorganism, such as a bacterium, yeast, or filamentous fungus found in nature. In general, the wild-type glucoamylase of most interest herein is SEQ ID NO:25.

III. Glucoamylases of the Invention

The invention provides thermostabile and/or thermoactive glucoamylases for use in a variety of applications, including feed supplements and starch processing. The invention provides compositions and methods using a *Thielaviopsis punctuala* glucoamylase, SEQ ID NO:25, as well as variants there of, as more fully described below.

IV. Variant Glucoamylases of the Invention

Accordingly, the present invention provides variant glucoamylases with improved activity that can be used in a variety of applications, including saccharification reactions, animal and human nutritional and feed products and the production of biofuels such as bioethanol.

In general, the variant glucoamylases of the invention have modified, improved biochemical properties as compared to the wild type parental G16 glucoamylase (SEQ ID NO:25), G6P (SEQ ID NO:13) or G7P (SEQ ID NO:15) glucoamylase. The wild type G16 glucoamylase (SEQ ID NO:25) of the present invention is the wild type gluocoamylase, or "G1P" as set forth in SEQ ID NO:1 of the U.S. Patent Application Publication US 2018/0037879, hereby incorporated by reference in its entirety. The G6P mature protein (SEQ ID NO:13) of the present invention is the "G6P" (which comprises the set of amino acid substitutions of K23R/S30P/S39A/L44I/T49R/N51D/A111G/A117V/L119M/Q121P/T309D/N413S/A415Y/Q423P as compared to the wild type G16 glucoamylase) of the U.S. Patent Application Publication US 2018/0037879, hereby incorporated by reference in its entirety. The biochemical properties of the variant glucoamylases that can be improved herein include, but are not limited to, pH activity, pH stability, thermostability, specific activity, activity and thermoactivity, expression, secretion, formulation stability (including liquid, solid and pellets), performance in animals and/or animal feed and protease stability.

The variant glucoamylases of the invention have one or more improved properties as compared to a parent glucoamylase, such as a wild type (SEQ ID NO:25), G6P (SEQ ID NO:13) or G7P (SEQ ID NO:15) glucoamylase. By "improved" herein is meant a desirable change of at least one biochemical property. "Improved function" can be measured as a percentage increase or decrease of a particular activity, or as a "fold" change, with increases of desirable properties (e.g. thermoactivity, pH stability, thermostability) or decreases of undesirable properties (e.g. protease sensitivity). That is, a variant glucoamylase may have a 10% increase in thermostability or a 10% decrease in protease sensitivity, as compared to a parent glucoamylase. Alternatively, a variant glucoamylase may have a 2-fold increase in pH stability or a 3-fold decrease in protease sensitivity. In general, percentage changes are used to describe changes in biochemical activity of less than 100%, and fold-changes are used to describe changes in biochemical activity of greater than 100% (as compared to the parental enzyme, in many cases G6P or G7P). In the present invention, percentage changes (usually increases) of biochemical activity of at least about 10%, 20%, 30%, 40%, 50%, 60%, 70%, 80%, 90%, 95%, 98% and 99% can be accomplished. In the present invention, a "fold increase" (or decrease) is measured as compared to the starting or parent enzyme. For example, as shown in the FIG. 3B, a variant G6P protein, F555R, has a 1.70 fold increase in thermoactivity improvement as compared to G6P: this is calculated by [(thermoactivity of variant)/(thermoactivity of parent)]. In many embodiments, the improvement is at least one and a tenth fold (1.1), one and a half fold (1.5 fold), 2 fold, 3 fold, 4 fold, 5 fold, 6 fold, 7 fold, 8 fold, 9 fold, or 10 fold or higher.

The variant glucoamylases of the invention can have an improvement one or more of a number of biochemical properties, including, but not limited to, pH activity, pH stability, thermostability, specific activity, activity and thermoactivity, expression, secretion, formulation stability (including liquid, solid and pellets), performance in animals and/or animal feed and/or protease stability. In general, improvements are measured as compared to the parental wildtype, G6P or G7P enzyme using a glucoamylase activity assay, as outlined below, under conditions that challenge the variant glucoamylase against the parental enzyme.

A. Starch Assay to Determine Glucoamylase Thermoactivity

In some embodiments, a starch assay is employed to determine glucoamylase thermoactivity, such as the one described in the Examples section. Specifically, 115 µl of 2% heated soluble starch in pH 4.3 buffer (final starch concentration of 1.5%) is added to 96 deep well plates. 10 µl of supernatant enzyme is added to the starch reaction plates (see, for example, Example 6). The plates are incubated at 30° C. or 60° C., 400 rpm for 72 hrs. At 72 hrs, 10 µL of the incubated sample is added to 90 L of water for 10× detection dilution for reaction plates incubated at 30° C. and 60° C. From 10× detection dilution plate, transfer 10 µL of diluted samples and add 190 µL of GOPOD (glucose oxidase/peroxidase) and incubated for 30 minutes at 50° C. with 400 rpm agitation. Absorbance is read at 510 nm to determine glucose released due to breakdown of starch. Activity of a glucoamylase variant is compared to the parent glucoamylase enzyme under the same conditions to determine activity improvement. In some embodiments, the parent glucoamylase enzyme is a polypeptide of SEQ ID NO:25. In some embodiments, the parent glucoamylase enzyme is a polypeptide of SEQ ID NO:13. In some embodiments, the parent glucoamylase enzyme is a polypeptide of SEQ ID NO:15.

Accordingly, as shown in the FIGS. 3 and 4, a number of variant glucoamylases of the invention exhibit increased thermoactivity.

B. Thermostability

In many embodiments, the variant glucoamylases of the invention have increased thermostability, particularly under the conditions used in starch processing, such as saccharification, as is more fully outlined below. Thermostability is also a consideration in the production of animal and human feeds, for example, which frequently use high temperatures during the pelleting process for periods of time that traditionally inactivate wild type glucoamylases. "Thermostability" in this context means that the variant enzymes are more stable than the parent glucoamylase (e.g. wild type, G6P or G7P) under the same thermal challenge conditions, that is, the activity of the variant is higher than that of the parent enzyme under identical conditions (generally using the glucoamylase assay as outlined herein and as shown in the Examples).

A suitable thermostability assay is as follows. 50 µl of the enzymes from the lysate plates are added to 96 well Biorad PCR plates and are challenged at 57° C. (for G1), 59° C. (for G2), 62° C. (for G3), 67° C. (for G4) and 72° C. (for G5) in thermocyclers for 10 minutes. Following the 10 minutes incubation, 20 µl of the challenged lysate is added to 96 deep well starch reaction plates containing 150 µl of 2% corn starch in 0.1M sodium acetate, pH 4.5 (final starch concentration of 1.5%). The final volume is adjusted to 200 µl using 0.1M sodium acetate buffer, pH 4.5. The plates are incubated at 40° C., 800 rpm for 21-48 hrs. At 21-48 hrs, the plates are centrifuged at 4000 rpm for 5 minutes and 20 µl of reaction supernatant is taken out into 96 well shallow microtiter plates and 180 µl of D-Glucose assay reagent (GOPOD assay kit from Megazyme, Catalogue #K-GLUC) is added to each well. The plates are then incubated at 50° C. for 30 minutes. Following the incubation, the plates are read at 510 nm to monitor glucose released due to breakdown of starch. Activity of Glucoamylase variant is compared to the parent under the same conditions to determine thermo stability improvement.

In additional embodiments, when the enzyme is used in carbohydrate processing such as saccharification, the enzymes are generally more stable in the presence of the starch substrate. Thus, in these embodiments, the reactions are generally measured in days, with the variant glucoamylases showing significant stability at 24 hours, 48 hours and 72 hours at 60° C. in the presence of substrates as outlined below.

Taken together, the variant glucoamylases of the invention can exhibit increased thermostability as compared to a parent glucozylases (e.g. wild type, G6P or G7P) at 30° C., 35° C., 40° C., 45° C., 50° C., 55° C., 58° C., 60° C., 65° C., 66° C., 70° C., 75° C., 80° C. and/or 85° C. for a period of time, generally ranging from about 10 minutes to 72 hours, with 24, 45, 48 and 72 hours finding particular use in the invention.

C. pH Stability

In many embodiments, the variant glucoamylases of the invention have altered pH activity or stability as compared to the parent glucoamylase. "Increased pH stability" in this context means that the variant enzymes are more stable than the parent glucoamylase (e.g. wild type, G6P or G7P) under the same pH challenge conditions, that is, the activity of the variant is higher than that of the parent under identical conditions (generally using the glucoamylase assay as outlined herein and as shown in the Examples). For example, starch processing can be done at a variety of pHs, depending on the raw substrates and reaction conditions.

D. Specific Activity Assays

In some embodiments, the variant glucoamylases of the invention have increased specific activity as compared to a parent glucoamylase (e.g. wild type, G6P or G7P). By "specific activity" herein is meant the activity per amount of enzyme, generally determined by dividing the enzymatic activity of a sample (sometimes measured in "glucoamylase units") by the amount of glucoamylase enzyme, generally determined as is known in the art.

E. Protease Susceptibility

In some embodiments, the variant glucoamylases of the invention are less susceptible to protease degradation than the parent enzyme under identical conditions. In some cases, protease degradation during the production of variant glucoamylases in a production host organism by protease enzymes produced by the host organism can be a problem, thus resulting in lower yield of active enzyme. Similarly, depending on the use of the variant enzymes, for example in starch processing, there may be other proteases present in the raw substrates or other enzymes for use in combination that can degrade the glucoamylase during the starch processing.

This is generally determined as is known in the art, for example by allowing proteolytic degradation and then doing N-terminal sequencing on the resulting fragments to determine the cleavage site(s). In some cases, depending on the variant and the host production organism, there may not be significant proteolytic degradation.

As needed, as will be appreciated by those in the art, the specific mutations that can be made will depend on the endogenous proteases that the host organism produces, and also generally occurs in surface exposed loop structures or turns that are therefore accessible to proteases. For example, production of glucoamylases in *A. niger* fungal production organisms can lead to proteolytic degradation; see Wyss et al., Appl. And Environ. Microbiol. February 1999:359-366, hereby incorporated by reference in its entirety.

V. Specific Variant Glucoamylases

The present invention provides variant glucoamylase enzymes comprising at least one amino acid substitution and/or an amino acid truncation as compared to a parent glucoamylase. In some embodiments, the parent glucoamylase is a wild type glucoamylase (SEQ ID NO:25). In one embodiment, the variant glucoamylase enzyme is G6P comprising amino acid substitutions K23R/S30P/S39A/L44I/T49R/N51D/A111G/A117V/L119M/Q121P/T309D/N413S/A415Y/Q423P as compared to the wild type glucoamylase (SEQ ID NO:25). In another embodiment, the variant glucoamylase enzyme is G7P comprising amino acid substitutions K23R/S30P/S39A/L44I/T49R/N51D/A111G/A117V/L119M/Q121P/T309D/N413S/A415Y/Q423P, and further comprising a C-terminal amino acid truncation at position 493 as compared to the wild type glucoamylase (SEQ ID NO:25). In some embodiments, the parent glucoamylase is G6P. In some embodiments, the parent glucoamylase is G7P.

The present invention provides variant glucoamylase enzymes comprising an amino acid truncation at a position number selected from the group consisting of 493, 500, 502, 503, 506, 509, 510, 513, 514, 515, 519, 520, 522, 524, 525, 544, 549, 550, 551, 556, 558, 560, 563, 564 and 569. In some embodiments, the amino acid truncation described herein is a C-terminal amino acid truncation at a position number selected from the group consisting of 493, 500, 502, 503, 506, 509, 510, 513, 514, 515, 519, 520, 522, 524, 525, 544, 549, 550, 551, 556, 558, 560, 563, 564 and 569. In one embodiment, the variant glucoamylase enzyme comprises a C-terminal amino acid truncation at position 493, forming the G7P mature protein without the SBD as set forth in SEQ ID NO:15.

In some embodiments, the invention provides a composition comprising a variant glucoamylase enzyme, wherein the variant glucoamylase exhibits at least 95% identity to SEQ ID NO:15, wherein said variant glucoamylase enzyme has at least 1.1 fold better activity as compared to SEQ ID NO:25 under a condition selected from the group consisting of thermoactivity at about 30° C., thermoactivity at about 35° C., thermoactivity at about 40° C., thermoactivity at about 50° C., thermoactivity at about 60° C. and thermoactivity at about 70° C. In some embodiments, the variant glucoamylase exhibits at least 96%, 97%, 98%, 99% or 100% identity to SEQ ID NO:15, wherein said variant glucoamylase enzyme has at least 1.1 fold better activity as compared to SEQ ID NO:25 under a condition selected from the group consisting of thermoactivity at about 30° C., thermoactivity at about 35° C., thermoactivity at about 40° C., thermoactivity at about 50° C., thermoactivity at about 60° C. and thermoactivity at about 70° C.

In some embodiments, the present invention provides variant glucoamylase enzymes comprising an amino acid substitution at one or more (e.g., several) positions corresponding to positions 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492 as compared to a parent glucoamylase enzyme. In some embodiments, the variant glucoamylase enzyme has at least 95%, at least 96%, at least 97%, at least 98%, or at least 99% sequence identity to the parent polypeptide (e.g. SEQ ID NO:13, SEQ ID NO:15 or SEQ ID NO:25). In some embodiments, the parent glucoamylase enzyme is SEQ ID NO:15.

In some embodiments, the present invention provides variant glucoamylase enzymes comprising at least one amino acid substitution as compared to SEQ ID NO:15, wherein said amino acid substitution is at a position number selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, wherein said variant enzyme is at least 95% identical to SEQ ID NO:15. In some cases, the variant enzyme can comprise 1, 2, 3, 4, 5, 6, 7, 8, 9, 10, 11, 12, 13, 14, 15, 16, 17, 18, 19 or 20 amino acid substitutions at these positions.

In some embodiments, the present invention provides variant glucoamylase enzymes comprising at least one amino acid substitution as compared to SEQ ID NO:15, wherein said amino acid substitution is at a position number selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, wherein said variant glucoamylase enzyme has at least 1.1 fold better activity as compared to SEQ ID NO:15 under a condition selected from the group consisting of thermoactivity at about 30° C., thermoactivity at about 35° C., thermoactivity at about 40° C., thermoactivity at about 50° C., thermoactivity at about 60° C. and thermoactivity at about 70° C.; and wherein said variant enzyme is at least 95% identical to SEQ ID NO:15. In some cases, the variant enzyme can comprise 1, 2, 3, 4, 5, 6, 7, 8, 9, 10, 11, 12, 13, 14, 15, 16, 17, 18, 19 or 20 amino acid substitutions at these positions.

In some embodiments, the present invention provides the variant glucoamylase enzyme as described herein exhibiting at least 96%, 97%, 98%, or 99% identity to SEQ ID NO:15.

In some embodiments, the present invention provides the variant glucoamylase enzyme as described herein, wherein said amino acid substitution(s) occur at one of said positions, two of said positions, three of said positions, four of said positions, five of said positions, six of said positions, seven of said positions, eight of said positions, nine of said positions, ten of said positions, eleven of said positions, twelve of said positions, thirteen of said positions or fourteen of said positions.

In further embodiments, the present invention provides variant glucoamylase enzymes as described herein, wherein said amino acid substitution is at a position number selected from the group consisting of 5, 68, 188, 321, 419, 422, 7, 11, 19, 26, 31, 42, 44, 49, 53, 55, 57, 69, 72, 73, 78, 79, 85, 86, 88, 89, 92, 93, 94, 97, 98, 103, 106, 118, 119, 125, 141, 145, 149, 150, 153, 155, 161, 168, 170, 171, 178, 179, 186, 195, 204, 205, 208, 209, 213, 214, 219, 220, 224, 227, 246, 247, 256, 261, 262, 306, 307, 309, 311, 317, 342, 347, 348, 352, 353, 355, 362, 364, 370, 374, 381, 382, 388, 391, 394, 395, 399, 400, 407, 412, 418, 434, 436, 437, 440, 446, 452, 453, 460, 469, 470, 472, 475, 476, 478, and 492.

In additional embodiments, the present invention provides variant glucoamylase enzymes as described herein, wherein said amino acid substitution(s) is selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, T400L, Y412F, L420K, A422G, P423G, P423R, P423V, G457S, A491V, K5P, K5S, K5T, K5Y, K5Q, K5N, K5H, E68K, E68Y, E68S, S188T, S188H, Y321F, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453A, A460S, A469S, A470T, S472T, G475V, T476W, G478S, L492P, and L9P.

In some embodiments, the present invention provides variant glucoamylase enzymes as described herein, wherein said amino acid substitution(s) is selected from the group consisting of K5P, K5S, K5T, K5Y, K5Q, K5N, K5H, E68K, E68Y, E68S, S188T, S188H, Y321F, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, T98S, S103D, D106T, D118N, M119E, A125P, M141L, Y145A, L149I, N150D, A153S, T155A, Q161P, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, A262S, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Y412F, Q418T, S434T, T436S, E437A, D440Q, G446S, A452A, V453S, A460S, A469S, A470T, S472T, G475V, T476W, G478S, L492P.

In some embodiments, the present invention provides variant glucoamylase enzymes as described herein, wherein the variant glucoamylase enzymes comprise one or more (e.g., several) substitutions selected from the group consisting of S188H/Y321W/Q419P, K5T/S188T, K5T/E68K/S188H, K5Y/S188H, K5Q/E68K/S188T, K5N/E68Y/S188T, K5H/S188H, K5S/E68Y/S188H, K5S/E68Y/S188T, K5Y/E68Y, K5S/E68S/S188T, K5H/E68S/S188H, K5H/E68K/S188T, K5P/S188H, K5Y/E68K, K5T/S188H, K5S/S188H, E68Y/S188H, E68Y/S188T, K5T/Y321F, K5Q/S188H/Q419P, K5P/E68Y/S188T/A422S, K5N/S188H/Q419P, Y321W/A422S, E68K/Q419P, E68S/S188T/Y321W/A422S, K5Q/Q419P/A422S, S188T/Y321F, S188T/Q419P/A422S, K5H/S188T/Q419P/A422S, K5H/A422S, S188H/Y321W, Q419P/A422S, K5N/A422S, E68Y/S188H/Y321F/Q419P, K5Q/S188H, E11S/Y55F/M141L/N168S/T388Q, E11S/T31N/Y55F/M141L/N168S/T388Q, L19I/A195V, M141L/N168S/Y227F/T362Q/T388Q/D440Q, E11S/M141L, E11S/L19I/I44V/Y145A/T155A/D309S/L311V/Y412F/S472T, D309S/L311V, E11S/L19I/T31N/Y55F/A125P/N168S/Y227F, L19I/D309S/L311V/Y412F/A460S/S472T, E11S/L19I/N168S/Y227F/D309S/L311V/D440Q, L19I/Y412F, E11S/L19I/Y145A/A460S/S472T, E11S/M141L/N168S/D309S/L311V/T362Q/L364I/Y412F/A460S/S472T, E11S/Y55F/M141L/N168S/L311V/T362Q/L364I/A460S/S472T, E11S/L19I/Y55F/M141L/N168S/Y227F, L19I/T155A/A407S/Y412F/S472T, D53N/L149I/N150D/P186E/A317P, V42I/S103D/D106T/P186E/A317P/S434T/G478S, A317P/G478S, C26N/V42I/L149I/A317P/S355D/A374N, V42I/S103D/D106T/A317P, D53N/S434T, /S103D/A317P/V342I, A256V/A317P, V42I/P186E, A317P/V342I/G478S, I224V/A256V/A317P/G478S, V42I/L149I/N150D/A317P/G478S, V42I/S103D/P186E/A317P/V342I/S355D/A374N/A391G, P186E/A317P/G478S, D53N/G446S, A256V/A317P/G478S, V42I/D53N/T57S/L149I/A317P/G478S, C26N/V42I/D53N/T57S/N150D/P186E/A317P/V342I/G478S, V42I/S355D, V42I/N150D/P186E/A317P, V42I/S434T/G478S, C26N/D53N/T57S/S103D/Q161P/A317P/G478S, V42I/A256V/A317P/S434T, V42I/S103D/A317P/A391G/G478S, E68Y/I69L/G178T/Y179F/S213T/H214C, E68Y/I69L/E85Q/N86Q/F394Y7V395L, E68Y/I69L, D118N/M119E, E68Y/I69L/V97I/T98S/A246S/S247G/T261G/A262S/L347N/E348I, E68Y/I69L/S452A/V453S, E68Y/I69L/S452A/V453S, E68Y/I69L/E85Q/N86Q/L347N/E348I/Q418T/Q419P, E68Y/I69L/E85Q/N86Q/S204N/T205A/A208T/K209R/E381N/S382D/Q418T/Q419P/A469S/A470T, E381N/S382D/Q418T/Q419P/T436S/E437A/A469S/A470T, Q418T/Q419P/A469S/A470T, V170I/A171T/E381N/S382D/Q418T/Q419P/A469S/A470T, F394Y/V395L/Q418T/Q419P/T436S/E437A/A469S/ A470T, T78K/L79D/Q418T/Q419P/A469S/A470T, E68Y/I69L/V88I/T89S/T352S/V353I/Q399E/T400K/A469S/A470T, S72A/V73F/A153S/S306A/T476W, T370V/G475V, R49H/S72A/V73F/A92T/Y93K/A153S/S306A/T476W, E68Y/I69L/T219S/V220Q/A307E/S355D/L492P, E11S/V42I/L149I/I224V/A317P/T388Q/A460S/G478S, Y412F/Q418T/Q419P/A469S/A470T/, L19I/D53N/I69L/V88I/S188H/A195V/Y321W/Y412F, V42I/D118N/M119E/T261A/L311V/Y321W/S355D, E11S/T57S/T89S, E11S V42I/L79Y/D118N/M141L/L311V/A317P/Y321F, V42I/D53N/E68Y/A317P/L347N, I69L/S188H/A195V/A317P/Y321F/L364I/S434T, T57S/A195V/T261A/L311V/Y321F/L347N/E348I/S434T, E11S/V42I/T57S/E68Y/S188H/A195V/T261A, T57S/N168S/T261A/A317P/Y321W/V395L/Y412F, E11S/D53N/E68Y/D118N/S188H/A195V/Y412F/Q419P, E11S/V42I/D118N/M141L/N168S/Y321W/Y412F, E11S/D53N/T57S/E68Y/T89S/E381N/Y412F/Q419P/S434T, E11S/D53N/T57S/V88I/T89S/S188H/A195V/L311V/L347N/Y412F, A317P/Y412F, I69L/T89S/L311V/A317P/Y321F/Y412F/S434T, V42I/D53N/T57S/E68Y7V88I/Y412F, E11S/T57S/V88I/M141L/T261A/Y321W/L364I/Y412F, V42I/I69L/S188H/A317P/Y321F/Y412F, E11S/V42I/D53N/T57S/L79Y/T89S/L311V/Y321W/Y412F, L19I/M141L/N168S/S188H/A195V/L311V/S355D/S434T, S188H/A195V/T261A/L311V/Y321F/L347N/E348I, E11S/L19I/D53N/T57S/N168S/L347N, E11S/I69L/M119E/A195V/T261A/A317P/Y321F/L347N/Y412F, L79Y/V88I/T261A/A317P/Y321F/L364I/Y412F, E11S/V42I/E68Y/T89S/L311V/Y321F/T388Q/F394Y/V395L/Q419P, D53N/E68Y/V88I/M141L/N168S/Y321W/Y412F, E11S/I69L/L311V/A317P/Y321F/L347N/Y412F, D53N/T57S/M141L, D53N/V88I/T89S/D118N/E348I/S355D, E11S/S188H/A195V/A317P/L347N/E348I/Y412F/Q419P/S434T, E11S/D53N/I69L/V88I/A317P/Q419P, E68Y/I69L/V88I/N168S/L364I/Q419P, E11S/V42I/V88I/T261A/Y321F/E348I/S355D, E11S/V42I/T57S/I69L/A195V/L347N/E348I/S355D, L19I/T89S/A317P/Y321F/S434T, E11S/V42I/L79Y/L311V/A317P/Y321W/L347N/E348I/L364I/Y412F, D53N/T57S/L347N/E348I/Y412F, D53N/T57S/E68Y/L79Y/Y412F/S434T, L19I/V88I/T89S/A317P, M119E/M141L/N168S/L311V/Y321F, E11S/T89S/Y321W, E11S/M141L/T261A/A317P/Y412F/S434T, V42I/L79Y/S188H/A195V/L311V/Y321F/S355D, V42I/E68Y/V88I/T261A/Y321W/L347N/E348I, L19I/E68Y/I69L/M141L/Y321F/L347N/S355D/E381N/Y412F, V42I/D53N/I69L/L79Y/D118N/T261A/L311V/A317P/Y321F/L347N/Y412F, E68Y/S355D/L364I/S382D/T388Q/Q419P, E11S/L19I/V42I/E68Y/I69L/D118N/M141L/Y321W/L347N, /E11S/V42I/E68Y/M141L/A317P/Y321F/E348I/S355D, E11S/V42I/E68Y/I69L/V88I/T89S/D118N/M119E/S188H/A195V/A317P/L347N/Y412F/Q419P, V42I/V88I/L311V/A317P/Y321F/L347N/E348I/T388Q/V395L/S434T, T261A/A317P/Y321W/E348I, E11S/V42I/E68Y/I69L/D118N/M119E/Y412F, E11S/V42I/T57S/I69L/L311V, V42I/Y412F, E11S/L19I/E68Y/M119E/N168S/Y412F/Q419P, L19I/L311V/Y412F, E11S/V42I/M119E/Y412F, E11S/L19I/V42I/D53N/S188H/A195V/L311V/Y321F/Y412F, E11S/L19I/V42I/T57S/D118N/N168S/L311V/Y412F, L19I/V42I/D53N/T57S/N168S/A317P/Y321W/Y412F, D53N/T57S/E68Y/N168S/S188H/A195V/L311V/Y321W/Y412F/Q419P, L19I/D53N/T57S/L311V/Y321W/Y412F, E11S/T57S/Y321W/Y412F/Q419P, D53N/S188H/A195V/L311V/Y412F, V42I/D53N/S188H/A195V/L311V/Y321F/Y412F, L19I/M119E/N168S/S188H/A195V/L311V/Y412F/Q419P, E11S/V42I/S188H/A195V/L311V/A317P/Y321W/Y412F/Q419P, E11S/V42I/M119E/N168S/L311V/Y412F, E11S/V42I/N168S/L311V/A317P/Y321W/

Y412F/Q419P, E11S/V42I/D53N/E68Y/S188H/A195V/ L311V/A317P/Y321F/Y412F, E11S/L19I/D53N/N168S/ A195V/Y412F/Q419P, E11S/L19I/V42I/L311V/Y412F, V42I/D53N/N168S/L311V/Y412F, E11S/L311V/Y412F, E11S/D53N/T57S/L311V/Y321W/Y412F, E11S/L311V/ Y321W/Y412F, E11S/V42I/I69L/D118N/N168S/L311V/ A317P/Y412F/Q419P, E11S/L19I/V42I/E68Y/Y412F/ Q419P, E11S/L19I/D53N/L311V, E11S/L19I/V42I/L311V/ Y412F/Q419P, L19I/V42I/D53N/T57S/I69L/N168S/ S188H/A195V/L311V/A317P/Y321W, E11S/L19I/V42I/ T57S/L311V/A317P/Y321F/Y412F, L19I/V42I/I69L/ D118N/N168S/L311V/Y321W/Y412F/Q419P, E11S/V42I/ D53N/E68Y/S188H/A195V/Y412F, E11S/L19I/V42I/ D53N/T57S/N168S/L311V/Y321W/Y412F, E11S/V42I/ L311V/Y412F, E11S/L19I/V42I/N168S/A195V/L311V/ Y321F/Y412F, E11S/V42I/S188H/L311V/Y412F, L19I/ V42I/T57S/E68Y/M119E/S188H/A195V/L311V/Y321F/ Y412F, E11S/L19I/V42I/D53N/N168S/S188H/A195V, E11S/L19I/V42I/T57S/E68Y/A195V/L311V/Y321W, and E11S/L19I/V42I.

In one embodiment, the invention provides a variant glucoamylase enzyme as described herein, wherein said amino acid substitution is Y321F.

In a further embodiment, the invention provides a variant glucoamylase enzyme as described herein, wherein said amino acid substitutions are S188H/Y321W/Q419P.

In a further embodiment, the invention provides a variant glucoamylase enzyme as described herein, wherein said amino acid substitutions comprise Y321F, and further comprise at least one amino acid selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, T400L, Y412F, L420K, A422G, P423G, P423R, P423V, G457S, A491V, K5P, K5S, K5T, K5Y, K5Q, K5N, K5H, E68K, E68Y, E68S, S188T, S188H, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In a further embodiment, the invention provides a variant glucoamylase enzyme as described herein, wherein said amino acid substitutions comprise S188H/Y321W/Q419P and further comprise at least one amino acid selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, Y321F, T400L, Y412F, L420K, A422G, P423G, P423R, P423V, G457S, A491V, K5P, K5S, K5T, K5Y, K5Q, K5N, K5H, E68K, E68Y, E68S, S188T, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In some embodiment, the invention provides a C-terminally truncated variant glucoamylase enzyme of SEQ ID NO:13, wherein said truncation position is at a position number selected from the group consisting of 493, 500, 502, 503, 506, 509, 510, 513, 514, 519, 520, 522, 524, 525, 544, 549, 550, 551, 556, 558, 560, 563, 564 and 569.

In an additional embodiment, the invention provides a variant glucoamylase enzyme comprising at least one amino acid substitution as compared to SEQ ID NO:13, wherein said amino acid substitution is at a position selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 516, 518, 521, 522, 526, 533, 534, 535, 540, 542, 544, 545, 549, 550, 551, 555, 556, 557, 559, 563, 564, 569, 570, 581 584, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, and wherein said variant enzyme is at least 95% identical to SEQ ID NO:13. In some cases, the variant enzyme can comprise 1, 2, 3, 4, 5, 6, 7, 8, 9, 10, 11, 12, 13, 14, 15, 16, 17, 18, 19 or 20 amino acid substitutions at these positions.

In a further embodiment, the invention provides a variant glucoamylase enzyme comprising at least one amino acid substitution as compared to SEQ ID NO:13, wherein said amino acid substitution is at a position selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 516, 518, 521, 522, 526, 533, 534, 535, 540, 542, 544, 545, 549, 550, 551, 555, 556, 557, 559, 563, 564, 569, 570, 581 584, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, wherein said variant glucoamylase enzyme has at least 1.1 fold better activity as compared to SEQ ID NO:13 under a condition selected from the group consisting of thermoactivity at about 30° C., thermoactivity at about 35° C., thermoactivity at about 40° C., thermoactivity at about 50° C., thermoactivity at about 60° C. and thermoactivity at about 70° C.; and wherein said variant enzyme is at least 95% identical to SEQ ID NO:13. In some cases, the variant enzyme can comprise 1, 2, 3, 4, 5, 6, 7, 8, 9, 10, 11, 12, 13, 14, 15, 16, 17, 18, 19 or 20 amino acid substitutions at these positions.

In some embodiments, the present invention provides the variant glucoamylase enzyme as described herein exhibiting at least 96%, 97%, 98%, or 99% identity to SEQ ID NO:13.

In some embodiments, the present invention provides the variant glucoamylase enzyme as described herein, wherein said amino acid substitution(s) occur at one of said positions, two of said positions, three of said positions, four of said positions, five of said positions, six of said positions, seven of said positions, eight of said positions, nine of said positions, ten of said positions, eleven of said positions, twelve of said positions or thirteen of said positions.

In additional embodiments, the present invention provides variant glucoamylase enzymes as described herein, wherein said amino acid substitution(s) is selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321F, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In additional embodiments, the present invention provides variant glucoamylase enzymes as described herein, wherein said amino acid substitution(s) is selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321F, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, L9P, E11S, L19I, V42I, D53N, T57S, I69L, L79Y, V88I, T89S, D118N, M119E, M141L, N168S, A195V, T261A, L311V, A317P, L347N, E348I, S355D, L364I, E381N, S382D, T388Q, F394Y, V395L and S434T.

In some embodiments, the present invention provides variant glucoamylase enzymes as described herein, wherein the variant glucoamylase enzymes comprise one or more (e.g., several) substitutions selected from the group consisting of S188H/Y321W/Q419P, T98S/Q161P/F516L, T98S/Q161P/N570P, T98S/Q161P, T550D/F555S, V65I/Y412F/Y503S/S518I, Y412F/Y503S/I564T, Y412F/Y503E, Y412F/Y503E/S518I, V65I/Y412F/Y503S, V65I/Y503E, Y503D/S518I/I564N, Y503E/S518L, V65I/Y503E/S544Q, V65I/Y503S, Y503E/S544E, V65I/Y503E/S544E/I564N, V65I/Y412F/Y503E, Y503E/S518I/S544Q, V65I/Y503E/S518M, Y412F/S518L, Y503E/S544Q, V65I/Y412F/Y503E/S544E/I564T/G569I, Y412F/Y503S, Y503E/I564T, S549D/F555D/G559N, S549D/F555R, K508T/L526N/S549D/G559N, K508T/G559N, F555D/I556P/G559N, S549D/F555R/I556P/G559N, F555R/I556P, L526I/F555R/I556P, F555R/I556P/G559N, K508T/I556P/G559N, F555D/I556P, K508T/L526N/A534T/S549D/I556P, K508T/L526I/S549D/G559N, K508N/L526I/S549E/F555L/G559N, L526N/S549D/F555D/I556P, L526I/F555D/G559N, A38V/F555R, A39F/T540N/T542N, L498T/T542N/T581N/T584N, T542N/T581N/T584N, S535Y/T542N, T540N/T584N, T540N/T542N/T581N/T584N, L498T/T581N/T584N, L498T/T584N, L498T/T542N, T542N/T581N, P121S/T542N/T584N, L498T/T542N, S535Y/T540N/T542N/T581N, Q419P/P423R, L79F/Q419P, Q419P/P423V, Q419P/P423R/T533R, S36P/Q419P, Q419P/P423G, S36P/T400L/Q419P/P423G, S50Q/Q419P/P423R, S50Q/Q419P/P423R/G457S/E497V/P521S, Y321F/A422S, S188H/Q419P, K5H/Y321W, K5N/Y321F, K5P/S188H, E68S/S188H/A422S, S188T/Y321F/Q419P/A422S, K5H/S188H/Y321F/A422S, S188H/Y321W/Q419P, S188H/A422S, S188H/A422S/V545A, K5Q/A422S, K5S/E68K/Y321W, K5H/Y321F/A422S, S188H/Y321W/Q419P, K5Y/A422S, Q419P/A422S, K5Y/S188H/A422S, K5T/A422S, K5T/Y321W, Y321W/A422S, Q419P/A422S, K5P/Y321F, K5H/S188H/Y321F/A422S, E68K/A422S, Y321F/A422S, K5H/Y321F, K5T/Y321F/Q419P/A422S, K5T/E68Y/S188T, K5S/E68Y/S188H, K5N/S188H, K5T/E68S/S188T, K5H/E68Y/S188P, K5P/E68Y/S188T, K5T/E68K/S188H, K5P/E68K/S188T, K5H/E68Y/S188T, K5T/S188H, K5T/E68N/S188T, K5Y/E68Y/S188T, K5S/E68Y/S188T, K5Q/E68K/S188H, K5P/E68N/S188H, K5P/E68N/S188T, K5P/E68Y/S188H, K5Y/E68Y/S188H, K5S/S188T, K5H/E68N/S188H, K5P/S188H, K5H/S46T/E68K/S188H, K5H/E68K/S188T, K5Q/E68Y/S188T, K5Y/E68N/S188H, V42I/S188H/A195V/Y412F/Q419P, L19I/V42I/E68Y/N168S/S188H/A195V/Y412F, E11S/V42I/T57S/D118N/N168S/S188H/A195V/L311V, E11S/V42I/D53N/E68Y/N168S/S188H/A195V/L311V/Y412F, E11S/L19I/V42I/I69L/Y321W/Y412F/Q419P, E11S/L19I/V42I/E68Y/D118N/S188H/A195V/L311V/Y412F, E11S/L19I/T57S/M119E/S188H/A195V/L311V/Y412F, E11S/V42I/A317P/Y412F/Q419P, L19I/T57S/I69L/D118N/N168S/S188H/A195V/L311V/A317P/Y321F/Y412F/Q419P, E11S/E68Y/S188H/A195V/L311V/Y412F, E11S/L19I/V42I/E68Y/I69L/D118N/N168S/S188H/A195V/L311V/Y412F, E11S/L19I/V42I/S188H/A195V/L311V/Y321W/Y412F/Q419P, E11S/L19I/N168S/S188H/A195V/L311V/A317P/Y321F/Y412F, E11S/V42I/E68Y/Y412F, E11S/L19I/V42I/E68Y/Y412F, E11S/V42I/E68Y/S188H/A195V/Y412F, E11S/L19I/V42I/T57S/I69L/S188H/A195V/L311V/Y321W/Y412F, E11S/L19I/D53N/E68Y/S188H/A195V/L311V/Y412F, E11S/V42I/E68Y/S188H/A195V/L311V/Y412F/Q419P, E11S/L19I/V42I/E68Y/S188H/A195V/L311V/A317P/Y321W/Y412F/Q419P, E11S/L19I/D53N/

I69L/S188H/A195V/L311V/Q419P, E11S/V42I/E68Y/ N168S/L311V/A317P/Y321W/Y412F, E11S/E68Y/I69L/ S188H/A195V/L311V/A317P/Y321F/Y412F, E11S/V42I/ T57S/E68Y/I69L/S188H/A195V/L311V/A317P/Y321F, E11S/D53N/T57S/L311V/Y321F/Y412F/Q419P, E11S/ L19I/S188H/A195V/L311V/A317P/Y321W/Y412F/ Q419P, E11S/L19I/I69L/S188H/A195V/L311V/A317P, E11S/V42I/I69L/N168S/S188H/A195V/L311V/A317P/ Y412F/Q419P, E11S/V42I/E68Y/S188H/A195V/L311V/ Y412F, E11S/V42I/I69L/S188H/A195V/L311V/A195V/ L311V/A317P/Y321F/Y412F, E11S/Y412F, E11S/L19I/ V42I/E68Y/I69L/S188H/A195V/Y412F, E11S/L19I/V42I/ D53N/T57S/S188H/A195V/L311V/Y321W/Y412F, V42I/ E68Y/Y412F, E11S/L19I/V42I/D53N/T57S/E68Y/I69L/ N168S/S188H/A195V/L311V/A317P/Y321F, E11S/L19I/ V42I/D53N/T57S/I69L/S188H/A195V/L311V/A317P/ Y321W/Y412F, E11S/V42I/A317P/Y321F, E11S/V42I/ T57S/E68Y/D118N/S188H/A195V/L311V/Y412F, E11S/ L19I/V42I/E68Y/I69L/D118N/N168S/S188H/A195V/ L311V/Y412F/Q419P, E11S/V42I/D53N/E68Y/S188H/ A195V/L311V/Y412F, E11S/I69L/D118N/S188H/A195V/ L311V/Y412F, V42I/D53N/T57S/E68Y/M141L/N168S/ T261A/Y321W/E381N/Y412F, E11S/V42I/S188H/L347N/ Y412F/S434T, D53N/T57S/E68Y/D118N/M119E/L311V/ E348I/Y412F, D118N/N168S/S188H/L347N/E348I/ S382D/T388Q/V395L, E68Y/I69L/N168S/S188H/A195V/ L311V/A317P/Y321W/Y412F/Q419P, E11S/E68Y/V88I/ A317P/Y321F/S355D, D53N/I69L/L79Y/M119E/T261A/ L311V/L347N/E348I/Q419P, V42I/E68Y/I69L/D118N/ M119E/M141L/L311V/A317P/Y321F/L347N, E11S/L19I/ E68Y/I69L/L79Y/M141L/N168S/T261A/A317P/Y321W/ L347N, E11S/V42I/E68Y/I69L/L311V/Y321W/S434T, E11S/V42I/D53N/N168S/L311V/A317P/Y321W, E11S/ E68Y/I69L/D118N/N168S/Y321F/Y412F, V42I/D53N/ T57S/L311V/Y321W/S355D/Y412F/Q419P, V42I/E68Y/ L311V/L347N/L364I/Y412F, E11S/D118N/M119E/ M141L/L311V/Y321W/L347N, V42I/D53N/T57S/M119E/ M141L/A317P/Y321F/Q419P, T57S/I69L/T89S/S188H/ A195V/T261A/L311V/A317P/Y321W/F394Y/Y412F, Y321F/Y412F, V42I/T57S/E68Y/I69L/T89S/M119E/ T261A/A317P/Y412F/S434T, E11S/V42I/E68Y/L311V/ A317P/S434T, V42I/D53N/T57S/E68Y/I69L/S434T, V42I/ E68Y/Y321W, L311V/L347N/E348I/S355D/L364I/S434T, E11S/D53N/T57S/E68Y/V88I/T89S/M119E/A317P/ Y321W, D53N/E68Y/I69L/T89S/L311V/A317P/S355D/ Q419P, V42I/E68Y/A317P/Y321F/Y412F, L19I/I69L/ T89S/L311V/A317P/Y321F/S355D/L364I/Y412F, V42I/ D53N/T57S/E68Y/I69L/M141L/S188H/A195V/L311V/ A317P/Y321F/Y412F/S434T, T57S/V88I/A317P/Y321W/ Q419P, E11S/L19I/V42I/D53N/E68Y/L311V/A317P/ Y321W/Y412F, E11S/V42I/D53N/E68Y/I69L/S188H/ A195V/E348I, L19I/V42I/T57S/I69L/V88I/M119E/ T261A/A317P/Y321F/Y412F, D53N/E68Y/D118N/ M119E/M141L/T261A/L347N/E348I/S355D/L364I/ S434T, E11S/T261A/L347N/E348I/S355D/S434T, M119E/ S188H/E348I, E11S/A317P/Y321F/L347N, E11S/E68Y/ I69L/T261A/L364I, D118N/M119E/N168S/S188H/A195V/ L311V/Y321W/L347N/F394Y, E11S/L311V/Y321W/ E348I/S355D/L364I/Y412F, V42I/D53N/T57S/I69L/V88I/ L347N/E348I/F394Y/V395L/S434T, E11S/D53N/T89S/ N168S/S188H/T261A/L311V/A317P/Y321W/S355D/ Y412F, L19I/V42I/D53N/L79Y/T89S/N168S/T261A/ L311V/Y321W/Y412F/Q419P/S434T, L79Y/V88I/D118N/ M119E/T261A/Y321F/L364I/Y412F, V42I/E68Y/T89S/ M141L/T261A/L311V/Y321F/E348I/L364I, V42I/E68Y/ D118N/S188H/T261A/Y412F/S434T, E11S/D53N/E68Y/ I69L/T89S/Y321W/E348I/S355D, M119E/L311V/Y321F, L311V/L347N/E348I, E11S/V42I/A317P/Y321F/L347N/ Y412F, EliS/L19I/V42I/E68Y/A317P/Y321F/L364I/ Y412F, D53N/E68Y/T89S/T261A, I69L/S188H/A195V/ L311V/A317P/Y321W/V395L/Y412F, V42I/D53N/E68Y/ V88I/T89S/D118N/L311V/Y412F/S434T, E11S/V42I/ E68Y/I69L/L311V/E348I, V42I/Y321W, E68Y/T261A/ L311V/L347N/E348I/S434T, E11S/E68Y/I69L/L79Y, V42I/D53N/E68Y/S188H/A195V/T261A/L311V/Y321F/ S355D/S434T, L19I/V42I/S188H/A195V/S382D/V395L/ Q419P, E11S/L19I/V42I/D53N/T57S/M119E/L311V/ Y321W/L347N/F394Y/Y412F, L9P/E11S/D53N/T57S/ E68Y/M119E/M141L/E348I/Y412F and L19I/V42I/I69L/ L311V/Y321W/L347N.

In one embodiment, the invention provides a variant glucoamylase enzyme as described herein, wherein said amino acid substitution is Y321F.

In a further embodiment, the invention provides a variant glucoamylase enzyme as described herein, wherein said amino acid substitutions are S188H/Y321W/Q419P.

In a further embodiment, the invention provides a variant glucoamylase enzyme as described herein, wherein said amino acid substitutions comprise Y321F, and further comprise at least one amino acid substitution selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In a further embodiment, the invention provides a variant glucoamylase enzyme as described herein, wherein said amino acid substitutions comprise S188H/Y321W/Q419P, and further comprise at least one amino acid substitution selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188P, S188T, S188W, T192A, K212Y, S215A, T258S, A262S, H264M, I298V, Y321F, Y321L, T400L, Y412F, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551F, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In an additional embodiment, the present invention provides a variant glucoamylase enzyme comprising at least one amino acid substitution as compared to SEQ ID NO:13 as described herein, and further comprising a C-terminal amino acid truncation at a position number selected from the group consisting of 493, 500, 502, 503, 506, 509, 510, 513, 514, 519, 520, 522, 524, 525, 544, 549, 550, 551, 556, 558, 560, 563, 564 and 569.

In some embodiments, the variant glucoamylase comprises an amino acid substitution of the Valine at position −20 as compared to G6P or G7P (see sequence at FIG. 1).

In some embodiments, the substitution is with any other of the 19 naturally occurring amino acids, with some embodiments not utilizing cysteine (due to possible disulfide formation) or proline (due to steric effects). In some embodiments, the amino acid substitution is V-20A, V-20F, V-20G, V-20I, V-20K, V-20L, V-20M, V-20Q, V-20R, V-20T, or V-20W.

In some embodiments, the variant glucoamylase comprises an amino acid substitution of the Leucine at position −18 as compared to G6P or G7P (see sequence at FIG. 1). In some embodiments, the substitution is with any other of the 19 naturally occurring amino acids, with some embodiments not utilizing cysteine (due to possible disulfide formation) or proline (due to steric effects). In some embodiments, the amino acid substitution is L-18F, L-18I, or L-18Y.

In some embodiments, the variant glucoamylase comprises an amino acid substitution of the Lysine at position −17 as compared to G6P or G7P (see G6P/G7P sequence at FIG. 1). In some embodiments, the substitution is with any other of the 19 naturally occurring amino acids, with some embodiments not utilizing cysteine (due to possible disulfide formation) or proline (due to steric effects). In some embodiments, the amino acid substitution is K-17F, K-17N, or K-17Y.

In some embodiments, the variant glucoamylase comprises an amino acid substitution of the Alanine at position −15 as compared to G6P or G7P (see G6P/G7P sequence at FIG. 1). In some embodiments, the substitution is with any other of the 19 naturally occurring amino acids, with some embodiments not utilizing cysteine (due to possible disulfide formation) or proline (due to steric effects). In some embodiments, the amino acid substitution is A-15F, A-15I, A-15L, or A-15V.

In some embodiments, the variant glucoamylase comprises an amino acid substitution of the Alanine at position −13 as compared to G6P or G7P (see G6P/G7P sequence at FIG. 1). In some embodiments, the substitution is with any other of the 19 naturally occurring amino acids, with some embodiments not utilizing cysteine (due to possible disulfide formation) or proline (due to steric effects). In some embodiments, the amino acid substitution is A-13T.

In some embodiments, the variant glucoamylase comprises an amino acid substitution of the Alanine at position −12 as compared to G6P or G7P (see G6P/G7P sequence at FIG. 1). In some embodiments, the substitution is with any other of the 19 naturally occurring amino acids, with some embodiments not utilizing cysteine (due to possible disulfide formation) or proline (due to steric effects). In some embodiments, the amino acid substitution is A-12V.

In some embodiments, the variant glucoamylase comprises an amino acid substitution of the Threonine at position −10 as compared to G6P or G7P (see G6P/G7P sequence at FIG. 1). In some embodiments, the substitution is with any other of the 19 naturally occurring amino acids, with some embodiments not utilizing cysteine (due to possible disulfide formation) or proline (due to steric effects). In some embodiments, the amino acid substitution is T-10F or T-10V.

In some embodiments, the variant glucoamylase comprises an amino acid substitution of the Tryptophan at position −9 as compared to G6P or G7P (see G6P/G7P sequence at FIG. 1). In some embodiments, the substitution is with any other of the 19 naturally occurring amino acids, with some embodiments not utilizing cysteine (due to possible disulfide formation) or proline (due to steric effects). In some embodiments, the amino acid substitution is W-9Y.

In some embodiments, the variant glucoamylase comprises an amino acid substitution of the Valine at position −1 as compared to G6P or G7P (see G6P/G7P sequence at FIG. 1). In some embodiments, the substitution is with any other of the 19 naturally occurring amino acids, with some embodiments not utilizing cysteine (due to possible disulfide formation) or proline (due to steric effects). In some embodiments, the amino acid substitution is V-1F.

In some embodiments, the variant glucoamylase comprises an amino acid substitution of the Lysine at position 5 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is K5H, K5N, K5P, K5Q, K5S, K5T, or K5Y.

In some embodiments, the variant glucoamylase comprises an amino acid substitution of the Arginine at position 7 as compared to G6P (SEQ ID NO: 13) or G7P (SEQ ID NO: 15) mature protein. In some embodiments, the substitution is with any other of the 19 naturally occurring amino acids, with some embodiments not utilizing proline (due to steric effects). In some embodiments, the amino acid substitution is R7C.

In some embodiments, the variant glucoamylase comprises an amino acid substitution of the Leucine at position 9 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is L9P.

In some embodiments, the variant glucoamylase comprises an amino acid substitution of the Glutamic acid at position 11 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is E11S.

In some embodiments, the variant glucoamylase comprises an amino acid substitution of the Leucine at position 19 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is L19I.

In some embodiments, the variant glucoamylase comprises an amino acid substitution of the Cysteine at position 26 as compared to G6P (SEQ ID NO: 13) or G7P (SEQ ID NO: 15) mature protein. In some embodiments, the substitution is with any other of the 19 naturally occurring amino acids, with some embodiments not utilizing proline (due to steric effects). In some embodiments, the amino acid substitution is C26N.

In some embodiments, the variant glucoamylase comprises an amino acid substitution of the Asparagine at position 27 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is N27A.

In some embodiments, the variant glucoamylase comprises an amino acid substitution of the Threonine at position 31 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T31N.

In some embodiments, the variant glucoamylase comprises an amino acid substitution of the Serine at position 36 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is S36P.

In some embodiments, the variant glucoamylase comprises an amino acid substitution of the Alanine at position 38 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A38V.

In some embodiments, the variant glucoamylase comprises an amino acid substitution of the Alanine at position 39 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A39F.

In some embodiments, the variant glucoamylase comprises an amino acid substitution of the Valine at position 42 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V42I.

In some embodiments, the variant glucoamylase comprises an amino acid substitution of the Isoleucine at position 44 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is I44V.

In some embodiments, the variant glucoamylase comprises an amino acid substitution of the Serine at position 46 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S46T.

In some embodiments, the variant glucoamylase comprises an amino acid substitution of the Proline at position 47 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is P47T.

In some embodiments, the variant glucoamylase comprises an amino acid substitution of the Arginine at position 49 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is R49H.

In some embodiments, the variant glucoamylase comprises an amino acid substitution of the Serine at position 50 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S50Q.

In some embodiments, the variant glucoamylase comprises an amino acid substitution of the Aspartic acid at position 53 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is D53N.

In some embodiments, the variant glucoamylase comprises an amino acid substitution of the Tyrosine at position 55 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is Y55F.

In some embodiments, the variant glucoamylase comprises an amino acid substitution of the Threonine at position 57 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T57S.

In some embodiments, the variant glucoamylase comprises an amino acid substitution of the Valine at position 65 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V65I.

In some embodiments, the variant glucoamylase comprises an amino acid substitution of the Glutamic acid at position 68 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is E68K, E68N, E68S or E68Y.

In some embodiments, the variant glucoamylase comprises an amino acid substitution of the Isoleucine at position 69 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is I69L.

In some embodiments, the variant glucoamylase comprises an amino acid substitution of the Serine at position 72 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S72A.

In some embodiments, the variant glucoamylase comprises an amino acid substitution of the Valine at position 73 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V73F.

In some embodiments, the variant glucoamylase comprises an amino acid substitution of the Threonine at position 78 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T78K.

In some embodiments, the variant glucoamylase comprises an amino acid substitution of the Leucine at position 79 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is L79F, L79Y, or L79D.

In some embodiments, the variant glucoamylase comprises an amino acid substitution of the Glutamic acid at position 85 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is E85Q.

In some embodiments, the variant glucoamylase comprises an amino acid substitution of the Asparagine at position 86 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is N86Q.

In some embodiments, the variant glucoamylase comprises an amino acid substitution of the Valine at position 88 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V88I.

In some embodiments, the variant glucoamylase comprises an amino acid substitution of the Threonine at position 89 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T89N, or T89S.

In some embodiments, the variant glucoamylase comprises an amino acid substitution of the Alanine at position 92 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A92T.

In some embodiments, the variant glucoamylase comprises an amino acid substitution of the Tyrosine at position 93 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is Y93K.

In some embodiments, the variant glucoamylase comprises an amino acid substitution of the Leucine at position 94 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is L94V.

In some embodiments, the variant glucoamylase comprises an amino acid substitution of the Valine at position 97 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V97I.

In some embodiments, the variant glucoamylase comprises an amino acid substitution of the Threonine at position 98 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T98S.

In some embodiments, the variant glucoamylase comprises an amino acid substitution of the Serine at position 103 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S103D.

In some embodiments, the variant glucoamylase comprises an amino acid substitution of the Aspartic acid at position 106 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is D106T.

In some embodiments, the variant glucoamylase comprises an amino acid substitution of the Alanine at position 108 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A108S.

In some embodiments, the variant glucoamylase comprises an amino acid substitution of the Aspartic acid at position 118 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is D118N.

In some embodiments, the variant glucoamylase comprises an amino acid substitution of the Methionine at position 119 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is M119E.

In some embodiments, the variant glucoamylase comprises an amino acid substitution of the Proline at position 121 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is P121S.

In some embodiments, the variant glucoamylase comprises an amino acid substitution of the Phenylalanine at position 122 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is F122M.

In some embodiments, the variant glucoamylase comprises an amino acid substitution of the Glycine at position 124 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is G124P, G124S, or G124T.

In some embodiments, the variant glucoamylase comprises an amino acid substitution of the Alanine at position 125 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is A125P.

In some embodiments, the variant glucoamylase comprises an amino acid substitution of the Methionine at position 141 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is M141L.

In some embodiments, the variant glucoamylase comprises an amino acid substitution of the Tyrosine at position 145 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is Y145A.

In some embodiments, the variant glucoamylase comprises an amino acid substitution of the Leucine at position 149 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is L149I.

In some embodiments, the variant glucoamylase comprises an amino acid substitution of the Asparagine at position 150 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is N150D.

In some embodiments, the variant glucoamylase comprises an amino acid substitution of the Alanine at position 153 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A153S.

In some embodiments, the variant glucoamylase comprises an amino acid substitution of the Threonine at position 155 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T155A.

In some embodiments, the variant glucoamylase comprises an amino acid substitution of the Glycine at position 158 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is G158S.

In some embodiments, the variant glucoamylase comprises an amino acid substitution of the Glutamine at position 161 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is Q161P.

In some embodiments, the variant glucoamylase comprises an amino acid substitution of the Asparagine at position 168 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is N168S.

In some embodiments, the variant glucoamylase comprises an amino acid substitution of the Valine at position 170 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V170I.

In some embodiments, the variant glucoamylase comprises an amino acid substitution of the Alanine at position 171 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A171T.

In some embodiments, the variant glucoamylase comprises an amino acid substitution of the Glycine at position 178 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is G178T.

In some embodiments, the variant glucoamylase comprises an amino acid substitution of the Tyrosine at position 179 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is Y179F.

In some embodiments, the variant glucoamylase comprises an amino acid substitution of the Proline at position 186 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is P186E.

In some embodiments, the variant glucoamylase comprises an amino acid substitution of the Serine at position 188 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is S188H, S188P, S188T or S188W.

In some embodiments, the variant glucoamylase comprises an amino acid substitution of the Threonine at position 192 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T192A.

In some embodiments, the variant glucoamylase comprises an amino acid substitution of the Alanine at position 195 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A195V.

In some embodiments, the variant glucoamylase comprises an amino acid substitution of the Serine at position 204 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S204N.

In some embodiments, the variant glucoamylase comprises an amino acid substitution of the Threonine at position 205 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T205A.

In some embodiments, the variant glucoamylase comprises an amino acid substitution of the Alanine at position 208 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A208T.

In some embodiments, the variant glucoamylase comprises an amino acid substitution of the Lysine at position 209 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is K209R.

In some embodiments, the variant glucoamylase comprises an amino acid substitution of the Lysine at position 212 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is K212Y.

In some embodiments, the variant glucoamylase comprises an amino acid substitution of the Serine at position 213 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S213T.

In some embodiments, the variant glucoamylase comprises an amino acid substitution of the Histidine at position 214 as compared to G6P (SEQ ID NO: 13) or G7P (SEQ ID NO: 15) mature protein. In some embodiments, the substitution is with any other of the 19 naturally occurring amino acids, with some embodiments not utilizing proline (due to steric effects). In some embodiments, the amino acid substitution is H214C.

In some embodiments, the variant glucoamylase comprises an amino acid substitution of the Serine at position 215 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S215A.

In some embodiments, the variant glucoamylase comprises an amino acid substitution of the Threonine at position 219 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T219S.

In some embodiments, the variant glucoamylase comprises an amino acid substitution of the Valine at position 220 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V220Q.

In some embodiments, the variant glucoamylase comprises an amino acid substitution of the Isoleucine at position 224 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is I224V.

In some embodiments, the variant glucoamylase comprises an amino acid substitution of the Tyrosine at position 227 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is Y227F.

In some embodiments, the variant glucoamylase comprises an amino acid substitution of the Alanine at position 246 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A246S.

In some embodiments, the variant glucoamylase comprises an amino acid substitution of the Serine at position 247 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S247G.

In some embodiments, the variant glucoamylase comprises an amino acid substitution of the Alanine at position 256 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A256V.

In some embodiments, the variant glucoamylase comprises an amino acid substitution of the Threonine at position 258 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T258S.

In some embodiments, the variant glucoamylase comprises an amino acid substitution of the Threonine at position 261 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T261A, or T261G.

In some embodiments, the variant glucoamylase comprises an amino acid substitution of the Alanine at position 262 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A262S.

In some embodiments, the variant glucoamylase comprises an amino acid substitution of the Histidine at position 264 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is H264M.

In some embodiments, the variant glucoamylase comprises an amino acid substitution of the Isoleucine at position 298 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is I298V.

In some embodiments, the variant glucoamylase comprises an amino acid substitution of the Serine at position 306 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S306A.

In some embodiments, the variant glucoamylase comprises an amino acid substitution of the Alanine at position 307 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A307E.

In some embodiments, the variant glucoamylase comprises an amino acid substitution of the Aspartic acid at position 309 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is D309S.

In some embodiments, the variant glucoamylase comprises an amino acid substitution of the Leucine at position 311 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is L311V.

In some embodiments, the variant glucoamylase comprises an amino acid substitution of the Alanine at position 317 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is A317P.

In some embodiments, the variant glucoamylase comprises an amino acid substitution of the Tyrosine at position 321 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is Y321F, Y321L or Y321W.

In some embodiments, the variant glucoamylase comprises an amino acid substitution of the Valine at position 342 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V342I.

In some embodiments, the variant glucoamylase comprises an amino acid substitution of the Leucine at position 347 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is L347N.

In some embodiments, the variant glucoamylase comprises an amino acid substitution of the Glutamic acid at position 348 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is E348I.

In some embodiments, the variant glucoamylase comprises an amino acid substitution of the Threonine at position 352 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T352S.

In some embodiments, the variant glucoamylase comprises an amino acid substitution of the Valine at position 353 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V353I.

In some embodiments, the variant glucoamylase comprises an amino acid substitution of the Serine at position 355 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S355D.

In some embodiments, the variant glucoamylase comprises an amino acid substitution of the Threonine at position 362 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T362Q.

In some embodiments, the variant glucoamylase comprises an amino acid substitution of the Leucine at position 364 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is L364I.

In some embodiments, the variant glucoamylase comprises an amino acid substitution of the Threonine at position 370 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T370V.

In some embodiments, the variant glucoamylase comprises an amino acid substitution of the Alanine at position 374 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A374N.

In some embodiments, the variant glucoamylase comprises an amino acid substitution of the Glutamic acid at position 381 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is E381N.

In some embodiments, the variant glucoamylase comprises an amino acid substitution of the Serine at position 382 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S382D.

In some embodiments, the variant glucoamylase comprises an amino acid substitution of the Threonine at position 388 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T388Q.

In some embodiments, the variant glucoamylase comprises an amino acid substitution of the Alanine at position 391 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A391G.

In some embodiments, the variant glucoamylase comprises an amino acid substitution of the Phenylalanine at position 394 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is F394Y.

In some embodiments, the variant glucoamylase comprises an amino acid substitution of the Valine at position 395 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V395L.

In some embodiments, the variant glucoamylase comprises an amino acid substitution of the Glutamine at position 399 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is Q399E.

In some embodiments, the variant glucoamylase comprises an amino acid substitution of the Threonine at position 400 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T400L, or T400K.

In some embodiments, the variant glucoamylase comprises an amino acid substitution of the Alanine at position 407 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A407S.

In some embodiments, the variant glucoamylase comprises an amino acid substitution of the Tyrosine at position 412 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is Y412F.

In some embodiments, the variant glucoamylase comprises an amino acid substitution of the Glutamine at position 418 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is Q418T.

In some embodiments, the variant glucoamylase comprises an amino acid substitution of the Glutamine at position 419 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is Q419P.

In some embodiments, the variant glucoamylase comprises an amino acid substitution of the Leucine at position 420 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is L420K.

In some embodiments, the variant glucoamylase comprises an amino acid substitution of the Alanine at position 422 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A422G, or A422S.

In some embodiments, the variant glucoamylase comprises an amino acid substitution of the Proline at position 423 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is P423G, P423R or P423V.

In some embodiments, the variant glucoamylase comprises an amino acid substitution of the Serine at position 434 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S434T.

In some embodiments, the variant glucoamylase comprises an amino acid substitution of the Threonine at position 436 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T436S.

In some embodiments, the variant glucoamylase comprises an amino acid substitution of the Glutamic acid at position 437 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is E437A.

In some embodiments, the variant glucoamylase comprises an amino acid substitution of the Aspartic acid at position 440 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is D440Q.

In some embodiments, the variant glucoamylase comprises an amino acid substitution of the Glycine at position 446 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is G446S.

In some embodiments, the variant glucoamylase comprises an amino acid substitution of the Serine at position 452 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S452A.

In some embodiments, the variant glucoamylase comprises an amino acid substitution of the Valine at position 453 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V453S.

In some embodiments, the variant glucoamylase comprises an amino acid substitution of the Glycine at position 457 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is G457S.

In some embodiments, the variant glucoamylase comprises an amino acid substitution of the Alanine at position 460 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A460S.

In some embodiments, the variant glucoamylase comprises an amino acid substitution of the Alanine at position 469 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A469S.

In some embodiments, the variant glucoamylase comprises an amino acid substitution of the Alanine at position 470 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A470T.

In some embodiments, the variant glucoamylase comprises an amino acid substitution of the Serine at position 472 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S472T.

In some embodiments, the variant glucoamylase comprises an amino acid substitution of the Glycine at position 475 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is G475V.

In some embodiments, the variant glucoamylase comprises an amino acid substitution of the Threonine at position 476 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T476W.

In some embodiments, the variant glucoamylase comprises an amino acid substitution of the Glycine at position 478 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is G478S.

In some embodiments, the variant glucoamylase comprises an amino acid substitution of the Alanine at position 491 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is A491V.

In some embodiments, the variant glucoamylase comprises an amino acid substitution of the Leucine at position 492 as compared to G6P (SEQ ID NO: 13) or G7P (SEQ ID NO: 15) mature protein. In some embodiments, the substitution is with any other of the 19 naturally occurring amino acids, with some embodiments not utilizing cysteine (due to possible disulfide formation). In some embodiments, the amino acid substitution is L492P.

In some embodiments, the variant glucoamylase comprises an amino acid substitution of the Glutamic acid at position 497 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is E497V.

In some embodiments, the variant glucoamylase comprises an amino acid substitution of the Leucine at position 498 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is L498T.

In some embodiments, the variant glucoamylase comprises an amino acid substitution of the Tyrosine at position 503 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is Y503D, Y503E, Y503G, Y503K, Y503L, Y503N, Y503S, or Y503T.

In some embodiments, the variant glucoamylase comprises an amino acid substitution of the Lysine at position 508 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is K508N, K508S or K508T.

In some embodiments, the variant glucoamylase comprises an amino acid substitution of the Leucine at position 509 as compared to G6P (SEQ ID NO: 13) mature protein. In some embodiments, the substitution is with any other of the 19 naturally occurring amino acids, with some embodiments not utilizing cysteine (due to possible disulfide formation). In some embodiments, the amino acid substitution is L509P.

In some embodiments, the variant glucoamylase comprises an amino acid substitution of the Valine at position 510 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is V510G or V510S.

In some embodiments, the variant glucoamylase comprises an amino acid substitution of the Phenylalanine at position 516 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is F516L.

In some embodiments, the variant glucoamylase comprises an amino acid substitution of the Tyrosine at position 518 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S518I, S518L, or S518M.

In some embodiments, the variant glucoamylase comprises an amino acid substitution of the Proline at position 521 as compared to G6P (SEQ ID NO: 13) mature protein. In some embodiments, the substitution is with any other of the 19 naturally occurring amino acids, with some embodiments not utilizing cysteine (due to possible disulfide formation). In some embodiments, the amino acid substitution is P521S.

In some embodiments, the variant glucoamylase comprises an amino acid substitution of the Serine at position 522 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is S522G.

In some embodiments, the variant glucoamylase comprises an amino acid substitution of the Leucine at position 526 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is L526I, L526N or L526S.

In some embodiments, the variant glucoamylase comprises an amino acid substitution of the Threonine at position 533 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T533R.

In some embodiments, the variant glucoamylase comprises an amino acid substitution of the Alanine at position 534 as compared to G6P (SEQ ID NO: 13) mature protein.

In some embodiments, the substitution is with any other of the 19 naturally occurring amino acids, with some embodiments not utilizing cysteine (due to possible disulfide formation) or proline (due to steric effects). In some embodiments, the amino acid substitution is A534T.

In some embodiments, the variant glucoamylase comprises an amino acid substitution of the Serine at position 535 as compared to G6P (SEQ ID NO: 13) mature protein.

In some embodiments, the substitution is with any other of the 19 naturally occurring amino acids, with some embodiments not utilizing cysteine (due to possible disulfide formation) or proline (due to steric effects). In some embodiments, the amino acid substitution is S535Y.

In some embodiments, the variant glucoamylase comprises an amino acid substitution of the Threonine at position 540 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T540N.

In some embodiments, the variant glucoamylase comprises an amino acid substitution of the Threonine at position 542 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T542N.

In some embodiments, the variant glucoamylase comprises an amino acid substitution of the Serine at position 544 as compared to G6P (SEQ ID NO: 13) mature protein.

In some embodiments, the substitution is with any other of the 19 naturally occurring amino acids, with some embodiments not utilizing cysteine (due to possible disulfide formation) or proline (due to steric effects). In some embodiments, the amino acid substitution is S544E, S544N, or S544Q.

In some embodiments, the variant glucoamylase comprises an amino acid substitution of the Valine at position 545 as compared to G6P (SEQ ID NO: 13) mature protein.

In some embodiments, the substitution is with any other of the 19 naturally occurring amino acids, with some embodiments not utilizing cysteine (due to possible disulfide formation) or proline (due to steric effects). In some embodiments, the amino acid substitution is V545A or V545D.

In some embodiments, the variant glucoamylase comprises an amino acid substitution of the Serine at position 549 as compared to G6P (SEQ ID NO: 13) mature protein.

In some embodiments, the substitution is with any other of the 19 naturally occurring amino acids, with some embodiments not utilizing cysteine (due to possible disulfide formation) or proline (due to steric effects). In some embodiments, the amino acid substitution is S549D or S549E.

In some embodiments, the variant glucoamylase comprises an amino acid substitution of the Threonine at position 550 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T550D.

In some embodiments, the variant glucoamylase comprises an amino acid substitution of the Valine at position 551 as compared to G6P (SEQ ID NO: 13) mature protein.

In some embodiments, the substitution is with any other of the 19 naturally occurring amino acids, with some embodiments not utilizing cysteine (due to possible disulfide formation) or proline (due to steric effects). In some embodiments, the amino acid substitution is V551D, V551R or V551S.

In some embodiments, the variant glucoamylase comprises an amino acid substitution of the Phenylalanine at position 555 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is F555D, F555K, F555L, F555N, F555R, or F555S.

In some embodiments, the variant glucoamylase comprises an amino acid substitution of the Isoleucine at position 556 as compared to G6P (SEQ ID NO: 13) mature protein. In some embodiments, the substitution is with any other of the 19 naturally occurring amino acids, with some embodiments not utilizing cysteine (due to possible disulfide formation). In some embodiments, the amino acid substitution is I556D, I556P or I556R.

In some embodiments, the variant glucoamylase comprises an amino acid substitution of the Arginine at position 557 as compared to G6P (SEQ ID NO: 13) mature protein. In some embodiments, the substitution is with any other of the 19 naturally occurring amino acids, with some embodiments not utilizing cysteine (due to possible disulfide formation). In some embodiments, the amino acid substitution is R557P.

In some embodiments, the variant glucoamylase comprises an amino acid substitution of the Glycine at position 559 as compared to G6P (SEQ ID NO: 13) mature protein.

In some embodiments, the substitution is with any other of the 19 naturally occurring amino acids, with some embodiments not utilizing cysteine (due to possible disulfide formation) or proline (due to steric effects). In some embodiments, the amino acid substitution is G559N or G559S.

In some embodiments, the variant glucoamylase comprises an amino acid substitution of the Serine at position 563 as compared to G6P (SEQ ID NO: 13) mature protein.

In some embodiments, the substitution is with any other of the 19 naturally occurring amino acids, with some embodiments not utilizing cysteine (due to possible disulfide formation) or proline (due to steric effects). In some embodiments, the amino acid substitution is S563L.

In some embodiments, the variant glucoamylase comprises an amino acid substitution of the Isoleucine at position 564 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is I564N, I564S or I564T.

In some embodiments, the variant glucoamylase comprises an amino acid substitution of the Glycine at position 569 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is G569I.

In some embodiments, the variant glucoamylase comprises an amino acid substitution of the Asparagine at position 570 as compared to G6P (SEQ ID NO: 13) mature protein. In some embodiments, the substitution is with any other of the 19 naturally occurring amino acids, with some embodiments not utilizing cysteine (due to possible disulfide formation). In some embodiments, the amino acid substitution is N570P.

In some embodiments, the variant glucoamylase comprises an amino acid substitution of the Threonine at position 581 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T581N.

In some embodiments, the variant glucoamylase comprises an amino acid substitution of the Threonine at position 584 as compared to G6P (SEQ ID NO: 13) mature protein. In some embodiments, the substitution is with any other of the 19 naturally occurring amino acids, with some embodiments not utilizing cysteine (due to possible disulfide formation) or proline (due to steric effects). In some embodiments, the amino acid substitution is T584N.

The amino acid changes that may be present in addition to the specific substitutions described herein may be of a minor nature, that is conservative amino acid substitutions or insertions that do not significantly affect the folding and/or activity of the protein; small deletions, typically of 1 to about 30 amino acids; small amino- or carboxyl-terminal extensions, such as an amino-terminal methionine residue; a small linker peptide of up to about 20 to about 25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuA al, Ala/Glu, and Asp/Gly.

A. Parent glucoamylase

The parent glucoamylase enzyme may be (a) a polypeptide having at least 85% sequence identity to the polypeptide of SEQ ID NO:25, SEQ ID NO:13 or SEQ ID NO:15; (b) a polypeptide encoded by a polynucleotide that hybridizes under medium-high stringency conditions with (i) the mature polypeptide coding sequence of SEQ ID NO: 14 or SEQ ID NO:16, or (ii) the full-length complement of (i); or (c) a polypeptide encoded by a polynucleotide having at least 70% sequence identity to the mature polypeptide coding sequence of SEQ ID NO: 14 or SEQ ID NO:16. For hybridization methods and conditions, see for example, Sambrook et al., 1989, Molecular Cloning, A Laboratory Manual, 2d edition, Cold Spring Harbor, N.Y.

In some embodiments, the parent glucoamylase enzyme has a sequence identity to the wild type polypeptide of SEQ ID NO:25 of at least 85%, at least 90%, at least 91%, at least 92%, at least 93%, at least 94%, at least 95%, at least 96%, at least 97%, at least 98%, at least 99%, or 100%, and have glucoamylase activity. In one aspect, the amino acid sequence of the parent differs by up to 20 amino acids, e.g., 1, 2, 3, 4, 5, 6, 7, 8, 9, 10, 11, 12, 13, 14, 15, 16, 17, 18, 19 or 20 from the wild type polypeptide of SEQ ID NO: 25. In some aspects, the parent glucoamylase enzyme has an amino acid sequence comprising SEQ ID NO:13. In some aspects, the parent glucoamylase enzyme has an amino acid sequence comprising SEQ ID NO:15.

In some embodiments, the parent glucoamylase enzyme is encoded by a polynucleotide having a sequence identity to the mature wild type polypeptide coding sequence of at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In some embodiments, the parent glucoamylase enzyme is a *Thielaviopsis punctuala* glucoamylase, e.g., the glucoamylase of SEQ ID NO:25. In some embodiments, the parent glucoamylase enzyme is produced in *Pichia pastoris*. In some embodiments, the parent glucoamylase enzyme is produced in *Saccharomyces cerevisiae*. In some embodiments, the parent glucoamylase enzyme is produced in *Aspergillus niger*.

In one embodiment, the variant glucoamylase enzymes are more stable than the parent variant glucoamylase enzyme when exposed to temperatures of 30° C., 35° C., 40° C., 45° C., 50° C., 52° C., 55° C., 56° C., 58° C., 60° C., 65° C., 66° C., 70° C., 75° C., 80° C. and/or 85° C. for a period of time, generally ranging from about 1, 2, 3, 4, 5, 6, 7, 8, 9 or 10 minutes or longer, depending on the ultimate conditions for the use of the variant glucoamylase enzyme, with some embodiments utilizing thermal challenge times of 5 minutes to 10 minutes, 5 minutes to 15 minutes, 5 minutes to 60 minutes, 10 minutes to 60 minutes all finding use in the present invention. In some embodiments, a challenge of 85° C. and 5 minutes is used.

Accordingly, in some embodiments the variant glucoamylase enzymes have increased thermostability as compared to a parent variant glucoamylase enzyme (e.g. wild type, G6P or G7P mature glucoamylase protein), for at least 5 minutes at 50° C., at least 5-10 minutes at 52° C., at least 5-10 minutes at 55° C., at least 5-10 minutes at 58° C., at least 5-10 minutes at 56° C., at least 5-10 minutes at 60° C., at least 5-10 minutes at 66° C. and in some embodiments at least 5-10 minutes at 70° C.

In addition, pH can be a consideration for thermostability as well. Accordingly, in some embodiments the variant glucoamylase enzymes have increased thermostability as compared to a parent glucoamylase enzyme for at least 5 minutes at 52° C. at pH 4.5, or at least 5 minutes at 56° C. at pH 4.5. Accordingly, in some embodiments the variant glucoamylase enzymes have increased thermostability as compared to a parent glucoamylase enzyme for at least 10 minutes at 52° C. at pH 4.5, or at least 10 minutes at 56° C. at pH 4.5.

Accordingly, as shown in FIGS. 2, 3, 4 and 6, a number of variant glucoamylase enzymes of the invention exhibit increased thermoactivity.

B. Nucleic Acid Compositions

The present invention also provides compositions comprising a variant glucoamylase enzyme encoding nucleic acid of the present invention. Such variant glucoamylase polypeptide encoding nucleic acids can encode any of the variant glucoamylase enzymes recited in the present application, including under section "Variant Glucoamylases of the Invention" above. In some embodiments, the composition comprises a nucleic acid selected from the group consisting of the even numbered sequences in SEQ ID NOs: 2 to 24.

In some embodiments, the composition comprises a nucleic acid of SEQ ID NO:2.

In some embodiments, the composition comprises a nucleic acid of SEQ ID NO:4. In some embodiments, the composition comprises a nucleic acid of SEQ ID NO:6. In some embodiments, the composition comprises a nucleic acid of SEQ ID NO:8. In some embodiments, the composition comprises a nucleic acid of SEQ ID NO:10. In some embodiments, the composition comprises a nucleic acid of SEQ ID NO:12. In some embodiments, the composition comprises a nucleic acid of SEQ ID NO:14. In some embodiments, the composition comprises a nucleic acid of SEQ ID NO:16. In some embodiments, the composition comprises a nucleic acid of SEQ ID NO:18. In some embodiments, the composition comprises a nucleic acid of SEQ ID NO:20. In some embodiments, the composition comprises a nucleic acid of SEQ ID NO:22. In some embodiments, the composition comprises a nucleic acid of SEQ ID NO:24.

In some embodiments, the invention provides a nucleic acid encoding a preprotein comprising a signal peptide and a mature protein, wherein said signal peptide is SEQ ID NO:26 or a variant signal peptide as compared to SEQ ID NO:26, and said variant signal peptide has at least one amino acid substitution at a position number selected from the group consisting of −20, −18, −17, −15, −13, −12, −10, −9, and −1; and wherein said mature protein has SEQ ID NO:15, or is a variant glucoamylase enzyme as compared to SEQ ID NO:15, wherein said variant glucoamylase has at least one amino acid substitution at a position number selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492; and wherein said preprotein is at least 95% identical to SEQ ID NO:3.

In further embodiments, the invention provides the nucleic acid encoding the preprotein as described herein, wherein said preprotein exhibits at least 96%, 97%, 98%, or 99% identity to SEQ ID NO:3.

In an additional embodiment, the invention provides the nucleic acid encoding the preprotein as described herein, wherein said variant signal peptide has amino acid substitution(s) at one of said positions, two of said positions, three of said positions, four of said positions, or five of said positions.

In a further embodiment, the invention provides the nucleic acid encoding the preprotein as described herein, wherein said variant glucoamylase enzyme has amino acid substitution(s) at one of said positions, two of said positions, three of said positions, four of said positions, five of said positions, six of said positions, seven of said positions, eight of said positions, nine of said positions, ten of said positions, eleven of said positions, twelve of said positions, thirteen of said positions or fourteen of said positions.

In an additional embodiment, the invention provides the nucleic acid encoding the preprotein as described herein, wherein said variant signal peptide has at least one amino acid substitution at a position number −20 or −15.

In an additional embodiment, the invention provides the nucleic acid encoding the preprotein as described herein, wherein said variant signal peptide has amino acid substitution(s) selected from the group consisting of V-20A, V-20F, V-20G, V-20I, V-20K, V-20L, V-20M, V-20Q, V-20R, V-20T, V-20W, L-18F, L-18I, L-18Y, K-17F, K-17N, K-17Y, A-15F, A-15I, A-15L, A-15V, A-13T, A-12V, T-10F, T-10V, W-9Y, and V-1F.

In a further embodiment, the invention provides the nucleic acid encoding the preprotein as described herein, wherein said variant glucoamylase enzyme has amino acid substitution(s) selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, T400L, Y412F, L420K, A422G, P423G, P423R, P423V, G457S, A491V, K5P, K5S, K5T, K5Y, K5Q, K5N, K5H, E68K, E68Y, E68S, S188T, S188H, Y321F, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In some embodiments, the invention provides the nucleic acid encoding the preprotein as described herein, wherein said variant glucoamylase enzyme has amino acid substitution(s) at a position number selected from the group consisting of 5, 68, 188, 321, 419, 420, 422, 7, 11, 19, 26, 31, 42, 44, 49, 53, 55, 57, 69, 72, 73, 78, 79, 85, 86, 88, 89, 92, 93, 94, 97, 98, 103, 106, 118, 119, 125, 141, 145, 149, 150, 153, 155, 161, 168, 170, 171, 178, 179, 186, 195, 204, 205, 208, 209, 213, 214, 219, 220, 224, 227, 246, 247, 256, 261, 262, 306, 307, 309, 311, 317, 342, 347, 348, 352, 353, 355, 362, 364, 370, 374, 381, 382, 388, 391, 394, 395, 399, 400, 407, 412, 418, 434, 436, 437, 440, 446, 452, 453, 460, 469, 470, 472, 475, 476, 478, and 492.

In further embodiments, the invention provides the nucleic acid encoding the preprotein as described herein, wherein said variant glucoamylase enzyme has amino acid substitution(s) selected from the group consisting of K5P, K5S, K5T, K5Y, K5Q, K5N, K5H, E68K, E68Y, E68S, S188T, S188H, Y321F, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, T98S, S103D, D106T, D118N, M119E, A125P, M141L, Y145A, L149I, N150D, A153S, T155A, Q161P, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, A262S, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Y412F, Q418T, S434T, T436S, E437A, D440Q, G446S, S452A, V453S, A460S, A469S, A470T, S472T, G475V, T476W, G478S, and L492P.

In a further embodiments, the invention provides the nucleic acid encoding the preprotein as described herein, wherein said preprotein has amino acid substitution(s) selected from the group consisting of S188H/Y321W/Q419P, K5T/S188T, K5T/E68K/S188H, K5Y/S188H, K5Q/E68K/S188T, K5N/E68Y/S188T, K5H/S188H, K5S/E68Y/S188H, K5S/E68Y/S188T, K5Y/E68Y, K5S/E68S/S188T, K5H/E68S/S188H, K5H/E68K/S188T, K5P/S188H, K5Y/E68K, K5T/S188H, K5S/S188H, E68Y/S188H, E68Y/S188T, A-15F/K5T/Y321F, V-20F/A-15I, V-20F/K5Q/S188H/Q419P, A-15I/Y321F, V-20F/A422S, A-15F/K5P/E68Y/S188T/A422S, V-20F/A-15I/A422S, V-20T/A-15I/Q419P, V-20F/K5N/S188H/Q419P, V-20F/Y321W/A422S, V-20F/E68K/Q419P, A-15F/S188H/Y321W/Q419P, V-20F/Y321F, A-15F/Y321F, V-20F/E68S/S188T/Y321W/A422S, V-20F/A-15F/K5Q/Q419P/A422S, V-20I/A-15I/Y321F, S188T/Y321F, S188T/Q419P/A422S, V-20T/A-15I/K5Q, A-15I/Y321W, V-20F/A-15F/K5Q, V-20F/K5H/S188T/Q419P/A422S, V-20T/A-15I/K5H/A422S, A-15F/S188H/Y321W, A-15F/Q419P/A422S, V-20F/K5N/A422S, V-20F/A-15I/S188H, E68Y/S188H/Y321F/Q419P, V-20F/A-15F/K5N/A422S, V-20F/A-15I/Y321F, V-20F/K5Q/S188H, E11S/Y55F/M141L/N168S/T388Q, E11S/T31N/Y55F/M141L/N168S/T388Q, L19I/A195V, M141L/N168S/Y227F/T362Q/T388Q/D440Q, E11S/M141L, E11S/L19I/I44V/Y145A/T155A/D309S/L311V/Y412F/S472T, D309S/L311V, E11S/L19I/T31N/Y55F/A125P/N168S/Y227F, L19I/D309S/L311V/Y412F/A460S/S472T, E11S/L19I/N168S/Y227F/D309S/L311V/D440Q, L19I/Y412F, E11S/L19I/Y145A/A460S/S472T, E11S/M141L/N168S/D309S/L311V/T362Q/L364I/Y412F/A460S/S472T, E11S/Y55F/M141L/N168S/L311V/T362Q/L364I/A460S/S472T, E11S/L19I/Y55F/M141L/N168S/Y227F, L19I/T155A/A407S/Y412F/S472T, D53N/L149I/N150D/P186E/A317P, V42I/S103D/D106T/P186E/A317P/S434T/G478S, A317P/G478S, C26N/V42I/L149I/A317P/S355D/A374N, V42I/S103D/D106T/A317P, D53N/S434T, /S103D/A317P/V342I, A256V/A317P, V42I/P186E, A317P/V342I/G478S, I224V/A256V/A317P/G478S, V42I/L149I/N150D/A317P/G478S, V42I/S103D/P186E/A317P/V342I/S355D/A374N/A391G, P186E/A317P/G478S, D53N/G446S, A256V/A317P/G478S, V42I/D53N/T57S/L149I/A317P/G478S, C26N/V42I/D53N/T57S/N150D/P186E/A317P/V342I/G478S, V42I/S355D, V42I/N150D/P186E/A317P, V42I/S434T/G478S, C26N/D53N/T57S/S103D/Q161P/A317P/G478S, V42I/A256V/A317P/S434T, V42I/S103D/A317P/A391G/G478S, E68Y/I69L/G178T/Y179F/S213T/H214C, E68Y/I69L/E85Q/N86Q/F394Y/V395L, E68Y/I69L, D118N/M119E, E68Y/I69L/V97I/T98S/A246S/S247G/T261G/A262S/L347N/E348I, E68Y/I69L/S452A/V453S, E68Y/I69L/S452A/V453S, E68Y/I69L/E85Q/N86Q/L347N/E348I/Q419P, E68Y/I69L/E85Q/N86Q/S204N/T205A, A208T/K209R/E381N/S382D/Q418T/Q419P/A469S/A470T, E381N/S382D/Q418T/Q419P/T436S/E437A/A469S/A470T, Q418T/Q419P/A469S/A470T, V170I/A171T/E381N/S382D/Q418T/Q419P/A469S/A470T, F394Y/V395L/Q418T/Q419P/T436S/E437A/A469S/A470T, T78K/L79D/Q418T/Q419P/A469S/A470T, E68Y/I69L/V88I/T89S/T352S/V353I/Q399E/T400K/A469S/A470T, S72A/V73F/A153S/S306A/T476W, T370V/G475V, R49H/S72A/V73F/A92T/Y93K/A153S/S306A/T476W, E68Y/I69L/T219S/V220Q/A307E/S355D/L492P, E11S/V42I/L149I/I224V/A317P/T388Q/A460S/G478S, Y412F/Q418T/Q419P/A469S/A470T/, L19I/D53N/I69L/V88I/S188H/A195V/Y321W/Y412F, V42I/D118N/M119E/T261A/L311V/Y321W/S355D, E11S/T57S/T89S, E11S/V42I/L79Y/D118N/M141L/L311V/A317P/Y321F, V42I/D53N/E68Y/A317P/L347N, I69L/S188H/A195V/A317P/Y321F/L364I/S434T, T57S/A195V/T261A/L311V/Y321F/L347N/E348I/S434T, E11S/V42I/T57S/E68Y/S188H/A195V/T261A, T57S/N168S/T261A/A317P/Y321W/V395L/Y412F, E11S/D53N/E68Y/D118N/S188H/A195V/Y412F/Q419P, E11S/V42I/D118N/M141L/N168S/Y321W/Y412F, E11S/D53N/T57S/E68Y/T89S/E381N/Y412F/Q419P/S434T, E11S/D53N/T57S/V88I/T89S/S188H/A195V/L311V/L347N/Y412F, A317P/Y412F, I69L/T89S/L311V/A317P/Y321F/Y412F/S434T, V42I/D53N/T57S/E68Y7V88I/Y412F, E11S/T57S/V88I/M141L/T261A/Y321W/L364I/Y412F, V42I/I69L/S188H/A317P/Y321W/Y412F, E11S/V42I/D53N/T57S/L79Y/T89S/L311V/Y321W/Y412F, L19I/M141L/N168S/S188H/A195V/L311V/S355D/S434T, S188H/A195V/T261A/L311V/Y321F/L347N/E348I, E11S/L19I/D53N/T57S/N168S/L347N, E11S/I69L/M119E/A195V/T261A/A317P/Y321W/L347N/Y412F, L79Y/V88I/T261A/A317P/Y321F/L364I/Y412F, E11S/V42I/E68Y/T89S/L311V/Y321F/T388Q/F394Y7V395L/Q419P, D53N/E68Y/V88I/M141L/N168S/Y321W/Y412F, E11S/I69L/L311V/A317P/Y321F/L347N/Y412F, D53N/T57S/M141L, D53N7V88I/T89S/D118N/E348I/S355D, E11S/S188H/A195V/A317P/L347N/E348I/Y412F/Q419P/S434T, E11S/D53N/I69L7V88I/A317P/Q419P, E68Y/I69L7V88I/N168S/L364I/Q419P, E11S/V42I7V88I/T261A/Y321F/E348I/S355D, E11S/V42I/T57S/I69L/A195V/L347N/E348I/S355D, L19I/T89S/A317P/Y321F/S434T, E11S/V42I/L79Y/L311V/A317P/Y321W/L347N/E348I/L364I/Y412F, D53N/T57S/L347N/E348I/Y412F, D53N/T57S/E68Y/L79Y/Y412F/S434T, L19I/V88I/T89S/A317P, M119E/M141L/N168S/L311V/Y321F, E11S/T89S/Y321W, E11S/M141L/T261A/A317P/Y412F/S434T, V42I/L79Y/S188H/A195V/L311V/Y321F/S355D, V42I/E68Y/V88I/T261A/Y321W/L347N/E348I, L19I/E68Y/I69L/M141L/Y321F/L347N/S355D/E381N/Y412F, V42I/D53N/I69L/L79Y/D118N/T261A/L311V/A317P/Y32i F/L347N/Y412F, E68Y/S355D/L364I/S382D/T388Q/Q419P, E11S/L19I/V42J/E68Y/I69L/D118N/M141L/Y321W/L347N, /E11S/V42I/E68Y/M141L/A317P/Y321F/E348I/S355 D, E11S/V42/E68Y/I69L7V88/T89S/D118N/M119E/S188H/A195V/A317P/L347N/Y412F/Q419P, V42I/V88I/L311V/A317P/Y32i F/L347N/E348I/T388Q/V395L/S434T, T261A/A317P/Y321W/E348I, E11S/V42I/E68Y/I69L/D118N/M119E/Y412F, E11S/V42I/T57S/I69L/L311V, V42I/Y412F, E11S/L19I/E68Y/M119E/N168S/Y412F/Q419P, L19I/L311V/Y412F, E11S/V42I/M119E/Y412F, E11S/L19I7/V42I/D53N/S188H/A195V/L311V/Y321F/Y412F, E11S/L19I7/V42I/T57S/D118N/N168S/L311V/Y412F, L19I/V42I/D53N/T57S/N168S/A317P/Y321W/Y412F, D53N/T57S/E68Y/N168S/S188H/A195V/L311V/Y321W/Y412F/Q419P, L19I/D53N/T57S/L311V/Y321W/Y412F, E11S/T57S/Y321W/Y412F/Q419P, D53N/S188H/A195V/L311V/Y412F, V42I/D53N/S188H/A195V/L311V/Y321F/Y412F, L19I/M119E/N168S/S188H/A195V/L311V/Y412F/Q419P, E11S/V42I/S188H/

A195V/L311V/A317P/Y321W/Y412F/Q419P, E11S/V42J/ M119E/N168S/L311V/Y412F, E11S/V42I/N168S/L311V/ A317P/Y321W/Y412F/Q419P, E11S/V42J/D53N/E68Y/ S188H/A195V/L311V/A317P/Y321F/Y412F, E11S/L19I/ D53N/N168S/A195V/Y412F/Q419P, E11S/L19I/V42I/ L311V/Y412F, V42I/D53N/N168S/L311V/Y412F, E11S/ L311V/Y412F, E11S/D53N/T57S/L311V/Y321W/Y412F, E11S/L311V/Y321W/Y412F, E11S/V42I/I69L/D118N/ N168S/L311V/A317P/Y412F/Q419P, E11S/L19I/V42I/ E68Y/Y412F/Q419P, E11S/L19I/D53N/L311V, E11S/L19I/ V42I/L311V/Y412F/Q419P, L19I/V42I/D53N/T57S/I69L/ N168S/S188H/A195V/L311V/A317P/Y321W, E11S/L19I/ V42I/T57S/L311V/A317P/Y321F/Y412F, L19I/V42I/I69L/ D118N/N168S/L311V/Y321W/Y412F/Q419P, E11S/V42I/ D53N/E68Y/S188H/A195V/Y412F, E11S/L19I/V42I/ D53N/T57S/N168S/L311V/Y321W/Y412F, E11S/V42I/ L311V/Y412F, E11S/L19I/V42I/N168S/A195V/L311V/ Y321F/Y412F, E11S/V42I/S188H/L311V/Y412F, L19I/ V42I/T57S/E68Y/M119E/S188H/A195V/L311V/Y321F/ Y412F, E11S/L19I/V42I/D53N/N168S/S188H/A195V, E11S/L19I/V42I/T57S/E68Y/A195V/L311V/Y321W, and E11S/L19I/V42I.

In a further embodiment, the invention provides the nucleic acid encoding the preprotein as described herein, wherein said variant glucoamylase enzyme has an amino acid substitution Y321F.

In an additional embodiment, the invention provides the nucleic acid encoding the preprotein as described herein, wherein said variant glucoamylase enzyme has amino acid substitutions S188H/Y321W/Q419P.

In a further embodiment, the invention provides the nucleic acid encoding the preprotein as described herein, wherein said variant glucoamylase enzyme comprises an amino acid substitution Y321F, and further comprises at least one amino acid selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, T400L, Y412F, L420K, A422G, P423G, P423R, P423V, G457S, A491V, K5P, K5S, K5T, K5Y, K5Q, K5N, K5H, E68K, E68Y, E68S, S188T, S188H, Y321W, Q419P, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In an additional embodiment, the invention provides the nucleic acid encoding the preprotein as described herein, wherein said variant glucoamylase enzyme comprises amino acid substitutions S188H/Y321W/Q419P and further comprises at least one amino acid selected from the group consisting of N27A, S36P, A38V, A39F, S46T, P47T, S50Q, V65I, E68N, L79F, T89N, T98S, A108S, P121S, F122M, G124P, G124S, G124T, G158S, Q161P, S188P, S188W, T192A, K212Y, S215A, T258S, A262S, H264M, I298V, Y321L, Y321F, T400L, Y412F, L420K, A422G, P423G, P423R, P423V, G457S, A491V, K5P, K5S, K5T, K5Y, K5Q, K5N, K5H, E68K, E68Y, E68S, S188T, A422S, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In some embodiments, the invention provides the nucleic acid encoding the preprotein as described herein, wherein the preprotein comprises a sequence selected from the group consisting of SEQ ID NO:3, SEQ ID NO:9 and SEQ ID NO:11.

In another embodiment, the invention provides a nucleic acid encoding a preprotein comprising a signal peptide and a mature protein, wherein said signal peptide is SEQ ID:26 or a variant signal peptide as compared to SEQ ID NO:26, and said variant signal peptide has at least one amino acid substitution at a position number selected from the group consisting of −20, −18, −17, −15, −13, −12, −10, −9, and −1; and wherein said mature protein has SEQ ID NO:13 or is a variant glucoamylase enzyme as compared to SEQ ID NO:13, wherein said variant glucoamylase has at least one amino acid substitution at a position number selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 516, 518, 521, 522, 526, 533, 534, 535, 540, 542, 544, 545, 549, 550, 551, 555, 556, 557, 559, 563, 564, 569, 570, 581, 584; 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492; and wherein said preprotein is at least 95% identical to SEQ ID NO:1; and wherein said preprotein is not SEQ ID NO:1.

In a further embodiment, the invention provides the nucleic acid encoding the preprotein as described herein, wherein said preprotein exhibits at least 96%, 97%, 98%, or 99% identity to SEQ ID NO:1.

In a further embodiment, the invention provides the nucleic acid encoding the preprotein as described herein, wherein said variant signal peptide has amino acid substitution(s) at one of said positions, two of said positions, three of said positions, four of said positions, or five of said positions.

In a further embodiment, the invention provides the nucleic acid encoding the preprotein as described herein, wherein said variant glucoamylase enzyme has amino acid substitution(s) at one of said positions, two of said positions, three of said positions, four of said positions, five of said positions, six of said positions, seven of said positions, eight of said positions, nine of said positions, ten of said positions, eleven of said positions, twelve of said positions or thirteen of said positions.

In additional embodiments, the invention provides the nucleic acid encoding the preprotein as described herein, wherein said variant signal peptide has amino acid substitution(s) selected from the group consisting of V-20A, V-20F, V-20G, V-20I, V-20K, V-20L, V-20M, V-20Q, V-20R, V-20T, V-20W, L-18F, L-18I, L-18Y, K-17F, K-17N, K-17Y, A-15F, A-15I, A-15L, A-15V, A-13T, A-12V, T-10F, T-10V, W-9Y, and V-1F.

In further embodiments, the invention provides the nucleic acid encoding the preprotein as described herein, wherein said variant glucoamylase enzyme has amino acid substitution(s) selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321F, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In additional embodiments, the invention provides the nucleic acid encoding the preprotein as described herein, wherein said variant glucoamylase enzyme has amino acid substitution(s) selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321F, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, L9P, E11S, L19I, V42I, D53N, T57S, I69L, L79Y, V88I, T89S, D118N, M119E, M141L, N168S, A195V, T261A, L311V, A317P, L347N, E348I, S355D, L364I, E381N, S382D, T388Q, F394Y, V395L and S434T.

In additional embodiments, the invention provides the nucleic acid encoding the preprotein as described herein, wherein said preprotein has amino acid substitution(s) selected from the group consisting of S188H/Y321W/ Q419P, T98S/Q161P/F516L, T98S/Q161P/N570P, T98S/ Q161P, T550D/F555S, V-20A/T258S, V65I/Y412F/Y503S/ S518I, Y412F/Y503S/I564T, Y412F/Y503E, Y412F/ Y503E/S518I, V65I/Y412F/Y503S, V65I/Y503E, Y503D/ S518I/I564N, Y503E/S518L, V65I/Y503E/S544Q, V65I/ Y503S, Y503E/S544E, V65I/Y503E/S544E/I564N, V65I/ Y412F/Y503E, Y503E/S518I/S544Q, V65I/Y503E/S518M, Y412F/S518L, Y503E/S544Q, V65I/Y412F/Y503E/S544E/ I564T/G569I, Y412F/Y503S, Y503E/I564T, S549D/F555D/ G559N, S549D/F555R, K508T/L526N/S549D/G559N, K508T/G559N, F555D/I556P/G559N, S549D/F555R/ I556P/G559N, F555R/I556P, L526I/F555R/I556P, F555R/ I556P/G559N, K508T/I556P/G559N, F555D/I556P, K508T/L526N/A534T/S549D/I556P, K508T/L526I/ S549D/G559N, K508N/L526I/S549E/F555L/G559N, L526N/S549D/F555D/I556P, L526I/F555D/G559N, A38V/ F555R, A39F/T540N/T542N, L498T/T542N/T581N/ T584N, T542N/T581N/T584N, S535Y/T542N, T540N/ T584N, T540N/T542N/T581N/T584N, L498T/T581N/ T584N, L498T/T584N, L498T/T542N/T581N, P121S/ T542N/T584N, L498T/T542N, S535Y/T540N/T542N/ T581N, Q419P/P423R, L79F/Q419P, Q419P/P423V, Q419P/P423R/T533R, S36P/Q419P, Q419P/P423G, S36P/ T400L/Q419P/P423G, S50Q/Q419P/P423R, S50Q/Q419P/ P423R/G457S/E497V/P521S, V-20R/A-15I, A-15F/S188T, V-20F/A-15I/Y321F/A422S, V-20F/A-15F/S188H/Q419P, A-15F/K5H/Y321W, A-15F/K5N/Y321F, V-20F/Y321F, V-20F/A-15I, A-15F/K5P/S188H, V-20F/E68S/S188H/ A422S, V-20F/S188T/Y321F/Q419P/A422S, V-20F/K5H/ S188H/Y321F/A422S, V-20F/A422S, A-15I/S188H/ Y321W/Q419P, A-15F/S188H/A422S, V-20F/S188H/ A422S/V545A, V-20F/A-15I/Q419P, V-20F/K5Q/A422S, V-20R/A-15I/K5S/E68K/Y321W, A-15F/K5H/Y321F/ A422S, V-20F/A-15F/K5N, V-20F/S188H/Y321W/Q419P, A-15I/Y321F, A-15F/K5Y/A422S, V-20F/A-15F/Q419P/ A422S, V-20F/K5Y/S188H/A422S, V-20T/A-15I/K5T/ A422S, V-20T/A-15I/K5T/Y321W, V-20R/A-15F/Y321W/ A422S, A-15F/A-13T, V-20F/Q419P/A422S, A-15I/K5P/ Y321F, V-20F/A-15F/Y321W, V-20F/A-15F/K5H/S188H/ Y321F/A422S, A-15I/E68K/A422S, Y321F/A422S, V-20T/ A-15F/K5H/Y321F, V-20T/A-15I/K5T/Y321F/Q419P/ A422S, K5T/E68Y/S188T, K5S/E68Y/S188H, K5N/ S188H, K5T/E68S/S188T, K5H/E68Y/S188P, K5P/E68Y/ S188T, K5T/E68K/S188H, K5P/E68K/S188T, K5H/E68Y/ S188T, K5T/S188H, K5T/E68N/S188T, K5Y/E68Y/S188T, K5S/E68Y/S188T, K5Q/E68K/S188H, K5P/E68N/S188H, K5P/E68N/S188T, K5P/E68Y/S188H, K5Y/E68Y/S188H, K5S/S188T, K5H/E68N/S188H, K5P/S188H, K5H/S46T/ E68K/S188H, K5H/E68K/S188T, K5Q/E68Y/S188T, K5Y/ E68N/S188H, V42I/S188H/A195V/Y412F/Q419P, L19I/ V42I/E68Y/N168S/S188H/A195V/Y412F, E11S/V42I/ T57S/D118N/N168S/S188H/A195V/L311V, E11S/V42I/ D53N/E68Y/N168S/S188H/A195V/L311V/Y412F, E11S/ L19I/V42I/I69L/Y321W/Y412F/Q419P, E11S/L19I/V42I/ E68Y/D118N/S188H/A195V/L311V/Y412F, E11S/L19I/ T57S/M119E/S188H/A195V/L311V/Y412F, E11S/V42I/ A317P/Y412F/Q419P, L19I/T57S/I69L/D118N/N168S/ S188H/A195V/L311V/A317P/Y321F/Y412F/Q419P, E11S/E68Y/S188H/A195V/L311V/Y412F, E11S/L19I/ V42I/E68Y/I69L/D118N/N168S/S188H/A195V/L311V/ Y412F, E11S/L19I/V42I/S188H/A195V/L311V/Y321W/ Y412F/Q419P, E11S/L19I/N168S/S188H/A195V/L311V/ A317P/Y321F/Y412F, E11S/V42I/E68Y/Y412F, E11S/

L19I/V42I/E68Y/Y412F, E11S/V42I/E68Y/S188H/A195V/ Y412F, E11S/L19I/V42I/T57S/I69L/S188H/A195V/ L311V/Y321W/Y412F, E11S/L19I/D53N/E68Y/S188H/ A195V/L311V/Y412F, E11S/V42I/E68Y/S188H/A195V/ L311V/Y321W/Y412F, E11S/V42I/E68Y/S188H/L311V/ Y412F/Q419P, E11S/L19I/V42I/E68Y/S188H/A195V/ L311V/A317P/Y321W/Y412F/Q419P, E11S/L19I/D53N/ I69L/S188H/A195V/L311V/Q419P, E11S/V42I/E68Y/ N168S/L311V/A317P/Y321W/Y412F, E11S/E68Y/I69L/ S188H/A195V/L311V/A317P/Y321F/Y412F, E11S/V42I/ T57S/E68Y/I69L/S188H/A195V/L311V/A317P/Y321F, E11S/D53N/T57S/L311V/Y321F/Y412F/Q419P, E11S/ L19I/S188H/A195V/L311V/A317P/Y321W/Y412F/ Q419P, E11S/L19I/I69L/S188H/A195V/L311V/A317P, E11S/V42I/I69L/N168S/S188H/A195V/L311V/A317P/ Y412F/Q419P, E11S/V42I/E68Y/S188H/A195V/L311V/ Y412F, E11S/V42I/I69L/S188H/A195V/L311V/A195V/ L311V/A317P/Y321F/Y412F, E11S/Y412F, E11S/L19I/ V42I/E68Y/I69L/S188H/A195V/Y412F, E11S/L19I/V42I/ D53N/T57S/S188H/A195V/L311V/Y321W/Y412F, V42I/ E68Y/Y412F, E11S/L19I/V42I/D53N/T57S/E68Y/I69L/ N168S/S188H/A195V/L311V/A317P/Y321F, E11S/L19I/ V42I/D53N/T57S/I69L/S188H/A195V/L311V/A317P/ Y321W/Y412F, E11S/V42I/A317P/Y321F, E11S/V42I/ T57S/E68Y/D118N/S188H/A195V/L311V/Y412F, E11S/ L19I/V42I/E68Y/I69L/D118N/N168S/S188H/A195V/ L311V/Y412F/Q419P, E11S/V42I/D53N/E68Y/S188H/ A195V/L311V/Y412F, E11S/I69L/D118N/S188H/A195V/ L311V/Y412F, V42I/D53N/T57S/E68Y/M141L/N168S/ T261A/Y321W/E381N/Y412F, E11S/V42I/S188H/L347N/ Y412F/S434T, D53N/T57S/E68Y/D118N/M119E/L311V/ E348I/Y412F, D118N/N168S/S188H/L347N/E348I/ S382D/T388Q/V395L, E68Y/I69L/N168S/S188H/A195V/ L311V/A317P/Y321W/Y412F/Q419P, E11S/E68Y/V88I/ A317P/Y321F/S355D, D53N/I69L/L79Y/M119E/T261A/ L311V/L347N/E348I/Q419P, V42I/E68Y/I69L/D118N/ M119E/M141L/L311V/A317P/Y321F/L347N, E11S/L19I/ E68Y/I69L/L79Y/M141L/N168S/T261A/A317P/Y321W/ L347N, E11S/V42I/E68Y/I69L/L311V/Y321W/S434T, E11S/V42I/D53N/N168S/L311V/A317P/Y321W, E11S/ E68Y/I69L/D118N/N168S/Y321F/Y412F, V42I/D53N/ T57S/L311V/Y321W/S355D/Y412F/Q419P, V42I/E68Y/ L311V/L347N/L364I/Y412F, E11S/D118N/M119E/ M141L/L311V/Y321W/L347N, V42I/D53N/T57S/M119E/ M141L/A317P/Y321F/Q419P, T57S/I69L/T89S/S188H/ A195V/T261A/L311V/A317P/Y321W/F394Y/Y412F, Y321F/Y412F, V42I/T57S/E68Y/I69L/T89S/M119E/ T261A/A317P/Y412F/S434T, E11S/V42I/E68Y/L311V/ A317P/S434T, V42I/D53N/T57S/E68Y/I69L/S434T, V42I/ E68Y/Y321W, L311V/L347N/E348I/S355D/L364I/S434T, E11S/D53N/T57S/E68Y/V88I/T89S/M119E/A317P/ Y321W, D53N/E68Y/I69L/T89S/L311V/A317P/S355D/ Q419P, V42I/E68Y/A317P/Y321F/Y412F, L19I/I69L/ T89S/L311V/A317P/Y321F/S355D/L364I/Y412F, V42I/ D53N/T57S/E68Y/I69L/M141L/S188H/A195V/L311V/ A317P/Y321F/Y412F/S434T, T57S/V88I/A317P/Y321W/ Q419P, E11S/L19I/V42I/D53N/E68Y/L311V/A317P/ Y321W/Y412F, E11S/V42J/D53N/E68Y/I69L/S188H/ A95V/E348I, L19J/V42I/T57S/I69L7V88I/M119E/T261A/ A317P/Y321F/Y412F, D53N/E68Y/D118N/M119E/ M141L/T261A/L347N/E348I/S355D/L364I/S434T, E11S/ T261A/L347N/E348I/S355D/S434T, M119E/S188H/ E348I, E11S/A317P/Y321F/L347N, E11S/E68Y/I69 L/T261A/L364I, D118N/M119E/N168S/S188H/A195V/ L311V/Y321W/L347N/F394Y, E11S/L311V/Y321W/ E348I/S355D/L364I/Y412F, V42I/D53N/T57S/I69L/V88I/ L347N/E348I/F394Y/V395L/S434T, E11S/D53N/T89S/ N168S/S188H/T261A/L311V/A317P/Y321W/S355D/ Y412F, L19I/V42I/D53N/L79Y/T89S/N168S/T261A/ L311V/Y321W/Y412F/Q419P/S434T, L79Y/V88I/D118N/ M119E/T261A/Y321F/L364I/Y412F, V42I/E68Y/T89S/ M141L/T261A/L311V/Y321F/E348I/L364I, V42I/E68Y/ D118N/S188H/T261A/Y412F/S434T, E11S/D53N/E68Y/ I69L/T89S/Y321W/E348I/S355D, M119E/L311V/Y321F, L311V/L347N/E348I, E11S/V42I/A317P/Y321F/L347N/ Y412F, E11S/L19I7V42I/E68Y/A317P/Y321F/L364I/ Y412F, D53N/E68Y/T89S/T261A, I69L/S188H/A195V/ L311V/A317P/Y321W/V395L/Y412F, V42I/D53N/E68Y/ V88I/T89S/D118N/L311V/Y412F/S434T, E11S/V42I/ E68Y/I69L/L311V/E348I, V42I/Y321W, E68Y/T261A/ L311V/L347N/E348I/S434T, E11S/E68Y/I69L/L79Y, V42I/D53N/E68Y/S188H/A195V/T261A/L311V/Y321F/ S355D/S434T, L19I/V42I/S188H/A195V/S382D/V395L/ Q419P, E11S/L19I/V42I/D53N/T57S/M119E/L311V/ Y321W/L347N/F394Y/Y412F, L9P/E11S/D53N/T57S/ E68Y/M119E/M141L/E348I/Y412F and L19I/V42I/I69L/ L311V/Y321W/L347N.

In a further embodiment, the invention provides the nucleic acid encoding the preprotein as described herein, wherein said variant glucoamylase enzyme has an amino acid substitution Y321F.

In an additional embodiment, the invention provides the nucleic acid encoding the preprotein as described herein, wherein said variant glucoamylase enzyme has amino acid substitutions S188H/Y321W/Q419P.

In a further embodiment, the invention provides the nucleic acid encoding the preprotein as described herein, wherein said variant glucoamylase enzyme comprises an amino acid substitution Y321F, and further comprises at least one amino acid substitution selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188H, S188P, S188T, S188W, T192A, K212Y, S215A, T258S, A262S, H264M, I298V, Y321L, Y321W, T400L, Y412F, Q419P, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, A452A, V453S, A460S, A469S, A470T, S472T, G475V, T476W, G478S, L492P, and L9P.

In an additional embodiment, the invention provides the nucleic acid encoding the preprotein as described herein, wherein said variant glucoamylase enzyme comprises amino acid substitutions S188H/Y321W/Q419P, and further comprises at least one amino acid substitution selected from the group consisting of K5H, K5N, K5P, K5Q, K5S, K5T, K5Y, N27A, S36P, A38V, A39F, S46T, P47T, S50Q, V65I, E68K, E68N, E68S, E68Y, L79F, T89N, T98S, A108S, P121S, F122M, G124P, G124S, G124T, G158S, Q161P, S188P, S188T, S188W, T192A, K212Y, S215A, T258S, A262S, H264M, I298V, Y321F, Y321L, T400L, Y412F, L420K, A422G, A422S, P423G, P423R, P423V, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, I44V, R49H, D53N, Y55F, T57S, I69L, S72A, V73F, T78K, L79D, L79Y, E85Q, N86Q, V88I, T89S, A92T, Y93K, L94V, V97I, S103D, D106T, D118N, M119E, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227F, A246S, S247G, A256V, T261A, T261G, S306A, A307E, D309S, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P.

In some embodiments, the invention provides the nucleic acid encoding a preprotein as described herein, wherein the preprotein comprises a sequence having SEQ ID NO:5 or SEQ ID NO:7.

"Codon optimized" in this context is done in relation to a particular host organism and its generally preferred amino acid codons; that is, the host production organism, e.g. an *Aspergillus* species, may yield higher translation and/or secretion using *Aspergillus* preferred codons as compared to a yeast production organism.

In some embodiments, the invention provides the nucleic acid as described herein, wherein said nucleic acid is codon optimized for a host organism for expression of the variant glucoamylase enzyme in said organism.

In some embodiments, the compositions are enriched in such a variant glucoamylase enzyme encoding nucleic acid of the present invention. The term "enriched" indicates that the glucoamylase activity capable of being obtained from the composition has been increased, e.g., with an enrichment factor of at least 1. In some embodiments, the compositions are formulated to provide desirable characteristics such as low color, low odor and acceptable storage stability.

1. Preparation of Variants

The variants can be prepared generally by construction genes encoding the protein sequence using well known techniques, including site-directed mutagenesis of a parental gene and synthetic gene construction.

i. Regulatory Sequences

The present invention also relates to nucleic acid constructs comprising a polynucleotide encoding a variant of the present invention operably linked to one or more control sequences that direct the expression of the coding sequence in a suitable host cell under conditions compatible with the control sequences. The control sequence may include a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell. As will be appreciated by those in the art, the exact length of the promoter is not known, with promoters generally being located near the transcription site of the gene, and can be anywhere from roughly 100 to 1000 base pairs long. Thus, for the purposes outlined herein, the promoter is inclusive of at least 100 upstream base pairs of the sequence shown in the figures.

Examples of suitable promoters for directing transcription of the nucleic acid constructs of the present invention in a filamentous fungal host cell are promoters obtained from *Aspergillus* species genes, as is known in the art, including *A. nidulans, A. niger* and *A. oryzae*, as well as *Rhizomucor* species genes such as *R. miehei*, *Trichoderma* species genes including *T. reesei*, *Fusarium* species including *F. venenatum*. Yeast control sequences including promoters are also well known from *Saccharomyces cerevisiae*.

Suitable promoter sequences (as well as other control sequences) from these species include the promoters from amylases (α-amylase in particular), glucoamylases, proteases, phosphatases, endoglucanases, cellulases, etc. as are known in the art. In addition, as for codon-optimization, it may be desirable to use promoters (and other control sequences) that are endogeneous to the host production strain, operably linked to the nucleic acids encoding the variant glucoamylases. In many embodiments, the promoter that is operably attached to the coding sequence is not the native *Thielaviopsis* punctuala promoter sequence.

The control sequence may also be a transcription terminator, which is recognized by a host cell to terminate transcription. The terminator sequence is operably linked to the 3'-terminus of the polynucleotide encoding the variant. Any terminator that is functional in the host cell can be used.

In some embodiments, terminators (and other control sequences such as promoters) for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

In some embodiments, terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase.

The control sequence can also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence can also be a leader, a nontranslated region of an mRNA that is important for translation by the host cell. The leader sequence is operably linked to the 5'-terminus of the polynucleotide encoding the variant. Any leader that is functional in the host cell may be used.

In some embodiments, leaders for filamentous fungal host cells are obtained from the genes for *Aspergillus oryzae* TAKA amylase and *Aspergillus nidulans* triose phosphate isomerase.

In some embodiments, suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence can also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

In some embodiments, polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

The control sequence may also be a signal peptide coding region that encodes a signal peptide linked to the N-terminus of a variant and directs the variant glucoamylase being expressed into the cell's secretory pathway. In some embodiments, the signal peptide sequence is the wild type signal peptide sequence as set forth in SEQ ID NO:26. In some embodiments, the signal peptide is a variant signal peptide as compared to SEQ ID NO:26, and the variant signal peptide exhibits at least 50%, 55%, 60%, 65%, 70%, 75%, 80%, 85%, 90%, or 95% identity to SEQ ID NO:26. In some embodiments, the signal peptide is a variant signal peptide as compared to SEQ ID NO:26, and the variant signal peptide comprises at least one amino acid substitution(s) at a position number selected from the group consisting of $-20$, $-18$, $-17$, $-15$, $-13$, $-12$, $-10$, $-9$, and $-1$. In some embodiments, the signal peptide is a variant signal peptide as compared to SEQ ID NO:26, and the variant signal peptide has amino acid substitution(s) at one of said positions, two of said positions, three of said positions, four of said positions, five of said positions, six of said positions, seven of said positions or eight of said positions. In some embodiments, the signal peptide is a variant signal peptide as compared to SEQ ID NO:26, and the variant signal peptide has amino acid substitution(s) selected from the group consisting of V-20A, V-20F, V-20G, V-20I, V-20K, V-20L, V-20M, V-20Q, V-20R, V-20T, V-20W, L-18F, L-18I, L-18Y, K-17F, K-17N, K-17Y, A-15F, A-15I, A-15L, A-15V, A-13T, A-12V, T-10F, T-10V, W-9Y, and V-1F.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the Gpd (Glyceraldehyde-3-phosphate dehydrogenase) from Ascomycota such as *Aspergillus*, *Aspergillus niger* glucoamylase promoter, *Aspergillus oryzae* TAKA alpha-amylase promoter, and *Aspergillus oryzae* glucoamylase promoter can be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

2. Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector can be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used. Vectors contemplated for use with the methods of the invention include both integrating and non-integrating vectors.

In some embodiments, the vector contains one or more selectable markers that permit easy selection of transformed, transfected, transduced, or the like cells. In many embodiments, the selection genes encode resistance to antibiotics such as ampicillin, ampicillin, chloroamphenicol, hygromycin, tetracycline or kanamycin, etc.

In some embodiments, the invention provides an expression vector comprising the nucleic acid as described herein.

Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

In some embodiments, the vector contains an element(s) that permits integration of the vector into the host cell's genome or autonomous replication of the vector in the cell independent of the genome.

For integration into the host cell genome, the vector can rely on the polynucleotide's sequence encoding the variant or any other element of the vector for integration into the genome by homologous or non-homologous recombination. Alternatively, the vector can contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector can further comprise an origin of replication enabling the vector to replicate autonomously in the host cell in question. The origin of replication can be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention can be inserted into a host cell to increase production of a variant, including the use of multiple genes encoding the variant glucoamylase in a vector, multiple vectors transformed into a cell, or multiple integrations of a vector into the genome. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

C. Particular Constructs

For expression in *Saccharomyces cerevisiae*, we used *Saccharomyces cerevisiae* INSCV1 strain (ThermoFisher Scientific, USA: Catalogue #V8251-20) and pYES2/CT vector (ThermoFisher Scientific, USA: Catalogue #V8251-20). For expression in *Pichia pastoris*, we used X33 *Pichia* strain and pPiCZαA vector (EasySelect *Pichia* Expression Kit, Invitrogen by life technologies). All are commercially available and are also discussed in the Examples below.

1. Codon Optimization

Codon optimization can be employed with any of the variant glucoamylase enzymes of the present invention, in order to optimize expression in the host cell employed. Such methods are well known in the art and described in, for example, WO 2007/142954. In heterologous expression systems, optimization steps can improve the ability of the host to produce the desired variant glucoamylase enzymes. Protein expression is governed by a host of factors including those that affect transcription, mRNA processing, and stability and initiation of translation. The polynucleotide optimization steps can include steps to improve the ability of the host to produce the foreign protein as well as steps to assist the researcher in efficiently designing expression constructs. Optimization strategies can include, for example, the modification of translation initiation regions, alteration of mRNA structural elements, and the use of different codon biases.

In some embodiments, reduced heterologous protein expression occurs through interfering secondary structures. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

In some embodiments, restriction sites can effect heterologous protein expression. By modifying restriction sites that could interfere with subsequent sub-cloning of transcription units into host expression vectors a polynucleotide sequence can be optimized.

In some embodiments, the optimized nucleic acid sequence can express the variant glucoamylase enzymes of the invention, at a level which is at least 110%, 150%, 200%, 500%, 1,000%, 5,000% or even 10,000% of that expressed by nucleic acid sequence that has not been optimized.

D. Host Cells and Production Strains

As will be appreciated by those in the art, there are a wide variety of production host organisms for the recombinant production of the variant glucoamylase enzymes of the invention, including, but not limited to bacterial cells and fungal cells including yeast.

The present invention also relates to recombinant host cells, comprising a polynucleotide encoding a variant glucoamlyase of the present invention operably linked to one or more control sequences that direct the production of a variant of the present invention. A construct or vector comprising a polynucleotide is introduced into a host cell so that the construct or vector is maintained as a chromosomal integrant or as a self-replicating extrachromosomal vector as described earlier. The choice of a host cell will to a large extent depend upon the gene encoding the variant and the ability of the host production organism to yield high protein titers of expressed and/or secreted proteins. In some embodiments, the host cell exhibits transitory expression of the variant glucoamlyase. In some embodiments, the host cell is a stably transfected host or a host cell that stably (i.e., permanently) expresses the variant glucoamylase. In some embodiments, the host cell is a production host cell. The transformation and/or transfection of the host cells with the expression vectors comprising the coding region for the variant glucoamylases of the invention is done as is well known in the art (See Sambrook, id.).

In some embodiments, the invention provides a host cell comprising the nucleic acid as described herein. In some embodiments, the invention provides a host cell comprising the expression vector as described herein.

In some embodiments, the invention provides the host cell as described herein, wherein the host cell is selected from the group consisting of a bacterial cell, a fungal cell, or a yeast cell.

The host cell can be any cell useful in the recombinant production of a variant, e.g., a prokaryote or a eukaryote. Such host cells include but are not limited to bacterial, fungal, and yeast cells. The host cell can also be a eukaryote, such as a mammalian, insect, plant, or fungal cell.

The host cell can be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK). In many cases, host cells include *Aspergillus* species including *A. nidulans, A. niger* and *A. oryzae*, as well as *Rhizomucor* species such as *R. miehei, Trichoderma* species including *T. reesei* and *Fusarium* species genes including *F. venenatum*. The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

In some embodiments, the fungal host cell can be a yeast cell. "Yeast" as used herein includes ascosporogenous yeast (Endomycetales), basidiosporogenous yeast, and yeast belonging to the Fungi Imperfecti (Blastomycetes). The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

E. Protein Compositions

The present invention also provides compositions comprising a variant glucoamylase enzyme of the present invention. In some embodiments, the composition comprises a carrier and/or an excipient. In some embodiments, the compositions are enriched in such a variant glucoamylase enzyme of the present invention. The term "enriched" indicates that the glucoamylase activity of the composition has been increased, e.g., with an enrichment factor of at least 1. In some embodiments, the compositions are formulated to provide desirable characteristics such as low color, low odor and acceptable storage stability.

In some embodiments, the composition comprises a variant glucoamylase enzyme of the present invention as the major enzymatic component, e.g., a mono-component composition.

In some embodiments, the composition may comprise one or more additional enzymes, depending on the end use, including, but not limited to, aminopeptidase, alpha-amylase, beta-amylase, isoamylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, glucoamylase, polyphenoloxidase, pullulanase, proteolytic enzyme, ribonuclease, transglutaminase, and/or xylanase.

In some embodiments, the composition comprises an alpha-amylase and the variant glucoamylase enzyme according to the invention. In some embodiments, the composition comprises an isoamylase and the variant glucoamylase enzyme according to the invention. In another embodiment the composition comprises an alpha-amylase, an isoamylase and the variant glucoamylase according to the invention.

In some embodiments, the composition comprises the variant glucoamylase enzyme of the invention combined with a pullulanase. In some embodiments, the composition comprises the variant glucoamylase of the invention combined with a pullulanas and an isoamylase. In some embodiments, the composition comprises the variant glucoamylase of the invention combined with a pullulanase and an alpha-amylase.

In some embodiments, the composition comprises the variant glucoamylase enzyme of the invention further comprises acid, neutral and/or alkaline proteases. In another embodiment the composition comprises the variant glucoamylase according to the invention and a cocktail of enzymes including alpha-amylase, proteases, peptidase, lipase, cellulose, pancreatin, and others.

F. Formulations of Variant Glucoamylases

In some embodiments, the invention provides a formulation suitable for consumption by an animal, wherein said formulation comprises a variant glucoamylase enzyme as described herein, and at least one consumable components.

In some embodiments, the compositions can be prepared in accordance with methods known in the art and can be in the form of a liquid or a dry composition. For instance, the composition may be in the form of granulate or microgranulate. The variant can be stabilized in accordance with methods known in the art.

In some embodiments, the enzyme composition (i.e., polypeptide compositions) of the present invention can be in any form suitable for use, such as, for example, a crude fermentation broth with or without cells removed, a cell lysate with or without cellular debris, a semi-purified or purified enzyme composition, or a host cell, as a source of the enzymes.

In some embodiments, the enzyme composition can be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In some embodiments, the dosage of the polypeptide composition of the invention and other conditions under which the composition is used may be determined on the basis of methods known in the art.

The above compositions are suitable for use in liquefaction, saccharification, and/or fermentation processes, and in some embodiments, in starch conversion. In some embodiments, the compositions are useful for producing a food product, including a syrup, as well as fermentation products, such as ethanol. In some embodiments, the compositions are useful for the pharmaceutical industry, such as in digestive aids.

In addition, as outlined below, the novel glucoamylases of the invention can be combined with other enzymes, including, but not limited to, alpha-amylases, pullulanases, cellulases (xylanases, ligninases, etc.) as more fully described below.

G. Methods of Production

The present invention also relates to methods of producing a variant glucoamylase enzyme, comprising: (a) cultivating the host cell of the present invention as described herein under conditions suitable for expression of the variant glucoamylase polypeptide; and (b) optionally recovering the variant glucoamylase polypeptide.

The host cells are cultivated in a nutrient medium suitable for production of the variant glucoamylase polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the variant glucamylase polypeptide is secreted into the nutrient medium, the variant glucamylase polypeptide can be recovered directly from the medium. If the variant is not secreted, it can be recovered from cell lysates.

The variant glucamylase polypeptide can be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant glucamylase polypeptide.

The variant glucamylase polypeptide can be recovered using methods known in the art. For example, the variant glucamylase polypeptide can be recovered from the nutrient medium by conventional procedures including, but not limited to, collection, centrifugation, filtration, extraction, spray-drying, evaporation, or precipitation.

The variant can be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

H. Methods of Using Variant Glucoamylases

Glucoamylase is regularly used in food and fermentation industries for the saccharification of starch to glucose.

The saccharification process can use glucoamlyase alone. Alternatively, the saccharification process can be a synergetic action of a number of enzymes including glucoamylase in combination with amylase (particular α-amylase), and additional debranching enzymes such as pullulanases or isoamylases. Glucose isomerase can be further employed to convert glucose to fructose which is traditionally preferred due to its higher sweetness and easier metabolizability. For example, glucoamylase can be used in doughs to improve bread crust color and produce low-calorie beer. Another key application of glucoamylase is as a digestive aid when used together with a cocktail of other enzymes.

In some embodiments, the glucoamylase are used in animal feed stocks or in the production of animal feed stocks, including the components and use described in detail below.

In some embodiments, the invention provides a method of carbohydrate saccharification from a starch substrate comprising contacting said substrate with a variant glucoamylase enzyme as described herein, wherein said starch is degraded.

As discussed herein, the use of glucoamylase enzyme in animal feeds has a number of benefits, including a feed cost savings, such as reductions in dietary inorganic phosphate, energy and amino acids, including a fast and efficient breakdown of dietary glucose and increased nutrient availability from glucose, as well as production benefits such as body weight gain for the non-ruminant subjects. In some embodiments, the variant glucoamylase enzymes of the invention are formulated and added to feed or can be made as a component of the feed. In the former case, the feed stock addition of glucoamylase enzyme can be done by formulating the variant glucoamylase enzyme on a carrier feed such as wheat flour. In some embodiments, the animal feed stocks or supplements are feed to livestock, including but not limited to cattle, pigs, sheep, bird, cat, fish, dog, equine, pet, poultry, etc. In some embodiments, the variant glucoamylase enzymes of the invention can be fed to humans (See, for example http://www.globalhealingcenter.com/natural-health/glucoamylase/) as well as other commercially available products for human consumption such as Vegan-Zyme®.

In some embodiments, the dosage of the polypeptide composition of the invention and other conditions under which the composition is used may be determined on the basis of methods known in the art.

The above compositions are suitable for use in liquefaction, saccharification, and/or fermentation processes, and in some embodiments, in starch conversion. In some embodiments, the compositions are useful for producing a food product, including a syrup, as well as fermentation products, such as ethanol. In some embodiments, the compositions are useful for the pharmaceutical industry, such as digestive aids.

In one embodiment, the variant glucoamylase enzymes are added to animal feed stock and pelleted as is known in the art, such that the feed is formed with glucoamylase enzyme in it. In other embodiments, the variant glucoamylase enzyme can be sprayed or dosed in a liquid form into animal feed.

1. Industrial Applications

The variant glucoamylases of the present invention possess valuable properties allowing for a variety of industrial applications. In some embodiments, the glucoamylases may be used in feed stock production, beer making, ethanol production, biofuel production, and starch conversion processes.

In general, the major commercial application of glucoamylase is to catalyze starch saccharification resulting in glucose which can be used in food and fermentation processes. In general, this is a two step process, with the first step utilizing a dry solid starch slurry (30-35%, with optionally milling) that is gelatinized with a thermal treatment at 60 to 90° C. with liquifaction at 95-105° C. (generally pH 6.5) with an α-amylase. The α-amylase is an endo-acting enzyme, resulting in short-chain dextrins. These dextrins are then saccharified by glucoamylase to release glucose, a step that is usually done at 60° C. for 2-4 days. It is this last step that results in the need for a thermostable glucoamylase.

In some embodiments, the present invention provides a biofuel made by the use of a variant glucoamylase enzyme that produces glucose, that is then subjected to a fermentation step to result in ethanol production (usually using a yeast).

The variant glucoamylases may be used for starch processes, in particular starch conversion, especially liquefaction of starch (see, e.g., U.S. Pat. No. 3,912,590, EP 252730 and EP 063909, WO 99/19467, and WO 96/28567, which are all hereby incorporated by reference). Also contemplated are compositions for starch conversion purposes, which may in addition to the glucoamylase of the invention further comprise an alpha-amylase, a pullulanase and/or a protease.

Further, the glucoamylases of the invention are particularly useful in the production of sweeteners and ethanol (see, e.g., U.S. Pat. No. 5,231,017, which is hereby incorporated by reference), such as fuel, drinking and industrial ethanol, from starch or whole grains.

In some embodiments, the present invention relates to a use of the glucoamylase according to the invention for production of syrup and/or a fermentation product from a starch containing material. The starch material may in one embodiment be gelatinized. In another embodiment the starch material is ungelatinized.

2. Starch Processing

As discussed herein, the novel glucoamylase enzymes of the invention find particular use in starch processing. Native starch consists of microscopic granules, which are insoluble in water at room temperature. When aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolyzate is used in the production of, e.g., syrups or other feed supplements. Both dry and wet milling is well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction can be carried out in the presence of an alpha-amylase, and in some embodiments, the alpha-amylase is a bacterial alpha-amylase and/or acid fungal alpha-amylase. In an embodiment, a glucoamylase is also present during liquefaction. In some embodiments, viscosity reducing enzymes such as a xylanase and/or beta-glucanase is also present during liquefaction. In some embodiments, acid protease is also present. In some embodiments, acid protease is also present to reduce corn steeping time.

In some embodiments, the process of the invention further comprises, prior to the conversion of a starch-containing material to sugars/dextrins the steps of: (i) reducing the particle size of the starch-containing material; and (ii) forming a slurry comprising the starch-containing material and water.

3. Beer Making

The variant glucoamylase enzymes can also be used in a beer-making process and similar fermentations.

I. Distillation

Optionally, following fermentation, an alcohol (e.g., ethanol) can be extracted by, for example, distillation and optionally followed by one or more process steps.

1. Enzymes

The enzyme(s) and polypeptides described below are to be used in an "effective amount" in processes of the present invention or can be combined with the variant glucoamylase enzymes of the invention. In some embodiments, the the variant glucoamylase enzymes can be combined with enzymes including but not limited to alpha-amylases, bacterial alpha-amylases, bacterial hybrid alpha-amylases, fungal alpha-amylases, fungal hybrid alpha-amylases, carbohydrate-source generating Enzymes (Saccharifying Enzymes), glucoamylases, beta-amylases, maltogenic amylases, glucoamylases, pullulanases, and proteases.

a. Alpha-Amylases

Any alpha-amylase may be used, such as of fungal, bacterial or plant origin. In some embodiments, the alpha-amylase is an acid alpha-amylase, e.g., acid fungal or acid bacterial alpha-amylase. The term "acid alpha-amylase" means an alpha-amylase (EC 3.2.1.1) which added in an effective amount has activity optimum at a pH in the range of 3 to 7, from 3.5 to 6, or from 4-5.

b. Bacterial Alpha-Amylases

An alpha-amylase for use in the present invention may be a bacterial alpha-amylase, e.g., derived from *Bacillus*. In a preferred embodiment the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp.

c. Bacterial Hybrid Alpha-Amylases

The alpha-amylase can be a hybrid alpha-amylase, e.g., an alpha-amylase comprising 445 C-terminal amino acid residues of the *Bacillus licheniformis* alpha-amylase and the 37 N-terminal amino acid residues of the alpha-amylase derived from *Bacillus amyloliquefaciens*.

d. Fungal Alpha-Amylases

Fungal alpha-amylases include but are not limited to alpha-amylases derived from a strain of *Aspergillus*, such as, *Aspergillus kawachii, Aspergillus niger*, and *Aspergillus oryzae* alpha-amylases. In some embodiments, the alpha-amylase is derived from *Aspergillus kawachii* (Kaneko et al., 1996, J. Ferment. Bioeng. 81:292-298, "Molecular-cloning and determination of the nucleotide-sequence of a gene encoding an acid-stable alpha-amylase from *Aspergillus kawachii*"; and further as EMBL: #AB008370)

The fungal alpha-amylase may also be a wild-type enzyme comprising a starch-binding domain (SBD) and an alpha-amylase catalytic domain, or a variant thereof.

2. Fungal Hybrid Alpha-Amylases

In some embodiments, the fungal acid alpha-amylase is a hybrid alpha-amylase.

A hybrid alpha-amylase may comprise an alpha-amylase catalytic domain (CD) and a carbohydrate-binding domain/module (CBM), such as a SBD, and optionally a linker.

3. Commercial Alpha-Amylase Products

In some embodiments, commercial compositions comprising alpha-amylase include MYCOLASE™ (DSM), BAN™, TERMAMYL™ SC, FUNGAMYL™, LIQUOZYME™ X, LIQUOZYME™ SC and SAN™ SUPER, SAN™ EXTRA L (Novozymes A/S) and CLARASE™ L-40,000, DEX-LO™, SPEZYME™ FRED, SPEZYME™ AA, SPEZYME™ ALPHA, SPEZYME™ DELTA AA, GC358, GC980, SPEZYME™ CL and SPEZYME™ RSL (DuPont Industrial Biosciences), and the acid fungal alpha-amylase from *Aspergillus niger* referred to as SP288 (available from Novozymes A/S, Denmark).

4. Carbohydrate-Source Generating Enzymes (Saccharifying Enzymes)

The term "carbohydrate-source generating enzyme" includes glucoamylase (a glucose generator), beta-amylase and maltogenic amylase (both maltose generators) and also alpha-glucosidase, isoamylase and pullulanase. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate can be converted directly or indirectly to the desired fermentation product, preferably ethanol. A mixture of carbohydrate-source generating enzymes may be used. In some embodiments, blends include mixtures comprising at least a glucoamylase and an alpha-amylase, especially an acid amylase, even more preferred an acid fungal alpha-amylase.

In a conventional starch-to-ethanol process (i.e., including a liquefaction step), the ratio can be carried out as is known in the art, especially when saccharification and fermentation are carried out simultaneously.

5. Beta-Amylases

In some embodiments, a beta-amlyase can be included in the compositions of the invention. A beta-amylase (E.C 3.2.1.2) is the name traditionally given to exo-acting maltogenic amylases, which catalyze the hydrolysis of 1,4-alpha-glucosidic linkages in amylose, amylopectin and related glucose polymers.

Beta-amylases have been isolated from various plants and microorganisms (Fogarty and Kelly, 1979, Progress in Industrial Microbiology 15: 1 12-1 15). These beta-amylases are characterized by having a temperature optimum in the range from 40° C. to 65° C. and a pH optimum in the range from 4.5 to 7. A commercially available beta-amylase from barley is NOVOZYM™ WBA from Novozymes A/S, Denmark and SPEZYME™ BBA 1500 from DuPont Industrial Biosciences, USA.

6. Maltogenic Amylases

In some embodiments, a maltogenic amlyase can be included in the compositions of the invention and/or used in the pocesses of the invention. The amylase can be a maltogenic alpha-amylase (glucan 1,4-alpha-maltohydrolase, EC 3.2.1.133), which catalyzes the hydrolysis of amylose and amylopectin to maltose in the alpha-configuration. A maltogenic amylase from *Bacillus stearothermophilus* strain NCIB 1 1837 is commercially available from Novozymes A/S. Maltogenic.

The maltogenic amylase can be added in an amount of 0.05-5 mg total protein/gram DS or 0.05-5 MANU/g DS.

7. Phytases

In some embodiments, a glucoamylase can be included in the compositions of the invention. Any glucoamylase may be used in a process of the present invention. Phytases are enzymes that degrade phytates and/or phytic acid by specifically hydrolyzing the ester link between inositol and phosphorus. Phytase activity is credited with phosphorus and ion availability in many ingredients. In some embodiments, the glucoamylase is capable of liberating at least one inorganic phosphate from an inositol hexaphosphate (e.g., phytic acid). Phytases can be grouped according to their preference for a specific position of the phosphate ester group on the phytate molecule at which hydrolysis is initiated (e.g., 3-phytase (EC 3.1.3.8) or 6-phytases (EC 3.1.3.26)). An example of phytase is myo-inositol-hexakiphosphate-3-phosphohydrolase. Phytases can also include those in PCT application number PCT/US2016/040555, filed on Jun. 30, 2016, hereby incorporated by reference in its entirety, and in particular for the sequences of the phytases depicted therein.

In some embodiments, the glucoamylase is a commercially-available phytase, such commercially-available phytases include but are not limited to NATUPHOS (BASF), RONOZYME P (Novozymes A/S), PHYZYME (Danisco A/S, Verenium) and FINASE (AB Enzymes). The method for determining microbial phytase activity and the definition of a phytase unit is disclosed in Engelen et al., 1994, *Journal of AOAC International* 77: 760-764. In some embodiments, the phytase can be a wild-type phytase, an active variant or active fragment thereof.

8. Pullulanases

In some embodiments, a maltogenic amlyase can be included in the compositions of the invention and/or used in the pocesses of the invention. Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

In some embodiments, the pullulanase is a commercially-available pullulanase, such commercially-available pullulanases include but are not limited to PROMOZYME D, PROMOZYME™ D2 (Novozymes A/S, Denmark), OPTIMAX L-1000, OPTIMAX L-300 (DuPont Industrial Biosciences), and AMANO 8 (Amano, Japan).

9. Proteases

A protease can be added during saccharification, fermentation, simultaneous saccharification and fermentation. The protease may be any protease. In some embodiments, the protease is an acid protease of microbial origin, for example of fungal or bacterial origin. In some embodiments, the protease is an acid fungal protease, but also other proteases can be used.

Suitable proteases include but are not limited to microbial proteases, such as fungal and bacterial proteases.

In some embodiments, the proteases are acidic proteases, i.e., proteases characterized by the ability to hydrolyze proteins under acidic conditions below pH 7.

The protease can be a neutral or alkaline protease, such as a protease derived from a strain of *Bacillus*. In some embodiments, the particular protease is derived from *Bacillus amyloliquefaciens* and has the sequence obtainable at the Swissprot Database, Accession no. P06832.

In some embodiments, the protease is a protease preparation derived from a strain of *Aspergillus*, such as *Aspergillus oryzae*. In another embodiment the protease is derived from a strain of *Rhizomucor*, such as *Rhizomucor miehei*. In some embodiments the protease is a protease preparation, such as a mixture of a proteolytic preparation derived from a strain of *Aspergillus*, such as *Aspergillus oryzae*, and a protease derived from a strain of *Rhizomucor*, such as *Rhizomucor miehei*.

In some embodiments, the protease is a commercially-available protease, such commercially-available proteases include but are not limited to ALCALASE®, ESPERASE™, FLAVOURZYME™, NEUTRASE®, NOVOZYM™ FM 2.0L, and iZyme BA (available from Novozymes A/S, Denmark) and GC106™ and SPEZYME™ FAN from DuPont Industrial Biosciences, USA, and RENNI LASE® from DSM.

VI. Examples

Example 1: Design and Construction of Glucoamylase G7P

The starting gene is G16 G6P as set forth in SEQ ID NO:1. To improve the overall activity of G16 G6P, G7P was designed rationally to truncate the SBD of G6P. The sequence alignment of G6P and G7P is shown in FIG. 1. G7P was subsequently constructed using gene specific primers with 5'EcoR1 and 3'Not 1 cloning site. Following PCR and restriction digestion, it was cloned into pPiCZαA vector (EasySelect *Pichia* Expression Kit, Invitrogen by life technologies). The recombinant plasmid was linearized using Pme1 restriction enzyme and was transformed into X33 *Pichia* strain from the same expression kit mentioned earlier. The transformants were then selected on YPD+Zeocine agar plates after 3 days of growth at 30° C.

Example 2: Preparation of Glucoamylase G6P and G7P Produced by *Pichia pastoris* in HTP Glucoamylase-encoding genes from single colonies were inoculated into individual wells of 24 well plates containing 2000 μl of BMGY medium according to ThermoFisher Scientific receipe. The cultures were grown for 18 hrs at 30° C., 200 rpm and 85% humidity. After 18 hrs, 24 wells plates were centrifuged and the liquid media was decanted. 2000 μl of BMMY medium was added into the pellet according to ThermoFisher Scientific recipe. 200 μl of 10% methanol was added to each plate. The plates were incubated at 30° C., 200 rpm and 85% humidity incubator. At every 24 hrs, 200 μl of 10% methanol was added to each plate. Harvest plate at 72 hrs by centrifuging plates at 4,000 rpm at 4° C. for 10 minutes. The supernatants were transferred to costar deep wells plates and stored at −20° C. prior to activity assay.

Example 3: Starch Assay to Determine *Pichia pastoris* Produced Glucoamylase G6P and G7P Thermoactivity at 40° C.

115 μL of 2% heated soluble starch (final concentration of 1.5% starch), 10 μL of 4× diluted enzyme supernatant plus 25 μL pH 4.3 buffer were incubated for 0.5 hours at 40° C. with 400 rpm agitation. 20 μL of the incubated sample was added to 90 μL of water for 10× detection dilution for reaction plates incubated at 40° C. 10 μL of diluted samples was transferred from 5× detection dilution plate, mixed with 190 μL of GOPOD (glucose oxidase/peroxidase) and then incubated for 30 minutes at 50° C. with 400 RPM agitation. Absorbance was read at 510 nm to determine glucose released.

As shown in FIG. 2, G7P exhibited >3 fold improved thermoactivity than G6P.

Example 4: Glucoamylase G6 and G7 Mutant Collection Design and Construction

To improve the overall activity of G16 G6P and G7P, multiple mutant collections were designed during G6 improvement and multiple mutant collections were designed during G7 improvement based on analyzing sequence, structural and experimental data of G16. The design includes one to multiple specific mutations per mutant. The mutant collections were subsequently constructed using the QuickChange® Lightning kit (Agilent Technologies, Santa Clara, Calif.) and subsequently cloned into the pYES2/CT vector (ThermoFisher Scientific, USA: Catalogue #V8251-20).

Example 5: Preparation of Glucoamylase Produced by *Saccharomyces cerevisiae* in HTP The *Saccharomyces cerevisiae* INSCV1 strain (ThermoFisher Scientific, USA: Catalogue #V8251-20) containing recombinant glucoamylase-encoding genes from single colonies were inoculated into individual wells of 96 well plates containing 300 μl synthetic minimal defined medium (SC) with 2% glucose and no uracil supplementation. The cultures were grown overnight at 30° C., 200 rpm and 85% humidity. Appropriate volume of overnight culture from each well needed to obtain an $OD_{600}$ of 0.4 was added to corresponding wells of the new 96 well plates containing 350 μl of induction medium (SC selective medium containing 2% galactose). The plates were then incubated for 48 hrs at 30° C., 250 rpm and 85% humidity. The cells were then pelleted using centrifugation at 4000 rpm for 10 min at 4° C. The supernatants were transferred to round bottom plates and stored at −20° C. prior to activity assay.

Example 6: Starch Assay to Determine *Saccharomyces cerevisiae* Produced

Glucoamylase Thermoactivity at 30° C. and 60° C.

115 μL of 2% heated soluble starch (final concentration of 1.5% starch), 10 μL supernatant enzyme plus 25 μL pH 4.3 buffer were incubated for 72 hours at 30° C. or 60° C. with 400 rpm agitation. 10 µL of the incubated sample was added to 90 µL of water for 10× detection dilution for reaction plates incubated at 30° C. and 60° C. 10 µL of diluted samples was transferred from 10× detection dilution plate, mixed with 190 µL of GOPOD (glucose oxidase/peroxidase) and then incubated for 30 minutes at 50° C. with 400 RPM agitation. Absorbance was read at 510 nm to determine glucose released.

G6 variants identified with improved thermoactivity at 30° C. and/or 60° C. are shown in FIGS. 3A-3S and G7 variants identified with improved thermoactivity at 30° C. and/or 60° C. are shown in FIGS. 4A-4K.

Example 7: Design and Construction of 2 Glucoamylase Variants

2 Variants were designed based on the beneficial variants identified in *Saccharomyces cerevisiae* and structure analysis to improve the specific activity of Glucoamylase G6P with the SBD. The variants were subsequently constructed using gene specific primers with 5'EcoR1 and 3'Not 1 cloning site. Following PCR and restriction digestion, it was cloned into pPiCZαA vector (EasySelect *Pichia* Expression Kit, Invitrogen by life technologies). The recombinant plasmid was linearized using Pme1 restriction enzyme and was transformed into X33 *Pichia* strain from the same expression kit mentioned earlier. The transformants were then selected on YPD+Zeocine agar plates after 3 days of growth at 30° C.

Example 8: Preparation of Glucoamylase Variants Produced by *Pichia pastoris* in HTP Glucoamylase-encoding genes from single colonies were inoculated into individual wells of 24 well plates containing 2000 µl of BMGY medium according to ThermoFisher Scientific receipe. The cultures were grown for 18 hrs at 30° C., 200 rpm and 85% humidity. After 18 hrs, 24 well plates were centrifuged and the liquid media was decanted. 2000 µl of BMMY medium was added to the pellet according to ThermoFisher Scientific receipe. 200 µl of 10% methanol was added to each plate. The plates were incubated at 30° C., 200 rpm and 85% humidity. At every 24 hrs, 200 µl of 10% methanol was added to each plate. Harvest plate at 72 hrs by centrifuging plates at 4,000 rpm at 4° C. for 10 minutes. The supernatants were transferred to costar deep wells plates and stored at −20° C. prior to activity assay.

Example 9: Starch Assay to Determine *Pichia pastoris* Produced Glucoamylase Variants Specific Activity at 40° C.

Normalize all protein samples reference to G6P using SDS-PAGE protein quantification. 115 µL of 2% heated soluble starch (final concentration of 1.5% starch), 10 µL of 4× diluted enzyme supernatant plus 25 µL pH 4.3 buffer were incubated for 0.5 hours at 40° C. with 400 rpm agitation. 20 µL of the incubated sample was added to 90 µL of water for 10× detection dilution for reaction plates incubated at 40° C. 10 µL of diluted samples was transferred from 5× detection dilution plate, mixed with 190 µL of GOPOD (glucose oxidase/peroxidase) and incubated for 30 minutes at 50° C. with 400 RPM agitation. Absorbance was read at 510 nm to determine glucose released.

Figure 6:
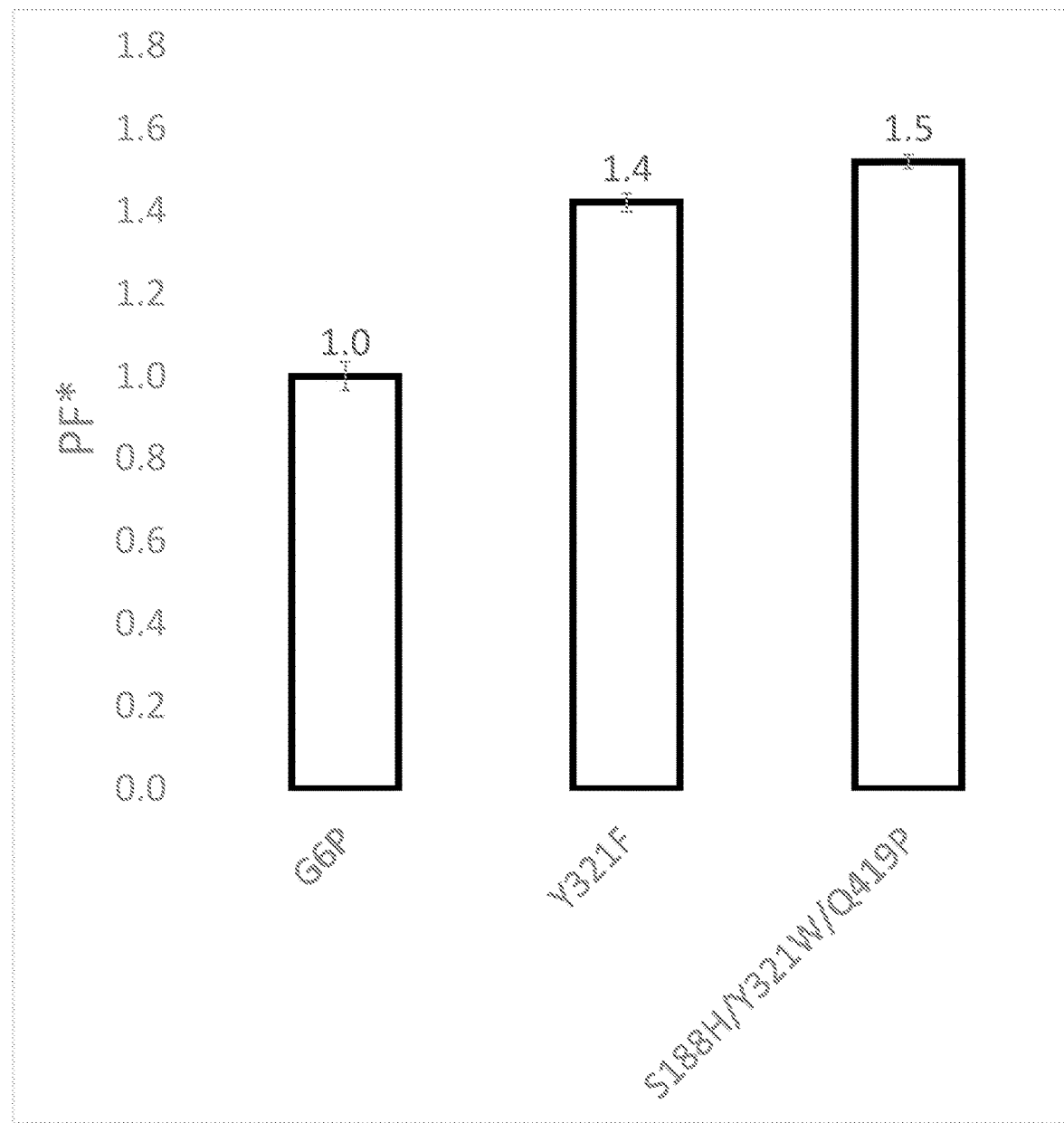
FIG. 6 provides data regarding specific activity comparison of *Pichia pastoris* produced variants (Y321F and S188HG/Y321W/Q419P) and G6P at 40° C.

As shown in FIG. 6, the two variants exhibited >1.4-1.5 fold improved specific activity than G6P. Although the experiments were performed on the variants with the SBD, the same variants without the SBD may have similar specific activity improvement over G7P.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only.

What is claimed is:

1. A composition comprising a variant glucoamylase enzyme, wherein the variant glucoamylase exhibits at least 95% identity to SEQ ID NO:15, wherein said variant glucoamylase enzyme has at least 1.1 fold better activity as compared to SEQ ID NO:25 under a condition selected from the group consisting of thermoactivity at about 30° C., thermoactivity at about 35° C., thermoactivity at about 40° C., thermoactivity at about 50° C., thermoactivity at about 60° C. and thermoactivity at about 70° C., wherein the variant glucoamylase enzyme does not include a starch binding domain; wherein the variant glucoamylase enzyme is not naturally occurring; and wherein an amino acid substitution(s) is selected from the group consisting of S188H/Y321W/Q419P, K5T/S188T, K5T/E68K/S188H, K5Y/S188H, K5Q/E68K/S188T, K5N/E68Y/S188T, K5H/S188H, K5S/E68Y/S188H, K5S/E68Y/S188T, K5Y/E68Y, K5S/E68S/S188T, K5H/E68S/S188H, K5H/E68K/S188T, K5P/S188H, K5Y/E68K, K5T/S188H, K5S/S188H, E68Y/S188H, E68Y/S188T, K5T/Y321F, K5Q/S188H/Q419P, K5P/E68Y/S188T/A422S, K5N/S188H/Q419P, Y321W/A422S, E68K/Q419P, E68S/S188T/Y321W/A422S, K5Q/Q419P/A422S, S188T/Y321F, S188T/Q419P/A422S, K5H/S188T/Q419P/A422S, K5H/A422S, S188H/Y321W, Q419P/A422S, K5N/A422S, E68Y/S188H/Y321F/Q419P, K5Q/S188H, E11S/Y55F/M141L/N168S/T388Q, E11S/T31N/Y55F/M141L/N168S/T388Q, L19I/A195V, M141L/N168S/Y227F/T362Q/T388Q/D440Q, E11S/M141L, E11S/L19I/I44V/Y145A/T155A/D309S/L311V/Y412F/S472T, D309S/L311V, E11S/L19I/T31N/Y55F/A125P/N168S/Y227F, L19I/D309S/L311V/Y412F/A460S/S472T, E11S/L19I/N168S/Y227F/D309S/L311V/D440Q, L19I/Y412F, E11S/L19I/Y145A/A460S/S472T, E11S/M141L/N168S/D309S/L311V/T362Q/L364I/Y412F/A460S/S472T, E11S/Y55F/M141L/N168S/L311V/T362Q/L364I/A460S/S472T, E11S/L19I/Y55F/M141L/N168S/Y227F, L19I/T155A/A407S/Y412F/S472T, D53N/L149I/N150D/P186E/A317P, V42I/S103D/D106T/P186E/A317P/S434T/G478S, A317P/G478S, C26N/V42I/L149I/A317P/S355D/A374N, V42I/S103D/D106T/A317P, D53N/S434T./S103D/A317P/V342I, A256V/A317P, V42I/P186E, A317P/V342I/G478S, I224V/A256V/A317P/G478S, V42I/L149I/N150D/A317P/G478S, V42I/S103D/P186E/A317P/V342I/S355D/A374N/A391G, P186E/A317P/G478S, D53N/G446S, A256V/A317P/G478S, V42I/D53N/T57S/L149I/A317P/G478S, C26N/V42I/D53N/T57S/N150D/P186E/A317P/V342I/G478S, V42I/S355D, V42I/N150D/P186E/A317P, V42I/S434T/G478S, C26N/D53N/T57S/S103D/Q161P/A317P/G478S, V42I/A256V/A317P/S434T, V42I/S103D/A317P/A391G/G478S, E68Y/I69L/G178T/Y179F/S213T/H214C, E68Y/I69L/E85Q/N86Q/F394Y/V395L, E68Y/I69L, D118N/M119E, E68Y/I69L/V97I/T98S/A246S/S247G/T261G/A262S/L347N/E348I, E68Y/I69L/S452A/V453S, E68Y/I69L/S452A/V453S, E68Y/I69L/E85Q/N86Q/L347N/E348I/Q418T/Q419P, E68Y/I69L/E85Q/N86Q/S204N/T205A, A208T/K209R/E381N/S382D/Q418T/Q419P/A469S/A470T, E381N/S382D/Q418T/Q419P/T436S/E437A/A469S/A470T, Q418T/Q419P/A469S/A470T, V170I/A171T/E381N/S382D/Q418T/Q419P/A469S/A470T, F394Y/V395L/Q418T/Q419P/T436S/E437A/A469S/A470T, T78K/L79D/Q418T/Q419P/A469S/A470T, E68Y/I69L/V88I/T89S/T352S/V353I/Q399E/T400K/A469S/A470T, S72A/V73F/A153S/S306A/T476W, T370V/G475V, R49H/S72A/V73F/A92T/Y93K/A153S/

S306A/T476W, E68Y/I69L/T219S/V220Q/A307E/S355D/ L492P, E11S/V42I/L149I/I224V/A317P/T388Q/A460S/ G478S, Y412F/Q418T/Q419P/A469S/A470T/L19I/D53N/ I69L/V88I/S188H/A195V/Y321W/Y412F, V42I/D118N/ M119E/T261A/L311V/Y321W/S355D, E11S/T57S/T89S, E11S/V42I/L79Y/D118N/M141L/L311V/A317P/Y321F, V42I/D53N/E68Y/A317P/L347N, I69L/S188H/A195V/ A317P/Y321F/L364I/S434T, T57S/A195V/T261A/L311V/ Y321F/L347N/E348I/S434T, E11S/V42I/T57S/E68Y/ S188H/A195V/T261A, T57S/N168S/T261A/A317P/ Y321W/V395L/Y412F, E11S/D53N/E68Y/D118N/S188H/ A195V/Y412F/Q419P, E11S/V42I/D118N/M141L/N168S/ Y321W/Y412F, E11S/D53N/T57S/E68Y/T89S/E381N/ Y412F/Q419P/S434T, E11S/D53N/T57S/V88I/T89S/ S188H/A195V/L311V/L347N/Y412F, A317P/Y412F, I69L/ T89S/L311V/A317P/Y321F/Y412F/S434T, V42I/D53N/ T57S/E68Y/V88I/Y412F, E11S/T57S/V88I/M141L/ T261A/Y321W/L364I/Y412F, V42I/I69L/S188H/A317P/ Y321W/Y412F, E11S/V42I/D53N/T57S/L79Y/T89S/ L311V/Y321W/Y412F, L19I/M141L/N168S/S188H/ A195V/L311V/S355D/S434T, S188H/A195V/T261A/ L311V/Y321F/L347N/E348I, E11S/L19I/D53N/T57S/ N168S/L347N, E11S/I69L/M119E/A195V/T261A/A317P/ Y321W/L347N/Y412F, L79Y/V88I/T261A/A317P/Y321F/ L364I/Y412F, E11S/V42I I/E68Y/T89S/L311V/Y321F/ T388Q/F394Y/V395L/Q419P, D53N/E68Y/V88I/M141L/ N168S/Y321W/Y412F, E11S/I69L/L311V/A317P/Y321F/ L347N/Y412F, D53N/T57S/M141L, D53N/V88I/T89S/ D118N/E348I/S355D, E11S/S188H/A195V/A317P/L347N/ E348I/Y412F/Q419P/S434T, E11S/D53N/I69L/V88I/ A317P/Q419P, E68Y/I69L/V88I/N168S/L364I/Q419P, E11S/V42I/V88I/T261A/Y321F/E348I/S355D, E11S/V42I/ T57S/I69L/A195V/L347N/E348I/S355D, L19I/T89S/ A317P/Y321F/S434T, E11S/V42I/L79Y/L311V/A317P/ Y321W/L347N/E348I/L364I/Y412F, D53N/T57S/L347N/ E348I/Y412F, D53N/T57S/E68Y/L79Y/Y412F/S434T, L19I/V88I/T89S/A317P, M119E/M141L/N168S/L311V/ Y321F, E11S/T89S/Y321W, E11S/M141L/T261A/A317P/ Y412F/S434T, V42I/L79Y/S188H/A195V/L311V/Y321F/ S355D, V42I/E68Y/V88I/T261A/Y321W/L347N/E348I, L19I/E68Y/I69L/M141L/Y321F/L347N/S355D/E381N/ Y412F, V42I/D53N/I69L/L79Y/D118N/T261A/L311V/ A317P/Y321F/L347N/Y412F, E68Y/S355D/L364I/S382D/ T388Q/Q419P, E11S/L19I/V42I/E68Y/I69L/D118N/ M141L/Y321W/L347N,/E11S/V42I/E68Y/M141L/A317P/ Y321F/E348I/S355D, E11S/V42I/E68Y/I69L/V88I/T89S/ D118N/M119E/S188H/A195V/A317P/L347N/Y412F/ Q419P, V42I/V88I/L311V/A317P/Y321F/L347N/E348I/ T388Q/V395L/S434T, T261A/A317P/Y321W/E348I, E11S/V42I/E68Y/I69L/D118N/M119E/Y412F, E11S/V42I/ T57S/I69L/L311V, V42I/Y412F, E11S/L19I/E68Y/M119E/ N168S/Y412F/Q419P, L19I/L311V/Y412F, E11S/V42I/ M119E/Y412F, E11S/L19I/V42I/D53N/S188H/A195V/ L311V/Y321F/Y412F, E11S/L19I/V42I/T57S/D118N/ N168S/L311V/Y412F, L19I/V42I/D53N/T57S/N168S/ A317P/Y321W/Y412F, D53N/T57S/E68Y/N168S/S188H/ A195V/L311V/Y321W/Y412F/Q419P, L19I/D53N/T57S/ L311V/Y321W/Y412F, E11S/T57S/Y321W/Y412F/Q419P, D53N/S188H/A195V/L311V/Y412F, V42I/D53N/S188H/ A195V/L311V/Y321F/Y412F, L19I/M119E/N168S/ S188H/A195V/L311V/Y412F/Q419P, E11S/V42I/S188H/ A195V/L311V/A317P/Y321W/Y412F/Q419P, E11S/V42I/ M119E/N168S/L311V/Y412F, E11S/V42I/N168S/S188H/ A317P/Y321W/Y412F/Q419P, E11S/V42I/D53N/E68Y/ S188H/A195V/L311V/A317P/Y321F/Y412F, E11S/L19I/ D53N/N168S/A195V/412F/Q419P, E11S/L19I/V42I/ L311V/Y412F, V42I/D53N/N168S/L311V/Y412F, E11S/ L311V/Y412F, E11S/D53N/T57S/L311V/Y321W/Y412F, E11S/L311V/Y321W/Y412F, E11S/V42I/I69L/D118N/ N168S/L311V/A317P/Y412F/Q419P, E11S/L19I/V42I/ E68Y/Y412F/Q419P, E11S/L19I/D53N/L311V, E11S/L19I/ V42I/L311V/Y412F/Q419P, L19I/V42I/D53N/T57S/I69L/ N168S/S188H/A195V/L311V/A317P/Y321W, E11S/L19I/ V42I/T57S/L311V/A317P/Y321F/Y412F, L19I/V42I/I69L/ D118N/N168S/L311V/Y321W/Y412F/Q419P, E11S/V42I/ D53N/E68Y/S188H/A195V/Y412F, E11S/L19I/V42I/ D53N/T57S/N168S/L311V/Y321W/Y412F, E11S/V42I/ L311V/Y412F, E11S/L19I/V42I/N168S/A195V/L311V/ Y321F/Y412F, E11S/V42I/S188H/L311V/Y412F, L19I/ V42I/T57S/E68Y/M119E/S188H/A195V/L311V/Y321F/ Y412F, E11S/L19I/V42I/D53N/N168S/S188H/A195V, E11S/L19I/V42I/T57S/E68Y/A195V/L311V/Y321W, and E11S/L19I/V42I.

2. A composition comprising a variant glucoamylase enzyme, wherein the variant glucoamylase exhibits at least 95% identity to SEQ ID NO:15, wherein said variant glucoamylase enzyme has at least 1.1 fold better activity as compared to SEQ ID NO:25 under a condition selected from the group consisting of thermoactivity at about 30° C., thermoactivity at about 35° C., thermoactivity at about 40° C., thermoactivity at about 50° C., thermoactivity at about 60° C. and thermoactivity at about 70° C., wherein the variant glucoamylase enzyme consists of a catalytic domain; wherein the variant glucoamylase enzyme is not naturally occurring; and wherein an amino acid substitution(s) is selected from the group consisting of S188H/Y321W/ Q419P, K5T/S188T, K5T/E68K/S188H, K5Y/S188H, K5Q/ E68K/S188T, K5N/E68Y/S188T, K5H/S188H, K5S/E68Y/ S188H, K5S/E68Y/S188T, K5Y/E68Y, K5S/E68S/S188T, K5H/E68S/S188H, K5H/E68K/S188T, K5P/S188H, K5Y/ E68K, K5T/S188H, K5S/S188H, E68Y/S188H, E68Y/ S188T, K5T/Y321F, K5Q/S188H/Q419P, K5P/E68Y/ S188T/A422S, K5N/S188H/Q419P, Y321W/A422S, E68K/ Q419P, E68S/S188T/Y321W/A422S, K5Q/Q419P/A422S, S188T/Y321F, S188T/Q419P/A422S, K5H/S188T/Q419P/ A422S, K5H/A422S, S188H/Y321W, Q419P/A422S, K5N/ A422S, E68Y/S188H/Y321F/Q419P, K5Q/S188H, E11S/ Y55F/M141L/N168S/T388Q, E11S/T31N/Y55F/M141L/ N168S/T388Q, L19I/A195V, M141L/N168S/Y227F/ T362Q/T388Q/D440Q, E11S/M141L, E11S/L19I/144V/ Y145A/T155A/D309S/L311V/Y412F/S472T, D309S/ L311V, E11S/L19I/T31N/Y55F/A125P/N168S/Y227F, L19I/D309S/L311V/Y412F/A460S/S472T, E11S/L19I/ N168S/Y227F/D309S/L311V/D440Q, L19I/Y412F, E11S/ L19I/Y145A/A460S/S472T, E11S/M141L/N168S/D309S/ L311V/T362Q/L364I/Y412F/A460S/S472T, E11S/Y55F/ M141L/N168S/L311V/T362Q/L364I/A460S/S472T, E11S/ L19I/Y55F/M141L/N168S/Y227F, L19I/T155A/A407S/ Y412F/S472T, D53N/L149I/N150D/P186E/A317P, V42I/ S103D/D106T/P186E/A317P/S434T/G478S, A317P/ G478S, C26N/V42I/L149I/A317P/S355D/A374N, V42I/ S103D/D106T/A317P, D53N/S434T, S103D/A317P/V342I, A256V/A317P, V42I/P186E, A317P/V342I/G478S, I224V/ A256V/A317P/G478S, V42I/L149I/N150D/A317P/G478S, V42I/S103D/P186E/A317P/V342I/S355D/A374N/A391G, P186E/A317P/G478S, D53N/G446S, A256V/A317P/ G478S, V42I/D53N/T57S/L149I/A317P/G478S, C26N/ V42I/D53N/T57S/N150D/P186E/A317P/V342I/G478S, V42I/S355D, V42I/N150D/P186E/A317P, V42I/S434T/ G478S, C26N/D53N/T57S/S103D/Q161P/A317P/G478S, V42I/A256V/A317P/S434T, V42I/S103D/A317P/A391G/ G478S, E68Y/I69L/G178T/Y179F/S213T/H214C, E68Y/ I69L/E85Q/N86Q/F394Y/V395L, E68Y/I69L, D118N/ M119E, E68Y/I69L/V97I/T98S/A246S/S247G/T261G/

A262S/L347N/E348I, E68Y/I69L/S452A/V453S, E68Y/I69L/S452A/V453S, E68Y/I69L/E85Q/N86Q/L347N/E348I/Q418T/Q419P, E68Y/I69L/E85Q/N86Q/S204N/T205A, A208T/K209R/E381N/S382D/Q418T/Q419P/A469S/A470T, E381N/S382D/Q418T/Q419P/T436S/E437A/A469S/A470T, Q418T/Q419P/A469S/A470T, V170I/A171T/E381N/S382D/Q418T/Q419P/A469S/A470T, F394Y/V395L/Q418T/Q419P/T436S/E437A/A469S/A470T, T78K/L79D/Q418T/Q419P/A469S/A470T, E68Y/I69L/V88I/T89S/T352S/V353I/Q399E/T400K/A469S/A470T, S72A/V73F/A153S/S306A/T476W, T370V/G475V, R49H/S72A/V73F/A92T/Y93K/A153S/S306A/T476W, E68Y/I69L/T219S/V220Q/A307E/S355D/L492P, E11S/V42I/L149I/I224V/A317P/T388Q/A460S/G478S, Y412F/Q418T/Q419P/A469S/A470T, L19I/D53N/I69L/V88I/S188H/A195V/Y321W/Y412F, V42I/D118N/M119E/T261A/L311V/Y321W/S355D, E11S/T57S/T89S, E11S/V42I/L79Y/D118N/M141L/L311V/A317P/Y321F, V42I/D53N/E68Y/A317P/L347N, I69L/S188H/A195V/A317P/Y321F/L364I/S434T, T57S/A195V/T261A/L311V/Y321F/L347N/E348I/S434T, E11S/V42I/T57S/E68Y/S188H/A195V/T261A, T57S/N168S/T261A/A317P/Y321W/V395L/Y412F, E11S/D53N/E68Y/D118N/S188H/A195V/Y412F/Q419P, E11S/V42I/D118N/M141L/N168S/Y321W/Y412F, E11S/D53N/T57S/E68Y/T89S/E381N/Y412F/Q419P/S434T, E11S/D53N/T57S/V88I/T89S/S188H/A195V/L311V/L347N/Y412F, A317P/Y412F, I69L/T89S/L311V/A317P/Y321F/Y412F/S434T, V42I/D53N/T57S/E68Y/V88I/Y412F, E11S/T57S/V88I/M141L/T261A/Y321W/L364I/Y412F, V42I/169L/S188H/A317P/Y321W/Y412F, E11S/V42I/D53N/T57S/L79Y/T89S/L311V/Y321W/Y412F, L19I/M141L/N168S/S188H/A195V/L311V/S355D/S434T, S188H/A195V/T261A/L311V/Y321F/L347N/E348I, E11S/L19I/D53N/T57S/N168S/L347N, E11S/169L/M119E/A195V/T261A/A317P/Y321W/L347N/Y412F, L79Y/V88I/T261A/A317P/Y321F/L364I/Y412F, E11S/V42I/E68Y/T89S/L311V/Y321F/T388Q/F394Y/V395L/Q419P, D53N/E68Y/V88I/M141L/N168S/Y321W/Y412F, E11S/I69L/L311V/A317P/Y321F/L347N/Y412F, D53N/T57S/M141L, D53N/V88I/T89S/D118N/E348I/S355D, E11S/S188H/A195V/A317P/L347N/E348I/Y412F/Q419P/S434T, E11S/D53N/169L/V88I/A317P/Q419P, E68Y/I69L/V88I/N168S/L364I/Q419P, E11S/V42I/V88I/T261A/Y321F/E348I/S355D, E11S/V42I/T57S/I69L/A195V/L347N/E348I/S355D, L19I/T89S/A317P/Y321F/S434T, E11S/V42I/L79Y/L311V/A317P/Y321W/L347N/E348I/L364I/Y412F, D53N/T57S/L347N/E348I/Y412F, D53N/T57S/E68Y/L79Y/Y412F/S434T, L19I/V88I/T89S/A317P, M119E/M141L/N168S/L311V/Y321F, E11S/T89S/Y321W, E11S/M141L/T261A/A317P/Y412F/S434T, V42I/L79Y/S188H/A195V/L311V/Y321F/S355D, V42I/E68Y/V88I/T261A/Y321W/L347N/E348I, L19I/E68Y/169L/M141L/Y321F/L347N/S355D/E381N/Y412F, V42I/D53N/I69L/L79Y/D118N/T261A/L311V/A317P/Y321F/L347N/Y412F, E68Y/S355D/L364I/S382D/T388Q/Q419P, E11S/L19I/V42I, E68Y/169L/D118N/M141L/Y321W/L347N,/E11S/V42I/E68Y/M141L/A317P/Y321F/E348I/S355D, E11S/V42I/E68Y/I69L/V88I/T89S/D118N/M119E/S188H/A195V/A317P/L347N/Y412F/Q419P, V42I/V88I/L311V/A317P/Y321F/L347N/E348I/T388Q/V395L/S434T, T261A/A317P/Y321W/E348I, E11S/V42I/E68Y/169L/D118N/M119E/Y412F, E11S/V42I/T57S/169L/L311V, V42I/Y412F, E11S/L19I/E68Y/M119E/N168S/Y412F/Q419P, L19I/L311V/Y412F, E11S/V42I/M119E/Y412F, E11S/L19I/V42I/D53N/S188H/A195V/L311V/Y321F/Y412F, E11S/L19I/V42I/T57S/D118N/N168S/L311V/Y412F, L19I/V42I/D53N/T57S/N168S/A317P/Y321W/Y412F, D53N/T57S/E68Y/N168S/S188H/A195V/L311V/Y321W/Y412F/Q419P, L19I/D53N/T57S/L311V/Y321W/Y412F, E11S/T57S/Y321W/Y412F/Q419P, D53N/S188H/A195V/L311V/Y412F, V42I/D53N/S188H/A195V/L311V/Y321F/Y412F, L19I/M119E/N168S/S188H/A195V/L311V/Y412F/Q419P, E11S/V42I/S188H/A195V/L311V/A317P/Y321W/Y412F/Q419P, E11S/V42I/M119E/N168S/L311V/Y412F, E11S/V42I/N168S/L311V/A317P/Y321W/Y412F/Q419P, E11S/V42I/D53N/E68Y/S188H/A195V/L311V/A317P/Y321F/Y412F, E11S/L19I/D53N/N168S/A195V/Y412F/Q419P, E11S/L19I/V42I/L311V/Y412F, V42I/D53N/N168S/L311V/Y412F, E11S/L311V/Y412F, E11S/D53N/T57S/L311V/Y321W/Y412F, E11S/L311V/Y321W/Y412F, E11S/V42I/L19I/D118N/N168S/L311V/A317P/Y412F/Q419P, E11S/L19I/V42I/E68Y/Y412F/Q419P, E11S/L19I/D53N/L311V, E11S/L19I/V42I/L311V/Y412F/Q419P, L19I/V42I/D53N/T57S/I69L/N168S/S188H/A195V/L311V/A317P/Y321W, E11S/L19I/V42I/T57S/L311V/A317P/Y321F/Y412F, L19I/V42I/169L/D118N/N168S/L311V/Y321W/Y412F/Q419P, E11S/V42I/D53N/E68Y/S188H/A195V/Y412F, E11S/L19I/V42I/D53N/T57S/N168S/L311V/Y321W/Y412F, E11S/V42I/L311V/Y412F, E11S/L19I/V42I/N168S/A195V/L311V/Y321F/Y412F, E11S/V42I/S188H/L311V/Y412F, L19I/V42I/T57S/E68Y/M119E/S188H/A195V/L311V/Y321F/Y412F, E11S/L19I/V42I/D53N/N168S/S188H/A195V, E11S/L19I/V42I/T57S/E68Y/A195V/L311V/Y321W, and E11S/L19I/V42I.

3. A composition comprising a variant glucoamylase enzyme comprising at least one amino acid substitution as compared to SEQ ID NO:15, wherein said amino acid substitution is at a position number selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, wherein said variant enzyme is at least 95% identical to SEQ ID NO:15, wherein the variant glucoamylase enzyme does not include a starch binding domain; wherein the variant glucoamylase enzyme is not naturally occurring; and wherein said amino acid substitution(s) is selected from the group consisting of S188H/Y321W/Q419P, K5T/S188T, K5T/E68K/S188H, K5Y/S188H, K5Q/E68K/S188T, K5N/E68Y/S188T, K5H/S188H, K5S/E68Y/S188H, K5S/E68Y/S188T, K5Y/E68Y, K5S/E68S/S188T, K5H/E68S/S188H, K5H/E68K/S188T, K5P/S188H, K5Y/E68K, K5T/S188H, K5S/S188H, E68Y/S188H, E68Y/S188T, K5T/Y321F, K5Q/S188H/Q419P, K5P/E68Y/S188T/A422S, K5N/S188H/Q419P, Y321W/A422S, E68K/Q419P, E68S/S188T/Y321W/A422S, K5Q/Q419P/A422S, S188T/Y321F, S188T/Q419P/A422S, K5H/S188T/Q419P/A422S, K5H/A422S, S188H/Y321W, Q419P/A422S, K5N/A422S, E68Y/S188H/Y321F/Q419P, K5Q/S188H, E11S/Y55F/M141L/N168S/T388Q, E11S/T31N/Y55F/M141L/N168S/T388Q, L19I/A195V, M141L/N168S/Y227F/T362Q/T388Q/D440Q, E11S/M141L, E11S/L19I/144V/Y145A/T155A/D309S/L311V/Y412F/S472T, D309S/L311V, E11S/L19I/T31N/Y55F/A125P/N168S/Y227F, L19I/D309S/L311V/Y412F/A460S/S472T, E11S/L19I/N168S/Y227F/D309S/L311V/D440Q, L19I/Y412F, E11S/L19I/Y145A/A460S/S472T, E11S/M141L/N168S/

D309S/L311V/T362Q/L364I/Y412F/A460S/S472T, E11S/Y55F/M141L/N168S/L311V/T362Q/L364I/A460S/S472T, E11S/L19I/Y55F/M141L/N168S/Y227F, L19I/T155A/A407S/Y412F/S472T, D53N/L149I/N150D/P186E/A317P, V42I/S103D/D106T/P186E/A317P/S434T/G478S, A317P/G478S, C26N/V42I/L149I/A317P/S355D/A374N, V42I/S103D/D106T/A317P, D53N/S434T/S103D/A317P/V342I, A256V/A317P, V42I/P186E, A317P/V342I/G478S, I224V/A256V/A317P/G478S, V42I/L149I/N150D/A317P/G478S, V42I/S103D/P186E/A317P/V342I/S355D/A374N/A391G, P186E/A317P/G478S, D53N/G446S, A256V/A317P/G478S, V42I/D53N/T57S/L149I/A317P/G478S, C26N/V42I/D53N/T57S/N150D/P186E/A317P/V342I/G478S, V42I/S355D, V42I/N150D/P186E/A317P, V42I/S434T/G478S, C26N/D53N/T57S/S103D/Q161P/A317P/G478S, V42I/A256V/A317P/S434T, V42I/S103D/A317P/A391G/G478S, E68Y/I69L/G178T/Y179F/S213T/H214C, E68Y/I69L/E85Q/N86Q/F394Y/V395L, E68Y/I69L, D118N/M119E, E68Y/I69L/V97I/T98S/A246S/S247G/T261G/A262S/L347N/E348I, E68Y/I69L/S452A/V453S, E68Y/I69L/S452A/V453S, E68Y/I69L/E85Q/N86Q/L347N/E348I/Q418T/Q419P, E68Y/I69L/E85Q/N86Q/S204N/T205A, A208T/K209R/E381N/S382D/Q418T/Q419P/A469S/A470T, E381N/S382D/Q418T/Q419P/T436S/E437A/A469S/A470T, Q418T/Q419P/A469S/A470T, V170I/A171T/E381N/S382D/Q418T/Q419P/A469S/A470T, F394Y/V395L/Q418T/Q419P/T436S/E437A/A469S/A470T, T78K/L79D/Q418T/Q419P/A469S/A470T, E68Y/I69L/V88I/T89S/T352S/V353I/Q399E/T400K/A469S/A470T, S72A/V73F/A153S/S306A/T476W, T370V/G475V, R49H/S72A/V73F/A92T/Y93K/A153S/S306A/T476W, E68Y/I69L/T219S/V220Q/A307E/S355D/L492P, E11S/V42I/L149I/I224V/A317P/T388Q/A460S/G478S, Y412F/Q418T/Q419P/A469S/A470T/L19I/D53N/I69L/V88I/S188H/A195V/Y321W/Y412F, V42I/D118N/M119E/T261A/L311V/Y321W/S355D, E11S/T57S/T89S, E11S/V42I/L79Y/D118N/M141L/L311V/A317P/Y321F, V42I/D53N/E68Y/A317P/L347N, I69L/S188H/A195V/A317P/Y321F/L364I/S434T, T57S/A195V/T261A/L311V/Y321F/L347N/E348I/S434T, E11S/V42I/T57S/E68Y/S188H/A195V/T261A, T57S/N168S/T261A/A317P/Y321W/V395L/Y412F, E11S/D53N/E68Y/D118N/S188H/A195V/Y412F/Q419P, E11S/V42I/D118N/M141L/N168S/Y321W/Y412F, E11S/D53N/T57S/E68Y/T89S/E381N/Y412F/Q419P/S434T, E11S/D53N/T57S/V88I/T89S/S188H/A195V/L311V/L347N/Y412F, A317P/Y412F, I69L/T89S/L311V/A317P/Y321F/Y412F/S434T, V42I/D53N/T57S/E68Y/V88I/Y412F, E11S/T57S/V88I/M141L/T261A/Y321W/L364I/Y412F, V42I/I69L/S188H/A317P/Y321W/Y412F, E11S/V42I/D53N/T57S/L79Y/T89S/L311V/Y321W/Y412F, L19I/M141L/N168S/S188H/A195V/L311V/S355D/S434T, S188H/A195V/T261A/L311V/Y321F/L347N/E348I, E11S/L19I/D53N/T57S/N168S/L347N, E11S/I69L/M119E/A195V/T261A/A317P/Y321W/L347N/Y412F, L79Y/V88I/T261A/A317P/Y321F/L364I/Y412F, E11S/V42I/E68Y/T89S/L311V/Y321F/T388Q/F394Y/V395L/Q419P, D53N/E68Y/V88I/M141L/N168S/Y321W/Y412F, E11S/I69L/L311V/A317P/Y321F/L347N/Y412F, D53N/T57S/M141L, D53N/V88I/T89S/D118N/E348I/S355D, E11S/S188H/A195V/A317P/L347N/E348I/Y412F/Q419P/S434T, E11S/D53N/I69L/V88I/A317P/Q419P, E68Y/I69L/V88I/N168S/L364I/Q419P, E11S/V42I/V88I/T261A/Y321F/E348I/S355D, E11S/V42I/T57S/I69L/A195V/L347N/E348I/S355D, L19I/T89S/A317P/Y321F/S434T, E11S/V42I/L79Y/L311V/A317P/Y321W/L347N/E348I/L364I/Y412F, D53N/T57S/L347N/E348I/Y412F, D53N/T57S/E68Y/L79Y/Y412F/S434T, L19I/V88I/T89S/A317P, M119E/M141L/N168S/L311V/Y321F, E11S/T89S/Y321W, E11S/M141L/T261A/A317P/Y412F/S434T, V42I/L79Y/S188H/A195V/L311V/Y321F/S355D, V42I/E68Y/V88I/T261A/Y321W/L347N/E348I, L19I/E68Y/I69L/M141L/Y321F/L347N/S355D/E381N/Y412F, V42I/D53N/I69L/L79Y/D118N/T261A/L311V/A317P/Y321F/L347N/Y412F, E68Y/S355D/L364I/S382D/T388Q/Q419P, E11S/L19I/V42I/E68Y/I69L/D118N/M141L/Y321W/L347N, E11S/V42I/E68Y/M141L/A317P/Y321F/E348I/S355D, E11S/V42I/E68Y/I69L/V88I/T89S/D118N/M119E/S188H/A195V/A317P/L347N/Y412F/Q419P, V42I/V88I/L311V/A317P/Y321F/L347N/E348I/T388Q/V395L/S434T, T261A/A317P/Y321W/E348I, E11S/V42I/E68Y/I69L/D118N/M119E/Y412F, E11S/V42I/T57S/I69L/L311V, V42I/Y412F, E11S/L19I/E68Y/M119E/N168S/Y412F/Q419P, L19I/L311V/Y412F, E11S/V42I/M119E/Y412F, E11S/L19I/V42I/D53N/S188H/A195V/L311V/Y321F/Y412F, E11S/L19I/V42I/T57S/D118N/N168S/L311V/Y412F, L19I/V42I/D53N/T57S/N168S/A317P/Y321W/Y412F, D53N/T57S/E68Y/N168S/S188H/A195V/L311V/Y321W/Y412F/Q419P, L19I/D53N/T57S/L311V/Y321W/Y412F, E11S/T57S/Y321W/Y412F/Q419P, D53N/S188H/A195V/L311V/Y412F, V42I/D53N/S188H/A195V/L311V/Y321F/Y412F, L19I/M119E/N168S/S188H/A195V/L311V/Y412F/Q419P, E11S/V42I/S188H/A195V/L311V/A317P/Y321W/Y412F/Q419P, E11S/V42I/M119E/N168S/L311V/Y412F, E11S/V42I/N168S/L311V/A317P/Y321W/Y412F/Q419P, E11S/V42I/D53N/E68Y/S188H/A195V/L311V/A317P/Y321F/Y412F, E11S/L19I/D53N/N168S/A195V/Y412F/Q419P, E11S/L19I/V42I/L311V/Y412F, V42I/D53N/N168S/L311V/Y412F, E11S/L311V/Y412F, E11S/D53N/T57S/L311V/Y321W/Y412F, E11S/L311V/Y321W/Y412F, E11S/V42I/I69L/D118N/N168S/L311V/A317P/Y412F/Q419P, E11S/L19I/V42I/E68Y/Y412F/Q419P, E11S/L19I/D53N/L311V, E11S/L19I/V42I/L311V/Y412F/Q419P, L19I/V42I/D53N/T57S/I69L/N168S/S188H/A195V/L311V/A317P/Y321W, E11S/L19I/V42I/T57S/L311V/A317P/Y321F/Y412F, L19I/V42I/I69L/D118N/N168S/L311V/Y321W/Y412F/Q419P, E11S/V42I/D53N/E68Y/S188H/A195V/Y412F, E11S/L19I/V42I/D53N/T57S/N168S/L311V/Y321W/Y412F, E11S/V42I/L311V/Y412F, E11S/L19I/V42I/N168S/A195V/L311V/Y321F/Y412F, E11S/V42I/S188H/L311V/Y412F, L19I/V42I/T57S/E68Y/M119E/S188H/A195V/L311V/Y321F/Y412F, E11S/L19I/V42I/D53N/N168S/S188H/A195V, E11S/L19I/V42I/T57S/E68Y/A195V/L311V/Y321W, and E11S/L19I/V42I.

4. A composition comprising a variant glucoamylase enzyme comprising at least one amino acid substitution as compared to SEQ ID NO:15, wherein said amino acid substitution is at a position number selected from the group consisting of 5, 27, 36, 38, 39, 46, 47, 50, 65, 68, 79, 89, 98, 108, 121, 122, 124, 158, 161, 188, 192, 212, 215, 258, 262, 264, 298, 321, 400, 412, 419, 420, 422, 423, 457, 491, 497, 498, 503, 508, 509, 510, 7, 9, 11, 19, 26, 31, 42, 44, 49, 53, 55, 57, 69, 72, 73, 78, 85, 86, 88, 92, 93, 94, 97, 103, 106, 118, 119, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 309, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, wherein said variant glucoamylase enzyme has at least 1.1 fold better activity as compared to SEQ ID NO:15 under a condition selected from the group consisting of thermoactivity at about 30° C., thermoactivity at about 35° C., thermoactivity at about 40° C., thermoactivity at about 50° C., thermoactivity at about 60° C. and thermoactivity at about 70° C.; wherein said variant enzyme is at least 95% identical to SEQ ID NO:15, wherein the variant glucoamylase enzyme does not include a starch binding domain; wherein the variant glucoamylase enzyme is not naturally occurring; and wherein said amino acid substitution(s) is selected from the group consisting of S188H/Y321W/Q419P, K5T/S188T, K5T/E68K/S188H, K5Y/S188H, K5Q/E68K/S188T, K5N/E68Y/S188T, K5H/S188H, K5S/E68Y/S188H, K5S/E68Y/S188T, K5Y/E68Y, K5S/E68S/S188T, K5H/E68S/S188H, K5H/E68K/S188T, K5P/S188H, K5Y/E68K, K5T/S188H, K5S/S188H, E68Y/S188H, E68Y/S188T, K5T/Y321F, K5Q/S188H/Q419P, K5P/E68Y/S188T/A422S, K5N/S188H/Q419P, Y321W/A422S, E68K/Q419P, E68S/S188T/Y321W/A422S, K5Q/Q419P/A422S, S188T/Y321F, S188T/Q419P/A422S, K5H/S188T/Q419P/A422S, K5H/A422S, S188H/Y321W, Q419P/A422S, K5N/A422S, E68Y/S188H/Y321F/Q419P, K5Q/S188H, E11S/Y55F/M141L/N168S/T388Q, E11S/T31N/Y55F/M141L/N168S/T388Q, L19I/A195V, M141L/N168S/Y227F/T362Q/T388Q/D440Q, E11S/M141L, E11S/L19I/I44V/Y145A/T155A/D309S/L311V/Y412F/S472T, D309S/L311V, E11S/L19I/T31N/Y55F/A125P/N168S/Y227F, L19I/D309S/L311V/Y412F/A460S/S472T, E11S/L19I/N168S/Y227F/D309S/L311V/D440Q, L19I/Y412F, E11S/L19I/Y145A/A460S/S472T, E11S/M141L/N168S/D309S/L311V/T362Q/L364I/Y412F/A460S/S472T, E11S/Y55F/M141L/N168S/L311V/T362Q/L364I/A460S/S472T, E11S/L19I/Y55F/M141L/N168S/Y227F, L19I/T155A/A407S/Y412F/S472T, D53N/L149I/N150D/P186E/A317P, V42I/S103D/D106T/P186E/A317P/S434T/G478S, A317P/G478S, C26N/V42I/L149I/A317P/S355D/A374N, V42I/S103D/D106T/A317P, D53N/S434T/S103D/A317P/V342I, A256V/A317P, V42I/P186E, A317P/V342I/G478S, I224V/A256V/A317P/G478S, V42I/L149I/N150D/A317P/G478S, V42I/S103D/P186E/A317P/V342I/S355D/A374N/A391G, P186E/A317P/G478S, D53N/G446S, A256V/A317P/G478S, V42I/D53N/T57S/L149I/A317P/G478S, C26N/V42I/D53N/T57S/N150D/P186E/A317P/V342I/G478S, V42I/S355D, V42I/N150D/P186E/A317P, V42I/S434T/G478S, C26N/D53N/T57S/S103D/Q161P/A317P/G478S, V42I/A256V/A317P/S434T, V42I/S103D/A317P/A391G/G478S, E68Y/I69L/G178T/Y179F/S213T/H214C, E68Y/I69L/E85Q/N86Q/F394Y/V395L, E68Y/I69L, D118N/M119E, E68Y/I69L/V97I/T98S/A246S/S247G/T261G/A262S/L347N/E348I, E68Y/I69L/S452A/V453S, E68Y/I69L/S452A/V453S, E68Y/I69L/E85Q/N86Q/L347N/E348I/Q418T/Q419P, E68Y/I69L/E85Q/N86Q/S204N/T205A, A208T/K209R/E381N/S382D/Q418T/Q419P/A469S/A470T, E381N/S382D/Q418T/Q419P/T436S/E437A/A469S/A470T, Q418T/Q419P/A469S/A470T, V170I/A171T/E381N/S382D/Q418T/Q419P/A469S/A470T, F394Y/V395L/Q418T/Q419P/T436S/E437A/A469S/A470T, T78K/L79D/Q418T/Q419P/A469S/A470T, E68Y/I69L/V88I/T89S/T352S/V353I/Q399E/T400K/A469S/A470T, S72A/V73F/A153S/S306A/T476W, T370V/G475V, R49H/S72A/V73F/A92T/Y93K/A153S/S306A/T476W, E68Y/I69L/T219S/V220/A307E/S355D/L492P, E11S/V42I/L149I/I224V/A317P/T388Q/A460S/G478S, Y412F/Q418T/Q419P/A469S/A470T/L19I/D53N/I69L/V88I/S188H/A195V/Y321W/Y412F, V42I/D118N/M119E/T261A/L311V/Y321W/S355D, E11S/T57S/T89S, E11S/V42I/L79Y/D118N/M141L/L311V/A317P/Y321F, V42I/D53N/E68Y/A317P/L347N, I69L/S188H/A195V/A317P/Y321F/L364I/S434T, T57S/A195V/T261A/L311V/Y321F/L347N/E348I/S434T, E11S/V42I/T57S/E68Y/S188H/A195V/T261A, T57S/N168S/T261A/A317P/Y321W/V395L/Y412F, E11S/D53N/E68Y/D118N/S188H/A195V/Y412F/Q419P, E11S/V42I/D118N/M141L/N168S/Y321W/Y412F, E11S/D53N/T57S/E68Y/T89S/E381N/Y412F/Q419P/S434T, E11S/D53N/T57S/V88I/T89S/S188H/A195V/L311V/L347N/Y412F, A317P/Y412F, I69L/T89S/L311V/A317P/Y321F/Y412F/S434T, V42I/D53N/T57S/E68Y/V88I/Y412F, E11S/T57S/V88I/M141L/T261A/Y321W/L364I/Y412F, V42I/I69L/S188H/A317P/Y321W/Y412F, E11S/V42I/D53N/T57S/L79Y/T89S/L311V/Y321W/Y412F, L19I/M141L/N168S/S188H/A195V/L311V/S355D/S434T, S188H/A195V/T261A/L311V/Y321F/L347N/E348I, E11S/L19I/D53N/T57S/N168S/L347N, E11S/I69L/M119E/A195V/T261A/A317P/Y321W/L347N/Y412F, L79Y/V88I/T261A/A317P/Y321F/L364I/Y412F, E11S/V42I/E68Y/T89S/L311V/Y321F/T388Q/F394Y/V395L/Q419P, D53N/E68Y/V88I/M141L/N168S/Y321W/Y412F, E11S/I69L/L311V/A317P/Y321F/L347N/Y412F, D53N/T57S/M141L, D53N/V88I/T89S/D118N/E348I/S355D, E11S/S188H/A195V/A317P/L347N/E348I/Y412F/Q419P/S434T, E11S/D53N/I69L/V88I/A317P/Q419P, E68Y/I69L/V88I/N168S/L364I/Q419P, E11S/V42I/V88I/T261A/Y321F/E348I/S355D, E11S/V42I/T57S/I69L/A195V/L347N/E348I/S355D, L19I/T89S/A317P/Y321F/S434T, E11S/V42I/L79Y/L311V/A317P/Y321W/L347N/E348I/L364I/Y412F, D53N/T57S/L347N/E348I/Y412F, D53N/T57S/E68Y/L79Y/Y412F/S434T, L19I/V88I/T89S/A317P, M119E/M141L/N168S/L311V/Y321F, E11S/T89S/Y321W, E11S/M141L/T261A/A317P/Y412F/S434T, V42I/L79Y/S188H/A195V/L311V/Y321F/S355D, V42I/E68Y/V88I/T261A/Y321W/L347N/E348I, L19I/E68Y/I69L/M141L/Y321F/L347N/S355D/E381N/Y412F, V42I/D53N/I69L/L79Y/D118N/T261A/L311V/A317P/Y321F/L347N/Y412F, E68Y/S355D/L364I/S382D/T388Q/Q419P, E11S/L19I/V42I/E68Y/I69L/D118N/M141L/Y321W/L347N, E11S/V42I/E68Y/M141L/A317P/Y321F/E348I/S355D, E11S/V42I/E68Y/I69L/V88I/T89S/D118N/M119E/S188H/A195V/A317P/L347N/Y412F/Q419P, V42I/V88I/L311V/A317P/Y321F/L347N/E348I/T388Q/V395L/S434T, T261A/A317P/Y321W/E348I, E11S/V42I/E68Y/I69L/D118N/M119E/Y412F, E11S/V42I/T57S/I69L/L311V, V42I/Y412F, E11S/L19I/E68Y/M119E/N168S/Y412F/Q419P, L19I/L311V/Y412F, E11S/V42I/M119E/Y412F, E11S/L19I/V42I/D53N/S188H/A195V/L311V/Y321F/Y412F, E11S/L19I/V42I/T57S/D118N/N168S/L311V/Y412F, L19I/V42I/D53N/T57S/N168S/A317P/Y321W/Y412F, D53N/T57S/E68Y/N168S/S188H/A195V/L311V/Y321W/Y412F/Q419P, L19I/D53N/T57S/L311V/Y321W/Y412F, E11S/T57S/Y321W/Y412F/Q419P, D53N/S188H/A195V/L311V/Y412F, V42I/D53N/S188H/A195V/L311V/Y321F/Y412F, L19I/M119E/N168S/S188H/A195V/L311V/Y412F/Q419P, E11S/V42I/S188H/A195V/L311V/A317P/Y321W/Y412F/Q419P, E11S/V42I/M119E/N168S/L311V/Y412F, E11S/V42I/N168S/L311V/A317P/Y321W/Y412F/Q419P, E11S/V42I/D53N/E68Y/S188H/A195V/L311V/A317P/Y321F/Y412F, E11S/L19I/D53N/N168S/A195V/Y412F/Q419P, E11S/L19I/V42I/L311V/Y412F, V42I/D53N/N168S/L311V/Y412F, E11S/L311V/Y412F, E11S/D53N/T57S/L311V/Y321W/Y412F, E11S/L311V/Y321W/Y412F, E11S/V42I/I69L/D118N/N168S/L311V/A317P/Y412F/Q419P, E11S/L19I/V42I/E68Y/Y412F/Q419P, E11S/L19I/D53N/L311V, E11S/L19I/V42I/L311V/Y412F/Q419P, L19I/V42I/D53N/T57S/I69L/N168S/S188H/A195V/L311V/A317P/Y321W, E11S/L19I/V42I/T57S/L311V/A317P/Y321F/Y412F, L19I/V42I/I69L/D118N/N168S/L311V/Y321W/Y412F/Q419P, E11S/V42I/D53N/E68Y/S188H/A195V/Y412F, E11S/L19I/V42I/D53N/T57S/N168S/L311V/Y321W/Y412F, E11S/V42I/

L311V/Y412F, E11S/L19I/V42I/N168S/A195V/L311V/ Y321F/Y412F, E11S/V42I/S188H/L311V/Y412F, L19I/ V42I/T57S/E68Y/M119E/S188H/A195V/L311V/Y321F/ Y412F, E11S/L19I/V42I/D53N/N168S/S188H/A195V, E11S/L19I/V42I/T57S/E68Y/A195V/L311V/Y321W, and E11S/L19I/V42I.

5. The composition according to claim 3, wherein said variant glucoamylase enzyme exhibits at least 96% identity to SEQ ID NO:15.

6. A nucleic acid encoding said variant glucoamylase enzyme of claim 3.

7. The nucleic acid of claim 6, wherein said nucleic acid is codon optimized for a host organism for expression of the variant glucoamylase enzyme in said organism.

8. An expression vector comprising the nucleic acid of claim 6.

9. A host cell comprising the nucleic acid of claim 6.

10. A host cell comprising the expression vector of claim 8.

11. The host cell of claim 9, wherein said host cell is selected from the group consisting of a bacterial cell, a fungal cell, and a yeast cell.

12. A method of making a variant glucoamylase enzyme comprising: a) culturing the host cell of claim 9 under conditions wherein said variant glucoamylase enzyme is expressed; and b) recovering said variant glucoamylase enzyme.

13. A composition comprising a C-terminally truncated variant glucoamylase enzyme of SEQ ID NO:13, wherein said truncation position is at a position number selected from the group consisting of 493, 500, 502, 503, 506, 509, 510, 513, 514, 519, 520, 522, 524, 525, 544, 549, 550, 551, 556, 558, 560, 563, 564 and 569; and wherein amino acid substitutions are selected from the group consisting of S188H/Y321W/Q419P, K5T/S188T, K5T/E68K/S188H, K5Y/S188H, K5Q/E68K/S188T, K5N/E68Y/S188T, K5H/ S188H, K5S/E68Y/S188H, K5S/E68Y/S188T, K5Y/E68Y, K5S/E68S/S188T, K5H/E68S/S188H, K5H/E68K/S188T, K5P/S188H, K5Y/E68K, K5T/S188H, K5S/S188H, E68Y/ S188H, E68Y/S188T, K5T/Y321F, K5Q/S188H/Q419P, K5P/E68Y/S188T/A422S, K5N/S188H/Q419P, Y321W/ A422S, E68K/Q419P, E68S/S188T/Y321W/A422S, K5Q/ Q419P/A422S, S188T/Y321F, S188T/Q419P/A422S, K5H/ S188T/Q419P/A422S, K5H/A422S, S188H/Y321W, Q419P/A422S, K5N/A422S, E68Y/S188H/Y321F/Q419P, K5Q/S188H, E11S/Y55F/M141L/N168S/T388Q, E11S/ T31N/Y55F/M141L/N168S/T388Q, L19I/A195V, M141L/ N168S/Y227F/T362Q/T388Q/D440Q, E11S/M141L, E11S/ L19I/144V/Y145A/T155A/D309S/L311V/Y412F/S472T, D309S/L311V, E11S/L19I/T31N/Y55F/A125P/N168S/ Y227F, L19I/D309S/L311V/Y412F/A460S/S472T, E11S/ L19I/N168S/Y227F/D309S/L311V/D440Q, L19I/Y412F, E11S/L19I/Y145A/A460S/S472T, E11S/M141L/N165S/ D309S/L311V/T362Q/L364I/Y412F/A460S/S472T E11S/ Y55F/M141L/N168S/L311V/T362Q/L364I/A460S/S472T, E11S/L19I/Y55F/M141L/N168S/Y227F, L19I/T155A/ A407S/Y412F/S472T, D53N/L149I/N150D/P186E/A317P, V42I/S103D/D106T/P186E/A317P/S434T/G478S, A317P/ G478S, C26N/V42I/L149I/A317P/S355D/A374N, V42I/ S103D/D106T/A317P, D53N/S434T/S103D/A317P/V342I, A256V/A317P, V42I/P186E, A317P/V342I/G478S, I224V/ A256V/A317P/G478S, V42I/L149I/N150D/A317P/G478S, V42I/S103D/P186E/A317P/V342I/S355D/A374N/A391G, P186E/A317P/G478S, D53N/G446S, A256V/A317P/ G478S, V42I/D53N/T57S/L149I/A317P/G478S, C26N/ V42I/D53N/T57S/N150D/P186E/A317P/V342I/G478S, V42I/S355D, V42I/N150D/P186E/A317P, V42I/S434T/ G478S, C26N/D53N/T57S/S103D/Q161P/A317P/G478S, V42I/A256V/A317P/S434T, V42I/S103D/A317P/A391G/ G478S, E68Y/I69L/G178T/Y179F/S213T/H214C, E68Y/ I69L/E85Q/N86Q/F394Y/V395L, E68Y/I69L, D118N/ M119E, E68Y/I69L/V97I/T98S/A246S/S247G/T261G/ A262S/L347N/E348I, E68Y/I69L/S452A/V453S, E68Y/ I69L/S452A/V453S, E68Y/I69L/E85Q/N86Q/L347N/ E348I/Q418T/Q419P, E68Y/I69L/E85Q/N86Q/S204N/ T205A, A208T/K209R/E381N/S382D/Q418T/Q419P/ A469S/A470T, E381N/S382D/Q418T/Q419P/T436S/ E437A/A469S/A470T, Q418T/Q419P/A469S/A470T, V170I/A171T/E381N/S382D/Q418T/Q419P/A469S/ A470T, F394Y/V395L/Q418T/Q419P/T436S/E437A/ A469S/A470T, T78K/L79D/Q418T/Q419P/A469S/A470T, E68Y/I69L/V88I/T98S/T352S/V353I/Q399E/T400K/ A469S/A470T, S72A/V73F/A153S/S306A/T476W, T370V/ G475V, R49H/S72A/V73F/A92T/Y93K/A153S/S306A/ T476W, E68Y/I69L/T219S/V220Q/A307E/S355D/L492P, E11S/V42I/L149I/I224V/A317P/T388Q/A460S/G478S, Y412F/Q418T/Q419P/A469S/A470T/, L19I/D53N/I69L/ V88I/S188H/A195V/Y321W/Y412F, V42I/D118N/M119E/ T261A/L311V/Y321W/S355D, E11S/T57S/T89S, E11S/ V42I/L79Y/D118N/M141L/L311V/A317P/Y321F, V42I/ D53N/E68Y/A317P/L347N, I69L/S188H/A195V/A317P/ Y321F/L364I/S434T, T57S/A195V/T261A/L311V/Y321F/ L347N/E348I/S434T, E11S/V42I/T57S/E68Y/S188H/ A195V/T261A, T57S/N168S/T261A/A317P/Y321W/ V395L/Y412F, E11S/D53N/E68Y/D118N/S188H/A195V/ Y412F/Q419P, E11S/V42I/D118N/M141L/N168S/Y321W/ Y412F, E11S/D53N/T57S/E68Y/T89S/E381N/Y412F/ Q419P/S434T, E11S/D53N/T57S/V88I/T89S/S188H/ A195V/L311V/L347N/Y412F, A317P/Y412F, I69L/T89S/ L311V/A317P/Y321F/Y412F/S434T, V42I/D53N/T57S/ E68Y/V88I/Y412F, E11S/T57S/V88I/M141L/T261A/ Y321W/L364I/Y412F, V42I/I69L/S188H/A317P/Y321W/ Y412F, E11S/V42I/D53N/T57S/L79Y/T89S/L311V/ Y321W/Y412F, L19I/M141L/N168S/S188H/A195V/ L311V/S355D/S434T, S188H/A195V/T261A/L311V/ Y321F/L347N/E348I, E11S/L19I/D53N/T57S/N168S/ L347N, E11S/I69L/M119E/A195V/T261A/A317P/Y321W/ L347N/Y412F, L79Y/V88I/T261A/A317P/Y321F/L364I/ Y412F, E11S/V42I/E68Y/T89S/L311V/Y321F/T388Q/ F394Y/V395L/Q419P, D53N/E68Y/V88I/M141L/N168S/ Y321W/Y412F, E11S/I69L/L311V/A317P/Y321F/L347N/ Y412F, D53N/T57S/M141L, D53N/V88I/T89S/D118N/ E348I/S355D, E11S/S188H/A195V/A317P/L347N/E348I/ Y412F/Q419P/S434T, E11S/D53N/I69L/V88I/A317P/ Q419P, E68Y/I69L/V88I/N168S/L364I/Q419P, E11S/V42I/ V88I/T261A/Y321F/E348I/S355D, E11S/V42I/T57S/I69L/ A195V/L347N/E348I/S355D, L19I/T89S/A317P/Y321F/ S434T, E11S/V42I/L79Y/L311V/A317P/Y321W/L347N/ E348I/L364I/Y412F, D53N/T57S/L347N/E348I/Y412F, D53N/T57S/E68Y/L79Y/Y412F/S434T, L19I/V88I/T89S/ A317P, M119E/M141L/N168S/L311V/Y321F, E11S/T89S/ Y321W, E11S/M141L/T261A/A317P/Y412F/S434T, V42I/ L79Y/S188H/A195V/L311V/Y321F/S355D, V42I/E68Y/ V88I/T261A/Y321W/L347N/E348I, L19I/E68Y/I69L/ M141L/Y321F/L347N/S355D/E381N/Y412F, V42I/D53N/ I69L/L79Y/D118N/T261A/L311V/A317P/Y321F/L347N/ Y412F, E68Y/S355D/L364I/S382D/T388Q/Q419P, E11S/ L19I/V42I/E68Y/I69L/D118N/M141L/Y321W/L347N, E11S/V42I/E68Y/M141L/A317P/Y321F/E348I/S355D, E11S/V42I/E68Y/I69L/V88I/T89S/D118N/M119E/S188H/ A195V/A317P/L347N/Y412F/Q419P, V42I/V88I/L311V/ A317P/Y321F/L347N/E348I/T388Q/V395L/S434T, T261A/A317P/Y321W/E348I, E11S/V42I/E68Y/I69L/ D118N/M119E/Y412F, E11S/V42I/T57S/I69L/L311V, V42I/Y412F, E11S/L19I/E68Y/M119E/N168S/Y412F/ Q419P, L19I/L311V/Y412F, E11S/V42I/M119E/Y412F, E11S/L19I/V42I/D53N/S188H/A195V/L311V/Y321F/ Y412F, E11S/L19I/V42I/T57S/D118N/N168S/L311V/ Y412F, L19I/V42I/D53N/T57S/N168S/A317P/Y321W/ Y412F, D53N/T57S/E68Y/N168S/S188H/A195V/L311V/ Y321W/Y412F/Q419P, L19I/D53N/T57S/L311V/Y321W/ Y412F, E11S/T57S/Y321W/Y412F/Q419P, D53N/S188H/ A195V/L311V/Y412F, V42I/D53N/S188H/A195V/L311V/ Y321F/Y412F, L19I/M119E/N168S/S188H/A195V/ L311V/Y412F/Q419P, E11S/V42I/S188H/A195V/L311V/ A317P/Y321W/Y412F/Q419P, E11S/V42I/M119E/N168S/ L311V/Y412F, E11S/V42I/N168S/L311V/A317P/Y321W/ Y412F/Q419P, E11S/V42I/D53N/E68Y/S188H/A195V/ L311V/A317P/Y321F/Y412F, E11S/L19I/D53N/N168S/ A195V/Y412F/Q419P, E11S/L19I/V42I/L311V/Y412F, V42I/D53N/N168S/L311V/Y412F, E11S/L311V/Y412F, E11S/D53N/T57S/L311V/Y321W/Y412F, E11S/L311V/ Y321W/Y412F, E11S/V42I/I69L/D118N/N168S/L311V/ A317P/Y412F/Q419P, E11S/L19I/V42I/E68Y/Y412F/ Q419P, E11S/L19I/D53N/L311V, E11S/L19I/V42I/L311V/ Y412F/Q419P, L19I/V42I/D53N/T575/I69L/N168S/ S188H/A195V/L311V/A317P/Y321W, E11S/L19I/V42I/ T57S/L311V/A317P/Y321F/Y412F, L19I/V42I/I69L/ D118N/N168S/L311V/Y321W/Y412F/Q419P, E11S/V42I/ D53N/E68Y/S188H/A195V/Y412F, E11S/L19I/V42I/ D53N/T57S/N168S/L311V/Y321W/Y412F, E11S/V42I/ L311V/Y412F, E11S/L19I/V42I/N168S/A195V/L311V/ Y321F/Y412F, E11S/V42I/S188H/L311V/Y412F, L19I/ V42I/T57S/E68Y/M119E/S188H/A195V/L311V/Y321F/ Y412F, E11S/L19I/V42I/D53N/N168S/S188H/A195V, E11S/L19I/V42I/T57S/E68Y/A195V/L311V/Y321W, and E11S/L19I/V42I.

14. A composition comprising a variant glucoamylase enzyme comprising at least one amino acid substitution as compared to SEQ ID NO:13, wherein said amino acid substitution is at a position selected from the group consisting of 5, 27, 36, 38, 46, 47, 50, 65, 68, 79, 89, 98, 108, 122, 124, 158, 161, 188, 192, 212, 215, 258, 262, 264, 298, 321, 400, 412, 420, 422, 457, 491, 497, 498, 503, 508, 509, 510, 516, 518, 521, 522, 526, 533, 534, 535, 540, 542, 544, 545, 549, 550, 551, 555, 556, 557, 559, 563, 564, 569, 570, 581 584, 7, 9, 11, 19, 26, 31, 42, 53, 55, 57, 69, 72, 73, 78, 85, 86, 88, 92, 93, 94, 97, 103, 106, 118, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, wherein said variant enzyme is at least 95% identical to SEQ ID NO:13, and wherein the variant glucoamylase enzyme is not naturally occurring; and wherein amino acid substitutions are selected from the group consisting of T98S/Q161P/F516L, T98S/Q161P/N570P, T98S/ Q161P, T550D/F555S, V65I/Y412F/Y503S/S518I, Y412F/ Y503S/I564T, Y412F/Y503E, Y412F/Y503E/S518I, V65I/ Y412F/Y503S, V65I/Y503E, Y503D/S518I/I564N, Y503E/ S518L, V65I/Y503E/S544Q, V65I/Y503S, Y503E/S544E, V65I/Y503E/S544E/I564N, V65I/Y412F/Y503E, Y503E/ S518I/S544Q, V65I/Y503E/S518M, Y412F/S518L, Y503E/ S544Q, V65I/Y412F/Y503E/S544E/I564T/G569I, Y412F/ Y503S, Y503E/I564T, S549D/F555D/G559N, S549D/ F555R, K508T/L526N/S549D/G559N, K508T/G559N, F555D/I556P/G559N, S549D/F555R/I556P/G559N, F555R/I556P, L526I/F555R/I556P, F555R/I556P/G559N, K508T/I556P/G559N, F555D/I556P, K508T/L526N/ A534T/S549D/I556P, K508T/L526I/S549D/G559N, K508N/L526I/S549E/F555L/G559N, L526N/S549D/ F555D/I556P, L526I/F555D/G559N, A38V/F555R, L498T/ T542N/T581N/T584N, T542N/T581N/T584N, S535Y/ T542N, T540N/T584N, T540N/T542N/T581N/T584N, L498T/T581N/T584N, L498T/T584N, L498T/T542N/ T581N, L498T/T542N, S535Y/T540N/T542N/T581N, Y321F/A422S, K5H/Y321W, K5N/Y321F, K5P/S188H, E68S/S188H/A422S, K5H/S188H/Y321F/A422S, S188H/ A422S, S188H/A422S/V545A, K5Q/A422S, K5S/E68K/ Y321W, K5H/Y321F/A422S, K5Y/A422S, K5Y/S188H/ A422S, K5T/A422S, K5T/Y321W, Y321W/A422S, K5P/ Y321F, K5H/S188H/Y321F/A422S, E68K/A422S, Y321F/ A422S, K5H/Y321F, K5T/E68Y/S188T, K5S/E68Y/ S188H, K5N/S188H, K5T/E68S/S188T, K5H/E68Y/S188P, K5P/E68Y/S188T, K5T/E68K/S188H, K5P/E68K/S188T, K5H/E68Y/S188T, K5T/S188H, K5T/E68N/S188T, K5Y/ E68Y/S188T, K5S/E68Y/S188T, K5Q/E68K/S188H, K5P/ E68N/S188H, K5P/E68N/S188T, K5P/E68Y/S188H, K5Y/ E68Y/S188H, K5S/S188T, K5H/E68N/S188H, K5P/ S188H, K5H/S46T/E68K/S188H, K5H/E68K/S188T, K5O1E68Y/S188T, K5Y/E68N/S188H, L19I/V42I/E68Y/ N168S/S188H/A195V/Y412F, E11S/V42I/T57S/D118N/ N168S/S188H/A195V/L311V, E11S/V42I/D53N/E68Y/ N168S/S188H/A195V/L311V/Y412F, E11S/L19I/V42I/ E68Y/D118N/S188H/A195V/L311V/Y412F, E11S/E68Y/ S188H/A195V/L311V/Y412F, E11S/L19I/V42I/E68Y/ L19I/D118N/N168S/S188H/A195V/L311V/Y412F, E11S/ L19I/N168S/S188H/A195V/L311V/A317P/Y321F/Y412F, E11S/V42I/E68Y/Y412F, E11S/L19I/V42I/E68Y/Y412F, E11S/V42I/E68Y/S188H/A195V/Y412F, E11S/L19I/V42I/ T57S/L19I/S188H/A195V/L311V/Y321W/Y412F, E11S/ L19I/D53N/E68Y/S188H/A195V/L311V/Y412F, E11S/ V42I/E68Y/S188H/A195V/L311V/Y321W/Y412F, E11S/ V42I/E68Y/N168S/L311V/A317P/Y321W/Y412F, E11S/ E68Y/L19I/S188H/A195V/L311V/A317P/Y321F/Y412F, E11S/V42I/T57S/E68Y/L19I/S188H/A195V/L311V/ A317P/Y321F, E11S/L19I/L19I/S188H/A195V/L311V/ A317P, E11S/V42I/E68Y/S188H/A195V/L311V/Y412F, E11S/V42I/L19I/S188H/A195V/L311V/A317P/Y321F/ Y412F, E11S/Y412F, E11S/L19I/V42I/E68Y/L19I/S188H/ A195V/Y412F, E11S/L19I/V42I/D53N/T57S/S188H/ A195V/L311V/Y321W/Y412F, V42I/E68Y/Y412F, E11S/ L19I/V42I/D53N/T57S/E68Y/L19I/N168S/S188H/A195V/ L311V/A317P/Y321F, E11S/L19I/V42I/D53N/T57S/L19I/ S188H/A195V/L311V/A317P/Y321W/Y412F, E11S/V42I/ A317P/Y321F, E11S/V42I/T57S/E68Y/D118N/S188H/ A195V/L311V/Y412F, E11S/V42I/D53N/E68Y/S188H/ A195V/L311V/Y412F, E11S/L19I/D118N/S188H/A195V/ L311V/Y412F, V42I/D53N/T57S/E68Y/M141L/N168S/ T261A/Y321W/E381N/Y412F, E11S/V42I/S188H/L347N/ Y412F/S434T, D118N/N168S/S188H/L347N/E348I/ S382D/T388Q/V395L, E11S/E68Y/V88I/A317P/Y321F/ S355D, E11S/L19I/E68Y/L19I/L79Y/M141L/N168S/ T261A/A317P/Y321W/L347N, E11S/V42I/E68Y/L19I/ L311V/Y321W/S434T, E11S/V42I/D53N/N168S/L311V/ A317P/Y321W, E11S/E68Y/L19I/D118N/N168S/Y321F/ Y412F, V42I/E68Y/L311V/L347N/L364I/Y412F, T57S/ I69L/T89S/S188H/A195V/T261A/L311V/A317P/Y321W/ F394Y/Y412F, Y321F/Y412F, E11S/V42I/E68Y/L311V/ A317P/S434T, V42I/D53N/T57S/E68Y/I69L/S434T, V42I/ E68Y/Y321W, L311V/L347N/E348I/S355D/L364I/S434T, V42I/E68Y/A317P/Y321F/Y412F, L19I/L19I/T89S/ L311V/A317P/Y321F/S355D/L364I/Y412F, V42I/D53N/ T57S/E68Y/L19I/M141L/S188H/A195V/L311V/A317P/ Y321F/Y412F/S434T, E11S/L19I/V42I/D53N/E68Y/ L311V/A317P/Y321W/Y412F, E11S/V42I/D53N/E68Y/ L19I/S188H/A195V/E348I, E11S/T261A/L347N/E348I/

S355D/S434T, E11S/A317P/Y321F/L347N, E11S/E68Y/ L19I/T261A/L364I, E11S/L311V/Y321W/E348I/S355D/ L364I/Y412F, V42I/D53N/T57S/L19I/V88I/L347N/E348I/ F394Y/V395L/S434T, E11S/D53N/T89S/N168S/S188H/ T261A/L311V/A317P/Y321W/S355D/Y412F, V42I/E68Y/ T89S/M141L/T261A/L311V/Y321F/E348I/L364I, V42I/ E68Y/D118N/S188H/T261A/Y412F/S434T, E11S/D53N/ E68Y/L19I/T89S/Y321W/E348I/S355D, L311V/L347N/ E348I, E11S/V42I/A317P/Y321F/L347N/Y412F, E11S/ L19I/V42I/E68Y/A317P/Y321F/L364I/Y412F, D53N/ E68Y/T89S/T261A, L19I/S188H/A195V/L311V/A317P/ Y321W/V395L/Y412F, V42I/D53N/E68Y/V88I/T89S/ D118N/L311V/Y412F/S434T, E11S/V42I/E68Y/L19I/ L311V/E348I, V42I/Y321W, E68Y/T261A/L311V/L347N/ E348I/S434T, E11S/E68Y/L19I/L79Y, and V42I/D53N/ E68Y/S188H/A195V/T261A/L311V/Y321F/S355D/ S434T.

15. A composition comprising a variant glucoamylase enzyme comprising at least one amino acid substitution as compared to SEQ ID NO:13, wherein said amino acid substitution is at a position selected from the group consisting of 5, 27, 36, 38, 46, 47, 50, 65, 68, 79, 89, 98, 108, 122, 124, 158, 161, 188, 192, 212, 215, 258, 262, 264, 298, 321, 400, 412, 420, 422, 457, 491, 497, 498, 503, 508, 509, 510, 516, 518, 521, 522, 526, 533, 534, 535, 540, 542, 544, 545, 549, 550, 551, 555, 556, 557, 559, 563, 564, 569, 570, 581 584, 7, 9, 11, 19, 26, 31, 42, 53, 55, 57, 69, 72, 73, 78, 85, 86, 88, 92, 93, 94, 97, 103, 106, 118, 125, 141, 145, 149, 150, 153, 155, 168, 170, 171, 178, 179, 186, 195, 204, 205, 208, 209, 213, 214, 219, 220, 224, 227, 246, 247, 256, 261, 306, 307, 311, 317, 342, 347, 348, 352, 353, 355, 362, 364, 370, 374, 381, 382, 388, 391, 394, 395, 399, 407, 418, 434, 436, 437, 440, 446, 452, 453, 460, 469, 470, 472, 475, 476, 478 and 492, wherein said variant glucoamylase enzyme has at least 1.1 fold better activity as compared to SEQ ID NO:13 under a condition selected from the group consisting of thermoactivity at about 30° C., thermoactivity at about 35° C., thermoactivity at about 40° C., thermoactivity at about 50° C., thermoactivity at about 60° C. and thermoactivity at about 70° C.; wherein said variant enzyme is at least 95% identical to SEQ ID NO:13, wherein the variant glucoamylase enzyme is not naturally occurring; and wherein amino acid substitutions are selected from the group consisting of T98S/Q161P/F516L, T98S/Q161P/N570P, T98S/ Q161P, T550D/F555S, V65I/Y412F/Y503S/S518I, Y412F/ Y503S/I564 T, Y412F/Y503E, Y412F/Y503E/S518I, V65I/ Y412F/Y503S, V65I/Y503E, Y503D/S518I/I564N, Y503E/ S518L, V65I/Y503E/S544Q V65I/Y503S, Y503E/S544E, V65I/Y503E/S544E/I564N, V65I/Y412F/Y503E, Y503E/ S518I/S544Q, V65I/Y503E/S518M, Y412F/S518L, Y503E/ S544Q, V65I/Y412F/Y503E/S544E/I564 T/G569I, Y412F/ Y503S, Y503E/I564 T, S549D/F555D/G559N, S549D/ F555R, K508T/L526N/S549D/G559N, K508T/G559N, F555D/I556P/G559N, S549D/F555R/I556P/G559N, F555R/I556P, L526I/F555R/I556P, F555R/I556P/G559N, K508T/I556P/G559N, F555D/I556P, K508T/L526N/ A534T/S549D/I556P, K508T/L526I/S549D/G559N, K508N/L526I/S549E/F555L/G559N, L526N/S549D/ F555D/I556P, L526I/F555D/G559N, A38V/F555R, L498T/ T542N/T581N/T584N, T542N/T581N/T584N, S535Y/ T542N, T540N/T584N, T540N/T542N/T581N/T584N, L498T/T581N/T584N, L498T/T584N, L498T/T542N/ T581N, L498T/T542N, S535Y/T540N/T542N/T581N, Y321F/A422S, K5H/Y321W, K5N/Y321F, K5P/S188H, E68S/S188H/A422S, K5H/S188H/Y321F/A422S, S188H/ A422S, S188H/A422S/V545A, K5Q/A422S, K5S/E68K/ Y321W, K5H/Y321F/A422S, K5Y/A422S, K5Y/S188H/ A422S, K5T/A422S, K5T/Y321W, Y321W/A422S, K5P/ Y321F, K5H/S188H/Y321F/A422S, E68K/A422S, Y321F/ A422S, K5H/Y321F, K5T/E68Y/S188T, K5S/E68Y/ S188H, K5N/S188H, K5T/E68S/S188T, K5H/E68Y/S188P, K5P/E68Y/S188T, K5T/E68K/S188H, K5P/E68K/S188T, K5H/E68Y/S188T, K5T/S188H, K5T/E68N/S188T, K5Y/ E68Y/S188T, K5S/E68Y/S188T, K5Q/E68K/S188H, K5P/ E68N/S188H, K5P/E68N/S188T, K5P/E68Y/S188H, K5Y/ E68Y/S188H, K5S/S188T, K5H/E68N/S188H, K5P/ S188H, K5H/S46T/E68K/S188H, K5H/E68K/S188T, K5Q/ E68Y/S188T, K5Y/E68N/S188H, L19I/V42I/E68Y/N168S/ S188H/A195V/Y412F, E11S/V42I/T57S/D118N/N168S/ S188H/A195V/L311V, E11S/V42I/D53N/E68Y/N168S/ S188H/A195V/L311V/Y412F, E11S/L19I/V42I/E68Y/ D118N/S188H/A195V/L311V/Y412F, E11S/E68Y/S188H/ A195V/L311V/Y412F, E11S/L19I/V42I/E68Y/L19I/ D118N/N168S/S188H/A195V/L311V/Y412F, E11S/L19I/ N168S/S188H/A195V/L311V/A317P/Y321F/Y412F, E11S/V42I/E68Y/Y412F, E11S/L19I/V42I/E68Y/Y412F, E11S/V42I/E68Y/S188H/A195V/Y412F, E11S/L19I/V42I/ T57S/169L/S188H/A195V/L311V/Y321W/Y412F, E11S/ L19I/D53N/E68Y/S188H/A195V/L311V/Y412F, E11S/ V42I/E68Y/S188H/A195V/L311V/Y321W/Y412F, E11S/ V42I/E68Y/N168S/L311V/A317P/Y321W/Y412F, E11S/ E68Y/169L/S188H/A195V/L311V/A317P/Y321F/Y412F, E11S/V42I/T57S/E68Y/L19I/S188H/A195V/L311V/ A317P/Y321F, E11S/L19I/L19I/S188H/A195V/L311V/ A317P, E11S/V42I/E68Y/S188H/A195V/L311V/Y412F, E11S/V42I/L19I/S188H/A195V/L311V/A317P/Y321F/ Y412F, E11S/Y412F, E11S/L19I/V42I/E68Y/L19I/S188H/ A195V/Y412F, E11S/L19I/V42I/D53N/T57S/S188H/ A195V/L311V/Y321W/Y412F, V42I/E68Y/Y412F, E11S/ L19I/V42I/D53N/T57S/E68Y/L19I/N168S/S188H/A195V/ L311V/A317P/Y321F, E11S/L19I/V42I/D53N/T57S/L19I/ S188H/A195V/L311V/A317P/Y321W/Y412F, E11S/V42I/ A317P/Y321F, E11S/V42I/T57S/E68Y/D118N/S188H/ A195V/L311V/Y412F, E11S/V42I/D53N/E68Y/S188H/ A195V/L311V/Y412F, E11S/L19I/D118N/S188H/A195V/ L311V/Y412F, V42I/D53N/T57S/E68Y/M141L/N168S/ T261A/Y321W/E381N/Y412F, E11S/V42I/S188H/L347N/ Y412F/S434T, D118N/N168S/S188H/L347N/E348I/ S382D/T388Q/V395L, E11S/E68Y/V88I/A317P/Y321F/ S355D, E11S/L19I/E68Y/L19I/L79Y/M141L/N168S/ T261A/A317P/Y321W/L347N, E11S/V42I/E68Y/L19I/ L311V/Y321W/S434T, E11S/V42I/D53N/N168S/L311V/ A317P/Y321W, E11S/E68Y/L19I/D118N/N168S/Y321F/ Y412F, V42I/E68Y/L311V/L347N/L364I/Y412F, T57S/ L19I/T89S/S188H/A195V/T261A/L311V/A317P/Y321W/ F394Y/Y412F, Y321F/Y412F, E11S/V42I/E68Y/L311V/ A317P/S434T, V42I/D53N/T57S/E68Y/L19I/S434T, V42I/ E68Y/Y321W, L311V/L347N/E348I/S355D/L364I/S434T, V42I/E68Y/A317P/Y321F/Y412F, L19I/L19I/T89S/ L311V/A317P/Y321F/S355D/L364I/Y412F, V42I/D53N/ T57S/E68Y/L19I/M141L/S188H/A195V/L311V/A317P/ Y321F/Y412F/S434T, E11S/L19I/V42I/D53N/E68Y/ L311V/A317P/Y321W/Y412F, E11S/V42I/D53N/E68Y/ L19I/S188H/A195V/E348I, E11S/T261A/L347N/E348I/ S355D/S434T, E11S/A317P/Y321F/L347N, E11S/E68Y/ L19I/T261A/L364I, E11S/L311V/Y321W/E348I/S355D/ L364I/Y412F, V42I/D53N/T57S/L19I/V88I/L347N/E348I/ F394Y/V395L/S434T, E11S/D53N/T89S/N168S/S188H/ T261A/L311V/A317P/Y321W/S355D/Y412F, V42I/E68Y/ T89S/M141L/T261A/L311V/Y321F/E348I/L364I, V42I/ E68Y/D118N/S188H/T261A/Y412F/S434T, E11S/D53N/ E68Y/L19I/T89S/Y321W/E348I/S355D, L311V/L347N/ E348I, E11S/V42I/A317P/Y321F/L347N/Y412F, E11S/ L19I/V42I/E68Y/A317P/Y321F/L364I/Y412F, D53N/

E68Y/T89S/T261A, L19I/S188H/A195V/L311V/A317P/Y321W/V395L/Y412F, V42I/D53N/E68Y/V88I/T89S/D118N/L311V/Y412F/S434T, E11S/V42I/E68Y/I69L/L311V/E348I, V42I/Y321W, E68Y/T261A/L311V/L347N/E348I/S434T, E11S/E68Y/L19I/L79Y, and V42I/D53N/E68Y/S188H/A195V/T261A/L311V/Y321F/S355D/S434T.

16. The composition according to claim 14, wherein said variant enzyme is at least 96% identical to SEQ ID NO:13.

17. A host cell comprising the nucleic acid sequence encoding the variant glucoamylase of claim 14.

18. A host cell comprising an expression vector, wherein the expression vector comprises the nucleic acid sequence encoding the variant glucoamylase of claim 14.

19. The host cell of claim 17, wherein said host cell is selected from the group consisting of a bacterial cell, a fungal cell, and a yeast cell.

20. A method of making a variant glucoamylase enzyme comprising: a) culturing the host cell of claim 17 under conditions wherein said variant glucoamylase enzyme is expressed; and b) recovering said variant glucoamylase enzyme.

21. The composition according to claim 14, wherein said amino acid substitution(s) is selected from the group consisting of K5H, K5N, K5P, K5Q, K5S, K5T, K5Y, N27A, S36P, A38V, S46T, P47T, S50Q, V65I, E68K, E68N, E68S, E68Y, L79F, T89N, T98S, A108S, F122M, G124P, G124S, G124T, G158S, Q161P, S188H, S188P, S188T, S188W, T192A, K212Y, S215A, T258S, A262S, H264M, I298V, Y321F, Y321L, Y321W, T400L, Y412F, L420K, A422G, A422S, G457S, A491V, E497V, L498T, Y503D, Y503E, Y503G, Y503K, Y503L, Y503N, Y503S, Y503T, K508N, K508S, K508T, L509P, V510G, V510S, F516L, S518I, S518L, S518M, P521S, S522G, L526I, L526N, L526S, T533R, A534T, S535Y, T540N, T542N, S544E, S544N, S544Q, V545A, V545D, S549D, S549E, T550D, V551D, V551R, V551S, F555D, F555K, F555L, F555N, F555R, F555S, I556D, I556P, I556R, R557P, G559N, G559S, S563L, I564N, I564S, I564T, G569I, N570P, T581N, T584N, R7C, E11S, L19I, C26N, T31N, V42I, D53N, Y55F, T57S, I69L, S72A, V73F, T78K, L79D, L79Y, E85Q, N86Q, V88I, T89S, A92T, Y93K, L94V, V97I, S103D, D106T, D118N, A125P, M141L, Y145A, L149I, N150D, A153S, T155A, N168S, V170I, A171T, G178T, Y179F, P186E, A195V, S204N, T205A, A208T, K209R, S213T, H214C, T219S, V220Q, I224V, Y227A, A246S, S247G, A256V, T261A, T261G, S306A, A307E, L311V, A317P, V342I, L347N, E348I, T352S, V353I, S355D, T362Q, L364I, T370V, A374N, E381N, S382D, T388Q, A391G, F394Y, V395L, Q399E, T400K, A407S, Q418T, S434T, T436S, E437A, D440Q, G446S, S452A, V453S, A460S, A469S, A470T, S472T, G475V, T476W, G478S, L492P, and L9P, and wherein the variant glucoamylase enzyme is not naturally occurring.

* * * * *

SEQUENCE LISTING

<160> NUMBER OF SEQ ID NOS: 26

<210> SEQ ID NO 1
<211> LENGTH: 620
<212> TYPE: PRT
<213> ORGANISM: Artificial Sequence
<220> FEATURE:
<223> OTHER INFORMATION: G6P preprotein amino acid sequence

<400> SEQUENCE: 1

Met Val Phe Leu Lys Ser Ala Ile Ala Ala Ser Thr Trp Leu Leu Ala
1               5                   10                  15

Ala Thr Gly Val Val Ala Ser Pro Val Ser Lys Arg Ala Thr Leu Asp
            20                  25                  30

Glu Phe Ile Ser Thr Glu Arg Pro Leu Ala Leu Glu Arg Leu Leu Cys
            35                  40                  45

Asn Ile Gly Pro Thr Gly Cys Arg Ala Ser Gly Ala Ala Ser Gly Val
50                  55                  60

Val Ile Ala Ser Pro Ser Arg Ser Asp Pro Asp Tyr Tyr Tyr Thr Trp
65                  70                  75                  80

Thr Arg Asp Ala Ala Leu Val Phe Lys Glu Ile Val Asp Ser Val Glu
                85                  90                  95

Thr Asn Thr Thr Leu Leu Leu Pro Glu Ile Glu Asn Tyr Val Thr Ala
                100                 105                 110

Gln Ala Tyr Leu Gln Thr Val Thr Asn Pro Ser Gly Ser Leu Ser Asp
            115                 120                 125

Gly Ala Gly Leu Gly Glu Pro Lys Phe Asn Val Asp Met Thr Pro Phe
130                 135                 140

Thr Gly Ala Trp Gly Arg Pro Gln Arg Asp Gly Pro Ala Leu Arg Ala
145                 150                 155                 160

Thr Ala Met Ile Ala Tyr Tyr Asn Tyr Leu Leu Asn Asn Asn Ala Thr
                165                 170                 175

Thr Asp Cys Gly Leu Trp Gln Ile Ile Gln Asn Asp Leu Asn Tyr Val
                180                 185                 190

Ala Gln Tyr Trp Asn Gln Thr Gly Tyr Asp Leu Trp Glu Glu Val Pro
            195                 200                 205

Gly Ser Ser Phe Phe Thr Val Ala Ala Gln Tyr Arg Ala Leu Val Glu
210                 215                 220

Gly Ser Thr Leu Ala Ala Lys Leu Gly Lys Ser His Ser Ala Tyr Asp
225                 230                 235                 240

Thr Val Ala Pro Gln Ile Leu Cys Tyr Leu Gln Ser Phe Trp Ser Ser
                245                 250                 255

Ser Lys Gly Tyr Ile Val Ala Asn Thr Gln Thr Ala Ser Trp Val Ser
            260                 265                 270

Arg Ser Gly Leu Asp Ala Asn Thr Pro Leu Thr Ala Ile His Leu Phe
275                 280                 285

Asp Pro Glu Leu Gly Cys Asp Asp Ser Thr Phe Gln Pro Cys Ser Pro
290                 295                 300

Lys Gln Leu Ile Thr Thr Lys Lys Leu Val Asp Ser Phe Arg Ser Ile
305                 310                 315                 320

Tyr Ala Ile Asn Ser Gly Lys Ser Ala Gly Asp Ala Leu Ala Val Gly
                325                 330                 335

Arg Tyr Ala Glu Asp Val Tyr Tyr Asn Gly Asn Pro Trp Tyr Leu Cys
            340                 345                 350

Thr Leu Ala Val Ala Glu Gln Leu Tyr Asp Ala Val Tyr Thr Trp Lys
            355                 360                 365

Leu Glu Gly Ser Ile Thr Val Thr Ser Val Ser Leu Pro Phe Phe Thr
370                 375                 380

Asp Leu Leu Pro Ser Leu Thr Thr Gly Thr Tyr Ala Ser Gly Ser Thr
385                 390                 395                 400

Thr Phe Glu Ser Ile Ile Ser Ala Val Thr Thr Tyr Ala Asp Gly Phe
                405                 410                 415

Val Ser Ile Val Gln Thr Tyr Thr Pro Ser Asp Gly Ala Leu Ser Glu
            420                 425                 430

Gln Tyr Ser Lys Tyr Asn Gly Gln Gln Leu Ser Ala Pro Asp Leu Thr

Trp Ser Tyr Ala Ala Phe Leu Ser Ala Thr Glu Arg Arg Asp Ser Val
            450                 455                 460
Val Pro Ala Gly Trp Ala Gly Ala Ser Ser Val Ser Val Pro Gly Ala
465                 470                 475                 480
Cys Ala Ala Thr Thr Val Val Gly Thr Tyr Ala Ala Ser Asn Cys
                    485                 490                 495
Gly Thr Pro Gly Ser Gly Ser Gly Gly Asn Gly Gly Ser Ser Gly Asn
                500                 505                 510
Ala Leu Val Thr Phe Asn Glu Leu Ala Thr Thr Tyr Tyr Gly Glu Asn
            515                 520                 525
Ile Lys Leu Val Gly Ser Thr Ala Ala Phe Gly Ser Trp Ser Pro Ser
            530                 535                 540
Ala Gly Ile Leu Leu Ser Ala Ser Ser Tyr Thr Ala Ser Asn Pro Leu
545                 550                 555                 560
Trp Thr Thr Thr Val Ser Val Pro Gln Gly Ser Thr Val Glu Phe Lys
                    565                 570                 575
Phe Ile Arg Val Gly Ser Asp Gly Ser Ile Thr Trp Glu Ser Gly Asn
                580                 585                 590
Asn Lys Val Leu Thr Val Gly Ser Ser Ala Thr Ser Val Thr Val Ser
            595                 600                 605
Ala Ser Trp Asn Gly Ala Tyr Ser Val Ser Ser Ser
610                 615                 620

<210> SEQ ID NO 2
<211> LENGTH: 1866
<212> TYPE: DNA
<213> ORGANISM: Artificial Sequence
<220> FEATURE:
<223> OTHER INFORMATION: G6P preprotein-encoding nucleic acid sequence

<400> SEQUENCE: 2 atggtttttcc tcaagtcggc catcgccgct tccacctggc tcttggctgc cactggcgtc      60
gttgcctcgc ctgttttccaa gcgcgctacg ctggacgagt tcatcagcac cgagcgtccc     120
ttggctctgg agcgcctgct ctgcaacatt ggtcctactg gttgccgtgc ttcgggagct     180
gcctcgggag tcgttatcgc ctcgccgtcc cgcagcgatc cggactacta ctacacttgg     240
acccgtgatg ctgctctggt cttttaaggag attgtcgact ctgtcgagac taacaccact     300
ctgctgctgc cagagattga gaactacgtt actgcccagg cttacctgca gaccgtgacg     360 aaccctcgg gttcgctgtc ggatggtgct ggtctgggcg agcccaagtt caacgtcgat     420
atgactccct tcactggtgc ctggggtcgt cctcagcgtg atggtccggc tctgcgtgct     480
acggctatga tcgcctacta caactacctg ctcaacaaca cgccactac cgactgtggt     540 ctgtggcaga ttatccagaa cgacctgaat acgtcgctc agtactggaa ccaaactggt     600
tacgacctgt gggaggaggt tccgggttca tccttttttca ctgttgctgc tcagtacaga     660
gctctcgttg agggttctac ccttgctgcc aagctcggca agtctcactc ggcctacgac     720
actgtcgctc cgcagattct gtgctacttg cagagcttct ggtcatccag caagggctac     780
attgtcgcca cacccagac tgccagctgg gtctcgcggt ccggtcttga tgccaacact     840
cccttgactg ccatccacct atttgaccct gaacttggct gcgatgactc gactttccag     900
ccctgctcgc caagcagct tatcactact aagaagctcg ttgactcgtt ccgctccatc     960
tatgccatca actcgggcaa gtctgctggt gatgctttgg ctgttggtcg ttacgccgag    1020

```
gacgtctact acaacggcaa cccctggtac ctgtgcactt tggctgttgc agagcagctt    1080
tacgatgcag tttacacttg gaagctcgag ggctccatca ccgtcacctc tgtctcgctg    1140
cccttcttca ctgacctgct gccctcgctg accactggca cctacgcttc gggctcgacc    1200
accttcgaat ccatcatctc tgctgtgact acctacgctg atggctttgt cagtattgtc    1260
cagacctaca ctccctctga cggcgctctg tctgagcagt actccaagta caacggccag    1320
cagctgtcgg ctcccgacct gacctggtcg tacgccgctt cctatctgc cactgagcgc     1380 cgtgacagcg ttgtccctgc cggctgggct ggtgcctcgt ctgtctctgt gcccggcgcc    1440
tgcgctgcta ccaccgttgt cggaacctac gctgctgcct ccaactgcgg tactcctggc    1500
tctggctcgg gcggcaacgg tggctcgagc ggtaacgccc tggtgacttt caacgagctg    1560
gctactacct actacggcga gaacattaag cttgtcggca gcacagctgc tttcggttcg    1620
tggtcgccct cagctggtat tctcctgtct gcctcgtcgt acacggccag caaccctctg    1680
tggactacca ccgtgtcggt tccccagggc tcgaccgttg agttcaagtt catccgtgtt    1740
ggctccgacg gcagcatcac gtgggagagc ggcaacaaca aggtgttgac ggttggctct    1800
tcggccacga gcgtcactgt ttctgccagc tggaacggcg cctactcggt gtctagctct    1860
taatag                                                                1866
```

<210> SEQ ID NO 3
<211> LENGTH: 514
<212> TYPE: PRT
<213> ORGANISM: Artificial Sequence
<220> FEATURE:
<223> OTHER INFORMATION: G7P preprotein amino acid sequence

<400> SEQUENCE: 3

```
Met Val Phe Leu Lys Ser Ala Ile Ala Ala Ser Thr Trp Leu Leu Ala
1               5                   10                  15

Ala Thr Gly Val Val Ala Ser Pro Val Ser Lys Arg Ala Thr Leu Asp
            20                  25                  30

Glu Phe Ile Ser Thr Glu Arg Pro Leu Ala Leu Glu Arg Leu Leu Cys
        35                  40                  45

Asn Ile Gly Pro Thr Gly Cys Arg Ala Ser Gly Ala Ala Ser Gly Val
    50                  55                  60

Val Ile Ala Ser Pro Ser Arg Ser Asp Pro Asp Tyr Tyr Tyr Thr Trp
65                  70                  75                  80

Thr Arg Asp Ala Ala Leu Val Phe Lys Glu Ile Val Asp Ser Val Glu
                85                  90                  95

Thr Asn Thr Thr Leu Leu Leu Pro Glu Ile Glu Asn Tyr Val Thr Ala
            100                 105                 110

Gln Ala Tyr Leu Gln Thr Val Thr Asn Pro Ser Gly Ser Leu Ser Asp
        115                 120                 125

Gly Ala Gly Leu Gly Glu Pro Lys Phe Asn Val Asp Met Thr Pro Phe
    130                 135                 140

Thr Gly Ala Trp Gly Arg Pro Gln Arg Asp Gly Pro Ala Leu Arg Ala
145                 150                 155                 160

Thr Ala Met Ile Ala Tyr Tyr Asn Tyr Leu Leu Asn Asn Asn Ala Thr
                165                 170                 175

Thr Asp Cys Gly Leu Trp Gln Ile Ile Gln Asn Asp Leu Asn Tyr Val
            180                 185                 190

Ala Gln Tyr Trp Asn Gln Thr Gly Tyr Asp Leu Trp Glu Glu Val Pro
        195                 200                 205
```

```
Gly Ser Ser Phe Phe Thr Val Ala Ala Gln Tyr Arg Ala Leu Val Glu
    210                 215                 220
Gly Ser Thr Leu Ala Ala Lys Leu Gly Lys Ser His Ser Ala Tyr Asp
225                 230                 235                 240
Thr Val Ala Pro Gln Ile Leu Cys Tyr Leu Gln Ser Phe Trp Ser Ser
                245                 250                 255
Ser Lys Gly Tyr Ile Val Ala Asn Thr Gln Thr Ala Ser Trp Val Ser
            260                 265                 270
Arg Ser Gly Leu Asp Ala Asn Thr Pro Leu Thr Ala Ile His Leu Phe
        275                 280                 285
Asp Pro Glu Leu Gly Cys Asp Asp Ser Thr Phe Gln Pro Cys Ser Pro
290                 295                 300
Lys Gln Leu Ile Thr Thr Lys Lys Leu Val Asp Ser Phe Arg Ser Ile
305                 310                 315                 320
Tyr Ala Ile Asn Ser Gly Lys Ser Ala Gly Asp Ala Leu Ala Val Gly
                325                 330                 335
Arg Tyr Ala Glu Asp Val Tyr Tyr Asn Gly Asn Pro Trp Tyr Leu Cys
            340                 345                 350
Thr Leu Ala Val Ala Glu Gln Leu Tyr Asp Ala Val Tyr Thr Trp Lys
        355                 360                 365
Leu Glu Gly Ser Ile Thr Val Thr Ser Val Ser Leu Pro Phe Phe Thr
370                 375                 380
Asp Leu Leu Pro Ser Leu Thr Thr Gly Thr Tyr Ala Ser Gly Ser Thr
385                 390                 395                 400
Thr Phe Glu Ser Ile Ile Ser Ala Val Thr Thr Tyr Ala Asp Gly Phe
                405                 410                 415
Val Ser Ile Val Gln Thr Tyr Thr Pro Ser Asp Gly Ala Leu Ser Glu
            420                 425                 430
Gln Tyr Ser Lys Tyr Asn Gly Gln Gln Leu Ser Ala Pro Asp Leu Thr
        435                 440                 445
Trp Ser Tyr Ala Ala Phe Leu Ser Ala Thr Glu Arg Arg Asp Ser Val
450                 455                 460
Val Pro Ala Gly Trp Ala Gly Ala Ser Ser Val Ser Val Pro Gly Ala
465                 470                 475                 480
Cys Ala Ala Thr Thr Val Val Gly Thr Tyr Ala Ala Ala Ser Asn Cys
                485                 490                 495
Gly Thr Pro Gly Ser Gly Ser Gly Gly Asn Gly Gly Ser Ser Gly Asn
            500                 505                 510
Ala Leu

<210> SEQ ID NO 4
<211> LENGTH: 1548
<212> TYPE: DNA
<213> ORGANISM: Artificial Sequence
<220> FEATURE:
<223> OTHER INFORMATION: G7P preprotein-encoding nucleic acid sequence

<400> SEQUENCE: 4
atggttttcc tcaagtcggc catcgccgct tccacctggc tcttggctgc cactggcgtc      60
gttgcctcgc ctgtttccaa gcgcgctacg ctggacgagt catcagcac cgagcgtccc      120 ttggctctgg agcgcctgct ctgcaacatt ggtcctactg gttgccgtgc ttcgggagct      180
gcctcgggag tcgttatcgc ctcgccgtcc cgcagcgatc cggactacta ctacacttgg      240
acccgtgatg ctgctctggt ctttaaggag attgtcgact ctgtcgagac taacaccact      300
```

```
ctgctgctgc cagagattga gaactacgtt actgcccagg cttacctgca gaccgtgacg    360
aacccctcgg gttcgctgtc ggatggtgct ggtctgggcg agcccaagtt caacgtcgat    420
atgactccct tcactggtgc ctggggtcgt cctcagcgtg atggtccggc tctgcgtgct    480
acggctatga tcgcctacta caactacctg ctcaacaaca acgccactac cgactgtggt    540
ctgtggcaga ttatccagaa cgacctgaat tacgtcgctc agtactggaa ccaaactggt    600
tacgacctgt gggaggaggt tccgggttca tccttttttca ctgttgctgc tcagtacaga    660
gctctcgttg agggttctac ccttgctgcc aagctcggca agtctcactc ggcctacgac    720
actgtcgctc cgcagattct gtgctacttg cagagcttct ggtcatccag caagggctac    780
attgtcgcca acacccagac tgccagctgg gtctcgcggt ccggtcttga tgccaacact    840
cccttgactg ccatccacct atttgaccct gaacttggct gcgatgactc gactttccag    900
ccctgctcgc ccaagcagct tatcactact aagaagctcg ttgactcgtt ccgctccatc    960
tatgccatca actcgggcaa gtctgctggt gatgctttgg ctgttggtcg ttacgccgag    1020
gacgtctact acaacggcaa cccctggtac ctgtgcactt tggctgttgc agagcagctt    1080
tacgatgcag tttacacttg aagctcgag ggctccatca ccgtcacctc tgtctcgctg    1140
cccttcttca ctgacctgct gccctcgctg accactggca cctacgcttc gggctcgacc    1200
accttcgaat ccatcatctc tgctgtgact acctacgctg atggctttgt cagtattgtc    1260
cagacctaca ctccctctga cggcgctctg tctgagcagt actccaagta caacggccag    1320
cagctgtcgg ctcccgacct gacctggtcg tacgccgctt tcctatctgc cactgagcgc    1380
cgtgacagcg ttgtccctgc cggctgggct ggtgcctcgt ctgtctctgt gcccggcgcc    1440
tgcgctgcta ccaccgttgt cggaacctac gctgctgcct ccaactgcgg tactcctggc    1500
tctggctcgg gcggcaacgg tggctcgagc ggtaacgccc tgtaatag                 1548
```

<210> SEQ ID NO 5
<211> LENGTH: 620
<212> TYPE: PRT
<213> ORGANISM: Artificial Sequence
<220> FEATURE:
<223> OTHER INFORMATION: Variant1 (Y321F with Starch Binding Domain)
      preprotein amino acid sequence

<400> SEQUENCE: 5

Met Val Phe Leu Lys Ser Ala Ile Ala Ala Ser Thr Trp Leu Ala
1               5                   10                  15

Ala Thr Gly Val Val Ala Ser Pro Val Ser Lys Arg Ala Thr Leu Asp
            20                  25                  30

Glu Phe Ile Ser Thr Glu Arg Pro Leu Ala Leu Glu Arg Leu Leu Cys
        35                  40                  45

Asn Ile Gly Pro Thr Gly Cys Arg Ala Ser Gly Ala Ala Ser Gly Val
    50                  55                  60

Val Ile Ala Ser Pro Ser Arg Ser Asp Pro Asp Tyr Tyr Tyr Thr Trp
65                  70                  75                  80

Thr Arg Asp Ala Ala Leu Val Phe Lys Glu Ile Val Asp Ser Val Glu
                85                  90                  95

Thr Asn Thr Thr Leu Leu Leu Pro Glu Ile Glu Asn Tyr Val Thr Ala
            100                 105                 110

Gln Ala Tyr Leu Gln Thr Val Thr Asn Pro Ser Gly Ser Leu Ser Asp
        115                 120                 125

Gly Ala Gly Leu Gly Glu Pro Lys Phe Asn Val Asp Met Thr Pro Phe
    130                 135                 140

```
Thr Gly Ala Trp Gly Arg Pro Gln Arg Asp Gly Pro Ala Leu Arg Ala
145                 150                 155                 160

Thr Ala Met Ile Ala Tyr Tyr Asn Tyr Leu Leu Asn Asn Asn Ala Thr
            165                 170                 175

Thr Asp Cys Gly Leu Trp Gln Ile Ile Gln Asn Asp Leu Asn Tyr Val
            180                 185                 190

Ala Gln Tyr Trp Asn Gln Thr Gly Tyr Asp Leu Trp Glu Glu Val Pro
        195                 200                 205

Gly Ser Ser Phe Phe Thr Val Ala Ala Gln Tyr Arg Ala Leu Val Glu
        210                 215                 220

Gly Ser Thr Leu Ala Ala Lys Leu Gly Lys Ser His Ser Ala Tyr Asp
225                 230                 235                 240

Thr Val Ala Pro Gln Ile Leu Cys Tyr Leu Gln Ser Phe Trp Ser Ser
                245                 250                 255

Ser Lys Gly Tyr Ile Val Ala Asn Thr Gln Thr Ala Ser Trp Val Ser
                260                 265                 270

Arg Ser Gly Leu Asp Ala Asn Thr Pro Leu Thr Ala Ile His Leu Phe
            275                 280                 285

Asp Pro Glu Leu Gly Cys Asp Asp Ser Thr Phe Gln Pro Cys Ser Pro
290                 295                 300

Lys Gln Leu Ile Thr Thr Lys Lys Leu Val Asp Ser Phe Arg Ser Ile
305                 310                 315                 320

Tyr Ala Ile Asn Ser Gly Lys Ser Ala Gly Asp Ala Leu Ala Val Gly
                325                 330                 335

Arg Tyr Ala Glu Asp Val Phe Tyr Asn Gly Asn Pro Trp Tyr Leu Cys
            340                 345                 350

Thr Leu Ala Val Ala Glu Gln Leu Tyr Asp Ala Val Tyr Thr Trp Lys
            355                 360                 365

Leu Glu Gly Ser Ile Thr Val Thr Ser Val Ser Leu Pro Phe Phe Thr
370                 375                 380

Asp Leu Leu Pro Ser Leu Thr Thr Gly Thr Tyr Ala Ser Gly Ser Thr
385                 390                 395                 400

Thr Phe Glu Ser Ile Ile Ser Ala Val Thr Thr Tyr Ala Asp Gly Phe
                405                 410                 415

Val Ser Ile Val Gln Thr Tyr Thr Pro Ser Asp Gly Ala Leu Ser Glu
                420                 425                 430

Gln Tyr Ser Lys Tyr Asn Gly Gln Gln Leu Ser Ala Pro Asp Leu Thr
            435                 440                 445

Trp Ser Tyr Ala Ala Phe Leu Ser Ala Thr Glu Arg Arg Asp Ser Val
            450                 455                 460

Val Pro Ala Gly Trp Ala Gly Ala Ser Val Ser Val Pro Gly Ala
465                 470                 475                 480

Cys Ala Ala Thr Thr Val Val Gly Thr Tyr Ala Ala Ala Ser Asn Cys
                485                 490                 495

Gly Thr Pro Gly Ser Gly Ser Gly Gly Asn Gly Gly Ser Ser Gly Asn
                500                 505                 510

Ala Leu Val Thr Phe Asn Glu Leu Ala Thr Thr Tyr Tyr Gly Glu Asn
            515                 520                 525

Ile Lys Leu Val Gly Ser Thr Ala Ala Phe Gly Ser Trp Ser Pro Ser
            530                 535                 540

Ala Gly Ile Leu Leu Ser Ala Ser Ser Tyr Thr Ala Ser Asn Pro Leu
545                 550                 555                 560
```

```
Trp Thr Thr Thr Val Ser Val Pro Gln Gly Ser Thr Val Glu Phe Lys
            565                 570                 575

Phe Ile Arg Val Gly Ser Asp Gly Ser Ile Thr Trp Glu Ser Gly Asn
        580                 585                 590

Asn Lys Val Leu Thr Val Gly Ser Ser Ala Thr Ser Val Thr Val Ser
    595                 600                 605

Ala Ser Trp Asn Gly Ala Tyr Ser Val Ser Ser Ser
610                 615                 620

<210> SEQ ID NO 6
<211> LENGTH: 1866
<212> TYPE: DNA
<213> ORGANISM: Artificial Sequence
<220> FEATURE:
<223> OTHER INFORMATION: Variant1 (Y321F with Starch Binding Domain)
      preprotein-encoding nucleic acid sequence

<400> SEQUENCE: 6
atggttttcc tcaagtcggc catcgccgct tccacctggc tcttggctgc cactggcgtc      60
gttgcctcgc tgtttccaa gcgcgctacg ctggacgagt tcatcagcac cgagcgtccc     120
ttggctctgg agcgcctgct ctgcaacatt ggtcctactg gttgccgtgc ttcgggagct     180
gcctcgggag tcgttatcgc ctcgccgtcc cgcagcgatc cggactacta ctacacttgg     240
acccgtgatg ctgctctggt ctttaaggag attgtcgact ctgtcgagac taacaccact     300
ctgctgctgc agagattga gaactacgtt actgcccagg cttacctgca gaccgtgacg     360
aacccctcgg gttcgctgtc ggatggtgct ggtctgggcg agcccaagtt caacgtcgat     420
atgactccct tcactggtgc ctggggtcgt cctcagcgtg atggtccggc tctgcgtgct     480
acggctatga tcgcctacta caactacctg ctcaacaaca cgccactac cgactgtggt     540 ctgtggcaga ttatccagaa cgacctgaat tacgtcgctc agtactggaa ccaaactggt     600
tacgacctgt gggaggaggt tccgggttca tccttttca ctgttgctgc tcagtacaga     660
gctctcgttg agggttctac ccttgctgcc aagctcggca gtctcactc ggcctacgac     720 actgtcgctc gcagattct gtgctacttg cagagcttct ggtcatccag caagggctac     780
attgtcgcca acacccagac tgccagctgg gtctcgcggt ccggtcttga tgccaacact     840
cccttgactg ccatccacct atttgaccct gaacttggct gcgatgactc gactttccag     900
ccctgctcgc ccaagcagct tatcactact aagaagctcg ttgactcgtt ccgctccatc     960
tatgccatca actcgggcaa gtctgctggt gatgctttgg ctgttggtcg ttacgccgag    1020
gacgtcttct acaacggcaa ccctggtac ctgtgcactt ggctgttgc agagcagctt    1080 tacgatgcag tttacacttg gaagctcgag ggctccatca ccgtcacctc tgtctcgctg    1140
cccttcttca ctgacctgct gccctcgctg accactggca cctacgcttc gggctcgacc    1200
accttcgaat ccatcatctc tgctgtgact acctacgctg atggctttgt cagtattgtc    1260
cagacctaca ctccctctga cggcgctctg tctgagcagt actccaagta caacggccag    1320
cagctgtcgg ctcccgacct gacctggtcg tacgccgctt tcctatctgc cactgagcgc    1380
cgtgacagcg ttgtccctgc cggctgggct ggtgcctcgt ctgtctctgt gccggcgcc    1440 tgcgctgcta ccaccgttgt cggaacctac gctgctgcct ccaactgcgg tactcctggc    1500
tctggctcgg cggcaacgg tggctcgagc ggtaacgccc tggtgacttt caacgagctg    1560
gctactacct actacggcga gaacattaag cttgtcggca gcacagctgc tttcggttcg    1620
tggtcgccct cagctggtat tctcctgtct gcctcgtcgt acacggccag caaccctctg    1680
```

```
tggactacca ccgtgtcggt tccccagggc tcgaccgttg agttcaagtt catccgtgtt   1740
ggctccgacg gcagcatcac gtgggagagc ggcaacaaca aggtgttgac ggttggctct   1800
tcggccacga gcgtcactgt ttctgccagc tggaacggcg cctactcggt gtctagctct   1860
taatag                                                              1866
```

<210> SEQ ID NO 7
<211> LENGTH: 620
<212> TYPE: PRT
<213> ORGANISM: Artificial Sequence
<220> FEATURE:
<223> OTHER INFORMATION: Variant2 (S188H/Y321W/Q419P with Starch Binding
      Domain) preprotein amino acid sequence

<400> SEQUENCE: 7

```
Met Val Phe Leu Lys Ser Ala Ile Ala Ser Thr Trp Leu Leu Ala
1               5                   10                  15

Ala Thr Gly Val Val Ala Ser Pro Val Ser Lys Arg Ala Thr Leu Asp
                20                  25                  30

Glu Phe Ile Ser Thr Glu Arg Pro Leu Ala Leu Glu Arg Leu Leu Cys
            35                  40                  45

Asn Ile Gly Pro Thr Gly Cys Arg Ala Ser Gly Ala Ala Ser Gly Val
50                  55                  60

Val Ile Ala Ser Pro Ser Arg Ser Asp Pro Asp Tyr Tyr Tyr Thr Trp
65                  70                  75                  80

Thr Arg Asp Ala Ala Leu Val Phe Lys Glu Ile Val Asp Ser Val Glu
                85                  90                  95

Thr Asn Thr Thr Leu Leu Leu Pro Glu Ile Glu Asn Tyr Val Thr Ala
            100                 105                 110

Gln Ala Tyr Leu Gln Thr Val Thr Asn Pro Ser Gly Ser Leu Ser Asp
        115                 120                 125

Gly Ala Gly Leu Gly Glu Pro Lys Phe Asn Val Asp Met Thr Pro Phe
    130                 135                 140

Thr Gly Ala Trp Gly Arg Pro Gln Arg Asp Gly Pro Ala Leu Arg Ala
145                 150                 155                 160

Thr Ala Met Ile Ala Tyr Tyr Asn Tyr Leu Leu Asn Asn Asn Ala Thr
                165                 170                 175

Thr Asp Cys Gly Leu Trp Gln Ile Ile Gln Asn Asp Leu Asn Tyr Val
            180                 185                 190

Ala Gln Tyr Trp Asn Gln Thr Gly Tyr Asp Leu Trp Glu Glu Val Pro
        195                 200                 205

Gly His Ser Phe Phe Thr Val Ala Ala Gln Tyr Arg Ala Leu Val Glu
    210                 215                 220

Gly Ser Thr Leu Ala Ala Lys Leu Gly Lys Ser His Ser Ala Tyr Asp
225                 230                 235                 240

Thr Val Ala Pro Gln Ile Leu Cys Tyr Leu Gln Ser Phe Trp Ser Ser
                245                 250                 255

Ser Lys Gly Tyr Ile Val Ala Asn Thr Gln Thr Ala Ser Trp Val Ser
            260                 265                 270

Arg Ser Gly Leu Asp Ala Asn Thr Pro Leu Thr Ala Ile His Leu Phe
        275                 280                 285

Asp Pro Glu Leu Gly Cys Asp Asp Ser Thr Phe Gln Pro Cys Ser Pro
    290                 295                 300

Lys Gln Leu Ile Thr Thr Lys Lys Leu Val Asp Ser Phe Arg Ser Ile
305                 310                 315                 320
```

```
Tyr Ala Ile Asn Ser Gly Lys Ser Ala Gly Asp Ala Leu Ala Val Gly
                325                 330                 335

Arg Tyr Ala Glu Asp Val Trp Tyr Asn Gly Asn Pro Trp Tyr Leu Cys
            340                 345                 350

Thr Leu Ala Val Ala Glu Gln Leu Tyr Asp Ala Val Tyr Thr Trp Lys
        355                 360                 365

Leu Glu Gly Ser Ile Thr Val Thr Ser Val Ser Leu Pro Phe Phe Thr
    370                 375                 380

Asp Leu Leu Pro Ser Leu Thr Thr Gly Thr Tyr Ala Ser Gly Ser Thr
385                 390                 395                 400

Thr Phe Glu Ser Ile Ile Ser Ala Val Thr Thr Tyr Ala Asp Gly Phe
                405                 410                 415

Val Ser Ile Val Gln Thr Tyr Thr Pro Ser Asp Gly Ala Leu Ser Glu
            420                 425                 430

Gln Tyr Ser Lys Tyr Asn Gly Gln Pro Leu Ser Ala Pro Asp Leu Thr
        435                 440                 445

Trp Ser Tyr Ala Ala Phe Leu Ser Ala Thr Glu Arg Arg Asp Ser Val
    450                 455                 460

Val Pro Ala Gly Trp Ala Gly Ala Ser Ser Val Ser Val Pro Gly Ala
465                 470                 475                 480

Cys Ala Ala Thr Thr Val Val Gly Thr Tyr Ala Ala Ala Ser Asn Cys
                485                 490                 495

Gly Thr Pro Gly Ser Gly Ser Gly Asn Gly Ser Ser Gly Asn
            500                 505                 510

Ala Leu Val Thr Phe Asn Glu Leu Ala Thr Thr Tyr Tyr Gly Glu Asn
        515                 520                 525

Ile Lys Leu Val Gly Ser Thr Ala Ala Phe Gly Ser Trp Ser Pro Ser
    530                 535                 540

Ala Gly Ile Leu Leu Ser Ala Ser Ser Tyr Thr Ala Ser Asn Pro Leu
545                 550                 555                 560

Trp Thr Thr Thr Val Ser Val Pro Gln Gly Ser Thr Val Glu Phe Lys
                565                 570                 575

Phe Ile Arg Val Gly Ser Asp Gly Ser Ile Thr Trp Glu Ser Gly Asn
            580                 585                 590

Asn Lys Val Leu Thr Val Gly Ser Ser Ala Thr Ser Val Thr Val Ser
        595                 600                 605

Ala Ser Trp Asn Gly Ala Tyr Ser Val Ser Ser Ser
    610                 615                 620

<210> SEQ ID NO 8
<211> LENGTH: 1866
<212> TYPE: DNA
<213> ORGANISM: Artificial Sequence
<220> FEATURE:
<223> OTHER INFORMATION: Variant2 (S188H/Y321W/Q419P with Starch Binding
      Domain) preprotein-encoding nucleic acid sequence

<400> SEQUENCE: 8
atggttttcc tcaagtcggc catcgccgct tccacctggc tcttggctgc cactggcgtc      60
gttgcctcgc tgtttccaa gcgcgctacg ctggacgagt tcatcagcac cgagcgtccc      120
ttggctctgg agcgcctgct ctgcaacatt ggtcctactg gttgccgtgc ttcgggagct      180
gcctcgggag tcgttatcgc ctcgccgtcc cgcagcgatc cggactacta ctacacttgg      240
acccgtgatg ctgctctggt ctttaaggag attgtcgact ctgtcgagac taacaccact      300
ctgctgctgc cagagattga aactacgtt actgcccagg cttacctgca gaccgtgacg      360
```

```
aaccoctcgg gttcgctgtc ggatggtgct ggtctgggcg agcccaagtt caacgtcgat    420
atgactccct tcactggtgc ctggggtcgt cctcagcgtg atggtccggc tctgcgtgct    480
acggctatga tcgcctacta caactacctg ctcaacaaca acgccactac cgactgtggt    540
ctgtggcaga ttatccagaa cgacctgaat tacgtcgctc agtactggaa ccaaactggt    600
tacgacctgt gggaggaggt tccgggtcac tcctttttca ctgttgctgc tcagtacaga    660
gctctcgttg agggttctac ccttgctgcc aagctcggca gtctcactc ggcctacgac     720
actgtcgctc cgcagattct gtgctacttg cagagcttct ggtcatccag caagggctac    780
attgtcgcca cacccagac tgccagctgg gtctcgcgt ccggtcttga tgccaacact      840
cccttgactg ccatccacct atttgaccct gaacttggct gcgatgactc gactttccag    900
ccctgctcgc ccaagcagct tatcactact aagaagctcg ttgactcgtt ccgctccatc    960
tatgccatca actcgggcaa gtctgctggt gatgctttgg ctgttggtcg ttacgccgag    1020
gacgtctggt acaacggcaa cccctggtac ctgtgcactt ggctgttgc agagcagctt     1080
tacgatgcag tttacacttg gaagctcgag ggctccatca ccgtcacctc tgtctcgctg    1140
cccttcttca ctgacctgct gccctcgctg accactggca cctacgcttc gggctcgacc    1200
accttcgaat ccatcatctc tgctgtgact acctacgctg atggctttgt cagtattgtc    1260
cagacctaca ctccctctga cggcgctctg tctgagcagt actccaagta caacggccag    1320
cccctgtcgg ctcccgacct gacctggtcg tacgccgctt cctatctgc cactgagcgc     1380
cgtgacagcg ttgtccctgc cggctgggct ggtgcctcgt ctgtctctgt gcccggcgcc    1440
tgcgctgcta ccaccgttgt cggaacctac gctgctgcct ccaactgcgg tactcctggc    1500
tctggctcgg gcggcaacgg tggctcgagc ggtaacgccc tggtgacttt caacgagctg    1560
gctactacct actacggcga aacattaag cttgtcggca gcacagctgc tttcggttcg     1620
tggtcgccct cagctggtat tctcctgtct gcctcgtcgt acacggccag caaccctctg    1680
tggactacca ccgtgtcggt tccccagggc tcgaccgttg agttcaagtt catccgtgtt    1740
ggctccgacg gcagcatcac gtgggagagc ggcaacaaca aggtgttgac ggttggctct    1800
tcggccacga gcgtcactgt ttctgccagc tggaacggcg cctactcggt gtctagctct    1860
taatag                                                              1866
```

<210> SEQ ID NO 9
<211> LENGTH: 514
<212> TYPE: PRT
<213> ORGANISM: Artificial Sequence
<220> FEATURE:
<223> OTHER INFORMATION: Variant1 (Y321F without Starch Binding Domain)
      preprotein amino acid sequence

<400> SEQUENCE: 9

Met Val Phe Leu Lys Ser Ala Ile Ala Ala Ser Thr Trp Leu Leu Ala
1               5                   10                  15

Ala Thr Gly Val Val Ala Ser Pro Val Ser Lys Arg Ala Thr Leu Asp
            20                  25                  30

Glu Phe Ile Ser Thr Glu Arg Pro Leu Ala Leu Glu Arg Leu Leu Cys
        35                  40                  45

Asn Ile Gly Pro Thr Gly Cys Arg Ala Ser Gly Ala Ala Ser Gly Val
    50                  55                  60

Val Ile Ala Ser Pro Ser Arg Ser Asp Pro Asp Tyr Tyr Tyr Thr Trp
65                  70                  75                  80

```
Thr Arg Asp Ala Ala Leu Val Phe Lys Glu Ile Val Asp Ser Val Glu
                85                  90                  95

Thr Asn Thr Thr Leu Leu Leu Pro Glu Ile Glu Asn Tyr Val Thr Ala
            100                 105                 110

Gln Ala Tyr Leu Gln Thr Val Thr Asn Pro Ser Gly Ser Leu Ser Asp
        115                 120                 125

Gly Ala Gly Leu Gly Glu Pro Lys Phe Asn Val Asp Met Thr Pro Phe
    130                 135                 140

Thr Gly Ala Trp Gly Arg Pro Gln Arg Asp Gly Pro Ala Leu Arg Ala
145                 150                 155                 160

Thr Ala Met Ile Ala Tyr Tyr Asn Tyr Leu Leu Asn Asn Asn Ala Thr
                165                 170                 175

Thr Asp Cys Gly Leu Trp Gln Ile Ile Gln Asn Asp Leu Asn Tyr Val
            180                 185                 190

Ala Gln Tyr Trp Asn Gln Thr Gly Tyr Asp Leu Trp Glu Glu Val Pro
        195                 200                 205

Gly Ser Ser Phe Phe Thr Val Ala Ala Gln Tyr Arg Ala Leu Val Glu
    210                 215                 220

Gly Ser Thr Leu Ala Ala Lys Leu Gly Lys Ser His Ser Ala Tyr Asp
225                 230                 235                 240

Thr Val Ala Pro Gln Ile Leu Cys Tyr Leu Gln Ser Phe Trp Ser Ser
                245                 250                 255

Ser Lys Gly Tyr Ile Val Ala Asn Thr Gln Thr Ala Ser Trp Val Ser
            260                 265                 270

Arg Ser Gly Leu Asp Ala Asn Thr Pro Leu Thr Ala Ile His Leu Phe
        275                 280                 285

Asp Pro Glu Leu Gly Cys Asp Asp Ser Thr Phe Gln Pro Cys Ser Pro
    290                 295                 300

Lys Gln Leu Ile Thr Thr Lys Lys Leu Val Asp Ser Phe Arg Ser Ile
305                 310                 315                 320

Tyr Ala Ile Asn Ser Gly Lys Ser Ala Gly Asp Ala Leu Ala Val Gly
                325                 330                 335

Arg Tyr Ala Glu Asp Val Phe Tyr Asn Gly Asn Pro Trp Tyr Leu Cys
            340                 345                 350

Thr Leu Ala Val Ala Glu Gln Leu Tyr Asp Ala Val Tyr Thr Trp Lys
        355                 360                 365

Leu Glu Gly Ser Ile Thr Val Thr Ser Val Ser Leu Pro Phe Phe Thr
    370                 375                 380

Asp Leu Leu Pro Ser Leu Thr Thr Gly Thr Tyr Ala Ser Gly Ser Thr
385                 390                 395                 400

Thr Phe Glu Ser Ile Ile Ser Ala Val Thr Thr Tyr Ala Asp Gly Phe
                405                 410                 415

Val Ser Ile Val Gln Thr Tyr Thr Pro Ser Asp Gly Ala Leu Ser Glu
            420                 425                 430

Gln Tyr Ser Lys Tyr Asn Gly Gln Gln Leu Ser Ala Pro Asp Leu Thr
        435                 440                 445

Trp Ser Tyr Ala Ala Phe Leu Ser Ala Thr Glu Arg Arg Asp Ser Val
    450                 455                 460

Val Pro Ala Gly Trp Ala Gly Ala Ser Ser Val Ser Val Pro Gly Ala
465                 470                 475                 480

Cys Ala Ala Thr Thr Val Val Gly Thr Tyr Ala Ala Ala Ser Asn Cys
                485                 490                 495

Gly Thr Pro Gly Ser Gly Ser Gly Gly Asn Gly Gly Ser Ser Gly Asn
```

<210> SEQ ID NO 10
<211> LENGTH: 1548
<212> TYPE: DNA
<213> ORGANISM: Artificial Sequence
<220> FEATURE:
<223> OTHER INFORMATION: Variant1 (Y321F without Starch Binding Domain) preprotein-encoding nucleic acid sequence

<400> SEQUENCE: 10

```
atggttttcc tcaagtcggc catcgccgct tccacctggc tcttggctgc cactggcgtc      60
gttgcctcgc ctgtttccaa gcgcgctacg ctggacgagt tcatcagcac cgagcgtccc     120
ttggctctgg agcgcctgct ctgcaacatt ggtcctactg gttgccgtgc ttcgggagct     180
gcctcgggag tcgttatcgc ctcgccgtcc cgcagcgatc cggactacta ctacacttgg     240
acccgtgatg ctgctctggt ctttaaggag attgtcgact ctgtcgagac taacaccact     300
ctgctgctgc agagattga aactacgtt actgcccagg cttacctgca gaccgtgacg     360
aaccctcgg gttcgctgtc ggatggtgct ggtctgggcg agcccaagtt caacgtcgat     420
atgactccct tcactggtgc ctggggtcgt cctcagcgtg atggtccggc tctgcgtgct     480
acggctatga tcgcctacta caactacctg ctcaacaaca cgccactac cgactgtggt     540
ctgtggcaga ttatccagaa cgacctgaat tacgtcgctc agtactggaa ccaaactggt     600
tacgacctgt gggaggaggt tccgggttca tccttttca ctgttgctgc tcagtacaga     660
gctctcgttg agggttctac ccttgctgcc aagctcggca agtctcactc ggcctacgac     720
actgtcgctc cgcagattct gtgctacttg cagagcttct ggtcatccag caagggctac     780
attgtcgcca acacccagac tgccagctgg gtctcgcggt ccggtcttga tgccaacact     840
cccttgactg ccatccacct atttgaccct gaacttggct gcgatgactc gactttccag     900
ccctgctcgc caagcagct tatcactact aagaagctcg ttgactcgtt ccgctccatc     960
tatgccatca actcgggcaa gtctgctggt gatgctttgg ctgttggtcg ttacgccgag    1020
gacgtcttct acaacggcaa ccctggtac ctgtgcactt tggctgttgc agagcagctt    1080
tacgatgcag tttacacttg gaagctcgag ggctccatca ccgtcacctc tgtctcgctg    1140
cccttcttca ctgacctgct gccctcgctg accactggca cctacgcttc gggctcgacc    1200
accttcgaat ccatcatctc tgctgtgact acctacgctg atggctttgt cagtattgtc    1260
cagacctaca ctccctctga cggcgctctg tctgagcagt actccaagta caacggccag    1320
cagctgtcgg ctcccgacct gacctggtcg tacgccgctt tcctatctgc cactgagcgc    1380
cgtgacagcg ttgtccctgc cggctgggct ggtgcctcgt ctgtctctgt gcccggcgcc    1440
tgcgctgcta ccaccgttgt cggaacctac gctgctgcct ccaactgcgg tactcctggc    1500
tctggctcgg gcggcaacgg tggctcgagc ggtaacgccc tgtaatag                 1548
```

<210> SEQ ID NO 11
<211> LENGTH: 514
<212> TYPE: PRT
<213> ORGANISM: Artificial Sequence
<220> FEATURE:
<223> OTHER INFORMATION: Variant2 (S188H/Y321W/Q419P without Starch Binding Domain) preprotein amino acid sequence

<400> SEQUENCE: 11

Met Val Phe Leu Lys Ser Ala Ile Ala Ala Ser Thr Trp Leu Leu Ala

-continued

```
1               5                   10                  15
Ala Thr Gly Val Val Ala Ser Pro Val Ser Lys Arg Ala Thr Leu Asp
            20                  25                  30
Glu Phe Ile Ser Thr Glu Arg Pro Leu Ala Leu Glu Arg Leu Leu Cys
            35                  40                  45
Asn Ile Gly Pro Thr Gly Cys Arg Ala Ser Gly Ala Ser Gly Val
            50                  55                  60
Val Ile Ala Ser Pro Ser Arg Ser Asp Pro Asp Tyr Tyr Tyr Thr Trp
65                  70                  75                  80
Thr Arg Asp Ala Ala Leu Val Phe Lys Glu Ile Val Asp Ser Val Glu
                85                  90                  95
Thr Asn Thr Thr Leu Leu Leu Pro Glu Ile Glu Asn Tyr Val Thr Ala
            100                 105                 110
Gln Ala Tyr Leu Gln Thr Val Thr Asn Pro Ser Gly Ser Leu Ser Asp
            115                 120                 125
Gly Ala Gly Leu Gly Glu Pro Lys Phe Asn Val Asp Met Thr Pro Phe
130                 135                 140
Thr Gly Ala Trp Gly Arg Pro Gln Arg Asp Gly Pro Ala Leu Arg Ala
145                 150                 155                 160
Thr Ala Met Ile Ala Tyr Tyr Asn Tyr Leu Leu Asn Asn Asn Ala Thr
                165                 170                 175
Thr Asp Cys Gly Leu Trp Gln Ile Ile Gln Asn Asp Leu Asn Tyr Val
            180                 185                 190
Ala Gln Tyr Trp Asn Gln Thr Gly Tyr Asp Leu Trp Glu Glu Val Pro
            195                 200                 205
Gly His Ser Phe Phe Thr Val Ala Ala Gln Tyr Arg Ala Leu Val Glu
            210                 215                 220
Gly Ser Thr Leu Ala Ala Lys Leu Gly Lys Ser His Ser Ala Tyr Asp
225                 230                 235                 240
Thr Val Ala Pro Gln Ile Leu Cys Tyr Leu Gln Ser Phe Trp Ser Ser
                245                 250                 255
Ser Lys Gly Tyr Ile Val Ala Asn Thr Gln Thr Ala Ser Trp Val Ser
            260                 265                 270
Arg Ser Gly Leu Asp Ala Asn Thr Pro Leu Thr Ala Ile His Leu Phe
            275                 280                 285
Asp Pro Glu Leu Gly Cys Asp Asp Ser Thr Phe Gln Pro Cys Ser Pro
            290                 295                 300
Lys Gln Leu Ile Thr Thr Lys Lys Leu Val Asp Ser Phe Arg Ser Ile
305                 310                 315                 320
Tyr Ala Ile Asn Ser Gly Lys Ser Ala Gly Asp Ala Leu Ala Val Gly
                325                 330                 335
Arg Tyr Ala Glu Asp Val Trp Tyr Asn Gly Asn Pro Trp Tyr Leu Cys
            340                 345                 350
Thr Leu Ala Val Ala Glu Gln Leu Tyr Asp Ala Val Tyr Thr Trp Lys
            355                 360                 365
Leu Glu Gly Ser Ile Thr Val Thr Ser Val Ser Leu Pro Phe Phe Thr
            370                 375                 380
Asp Leu Leu Pro Ser Leu Thr Thr Gly Thr Tyr Ala Ser Gly Ser Thr
385                 390                 395                 400
Thr Phe Glu Ser Ile Ile Ser Ala Val Thr Thr Tyr Ala Asp Gly Phe
                405                 410                 415
Val Ser Ile Val Gln Thr Tyr Thr Pro Ser Asp Gly Ala Leu Ser Glu
            420                 425                 430
```

Gln Tyr Ser Lys Tyr Asn Gly Gln Pro Leu Ser Ala Pro Asp Leu Thr
        435                 440                 445

Trp Ser Tyr Ala Ala Phe Leu Ser Ala Thr Glu Arg Arg Asp Ser Val
    450                 455                 460

Val Pro Ala Gly Trp Ala Gly Ala Ser Ser Val Ser Val Pro Gly Ala
465                 470                 475                 480

Cys Ala Ala Thr Thr Val Val Gly Thr Tyr Ala Ala Ala Ser Asn Cys
                485                 490                 495

Gly Thr Pro Gly Ser Gly Ser Gly Asn Gly Gly Ser Ser Gly Asn
                500                 505                 510

Ala Leu

<210> SEQ ID NO 12
<211> LENGTH: 1548
<212> TYPE: DNA
<213> ORGANISM: Artificial Sequence
<220> FEATURE:
<223> OTHER INFORMATION: Variant2 (S188H/Y321W/Q419P without Starch
      Binding Domain) preprotein-encoding nucleic acid sequence

<400> SEQUENCE: 12

```
atggttttcc tcaagtcggc catcgccgct tccacctggc tcttggctgc cactggcgtc      60
gttgcctcgc ctgtttccaa gcgcgctacg ctggacgagt tcatcagcac cgagcgtccc     120
ttggctctgg agcgcctgct ctgcaacatt ggtcctactg gttgccgtgc ttcgggagct     180
gcctcgggag tcgttatcgc ctcgccgtcc cgcagcgatc cggactacta ctacacttgg     240
acccgtgatg ctgctctggt cttttaaggag attgtcgact ctgtcgagac taacaccact     300
ctgctgctgc cagagattga gaactacgtt actgcccagg cttacctgca gaccgtgacg     360
aacccctcgg gttcgctgtc ggatggtgct ggtctgggcg agcccaagtt caacgtcgat     420
atgactccct tcactggtgc ctggggtcgt cctcagcgtg atggtccggc tctgcgtgct     480
acggctatga tcgcctacta caactacctg ctcaacaaca cgccactac cgactgtggt     540 ctgtggcaga ttatccagaa cgacctgaat tacgtcgctc agtactggaa ccaaactggt     600
tacgacctgt gggaggaggt tccgggtcac tcctttttca ctgttgctgc tcagtacaga     660
gctctcgttg agggttctac ccttgctgcc aagctcggca gtctcactc ggcctacgac     720 actgtcgctc cgcagattct gtgctacttg cagagcttct ggtcatccag caagggctac     780
attgtcgcca cacccagac tgccagctgg gtctcgcggt ccggtcttga tgccaacact     840
cccttgactg ccatccacct atttgaccct gaacttggct cgatgactc gactttccag     900 ccctgctcgc ccaagcagct tatcactact aagaagctcg ttgactcgtt ccgctccatc     960
tatgccatca actcgggcaa gtctgctggt gatgctttgg ctgttggtcg ttacgccgag    1020
gacgtctggt acaacggcaa ccctggtac ctgtgcactt ggctgttgc agagcagctt    1080 tacgatgcag tttacacttg gaagctcgag gctccatca ccgtcacctc tgtctcgctg    1140
cccttcttca ctgacctgct gccctcgctg accactggca cctacgcttc gggctcgacc    1200
accttcgaat ccatcatctc tgctgtgact acctacgctg atggctttgt cagtattgtc    1260
cagacctaca ctcccctctga cggcgctctg tctgagcagt actccaagta caacggccag    1320 ccctgtcgg ctcccgacct gacctggtcg tacgccgctt tcctatctgc cactgagcgc    1380
cgtgacagcg ttgccctgc cggctgggct ggtgcctcgt ctgtctctgt gcccggcgcc    1440
tgcgctgcta ccaccgttgt cggaacctac gctgctgcct ccaactgcgg tactcctggc    1500
```
tctggctcgg gcggcaacgg tggctcgagc ggtaacgccc tgtaatag 1548

<210> SEQ ID NO 13
<211> LENGTH: 598
<212> TYPE: PRT
<213> ORGANISM: Artificial Sequence
<220> FEATURE:
<223> OTHER INFORMATION: G6P mature protein amino acid sequence

<400> SEQUENCE: 13

```
Ser Pro Val Ser Lys Arg Ala Thr Leu Asp Glu Phe Ile Ser Thr Glu
1               5                   10                  15

Arg Pro Leu Ala Leu Glu Arg Leu Leu Cys Asn Ile Gly Pro Thr Gly
            20                  25                  30

Cys Arg Ala Ser Gly Ala Ala Ser Gly Val Val Ile Ala Ser Pro Ser
        35                  40                  45

Arg Ser Asp Pro Asp Tyr Tyr Tyr Thr Trp Thr Arg Asp Ala Ala Leu
    50                  55                  60

Val Phe Lys Glu Ile Val Asp Ser Val Glu Thr Asn Thr Thr Leu Leu
65                  70                  75                  80

Leu Pro Glu Ile Glu Asn Tyr Val Thr Ala Gln Ala Tyr Leu Gln Thr
                85                  90                  95

Val Thr Asn Pro Ser Gly Ser Leu Ser Asp Gly Ala Gly Leu Gly Glu
            100                 105                 110

Pro Lys Phe Asn Val Asp Met Thr Pro Phe Thr Gly Ala Trp Gly Arg
        115                 120                 125

Pro Gln Arg Asp Gly Pro Ala Leu Arg Ala Thr Ala Met Ile Ala Tyr
    130                 135                 140

Tyr Asn Tyr Leu Leu Asn Asn Asn Ala Thr Thr Asp Cys Gly Leu Trp
145                 150                 155                 160

Gln Ile Ile Gln Asn Asp Leu Asn Tyr Val Ala Gln Tyr Trp Asn Gln
                165                 170                 175

Thr Gly Tyr Asp Leu Trp Glu Glu Val Pro Gly Ser Ser Phe Phe Thr
            180                 185                 190

Val Ala Ala Gln Tyr Arg Ala Leu Val Glu Gly Ser Thr Leu Ala Ala
        195                 200                 205

Lys Leu Gly Lys Ser His Ser Ala Tyr Asp Thr Val Ala Pro Gln Ile
    210                 215                 220

Leu Cys Tyr Leu Gln Ser Phe Trp Ser Ser Lys Gly Tyr Ile Val
225                 230                 235                 240

Ala Asn Thr Gln Thr Ala Ser Trp Val Ser Arg Ser Gly Leu Asp Ala
                245                 250                 255

Asn Thr Pro Leu Thr Ala Ile His Leu Phe Asp Pro Glu Leu Gly Cys
            260                 265                 270

Asp Asp Ser Thr Phe Gln Pro Cys Ser Pro Lys Gln Leu Ile Thr Thr
        275                 280                 285

Lys Lys Leu Val Asp Ser Phe Arg Ser Ile Tyr Ala Ile Asn Ser Gly
    290                 295                 300

Lys Ser Ala Gly Asp Ala Leu Ala Val Gly Arg Tyr Ala Glu Asp Val
305                 310                 315                 320

Tyr Tyr Asn Gly Asn Pro Trp Tyr Leu Cys Thr Leu Ala Val Ala Glu
                325                 330                 335

Gln Leu Tyr Asp Ala Val Tyr Thr Trp Lys Leu Glu Gly Ser Ile Thr
            340                 345                 350

Val Thr Ser Val Ser Leu Pro Phe Phe Thr Asp Leu Leu Pro Ser Leu
```

|  |  |  | 355 |  |  | 360 |  |  | 365 |  |  |
|---|---|---|---|---|---|---|---|---|---|---|---|

Thr Thr Gly Thr Tyr Ala Ser Gly Ser Thr Thr Phe Glu Ser Ile Ile
        370                  375                380

Ser Ala Val Thr Thr Tyr Ala Asp Gly Phe Val Ser Ile Val Gln Thr
385                  390                395                400

Tyr Thr Pro Ser Asp Gly Ala Leu Ser Glu Gln Tyr Ser Lys Tyr Asn
                405                410                415

Gly Gln Gln Leu Ser Ala Pro Asp Leu Thr Trp Ser Tyr Ala Ala Phe
        420                  425              430

Leu Ser Ala Thr Glu Arg Arg Asp Ser Val Val Pro Ala Gly Trp Ala
            435                440              445

Gly Ala Ser Ser Val Ser Val Pro Gly Ala Cys Ala Ala Thr Thr Val
450                  455                460

Val Gly Thr Tyr Ala Ala Ala Ser Asn Cys Gly Thr Pro Gly Ser Gly
465                  470                475                480

Ser Gly Gly Asn Gly Gly Ser Ser Gly Asn Ala Leu Val Thr Phe Asn
            485                490                495

Glu Leu Ala Thr Thr Tyr Tyr Gly Glu Asn Ile Lys Leu Val Gly Ser
        500                  505              510

Thr Ala Ala Phe Gly Ser Trp Ser Pro Ser Ala Gly Ile Leu Leu Ser
            515              520              525

Ala Ser Ser Tyr Thr Ala Ser Asn Pro Leu Trp Thr Thr Thr Val Ser
530                  535                540

Val Pro Gln Gly Ser Thr Val Glu Phe Lys Phe Ile Arg Val Gly Ser
545                  550                555                560

Asp Gly Ser Ile Thr Trp Glu Ser Gly Asn Asn Lys Val Leu Thr Val
                565                570                575

Gly Ser Ser Ala Thr Ser Val Thr Val Ser Ala Ser Trp Asn Gly Ala
                    580                585              590

Tyr Ser Val Ser Ser Ser
        595

```
<210> SEQ ID NO 14
<211> LENGTH: 1800
<212> TYPE: DNA
<213> ORGANISM: Artificial Sequence
<220> FEATURE:
<223> OTHER INFORMATION: G6P mature protein-encoding nucleic acid
      sequence

<400> SEQUENCE: 14
tcgcctgttt ccaagcgcgc tacgctggac gagttcatca gcaccgagcg tcccttggct      60
ctggagcgcc tgctctgcaa cattggtcct actggttgcc gtgcttcggg agctgcctcg     120
ggagtcgtta tcgcctcgcc gtcccgcagc gatccggact actactacac ttggacccgt     180
gatgctgctc tggtctttaa ggagattgtc gactctgtcg agactaacac cactctgctg     240
ctgccagaga ttgagaacta cgttactgcc caggcttacc tgcagaccgt gacgaacccc     300
tcgggttcgc tgtcggatgg tgctggtctg ggcgagccca agttcaacgt cgatatgact     360
cccttcactg gtgcctgggg tcgtcctcag cgtgatggtc cggctctgcg tgctacggct     420
atgatcgcct actacaacta cctgctcaac aacaacgcca ctaccgactg ggtctgtgg      480 cagattatcc agaacgacct gaattacgtc gctcagtact ggaaccaaac tggttacgac     540
ctgtgggagg aggttccggg ttcatccttt tcactgttg ctgctcagta cagagctctc      600
gttgagggtt ctacccttgc tgccaagctc ggcaagtctc actcggccta cgacactgtc     660
```

```
gctccgcaga ttctgtgcta cttgcagagc ttctggtcat ccagcaaggg ctacattgtc    720
gccaacaccc agactgccag ctgggtctcg cggtccggtc ttgatgccaa cactcccttg    780
actgccatcc acctatttga ccctgaactt ggctgcgatg actcgacttt ccagccctgc    840
tcgcccaagc agcttatcac tactaagaag ctcgttgact cgttccgctc catctatgcc    900
atcaactcgg gcaagtctgc tggtgatgct ttggctgttg gtcgttacgc cgaggacgtc    960
tactacaacg gcaaccccct gtacctgtgc actttggctg ttgcagagca gctttacgat   1020
gcagtttaca cttggaagct cgagggctcc atcaccgtca cctctgtctc gctgcccttc   1080
ttcactgacc tgctgccctc gctgaccact ggcacctacg cttcgggctc gaccaccttc   1140
gaatccatca tctctgctgt gactacctac gctgatggct ttgtcagtat tgtccagacc   1200
tacactccct ctgacggcgc tctgtctgag cagtactcca gtacaacgg ccagcagctg    1260 tcggctcccg acctgacctg gtcgtacgcc gctttcctat ctgccactga gcgccgtgac   1320
agcgttgtcc ctgccggctg ggctggtgcc tcgtctgtct ctgtgcccgg cgcctgcgct   1380
gctaccaccg ttgtcggaac ctacgctgct gcctccaact gcggtactcc tggctctggc   1440
tcgggcggca acggtggctc gagcggtaac gccctggtga cttttcaacga gctggctact   1500 acctactacg gcgagaacat taagcttgtc ggcagcacag ctgctttcgg ttcgtggtcg   1560
ccctcagctg gtattctcct gtctgcctcg tcgtacacgg ccagcaaccc tctgtggact   1620
accaccgtgt cggttcccca gggctcgacc gttgagttca agttcatccg tgttggctcc   1680
gacggcagca tcacgtggga gagcggcaac aacaaggtgt tgacggttgg ctcttcggcc   1740
acgagcgtca ctgtttctgc cagctggaac ggcgcctact cggtgtctag ctcttaatag   1800
```

<210> SEQ ID NO 15
<211> LENGTH: 492
<212> TYPE: PRT
<213> ORGANISM: Artificial Sequence
<220> FEATURE:
<223> OTHER INFORMATION: G7P mature protein amino acid sequence

<400> SEQUENCE: 15

```
Ser Pro Val Ser Lys Arg Ala Thr Leu Asp Glu Phe Ile Ser Thr Glu
1               5                   10                  15

Arg Pro Leu Ala Leu Glu Arg Leu Leu Cys Asn Ile Gly Pro Thr Gly
                20                  25                  30

Cys Arg Ala Ser Gly Ala Ala Ser Gly Val Val Ile Ala Ser Pro Ser
            35                  40                  45

Arg Ser Asp Pro Asp Tyr Tyr Tyr Thr Trp Thr Arg Asp Ala Ala Leu
        50                  55                  60

Val Phe Lys Glu Ile Val Asp Ser Val Glu Thr Asn Thr Thr Leu Leu
65                  70                  75                  80

Leu Pro Glu Ile Glu Asn Tyr Val Thr Ala Gln Ala Tyr Leu Gln Thr
                85                  90                  95

Val Thr Asn Pro Ser Gly Ser Leu Ser Asp Gly Ala Gly Leu Gly Glu
            100                 105                 110

Pro Lys Phe Asn Val Asp Met Thr Pro Phe Thr Gly Ala Trp Gly Arg
        115                 120                 125

Pro Gln Arg Asp Gly Pro Ala Leu Arg Ala Thr Ala Met Ile Ala Tyr
    130                 135                 140

Tyr Asn Tyr Leu Leu Asn Asn Asn Ala Thr Thr Asp Cys Gly Leu Trp
145                 150                 155                 160
```

| | | | | | | | | | | | |
|---|---|---|---|---|---|---|---|---|---|---|---|
|Gln|Ile|Ile|Gln|Asn|Asp|Leu|Asn|Tyr|Val|Ala|Gln|Tyr|Trp|Asn|Gln|
| | |165| | | | |170| | | | |175| | | |

Gln Ile Ile Gln Asn Asp Leu Asn Tyr Val Ala Gln Tyr Trp Asn Gln
            165                 170                 175

Thr Gly Tyr Asp Leu Trp Glu Glu Val Pro Gly Ser Ser Phe Phe Thr
        180                 185                 190

Val Ala Ala Gln Tyr Arg Ala Leu Val Glu Gly Ser Thr Leu Ala Ala
            195                 200                 205

Lys Leu Gly Lys Ser His Ser Ala Tyr Asp Thr Val Ala Pro Gln Ile
        210                 215                 220

Leu Cys Tyr Leu Gln Ser Phe Trp Ser Ser Lys Gly Tyr Ile Val
225                 230                 235                 240

Ala Asn Thr Gln Thr Ala Ser Trp Val Ser Arg Ser Gly Leu Asp Ala
            245                 250                 255

Asn Thr Pro Leu Thr Ala Ile His Leu Phe Asp Pro Glu Leu Gly Cys
            260                 265                 270

Asp Asp Ser Thr Phe Gln Pro Cys Ser Pro Lys Gln Leu Ile Thr Thr
        275                 280                 285

Lys Lys Leu Val Asp Ser Phe Arg Ser Ile Tyr Ala Ile Asn Ser Gly
        290                 295                 300

Lys Ser Ala Gly Asp Ala Leu Ala Val Gly Arg Tyr Ala Glu Asp Val
305                 310                 315                 320

Tyr Tyr Asn Gly Asn Pro Trp Tyr Leu Cys Thr Leu Ala Val Ala Glu
            325                 330                 335

Gln Leu Tyr Asp Ala Val Tyr Thr Trp Lys Leu Glu Gly Ser Ile Thr
            340                 345                 350

Val Thr Ser Val Ser Leu Pro Phe Phe Thr Asp Leu Leu Pro Ser Leu
        355                 360                 365

Thr Thr Gly Thr Tyr Ala Ser Gly Ser Thr Thr Phe Glu Ser Ile Ile
        370                 375                 380

Ser Ala Val Thr Thr Tyr Ala Asp Gly Phe Val Ser Ile Val Gln Thr
385                 390                 395                 400

Tyr Thr Pro Ser Asp Gly Ala Leu Ser Glu Gln Tyr Ser Lys Tyr Asn
            405                 410                 415

Gly Gln Gln Leu Ser Ala Pro Asp Leu Thr Trp Ser Tyr Ala Ala Phe
        420                 425                 430

Leu Ser Ala Thr Glu Arg Arg Asp Ser Val Val Pro Ala Gly Trp Ala
        435                 440                 445

Gly Ala Ser Ser Val Ser Val Pro Gly Ala Cys Ala Ala Thr Thr Val
        450                 455                 460

Val Gly Thr Tyr Ala Ala Ala Ser Asn Cys Gly Thr Pro Gly Ser Gly
465                 470                 475                 480

Ser Gly Gly Asn Gly Gly Ser Ser Gly Asn Ala Leu
            485                 490

<210> SEQ ID NO 16
<211> LENGTH: 1482
<212> TYPE: DNA
<213> ORGANISM: Artificial Sequence
<220> FEATURE:
<223> OTHER INFORMATION: G7P mature protein-encoding nucleic acid
      sequence

<400> SEQUENCE: 16
tcgcctgttt ccaagcgcgc tacgctggac gagttcatca gcaccgagcg tcccttggct      60
ctggagcgcc tgctctgcaa cattggtcct actggttgcc gtgcttcggg agctgcctcg     120
ggagtcgtta tcgcctcgcc gtcccgcagc gatccggact actactacac ttggacccgt     180

```
gatgctgctc tggtctttaa ggagattgtc gactctgtcg agactaacac cactctgctg    240
ctgccagaga ttgagaacta cgttactgcc caggcttacc tgcagaccgt gacgaacccc    300
tcgggttcgc tgtcggatgg tgctggtctg ggcgagccca agttcaacgt cgatatgact    360
cccttcactg gtgcctgggg tcgtcctcag cgtgatggtc cggctctgcg tgctacggct    420
atgatcgcct actacaacta cctgctcaac aacaacgcca ctaccgactg tggtctgtgg    480
cagattatcc agaacgacct gaattacgtc gctcagtact ggaaccaaac tggttacgac    540
ctgtgggagg aggttccggg ttcatccttt tcactgttg ctgctcagta cagagctctc     600
gttgagggtt ctacccttgc tgccaagctc ggcaagtctc actcggccta cgacactgtc    660
gctccgcaga ttctgtgcta cttgcagagc ttctggtcat ccagcaaggg ctacattgtc    720
gccaacaccc agactgccag ctgggtctcg cggtccggtc ttgatgccaa cactcccttg    780
actgccatcc acctatttga ccctgaactt ggctgcgatg actcgacttt ccagccctgc    840
tcgcccaagc agcttatcac tactaagaag ctcgttgact cgttccgctc catctatgcc    900
atcaactcgg gcaagtctgc tggtgatgct ttggctgttg gtcgttacgc cgaggacgtc    960
tactacaacg gcaaccctg gtacctgtgc actttggctg ttgcagagca gctttacgat    1020
gcagtttaca cttggaagct cgagggctcc atcaccgtca cctctgtctc gctgcccttc    1080
ttcactgacc tgctgccctc gctgaccact ggcacctacg cttcgggctc gaccaccttc    1140
gaatccatca tctctgctgt gactacctac gctgatggct tgtcagtat tgtccagacc     1200
tacactcccc tgacggcgc tctgtctgag cagtactcca agtacaacgg ccagcagctg    1260
tcggctcccg acctgacctg gtcgtacgcc gctttcctat ctgccactga gcgccgtgac    1320
agcgttgtcc ctgccggctg ggctggtgcc tcgtctgtct ctgtgcccgg cgcctgcgct    1380
gctaccaccg ttgtcggaac ctacgctgct gcctccaact gcggtactcc tggctctggc    1440
tcgggcggca acggtggctc gagcggtaac gccctgtaat ag                       1482
```

<210> SEQ ID NO 17
<211> LENGTH: 598
<212> TYPE: PRT
<213> ORGANISM: Artificial Sequence
<220> FEATURE:
<223> OTHER INFORMATION: Variant1 (Y321F with Starch Binding Domain)
      mature protein amino acid sequence

<400> SEQUENCE: 17

```
Ser Pro Val Ser Lys Arg Ala Thr Leu Asp Glu Phe Ile Ser Thr Glu
1               5                   10                  15

Arg Pro Leu Ala Leu Glu Arg Leu Leu Cys Asn Ile Gly Pro Thr Gly
            20                  25                  30

Cys Arg Ala Ser Gly Ala Ala Ser Gly Val Val Ile Ala Ser Pro Ser
        35                  40                  45

Arg Ser Asp Pro Asp Tyr Tyr Tyr Thr Trp Thr Arg Asp Ala Ala Leu
    50                  55                  60

Val Phe Lys Glu Ile Val Asp Ser Val Glu Thr Asn Thr Thr Leu Leu
65                  70                  75                  80

Leu Pro Glu Ile Glu Asn Tyr Val Thr Ala Gln Ala Tyr Leu Gln Thr
                85                  90                  95

Val Thr Asn Pro Ser Gly Ser Leu Ser Asp Gly Ala Gly Leu Gly Glu
            100                 105                 110

Pro Lys Phe Asn Val Asp Met Thr Pro Phe Thr Gly Ala Trp Gly Arg
        115                 120                 125
```

```
Pro Gln Arg Asp Gly Pro Ala Leu Arg Ala Thr Ala Met Ile Ala Tyr
    130                 135                 140

Tyr Asn Tyr Leu Leu Asn Asn Asn Ala Thr Thr Asp Cys Gly Leu Trp
145                 150                 155                 160

Gln Ile Ile Gln Asn Asp Leu Asn Tyr Val Ala Gln Tyr Trp Asn Gln
                165                 170                 175

Thr Gly Tyr Asp Leu Trp Glu Glu Val Pro Gly Ser Ser Phe Phe Thr
            180                 185                 190

Val Ala Ala Gln Tyr Arg Ala Leu Val Glu Gly Ser Thr Leu Ala Ala
        195                 200                 205

Lys Leu Gly Lys Ser His Ser Ala Tyr Asp Thr Val Ala Pro Gln Ile
    210                 215                 220

Leu Cys Tyr Leu Gln Ser Phe Trp Ser Ser Lys Gly Tyr Ile Val
225                 230                 235                 240

Ala Asn Thr Gln Thr Ala Ser Trp Val Ser Arg Ser Gly Leu Asp Ala
                245                 250                 255

Asn Thr Pro Leu Thr Ala Ile His Leu Phe Asp Pro Glu Leu Gly Cys
            260                 265                 270

Asp Asp Ser Thr Phe Gln Pro Cys Ser Pro Lys Gln Leu Ile Thr Thr
        275                 280                 285

Lys Lys Leu Val Asp Ser Phe Arg Ser Ile Tyr Ala Ile Asn Ser Gly
    290                 295                 300

Lys Ser Ala Gly Asp Ala Leu Ala Val Gly Arg Tyr Ala Glu Asp Val
305                 310                 315                 320

Phe Tyr Asn Gly Asn Pro Trp Tyr Leu Cys Thr Leu Ala Val Ala Glu
                325                 330                 335

Gln Leu Tyr Asp Ala Val Tyr Thr Trp Lys Leu Glu Gly Ser Ile Thr
            340                 345                 350

Val Thr Ser Val Ser Leu Pro Phe Phe Thr Asp Leu Leu Pro Ser Leu
        355                 360                 365

Thr Thr Gly Thr Tyr Ala Ser Gly Ser Thr Thr Phe Glu Ser Ile Ile
    370                 375                 380

Ser Ala Val Thr Thr Tyr Ala Asp Gly Phe Val Ser Ile Val Gln Thr
385                 390                 395                 400

Tyr Thr Pro Ser Asp Gly Ala Leu Ser Glu Gln Tyr Ser Lys Tyr Asn
                405                 410                 415

Gly Gln Gln Leu Ser Ala Pro Asp Leu Thr Trp Ser Tyr Ala Ala Phe
            420                 425                 430

Leu Ser Ala Thr Glu Arg Arg Asp Ser Val Val Pro Ala Gly Trp Ala
        435                 440                 445

Gly Ala Ser Ser Val Ser Val Pro Gly Ala Cys Ala Ala Thr Thr Val
    450                 455                 460

Val Gly Thr Tyr Ala Ala Ala Ser Asn Cys Gly Thr Pro Gly Ser Gly
465                 470                 475                 480

Ser Gly Gly Asn Gly Ser Ser Gly Asn Ala Leu Val Thr Phe Asn
                485                 490                 495

Glu Leu Ala Thr Thr Tyr Tyr Gly Glu Asn Ile Lys Leu Val Gly Ser
            500                 505                 510

Thr Ala Ala Phe Gly Ser Trp Ser Pro Ser Ala Gly Ile Leu Leu Ser
        515                 520                 525

Ala Ser Ser Tyr Thr Ala Ser Asn Pro Leu Trp Thr Thr Val Ser
    530                 535                 540
```

```
Val Pro Gln Gly Ser Thr Val Glu Phe Lys Phe Ile Arg Val Gly Ser
545                 550                 555                 560

Asp Gly Ser Ile Thr Trp Glu Ser Gly Asn Asn Lys Val Leu Thr Val
                565                 570                 575

Gly Ser Ser Ala Thr Ser Val Thr Val Ser Ala Ser Trp Asn Gly Ala
            580                 585                 590

Tyr Ser Val Ser Ser Ser
        595

<210> SEQ ID NO 18
<211> LENGTH: 1800
<212> TYPE: DNA
<213> ORGANISM: Artificial Sequence
<220> FEATURE:
<223> OTHER INFORMATION: Variant1 (Y321F with Starch Binding Domain)
      mature protein-encoding nucleic acid sequence

<400> SEQUENCE: 18
tcgcctgttt ccaagcgcgc tacgctggac gagttcatca gcaccgagcg tcccttggct      60
ctggagcgcc tgctctgcaa cattggtcct actggttgcc gtgcttcggg agctgcctcg     120
ggagtcgtta tcgcctcgcc gtcccgcagc gatccggact actactacac ttggacccgt     180
gatgctgctc tggtctttaa ggagattgtc gactctgtcg agactaacac cactctgctg     240
ctgccagaga ttgagaacta cgttactgcc caggcttacc tgcagaccgt gacgaaccc     300 tcgggttcgc tgtcggatgg tgctggtctg ggcgagccca agttcaacgt cgatatgact     360
cccttcactg gtgcctgggg tcgtcctcag cgtgatggtc cggctctgcg tgctacggct     420
atgatcgcct actacaacta cctgctcaac aacaacgcca ctaccgactg tggtctgtgg     480
cagattatcc agaacgacct gaattacgtc gctcagtact ggaaccaaac tggttacgac     540
ctgtgggagg aggttccggg ttcatccttt ttcactgttg ctgctcagta cagagctctc     600
gttgagggtt ctaccttgc tgccaagctc ggcaagtctc actcggccta cgacactgtc     660
gctccgcaga ttctgtgcta cttgcagagc ttctggtcat ccagcaaggg ctacattgtc     720
gccaacaccc agactgccag ctgggtctcg cggtccggtc ttgatgccaa cactcccttg     780
actgccatcc acctatttga ccctgaactt ggctgcgatg actcgacttt ccagcccctgc    840 tcgcccaagc agcttatcac tactaagaag ctcgttgact cgttccgctc catctatgcc     900
atcaactcgg gcaagtctgc tggtgatgct ttggctgttg tcgttacgc cgaggacgtc     960 ttctacaacg caaccccctg gtacctgtgc actttggctg ttgcagagca gctttacgat    1020
gcagtttaca cttggaagct cgagggctcc atcaccgtca cctctgtctc gctgcccttc    1080
ttcactgacc tgctgccctc gctgaccact ggcacctacg cttcgggctc gaccaccttc    1140
gaatccatca tctctgctgt gactacctac gctgatggct tgtcagtat tgtccagacc    1200 tacactccct ctgacggcgc tctgtctgag cagtactcca agtacaacgg ccagcagctg    1260
tcggctcccg acctgaccct gtcgtacgcc gcttttccta tctgccactg agcgccgtgac    1320 agcgttgtcc ctgccggctg gctggtgcc tcgtctgtct ctgtgcccgg cgcctgcgct     1380
gctaccaccg ttgtcggaac ctacgctgct gcctccaact gcggtactcc tggctctggc    1440
tcgggcggca acgtggctc gagcggtaac gccctggtga ctttcaacga gctgctact    1500 acctactacg cgagaacat taagcttgtc ggcagcacag ctgctttcgg ttcgtggtcg    1560
ccctcagctg gtattctcct gtctgcctcg tcgtacacgg ccagcaaccc tctgtggact    1620
accaccgtgt cggttcccca gggctcgacc gttgagttca gttcatccg tgttggctcc    1680
```

```
gacggcagca tcacgtggga gagcggcaac aacaaggtgt tgacggttgg ctcttcggcc   1740
acgagcgtca ctgtttctgc cagctggaac ggcgcctact cggtgtctag ctcttaatag   1800
```

<210> SEQ ID NO 19
<211> LENGTH: 598
<212> TYPE: PRT
<213> ORGANISM: Artificial Sequence
<220> FEATURE:
<223> OTHER INFORMATION: Variant2 (S188H/Y321W/Q419P with Starch Binding
      Domain) mature protein amino acid sequence

<400> SEQUENCE: 19

```
Ser Pro Val Ser Lys Arg Ala Thr Leu Asp Glu Phe Ile Ser Thr Glu
1               5                   10                  15

Arg Pro Leu Ala Leu Glu Arg Leu Leu Cys Asn Ile Gly Pro Thr Gly
            20                  25                  30

Cys Arg Ala Ser Gly Ala Ala Ser Gly Val Val Ile Ala Ser Pro Ser
        35                  40                  45

Arg Ser Asp Pro Asp Tyr Tyr Tyr Thr Trp Thr Arg Asp Ala Ala Leu
    50                  55                  60

Val Phe Lys Glu Ile Val Asp Ser Val Glu Thr Asn Thr Thr Leu Leu
65                  70                  75                  80

Leu Pro Glu Ile Glu Asn Tyr Val Thr Ala Gln Ala Tyr Leu Gln Thr
                85                  90                  95

Val Thr Asn Pro Ser Gly Ser Leu Ser Asp Gly Ala Gly Leu Gly Glu
            100                 105                 110

Pro Lys Phe Asn Val Asp Met Thr Pro Phe Thr Gly Ala Trp Gly Arg
        115                 120                 125

Pro Gln Arg Asp Gly Pro Ala Leu Arg Ala Thr Ala Met Ile Ala Tyr
    130                 135                 140

Tyr Asn Tyr Leu Leu Asn Asn Asn Ala Thr Thr Asp Cys Gly Leu Trp
145                 150                 155                 160

Gln Ile Ile Gln Asn Asp Leu Asn Tyr Val Ala Gln Tyr Trp Asn Gln
                165                 170                 175

Thr Gly Tyr Asp Leu Trp Glu Glu Val Pro Gly His Ser Phe Phe Thr
            180                 185                 190

Val Ala Ala Gln Tyr Arg Ala Leu Val Glu Gly Ser Thr Leu Ala Ala
        195                 200                 205

Lys Leu Gly Lys Ser His Ser Ala Tyr Asp Thr Val Ala Pro Gln Ile
    210                 215                 220

Leu Cys Tyr Leu Gln Ser Phe Trp Ser Ser Lys Gly Tyr Ile Val
225                 230                 235                 240

Ala Asn Thr Gln Thr Ala Ser Trp Val Ser Arg Ser Gly Leu Asp Ala
                245                 250                 255

Asn Thr Pro Leu Thr Ala Ile His Leu Phe Asp Pro Glu Leu Gly Cys
            260                 265                 270

Asp Asp Ser Thr Phe Gln Pro Cys Ser Pro Lys Gln Leu Ile Thr Thr
        275                 280                 285

Lys Lys Leu Val Asp Ser Phe Arg Ser Ile Tyr Ala Ile Asn Ser Gly
    290                 295                 300

Lys Ser Ala Gly Asp Ala Leu Ala Val Gly Arg Tyr Ala Glu Asp Val
305                 310                 315                 320

Trp Tyr Asn Gly Asn Pro Trp Tyr Leu Cys Thr Leu Ala Val Ala Glu
                325                 330                 335

Gln Leu Tyr Asp Ala Val Tyr Thr Trp Lys Leu Glu Gly Ser Ile Thr
```

```
                340             345              350
        Val Thr Ser Val Ser Leu Pro Phe Phe Thr Asp Leu Leu Pro Ser Leu
            355                  360                 365

Thr Thr Gly Thr Tyr Ala Ser Gly Ser Thr Thr Phe Glu Ser Ile Ile
            370                  375                 380

Ser Ala Val Thr Thr Tyr Ala Asp Gly Phe Val Ser Ile Val Gln Thr
        385                  390                 395                 400

Tyr Thr Pro Ser Asp Gly Ala Leu Ser Glu Gln Tyr Ser Lys Tyr Asn
                        405                 410                 415

Gly Gln Pro Leu Ser Ala Pro Asp Leu Thr Trp Ser Tyr Ala Ala Phe
                    420                 425                 430

Leu Ser Ala Thr Glu Arg Arg Asp Ser Val Val Pro Ala Gly Trp Ala
                    435                 440                 445

Gly Ala Ser Ser Val Ser Val Pro Gly Ala Cys Ala Ala Thr Thr Val
                    450                 455                 460

Val Gly Thr Tyr Ala Ala Ala Ser Asn Cys Gly Thr Pro Gly Ser Gly
        465                 470                 475                 480

Ser Gly Gly Asn Gly Gly Ser Ser Gly Asn Ala Leu Val Thr Phe Asn
                        485                 490                 495

Glu Leu Ala Thr Thr Tyr Tyr Gly Glu Asn Ile Lys Leu Val Gly Ser
                    500                 505                 510

Thr Ala Ala Phe Gly Ser Trp Ser Pro Ser Ala Gly Ile Leu Leu Ser
                    515                 520                 525

Ala Ser Ser Tyr Thr Ala Ser Asn Pro Leu Trp Thr Thr Thr Val Ser
                    530                 535                 540

Val Pro Gln Gly Ser Thr Val Glu Phe Lys Phe Ile Arg Val Gly Ser
        545                 550                 555                 560

Asp Gly Ser Ile Thr Trp Glu Ser Gly Asn Asn Lys Val Leu Thr Val
                        565                 570                 575

Gly Ser Ser Ala Thr Ser Val Thr Val Ser Ala Ser Trp Asn Gly Ala
                    580                 585                 590

Tyr Ser Val Ser Ser Ser
                    595

<210> SEQ ID NO 20
<211> LENGTH: 1800
<212> TYPE: DNA
<213> ORGANISM: Artificial Sequence
<220> FEATURE:
<223> OTHER INFORMATION: Variant2 (S188H/Y321W/Q419P with Starch Binding
      Domain) mature protein-encoding nucleic acid sequence

<400> SEQUENCE: 20
tcgcctgttt ccaagcgcgc tacgctggac gagttcatca gcaccgagcg tcccttggct    60
ctggagcgcc tgctctgcaa cattggtcct actggttgcc gtgcttcggg agctgcctcg   120
ggagtcgtta tcgcctcgcc gtcccgcagc gatccggact actactacac ttggacccgt   180
gatgctgctc tggtctttaa ggagattgtc gactctgtcg agactaacac cactctgctg   240
ctgccagaga ttgagaacta cgttactgcc caggcttacc tgcagaccgt gacgaacccc   300
tcgggttcgc tgtcggatgg tgctggtctg ggcgagccca gttcaacgt cgatatgact   360 cccttcactg gtgcctgggg tcgtcctcag cgtgatggtc cggctctgcg tgctacggct   420
atgatcgcct actacaacta cctgctcaac aacaacgcca ctaccgactg tggtctgtgg   480
cagattatcc agaacgacct gaattacgtc gctcagtact ggaaccaaac tggttacgac   540
```

```
ctgtgggagg aggttccggg tcactccttt tcactgttg ctgctcagta cagagctctc    600
gttgagggtt ctaccttgc tgccaagctc ggcaagtctc actcggccta cgacactgtc    660
gctccgcaga ttctgtgcta cttgcagagc ttctggtcat ccagcaaggg ctacattgtc    720
gccaacaccc agactgccag ctgggtctcg cggtccggtc ttgatgccaa cactcccttg    780
actgccatcc acctatttga ccctgaactt ggctgcgatg actcgacttt ccagccctgc    840
tcgcccaagc agcttatcac tactaagaag ctcgttgact cgttccgctc catctatgcc    900
atcaactcgg gcaagtctgc tggtgatgct ttggctgttg gtcgttacgc cgaggacgtc    960
tggtacaacg gcaaccctg gtacctgtgc actttggctg ttgcagagca gctttacgat   1020
gcagtttaca cttggaagct cgagggctcc atcaccgtca cctctgtctc gctgcccttc   1080
ttcactgacc tgctgccctc gctgaccact ggcacctacg cttcgggctc gaccaccttc   1140
gaatccatca tctctgctgt gactacctac gctgatggct tgtcagtat tgtccagacc   1200
tacactccct ctgacggcgc tctgtctgag cagtactcca agtacaacgg ccagcccctg   1260
tcggctcccg acctgacctg gtcgtacgcc gctttcctat ctgccactga gcgccgtgac   1320
agcgttgtcc ctgccggctg ggctggtgcc tcgtctgtct ctgtgcccgg cgcctgcgct   1380
gctaccaccg ttgtcggaac ctacgctgct gcctccaact gcggtactcc tggctctggc   1440
tcgggcggca acggtggctc gagcggtaac gccctggtga cttcaacga gctggctact   1500
acctactacg cgagaacat taagcttgtc ggcagcacag ctgctttcgg ttcgtggtcg   1560
ccctcagctg gtattctcct gtctgcctcg tcgtacacgg ccagcaaccc tctgtggact   1620
accaccgtgt cggttcccca gggctcgacc gttgagttca gttcatccg tgttggctcc   1680
gacggcagca tcacgtggga gagcggcaac aacaaggtgt tgacggttgg ctcttcggcc   1740
acgagcgtca ctgtttctgc cagctggaac ggcgcctact cggtgtctag ctcttaatag   1800
```

<210> SEQ ID NO 21
<211> LENGTH: 492
<212> TYPE: PRT
<213> ORGANISM: Artificial Sequence
<220> FEATURE:
<223> OTHER INFORMATION: Variant1 (Y321F without Starch Binding Domain) mature protein amino acid sequence

<400> SEQUENCE: 21

Ser Pro Val Ser Lys Arg Ala Thr Leu Asp Glu Phe Ile Ser Thr Glu
1               5                   10                  15

Arg Pro Leu Ala Leu Glu Arg Leu Leu Cys Asn Ile Gly Pro Thr Gly
            20                  25                  30

Cys Arg Ala Ser Gly Ala Ala Ser Gly Val Val Ile Ala Ser Pro Ser
        35                  40                  45

Arg Ser Asp Pro Asp Tyr Tyr Tyr Thr Trp Thr Arg Asp Ala Ala Leu
    50                  55                  60

Val Phe Lys Glu Ile Val Asp Ser Val Glu Thr Asn Thr Thr Leu Leu
65                  70                  75                  80

Leu Pro Glu Ile Glu Asn Tyr Val Thr Ala Gln Ala Tyr Leu Gln Thr
                85                  90                  95

Val Thr Asn Pro Ser Gly Ser Leu Ser Asp Gly Ala Gly Leu Gly Glu
            100                 105                 110

Pro Lys Phe Asn Val Asp Met Thr Pro Phe Thr Gly Ala Trp Gly Arg
        115                 120                 125

Pro Gln Arg Asp Gly Pro Ala Leu Arg Ala Thr Ala Met Ile Ala Tyr
    130                 135                 140

```
Tyr Asn Tyr Leu Leu Asn Asn Ala Thr Thr Asp Cys Gly Leu Trp
145                 150                 155                 160

Gln Ile Ile Gln Asn Asp Leu Asn Tyr Val Ala Gln Tyr Trp Asn Gln
        165                 170                 175

Thr Gly Tyr Asp Leu Trp Glu Glu Val Pro Gly Ser Ser Phe Phe Thr
            180                 185                 190

Val Ala Ala Gln Tyr Arg Ala Leu Val Glu Gly Ser Thr Leu Ala Ala
                195                 200                 205

Lys Leu Gly Lys Ser His Ser Ala Tyr Asp Thr Val Ala Pro Gln Ile
210                 215                 220

Leu Cys Tyr Leu Gln Ser Phe Trp Ser Ser Lys Gly Tyr Ile Val
225                 230                 235                 240

Ala Asn Thr Gln Thr Ala Ser Trp Val Ser Arg Ser Gly Leu Asp Ala
            245                 250                 255

Asn Thr Pro Leu Thr Ala Ile His Leu Phe Asp Pro Glu Leu Gly Cys
                260                 265                 270

Asp Asp Ser Thr Phe Gln Pro Cys Ser Pro Lys Gln Leu Ile Thr Thr
        275                 280                 285

Lys Lys Leu Val Asp Ser Phe Arg Ser Ile Tyr Ala Ile Asn Ser Gly
290                 295                 300

Lys Ser Ala Gly Asp Ala Leu Ala Val Gly Arg Tyr Ala Glu Asp Val
305                 310                 315                 320

Phe Tyr Asn Gly Asn Pro Trp Tyr Leu Cys Thr Leu Ala Val Ala Glu
                325                 330                 335

Gln Leu Tyr Asp Ala Val Tyr Thr Trp Lys Leu Glu Gly Ser Ile Thr
            340                 345                 350

Val Thr Ser Val Ser Leu Pro Phe Phe Thr Asp Leu Leu Pro Ser Leu
                355                 360                 365

Thr Thr Gly Thr Tyr Ala Ser Gly Ser Thr Thr Phe Glu Ser Ile Ile
        370                 375                 380

Ser Ala Val Thr Thr Tyr Ala Asp Gly Phe Val Ser Ile Val Gln Thr
385                 390                 395                 400

Tyr Thr Pro Ser Asp Gly Ala Leu Ser Glu Gln Tyr Ser Lys Tyr Asn
                405                 410                 415

Gly Gln Gln Leu Ser Ala Pro Asp Leu Thr Trp Ser Tyr Ala Ala Phe
            420                 425                 430

Leu Ser Ala Thr Glu Arg Arg Asp Ser Val Val Pro Ala Gly Trp Ala
                435                 440                 445

Gly Ala Ser Ser Val Ser Val Pro Gly Ala Cys Ala Ala Thr Thr Val
            450                 455                 460

Val Gly Thr Tyr Ala Ala Ala Ser Asn Cys Gly Thr Pro Gly Ser Gly
465                 470                 475                 480

Ser Gly Gly Asn Gly Gly Ser Ser Gly Asn Ala Leu
            485                 490
```

<210> SEQ ID NO 22
<211> LENGTH: 1482
<212> TYPE: DNA
<213> ORGANISM: Artificial Sequence
<220> FEATURE:
<223> OTHER INFORMATION: Variant1 (Y321F without Starch Binding Domain)
      mature protein-encoding nucleic acid sequence

<400> SEQUENCE: 22

```
tcgcctgttt ccaagcgcgc tacgctggac gagttcatca gcaccgagcg tcccttggct    60
```

```
ctggagcgcc tgctctgcaa cattggtcct actggttgcc gtgcttcggg agctgcctcg    120
ggagtcgtta tcgcctcgcc gtcccgcagc gatccggact actactacac ttggacccgt    180
gatgctgctc tggtctttaa ggagattgtc gactctgtcg agactaacac cactctgctg    240
ctgccagaga ttgagaacta cgttactgcc caggcttacc tgcagaccgt gacgaacccc    300
tcgggttcgc tgtcggatgg tgctggtctg ggcgagccca agttcaacgt cgatatgact    360
cccttcactg gtgcctgggg tcgtcctcag cgtgatggtc cggctctgcg tgctacggct    420
atgatcgcct actacaacta cctgctcaac aacaacgcca ctaccgactg ggtctgtgg     480 cagattatcc agaacgacct gaattacgtc gctcagtact ggaaccaaac tggttacgac    540
ctgtgggagg aggttccggg ttcatccttt tcactgttg ctgctcagta cagagctctc     600
gttgagggtt ctaccttgc tgccaagctc ggcaagtctc actcggccta cgacactgtc     660
gctccgcaga ttctgtgcta cttgcagagc ttctggtcat ccagcaaggg ctacattgtc    720
gccaacaccc agactgccag ctgggtctcg cggtccggtc ttgatgccaa cactcccttg    780
actgccatcc acctatttga ccctgaactt ggctgcgatg actcgacttt ccagccctgc    840
tcgcccaagc agcttatcac tactaagaag ctcgttgact cgttccgctc catctatgcc    900
atcaactcgg gcaagtctgc tggtgatgct ttggctgttg gtcgttacgc cgaggacgtc    960
ttctacaacg caaccccctg gtacctgtgc actttggctg ttgcagagca gctttacgat   1020
gcagtttaca cttggaagct cgagggctcc atcaccgtca cctctgtctc gctgcccttc   1080
ttcactgacc tgctgccctc gctgaccact ggcacctacg cttcgggctc gaccaccttc   1140
gaatccatca tctctgctgt gactacctac gctgatggct tgtcagtat tgtccagacc    1200 tacactccct ctgacggcgc tctgtctgag cagtactcca gtacaacgg ccagcagctg    1260 tcggctcccg acctgacctg gtcgtacgcc gctttcctat ctgccactga gcgccgtgac   1320
agcgttgtcc ctgccggctg ggctggtgcc tcgtctgtct ctgtgcccgg cgcctgcgct   1380
gctaccaccg ttgtcggaac ctacgctgct gcctccaact gcggtactcc tggctctggc   1440
tcgggcggca acggtggctc gagcggtaac gccctgtaat ag                      1482
```

```
<210> SEQ ID NO 23
<211> LENGTH: 492
<212> TYPE: PRT
<213> ORGANISM: Artificial Sequence
<220> FEATURE:
<223> OTHER INFORMATION: Variant2 (S188H/Y321W/Q419P without Starch
      Binding Domain) mature protein amino acid sequence

<400> SEQUENCE: 23

Ser Pro Val Ser Lys Arg Ala Thr Leu Asp Glu Phe Ile Ser Thr Glu
 1               5                  10                  15

Arg Pro Leu Ala Leu Glu Arg Leu Leu Cys Asn Ile Gly Pro Thr Gly
                20                  25                  30

Cys Arg Ala Ser Gly Ala Ala Ser Gly Val Val Ile Ala Ser Pro Ser
            35                  40                  45

Arg Ser Asp Pro Asp Tyr Tyr Tyr Thr Trp Thr Arg Asp Ala Ala Leu
        50                  55                  60

Val Phe Lys Glu Ile Val Asp Ser Val Glu Thr Asn Thr Thr Leu Leu
 65                  70                  75                  80

Leu Pro Glu Ile Glu Asn Tyr Val Thr Ala Gln Ala Tyr Leu Gln Thr
                85                  90                  95

Val Thr Asn Pro Ser Gly Ser Leu Ser Asp Gly Ala Gly Leu Gly Glu
```

```
                  100                 105                 110
Pro Lys Phe Asn Val Asp Met Thr Pro Phe Thr Gly Ala Trp Gly Arg
            115                 120                 125

Pro Gln Arg Asp Gly Pro Ala Leu Arg Ala Thr Ala Met Ile Ala Tyr
        130                 135                 140

Tyr Asn Tyr Leu Leu Asn Asn Ala Thr Thr Asp Cys Gly Leu Trp
145                 150                 155                 160

Gln Ile Ile Gln Asn Asp Leu Asn Tyr Val Ala Gln Tyr Trp Asn Gln
                165                 170                 175

Thr Gly Tyr Asp Leu Trp Glu Glu Val Pro Gly His Ser Phe Phe Thr
            180                 185                 190

Val Ala Ala Gln Tyr Arg Ala Leu Val Glu Gly Ser Thr Leu Ala Ala
        195                 200                 205

Lys Leu Gly Lys Ser His Ser Ala Tyr Asp Thr Val Ala Pro Gln Ile
210                 215                 220

Leu Cys Tyr Leu Gln Ser Phe Trp Ser Ser Lys Gly Tyr Ile Val
225                 230                 235                 240

Ala Asn Thr Gln Thr Ala Ser Trp Val Ser Arg Ser Gly Leu Asp Ala
            245                 250                 255

Asn Thr Pro Leu Thr Ala Ile His Leu Phe Asp Pro Glu Leu Gly Cys
        260                 265                 270

Asp Asp Ser Thr Phe Gln Pro Cys Ser Pro Lys Gln Leu Ile Thr Thr
    275                 280                 285

Lys Lys Leu Val Asp Ser Phe Arg Ser Ile Tyr Ala Ile Asn Ser Gly
290                 295                 300

Lys Ser Ala Gly Asp Ala Leu Ala Val Gly Arg Tyr Ala Glu Asp Val
305                 310                 315                 320

Trp Tyr Asn Gly Asn Pro Trp Tyr Leu Cys Thr Leu Ala Val Ala Glu
            325                 330                 335

Gln Leu Tyr Asp Ala Val Tyr Thr Trp Lys Leu Glu Gly Ser Ile Thr
        340                 345                 350

Val Thr Ser Val Ser Leu Pro Phe Phe Thr Asp Leu Leu Pro Ser Leu
    355                 360                 365

Thr Thr Gly Thr Tyr Ala Ser Gly Ser Thr Thr Phe Glu Ser Ile Ile
    370                 375                 380

Ser Ala Val Thr Thr Tyr Ala Asp Gly Phe Val Ser Ile Val Gln Thr
385                 390                 395                 400

Tyr Thr Pro Ser Asp Gly Ala Leu Ser Glu Gln Tyr Ser Lys Tyr Asn
            405                 410                 415

Gly Gln Pro Leu Ser Ala Pro Asp Leu Thr Trp Ser Tyr Ala Ala Phe
        420                 425                 430

Leu Ser Ala Thr Glu Arg Arg Asp Ser Val Val Pro Ala Gly Trp Ala
    435                 440                 445

Gly Ala Ser Ser Val Ser Val Pro Gly Ala Cys Ala Ala Thr Thr Val
450                 455                 460

Val Gly Thr Tyr Ala Ala Ala Ser Asn Cys Gly Thr Pro Gly Ser Gly
465                 470                 475                 480

Ser Gly Gly Asn Gly Gly Ser Ser Gly Asn Ala Leu
                485                 490

<210> SEQ ID NO 24
<211> LENGTH: 1482
<212> TYPE: DNA
<213> ORGANISM: Artificial Sequence
```

<220> FEATURE:
<223> OTHER INFORMATION: Variant2 (S188H/Y321W/Q419P without Starch
      Binding Domain) mature protein-encoding nucleic acid sequence

<400> SEQUENCE: 24

```
tcgcctgttt ccaagcgcgc tacgctggac gagttcatca gcaccgagcg tcccttggct     60
ctggagcgcc tgctctgcaa cattggtcct actggttgcc gtgcttcggg agctgcctcg    120
ggagtcgtta tcgcctcgcc gtcccgcagc gatccggact actactacac ttggacccgt    180
gatgctgctc tggtctttaa ggagattgtc gactctgtcg agactaacac cactctgctg    240
ctgccagaga ttgagaacta cgttactgcc caggcttacc tgcagaccgt gacgaacccc    300
tcgggttcgc tgtcggatgg tgctggtctg ggcgagccca agttcaacgt cgatatgact    360
cccttcactg gtgcctgggg tcgtcctcag cgtgatggtc cggctctgcg tgctacggct    420
atgatcgcct actacaacta cctgctcaac aacaacgcca ctaccgactg tggtctgtgg    480
cagattatcc agaacgacct gaattacgtc gctcagtact ggaaccaaac tggttacgac    540
ctgtgggagg aggttccggg tcactccttt ttcactgttg ctgctcagta cagagctctc    600
gttgagggtt ctacccttgc tgccaagctc ggcaagtctc actcggccta cgacactgtc    660
gctccgcaga ttctgtgcta cttgcagagc ttctggtcat ccagcaaggg ctacattgtc    720
gccaacaccc agactgccag ctgggtctcg cggtccggtc ttgatgccaa cactcccttg    780
actgccatcc acctatttga ccctgaactt ggctgcgatg actcgacttt ccagccctgc    840
tcgcccaagc agcttatcac tactaagaag ctcgttgact cgttccgctc catctatgcc    900
atcaactcgg gcaagtctgc tggtgatgct ttggctgttg tcgttacgc cgaggacgtc    960
tggtacaacg caaccccctg gtacctgtgc actttggctg ttgcagagca gctttacgat   1020
gcagtttaca cttggaagct cgagggctcc atcaccgtca cctctgtctc gctgcccttc   1080
ttcactgacc tgctgccctc gctgaccact ggcacctacg cttcgggctc gaccaccttc   1140
gaatccatca tctctgctgt gactacctac gctgatggct ttgtcagtat tgtccagacc   1200
tacactccct ctgacggcgc tctgtctgag cagtactcca agtacaacgg ccagcccctg   1260
tcggctcccg acctgacctg gtcgtacgcc gcttttcctat ctgccactga gcgccgtgac   1320
agcgttgtcc ctgccggctg ggctggtgcc tcgtctgtct ctgtgcccgg cgcctgcgct   1380
gctaccaccg ttgtcggaac ctacgctgct gcctccaact gcggtactcc tggctctggc   1440
tcgggcggca acggtggctc gagcggtaac gccctgtaat ag                      1482
```

<210> SEQ ID NO 25
<211> LENGTH: 598
<212> TYPE: PRT
<213> ORGANISM: Artificial Sequence
<220> FEATURE:
<223> OTHER INFORMATION: Amino acid sequence of wild type glucoamylase
      mature protein with Starch Binding Domain

<400> SEQUENCE: 25

```
Ser Pro Val Ser Lys Arg Ala Thr Leu Asp Glu Phe Ile Ser Thr Glu
 1               5                  10                  15

Arg Pro Leu Ala Leu Glu Lys Leu Leu Cys Asn Ile Gly Ser Thr Gly
                20                  25                  30

Cys Arg Ala Ser Gly Ala Ser Ser Gly Val Val Leu Ala Ser Pro Ser
            35                  40                  45

Thr Ser Asn Pro Asp Tyr Tyr Tyr Thr Trp Thr Arg Asp Ala Ala Leu
        50                  55                  60
```

```
Val Phe Lys Glu Ile Val Asp Ser Val Glu Thr Asn Thr Leu Leu
 65                  70                  75                  80

Leu Pro Glu Ile Glu Asn Tyr Val Thr Ala Gln Ala Tyr Leu Gln Thr
                 85                  90                  95

Val Thr Asn Pro Ser Gly Ser Leu Ser Asp Gly Ala Gly Leu Ala Glu
            100                 105                 110

Pro Lys Phe Asn Ala Asp Leu Thr Gln Phe Thr Gly Ala Trp Gly Arg
        115                 120                 125

Pro Gln Arg Asp Gly Pro Ala Leu Arg Ala Thr Ala Met Ile Ala Tyr
    130                 135                 140

Tyr Asn Tyr Leu Leu Asn Asn Ala Thr Thr Asp Cys Gly Leu Trp
145                 150                 155                 160

Gln Ile Ile Gln Asn Asp Leu Asn Tyr Val Ala Gln Tyr Trp Asn Gln
                165                 170                 175

Thr Gly Tyr Asp Leu Trp Glu Glu Val Pro Gly Ser Ser Phe Phe Thr
            180                 185                 190

Val Ala Ala Gln Tyr Arg Ala Leu Val Glu Gly Ser Thr Leu Ala Ala
        195                 200                 205

Lys Leu Gly Lys Ser His Ser Ala Tyr Asp Thr Val Ala Pro Gln Ile
    210                 215                 220

Leu Cys Tyr Leu Gln Ser Phe Trp Ser Ser Lys Gly Tyr Ile Val
225                 230                 235                 240

Ala Asn Thr Gln Thr Ala Ser Trp Val Ser Arg Ser Gly Leu Asp Ala
                245                 250                 255

Asn Thr Pro Leu Thr Ala Ile His Leu Phe Asp Pro Glu Leu Gly Cys
            260                 265                 270

Asp Asp Ser Thr Phe Gln Pro Cys Ser Pro Lys Gln Leu Ile Thr Thr
        275                 280                 285

Lys Lys Leu Val Asp Ser Phe Arg Ser Ile Tyr Ala Ile Asn Ser Gly
    290                 295                 300

Lys Ser Ala Gly Thr Ala Leu Ala Val Gly Arg Tyr Ala Glu Asp Val
305                 310                 315                 320

Tyr Tyr Asn Gly Asn Pro Trp Tyr Leu Cys Thr Leu Ala Val Ala Glu
                325                 330                 335

Gln Leu Tyr Asp Ala Val Tyr Thr Trp Lys Leu Glu Gly Ser Ile Thr
            340                 345                 350

Val Thr Ser Val Ser Leu Pro Phe Phe Thr Asp Leu Leu Pro Ser Leu
        355                 360                 365

Thr Thr Gly Thr Tyr Ala Ser Gly Ser Thr Thr Phe Glu Ser Ile Ile
    370                 375                 380

Ser Ala Val Thr Thr Tyr Ala Asp Gly Phe Val Ser Ile Val Gln Thr
385                 390                 395                 400

Tyr Thr Pro Ser Asp Gly Ala Leu Ser Glu Gln Tyr Asn Lys Ala Asn
                405                 410                 415

Gly Gln Gln Leu Ser Ala Gln Asp Leu Thr Trp Ser Tyr Ala Ala Phe
            420                 425                 430

Leu Ser Ala Thr Glu Arg Arg Asp Ser Val Val Pro Ala Gly Trp Ala
        435                 440                 445

Gly Ala Ser Ser Val Ser Val Pro Gly Ala Cys Ala Ala Thr Thr Val
    450                 455                 460

Val Gly Thr Tyr Ala Ala Ala Ser Asn Cys Gly Thr Pro Gly Ser Gly
465                 470                 475                 480

Ser Gly Gly Asn Gly Gly Ser Ser Gly Asn Ala Leu Val Thr Phe Asn
```

```
                    485                  490                  495
Glu Leu Ala Thr Thr Tyr Tyr Gly Glu Asn Ile Lys Leu Val Gly Ser
            500                  505                  510

Thr Ala Ala Phe Gly Ser Trp Ser Pro Ser Ala Gly Ile Leu Leu Ser
            515                  520                  525

Ala Ser Ser Tyr Thr Ala Ser Asn Pro Leu Trp Thr Thr Thr Val Ser
            530                  535                  540

Val Pro Gln Gly Ser Thr Val Glu Phe Lys Phe Ile Arg Val Gly Ser
545                  550                  555                  560

Asp Gly Ser Ile Thr Trp Glu Ser Gly Asn Asn Lys Val Leu Thr Val
                565                  570                  575

Gly Ser Ser Ala Thr Ser Val Thr Val Ser Ala Ser Trp Asn Gly Ala
                580                  585                  590

Tyr Ser Val Ser Ser Ser
                595

<210> SEQ ID NO 26
<211> LENGTH: 22
<212> TYPE: PRT
<213> ORGANISM: Artificial Sequence
<220> FEATURE:
<223> OTHER INFORMATION: Amino acid sequence of wild type signal peptide

<400> SEQUENCE: 26

Met Val Phe Leu Lys Ser Ala Ile Ala Ala Ser Thr Trp Leu Leu Ala
1               5                   10                  15

Ala Thr Gly Val Val Ala
            20
```